United States Patent
Liu et al.

(10) Patent No.: US 10,407,421 B2
(45) Date of Patent: Sep. 10, 2019

(54) BICYCLIC ARYL MONOBACTAM COMPOUNDS AND METHODS OF USE THEREOF FOR THE TREATMENT OF BACTERIAL INFECTIONS

(71) Applicant: Merck Sharp & Dohme Corp., Rahway, NJ (US)

(72) Inventors: Weiguo Liu, Princeton, NJ (US); Fa-Xiang Ding, Staten Island, NY (US); Wanying Sun, Edison, NJ (US); Reynalda Keh Dejesus, East Brunswick, NJ (US); Haifeng Tang, Metuchen, NJ (US); Xianhai Huang, Warren, NJ (US); Jinlong Jiang, Scotch Plains, NJ (US); Yan Guo, Westfield, NJ (US); Hongwu Wang, Westfield, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 16/076,781

(22) PCT Filed: Mar. 2, 2017

(86) PCT No.: PCT/US2017/020303
§ 371 (c)(1),
(2) Date: Aug. 9, 2018

(87) PCT Pub. No.: WO2017/155765
PCT Pub. Date: Sep. 14, 2017

(65) Prior Publication Data
US 2019/0071436 A1    Mar. 7, 2019

Related U.S. Application Data

(60) Provisional application No. 62/304,447, filed on Mar. 7, 2016.

(51) Int. Cl.
| | | |
|---|---|---|
| *C07D 417/14* | (2006.01) | |
| *A61K 45/06* | (2006.01) | |
| *C07D 471/04* | (2006.01) | |
| *C07C 53/18* | (2006.01) | |
| *A61P 31/04* | (2006.01) | |
| *A61K 31/424* | (2006.01) | |
| *A61K 31/431* | (2006.01) | |
| *A61K 31/439* | (2006.01) | |

(52) U.S. Cl.
CPC ............ *C07D 417/14* (2013.01); *A61K 45/06* (2013.01); *A61P 31/04* (2018.01); *C07C 53/18* (2013.01); *C07D 471/04* (2013.01); *A61K 31/424* (2013.01); *A61K 31/431* (2013.01); *A61K 31/439* (2013.01)

(58) Field of Classification Search
CPC .................................................. C07D 417/14

USPC ...................................................... 514/210.15
See application file for complete search history.

(56) References Cited

U.S. PATENT DOCUMENTS

| | | |
|---|---|---|
| 5,859,256 A | 1/1999 | Cho et al. |
| 9,174,978 B2 | 11/2015 | Aulakh et al. |
| 2014/0275007 A1 | 9/2014 | Glinka et al. |
| 2015/0018331 A1 | 1/2015 | Moser et al. |
| 2015/0045340 A1 | 2/2015 | Klenke et al. |

(Continued)

FOREIGN PATENT DOCUMENTS

| | | |
|---|---|---|
| EP | 0229012 B1 | 6/1991 |
| EP | 0531976 A1 | 3/1993 |
| WO | WO2007065288 A2 | 6/2007 |

(Continued)

OTHER PUBLICATIONS

Brown, Matthew, F. et al., Pyridone-Conjugated Monobactam Antibiotics with Gram-Negative Activity, Journal of Medicinal Chemistry, 2013, p. 5541-5552, vol. 56.

(Continued)

*Primary Examiner* — Taofiq A Solola
(74) *Attorney, Agent, or Firm* — Baerbel R. Brown; Catherine D. Fitch

(57) ABSTRACT

The present invention relates to bicyclic aryl monobactam compounds of Formula (I), and pharmaceutically acceptable salts thereof, wherein $A^1$, L, M, W, X, Y, Z, $R^x$ and $R^z$ are as defined herein. The present invention also relates to compositions which comprise a bicyclic aryl monobactam compound of the invention or a pharmaceutically acceptable salt thereof, and a pharmaceutically acceptable carrier. The invention further relates to methods for treating a bacterial infection comprising administering to the patient a therapeutically effective amount of a compound of the invention, either alone or in combination with a therapeutically effective amount of one or more beta-lactamase inhibitor compounds.

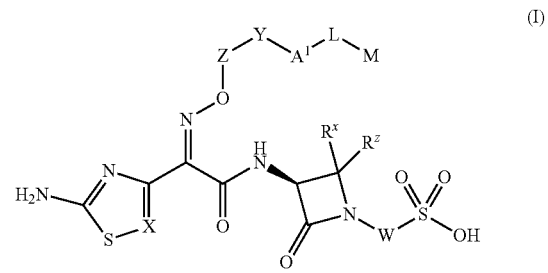

(I)

26 Claims, No Drawings

(56) References Cited

U.S. PATENT DOCUMENTS

2015/0266867 A1  9/2015  Aulakh et al.

FOREIGN PATENT DOCUMENTS

| WO | WO2012073138 A1 | 6/2012 |
| WO | WO2013110643 A1 | 8/2013 |
| WO | WO2017155765 A1 | 9/2017 |

OTHER PUBLICATIONS

Drawz, Sarah, M. et al., Three Decades of B-Lactamase Inhibitors, Clinical Microbiology Reviews, 2010, p. 160-201, vol. 23, No. 1.

International Search Report for PCT/US2017/020303 dated May 19, 2017, 10 pages.

Mitton-Fry, Mark, J. et al., Novel monobactams utilizing a siderophore uptake mechanism for the treatment of gram-negative infections, Bioorganic & Medicinal Chemistry Letters, 2012, p. 5989-5994, vol. 22.

Ready, Joseph, M. et al., Asymmetric Catalytic Synthesis of a-Aryloxy Alcohols: Kinetic Resolution of Terminal Epoxides via Highly Enantioselective Ring-Opening with Phenols, J. Am. Chem. Soc., 1999, p. 6086-6087, vol. 121.

Waley, S. G., B-Lactasmase: mechanism of action, The Chemistry of B-Lactams, M. I. Page (ed.), 1992, p. 198-228.

BICYCLIC ARYL MONOBACTAM COMPOUNDS AND METHODS OF USE THEREOF FOR THE TREATMENT OF BACTERIAL INFECTIONS

CROSS-REFERENCE TO RELATED APPLICATIONS

This application is a U.S. National Phase application under 35 U.S.C. § 371 of PCT Application PCT/US17/020303, filed Mar. 2, 2017, which claims priority from and the benefit of US Provisional Application U.S. Provisional Application No. U.S. Ser. No. 62/304,447 filed Mar. 7, 2016.

FIELD OF THE INVENTION

This invention relates to novel bicyclic aryl monobactam compounds, processes for their preparation and their use as therapeutic agents. More particularly, the invention relates to bicyclic aryl monobactam compounds and their use as antibiotic agents for the treatment of bacterial infections.

BACKGROUND OF THE INVENTION

The introduction of antibiotics for the treatment of bacterial infections is one of the great medical achievements of the 20$^{th}$ century. Over the past few decades, however, bacteria resistant to multiple antibiotics have begun to emerge throughout the world, threatening the effectiveness of antibiotic therapy. In the United States alone, at least 23,000 people each year die as a direct result of infections caused by antibiotic-resistant bacteria, and numerous others die from pre-existing conditions exacerbated by similar infections. *Antibiotic Resistance Threats in the United States,* 2013, Centers for Disease Control, Atlanta, Ga. New antibiotics are needed to combat the current and future threat of multidrug resistant bacteria.

β-lactams are the most widely used antibiotics for treatment of serious bacterial infections. These include carbapenems, cephalosporins, penicillins, and monobactams. As has been observed for other antibiotic classes, resistance to f-lactams has emerged. For most Gram-negative bacteria, this resistance is primarily driven by the expression of μ-lactamases, enzymes that hydrolyze β-lactam compounds. There are 4 different classes of β-lactamases (A, B, C, and D) capable of hydrolyzing overlapping but distinct subsets of β-lactams (Drawz and Bonomo, *Clin. Micro. Rev.,* 2010, 23:160-201). While the class B β-lactamases, also known as metallo β-lactamases (MBLs), are not the most prevalent β-lactamases found in the clinic, the frequency and distribution of their expression is on the rise and represents a significant medical threat because (i) MBLs have the ability to hydrolyze all β-lactams except monobactams, and (ii) unlike the class A and C β-lactamases, there are no inhibitors available for the MBLs.

Aztreonam, a monobactam, was first approved in the U.S in 1986 for the treatment of aerobic Gram-negative bacterial infections and remains the only monobactam in use in the U.S. today. However, aztreonam has poor activity against *Pseudomonas* and *Acinetobacter* strains. Because monobactams are inherently resistant to hydrolysis by MBLs, several companies have begun developing novel monobactam compounds for the treatment of infections caused by Gram-negative bacteria. Monobactam compounds comprising a siderophore moiety are disclosed in WO 2007/065288, WO2012/073138, *J Medicinal Chemistry* 56: 5541-5552 (2013), and *Bioorganic and Medicinal Chemistry Letters* 22:5989 (2012).

U.S. Patent Application Publication No. US 2014/0275007 discloses oxamazin monobactams and their use as antibacterial agents, and U.S. Patent Application Publication No. US 2015/0266867 also discloses novel monobactam compounds for the use as antibacterial agents. International Patent Application Publication No. WO 2013/110643 discloses novel amidine substituted monobactam derivatives and their use as antimicrobial agents.

The need for new antibiotics to overcome multidrug resistance continues. Compounds disclosed in this invention are designed to fill this medical need, through administration either on their own or in combination with one or more suitable β-lactamase inhibitors.

SUMMARY OF THE INVENTION

The invention relates to the design and synthesis of a series of bicyclic aryl monobactam analogs, a novel class of highly potent antibiotics effective against a broad range of Gram-negative bacteria. These compounds and their pharmaceutically acceptable salts may be useful as therapeutic agents for clinical treatment of various infections caused by Gram-negative bacteria, including strains that are multidrug resistant. The compounds can be used alone or in combination with one or more suitable β-lactamase inhibitors. More particularly, the present invention includes compounds of Formula I:

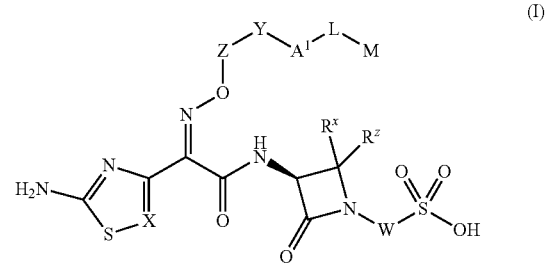

or a pharmaceutically acceptable salt thereof, wherein:

W is a bond or O;

$R^X$ and $R^Z$ are independently hydrogen, —$SC_1$-$C_3$alkyl, —$C_1$-$C_3$ alkyl, —($C_1$-$C_3$alkylene)$_n$$OC_1$-$C_3$alkyl, or —($C_1$-$C_3$alkylene)$_n$$NC_1$-$C_3$alkyl, wherein said —$SC_1$-$C_3$alkyl, $C_1$-$C_3$ alkyl, —($C_1$-$C_3$alkylene)$_n$$OC_1$-$C_3$alkyl and —($C_1$-$C_3$alkylene)$_n$$NC_1$-$C_3$alkyl are optionally substituted with one to seven fluorines;

or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and $C_4$-$C_7$ heterocycloalkyl are optionally substituted with one to three substituents independently selected from —F, —OH and —$OC_1$-$C_3$alkyl;

X is N or $CR^1$;

$R^1$ is hydrogen, $C_1$-$C_3$ alkyl, or halogen; wherein said $C_1$-$C_3$ alkyl is optionally substituted with one to three $R^a$;

each occurrence of $R^a$ is independently hydrogen, halogen, $C_1$-$C_3$alkyl, —$NR^cR^d$, —$OR^e$, or —$C(O)NR^cR^d$;

Z is $C_1$-$C_3$ alkylene, optionally substituted with one to three $R^b$;

each occurrence of $R^b$ is independently —$C_1$-$C_6$ alkyl, —$C_3$-$C_7$ cycloalkyl, —C(O)OR$^e$, —C(O)NR$^c$R$^d$, tetrazolyl, oxadiazolonyl, HetA, AryA, —S(O)$_m$R$^e$, —S(O)$_m$NR$^c$R$^d$, or P(O)(R$^e$)$_p$ wherein said —$C_1$-$C_6$ alkyl and —$C_3$-$C_7$ cycloalkyl are optionally substituted with one to three $R^a$ and wherein said AryA and HetA are optionally substituted with one to four $R^4$;

AryA is a 5- or 6-membered monocyclic aromatic ring with 0, 1, 2, or 3 heteroatom ring atoms independently selected from N, N as a quaternary salt, O and S;

HetA is a 4- to 6-membered saturated or monounsaturated monocyclic ring with 1, 2, or 3 heteroatom ring atoms independently selected from N, NH, N as a quaternary salt, O and S;

Y is a bond, O, NR$^2$, S, or CH$_2$;

$R^2$ is hydrogen, —$C_1$-$C_3$ alkyl, —C(O)R$^e$, —C(O)NR$^c$R$^d$, —S(O)$_m$R$^e$, or —S(O)$_m$NR$^c$R$^d$, wherein said —$C_1$-$C_3$ alkyl is optionally substituted with one to three $R^a$;

$A^1$ is a 9- to 11-membered bicyclic aromatic ring with 0, 1, 2, 3, or 4 heteroatom ring atoms independently selected from N, NH, N as a quaternary salt, O and S, optionally substituted with one to four $R^4$;

each occurrence of $R^4$ is independently:
(a) —$C_1$-$C_6$ alkyl,
(b) —$C_2$-$C_6$ alkenyl,
(c) —$C_2$-$C_6$ alkynyl,
(d) halogen,
(e) —OR$^e$,
(f) —S(O)$_m$R$^e$,
(g) —S(O)$_m$NR$^c$R$^d$,
(h) —C(O)R$^e$,
(i) —OC(O)R$^e$
(j) —C(O)OR$^e$,
(k) —CN,
(l) —C(O)NR$^c$R$^d$,
(m) —NR$^c$R$^d$,
(n) —NR$^c$C(O)R$^e$,
(o) —NR$^c$C(O)OR$^e$,
(p) —NR$^c$C(O)NR$^c$R$^d$,
(q) —NR$^c$S(O)$^m$R$^e$,
(r) =NH,
(s) —CF$_3$,
(t) —OCF$_3$,
(u) —OCHF$_2$,
(v) —$C_3$-$C_6$ cycloalkyl,
(w) —O—$C_3$-$C_6$cycloalkyl,
(x) —$C_1$-$C_3$alkylene-$C_3$-$C_6$cycloalkyl,
(y) —O—$C_1$-$C_3$ alkylene-$C_3$-$C_6$cycloalkyl,
(z) HetA,
(aa) —O-HetA,
(bb) —$C_1$-$C_3$alkylene-HetA,
(cc) —O—$C_1$-$C_3$alkylene-HetA,
(dd) AryA,
(ee) —O-AryA,
(ff) —$C_1$-$C_3$alkylene-AryA, or
(gg) —O—$C_1$-$C_3$alkylene-AryA,
wherein said $C_1$-$C_6$ alkyl, —$C_2$-$C_6$ alkenyl, —$C_2$-$C_6$ alkynyl, —$C_3$-$C_6$ cycloalkyl, —O—$C_3$-$C_6$cycloalkyl, —$C_1$-$C_3$alkylene-$C_3$-$C_6$cycloalkyl, —O—$C_1$-$C_3$ alkylene-$C_3$-$C_6$cycloalkyl, HetA, O-HetA, —$C_1$-$C_3$alkylene-HetA, —O—$C_1$-$C_3$ alkylene-HetA, AryA, —O-AryA, —$C_1$-$C_3$ alkylene-AryA, and —O—$C_1$-$C_3$alkylene-AryA are optionally substituted with one to three $R^a$;

L is a bond, —O—, —$C_1$-$C_6$alkylene-, —NHC(O)—, —C(O)—, —C(=NH)—, —S(O)$_m$—, —SC$_1$-$C_6$alkylene-, —NR$^3$(CH$_2$)$_n$—, —NHC(=NH)—, or —NHS(O)$_m$—, wherein —$C_1$-$C_6$alkylene-, —NHC(O)—, —C(=NH)—, —SC$_1$-$C_6$alkylene-, —NR$^3$(CH$_2$)$_n$—, —NHC(=NH)—, and —NHS(O)$_m$—, are optionally substituted with one to four $R^7$;

$R^3$ is hydrogen or —$C_1$-$C_3$ alkyl;

M is —CH$_2$OH, N(R$^3$)$_2$, N$^+$(C$_1$-$C_3$alkyl)$_3$, $C_2$-$C_6$alkyl, $C_3$-$C_7$ cycloalkyl, HetA, or AryA, wherein —CH$_2$OH, N(R$^3$)$_2$, N$^+$(C$_1$-$C_3$alkyl)$_3$, $C_2$-$C_6$alkyl, $C_3$-$C_7$ cycloalkyl, HetA, and AryA are optionally substituted with one to four $R^6$;

each occurrence of $R^6$ is independently selected from the group consisting of: halogen, —$C_1$-$C_6$alkyl, —(CH$_2$)$_n$NR$^c$R$^d$, —(CH$_2$)$_q$OR$^e$, —S(O)$_m$R$^e$, —S(O)$_m$NR$^c$R$^d$, —C(O)R$^e$, —OC(O)R$^e$, —C(O)OR$^e$, —CN, —C(O)NR$^c$R$^d$, —C(NH)NR$^c$R$^d$, —NR$^c$R$^d$, —N(R$^c$)(C(O)R$^e$), —N(R$^c$)(C(O)OR$^e$), —N(R$^c$)(C(O)NR$^c$R$^d$), —N(R$^c$)(S(O)$_m$R$^e$), HetA, and —$C_1$-$C_3$alkylene-HetA;

each occurrence of $R^7$ is independently selected from the group consisting of: halogen, —$C_1$-$C_6$alkyl, —(CH$_2$)$_n$NR$^c$R$^d$, —(CH$_2$)$_q$—OR$^e$, —S(O)$_m$R$^e$, —S(O)$_m$NR$^c$R$^d$, —C(O)R$^e$, —OC(O)R$^e$, —C(O)OR$^e$, —CN, —C(O)NR$^c$R$^d$, —C(NH)NR$^c$R$^d$, —NR$^c$R$^d$, —N(R$^c$)(C(O)R$^e$), —N(R$^c$)(C(O)OR$^e$), —N(R$^c$)(C(O)NR$^c$R$^d$), —N(R$^c$)(S(O)$_m$R$^e$), HetA, and —$C_1$-$C_3$alkylene-HetA;

each occurrence of R$^c$ and R$^d$ is independently: hydrogen, —$C_1$-$C_6$ alkyl, —$C_2$-$C_6$ alkenyl, —$C_3$-$C_6$ cycloalkyl, —$C_1$-$C_3$ alkylene-$C_3$-$C_6$ cycloalkyl, HetA, —$C_1$-$C_3$alkylene-HetA, AryA, —$C_1$-$C_3$ alkylene-AryA, or —$C_1$-$C_3$alkylene-HetA, wherein each R$^c$ and R$^d$ is optionally substituted with one to three R$^f$;

or, alternatively, R and R$^d$ together with the nitrogen atom to which they are attached, come together to form a 4- to 7-membered cycloheteroalkyl optionally containing one or two additional heteroatoms independently selected from O, S and —NR$^g$;

each occurrence of R$^e$ is independently: hydrogen, —$C_1$-$C_6$alkyl, —$C_2$-$C_6$ alkenyl, —OH, —OC$_1$-$C_6$ alkyl, —$C_3$-$C_6$ cycloalkyl, —$C_1$-$C_3$ alkylene-$C_3$-$C_6$ cycloalkyl, HetA, AryA, —$C_1$-$C_3$ alkylene-AryA, or —$C_1$-$C_3$ alkylene-HetA; wherein each R$^e$ is optionally substituted with one to three R$^h$;

each occurrence of R$^f$ is independently: halogen, —$C_1$-$C_6$alkyl, —OH, —OC$_1$-$C_4$ alkyl, —S(O)$_m$C$_1$-$C_4$ alkyl, —CN, —CF$_3$, —OCHF$_2$, or —OCF$_3$; wherein said —$C_1$-$C_6$ alkyl, —OC$_1$-$C_4$ alkyl and —S(O)$_m$C$_1$-$C_4$ alkyl are optionally substituted with one to three substituents independently selected from: —OH, halogen, cyano, and —S(O)$_2$CH$_3$;

each occurrence of R$^g$ is independently: hydrogen, —C(O)R$^e$, or —$C_1$-$C_6$ alkyl, wherein said —$C_1$-$C_6$alkyl is optionally substituted with one to five fluorines;

each occurrence of R$^h$ is independently: halogen, —$C_1$-$C_6$alkyl, —OH, —OC$_1$-$C_4$ alkyl, —S(O)$_m$C$_1$-$C_4$ alkyl, —CN, —CF$_3$, —OCHF$_2$, or —OCF$_3$; wherein said —$C_1$-$C_6$ alkyl, —OC$_1$-$C_4$ alkyl, and —S(O)$_m$C$_1$-$C_4$ alkyl are optionally substituted with one to three substituents independently selected from: —OH, halogen, cyano, and —S(O)$_2$CH$_3$;

each n is independently 0, 1, 2, 3 or 4;

each m is independently 0, 1 or 2, each p is 1 or 2; and each q is 0, 1, 2 or 3.

The present invention also includes compounds of Formula I:

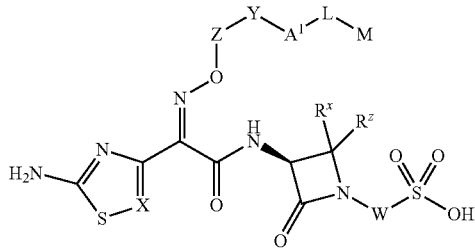

(I)

or a pharmaceutically acceptable salt thereof, wherein:

W is a bond or O;

$R^X$ and $R^Z$ are independently hydrogen, —$SC_1$-$C_3$alkyl, $C_1$-$C_3$ alkyl, —$(C_1$-$C_3$alkylene$)_nOC_1$-$C_3$alkyl, or —$(C_1$-$C_3$alkylene$)_nNC_1$-$C_3$alkyl, wherein said —$SC_1$-$C_3$alkyl, $C_1$-$C_3$ alkyl, —$(C_1$-$C_3$alkylene$)_nOC_1$-$C_3$alkyl and —$(C_1$-$C_3$alkylene$)_nNC_1$-$C_3$alkyl are optionally substituted with one to seven fluorines;

or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and $C_4$-$C_7$ heterocycloalkyl are optionally substituted with one to three substituents independently selected from —F, —OH and —$OC_1$-$C_3$alkyl;

X is N or $CR^1$;

$R^1$ is hydrogen, $C_1$-$C_3$ alkyl, or halogen; wherein said $C_1$-$C_3$ alkyl is optionally substituted with one to three $R^a$;

each occurrence of $R^a$ is independently hydrogen, halogen, $C_1$-$C_3$alkyl, —$NR^cR^d$ or —$OR^e$;

Z is $C_1$-$C_3$ alkylene, optionally substituted with one to three $R^b$;

each occurrence of $R^b$ is independently —$C_1$-$C_6$ alkyl, —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or $P(O)(R^e)_p$ wherein said —$C_1$-$C_6$ alkyl and —$C_3$-$C_7$ cycloalkyl are optionally substituted with one to three $R^a$ and wherein said AryA and HetA are optionally substituted with one to four $R^4$;

AryA is a 5- or 6-membered monocyclic aromatic ring with 0, 1, 2, or 3 heteroatom ring atoms independently selected from N, N as a quaternary salt, O and S;

HetA is a 4- to 6-membered saturated or monounsaturated monocyclic ring with 1, 2, or 3 heteroatom ring atoms independently selected from N, N as a quaternary salt, O and S;

Y is a bond, O, $NR^2$, S, or $CH_2$;

$R^2$ is hydrogen, —$C_1$-$C_3$ alkyl, —$C(O)R^e$, —$C(O)NR^cR^d$, —$S(O)_mR^e$, or —$S(O)_mNR^cR^d$, wherein said —$C_1$-$C_3$ alkyl is optionally substituted with one to three $R^a$;

$A^1$ is a 9- to 11-membered bicyclic aromatic ring with 0, 1, 2, 3, or 4 heteroatom ring atoms independently selected from N, N as a quaternary salt, O and S, optionally substituted with one to four $R^4$;

each occurrence of $R^4$ is independently:
(a) —$C_1$-$C_6$ alkyl,
(b) —$C_2$-$C_6$ alkenyl,
(c) —$C_2$-$C_6$ alkynyl,
(d) halogen,
(e) —$OR^e$,
(f) —$S(O)_mR^e$,
(g) —$S(O)_mNR^cR^d$,
(h) —$C(O)R^e$,
(i) —$OC(O)R^e$,
(j) —$C(O)OR^e$,
(k) —CN,
(l) —$C(O)NR^cR^d$,
(m) —$NR^cR^d$,
(n) —$NR^cC(O)R^e$,
(o) —$NR^cC(O)OR^e$,
(p) —$NR^cC(O)NR^cR^d$,
(q) —$NR^cS(O)_mR^e$,
(r) =NH,
(s) —$CF_3$,
(t) —$OCF_3$,
(u) —$OCHF_2$,
(v) —$C_3$-$C_6$ cycloalkyl,
(w) —O—$C_3$-$C_6$cycloalkyl,
(x) —$C_1$-$C_3$alkylene-$C_3$-$C_6$cycloalkyl,
(y) —O—$C_1$-$C_3$ alkylene-$C_3$-$C_6$cycloalkyl,
(z) HetA,
(aa) —O-HetA,
(bb) —$C_1$-$C_3$alkylene-HetA,
(cc) —O—$C_1$-$C_3$alkylene-HetA,
(dd) AryA,
(ee) —O-AryA,
(ff) —$C_1$-$C_3$ alkylene-AryA, or
(gg) —O—$C_1$-$C_3$alkylene-AryA,
wherein said $C_1$-$C_6$ alkyl, —$C_2$-$C_6$ alkenyl, —$C_2$-$C_6$ alkynyl, —$C_3$-$C_6$ cycloalkyl, —O—$C_3$-$C_6$cycloalkyl, —$C_1$-$C_3$alkylene-$C_3$-$C_6$cycloalkyl, —O—$C_1$-$C_3$ alkylene-$C_3$-$C_6$cycloalkyl, HetA, O-HetA, —$C_1$-$C_3$alkylene-HetA, —O—$C_1$-$C_3$ alkylene-HetA, AryA, —O-AryA, —$C_1$-$C_3$ alkylene-AryA, and —O—$C_1$-$C_3$alkylene-AryA are optionally substituted with one to three $R^a$;

L is a bond, —O—, —$C_1$-$C_6$alkylene-, —NHC(O)—, —C(O)—, —C(=NH)—, —$S(O)_m$—, —$SC_1$-$C_6$alkylene-, —$NR^3(CH_2)$—, —NHC(=NH)—, or —$NHS(O)_m$—

$R^3$ is hydrogen or —$C_1$-$C_3$ alkyl;

M is $N(R^3)_2$, $N^+(C_1$-$C_3$alkyl$)_3$, $C_2$-$C_6$alkyl, $C_3$-$C_7$ cycloalkyl, HetA, or AryA, wherein said $C_2$-$C_6$alkyl, $C_3$-$C_7$ cycloalkyl, HetA, and AryA are optionally substituted with one to four $R^6$ each occurrence of $R^6$ is independently selected from the group consisting of: halogen, —$C_1$-$C_6$alkyl, —$(CH_2)_nNR^cR^d$, —$OR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$C(NH)NR^cR^d$, —$NR^cR^d$, —$N(R^c)(C(O)R^e)$, —$N(R^c)(C(O)OR^e)$, —$N(R^c)(C(O)NR^cR^d)$, and —$N(R^c)(S(O)_mR^e)$;

each occurrence of $R^c$ and $R^d$ is independently: hydrogen, —$C_1$-$C_6$ alkyl, —$C_2$-$C_6$ alkenyl, —$C_3$-$C_6$ cycloalkyl, —$C_1$-$C_3$ alkylene-$C_3$-$C_6$ cycloalkyl, HetA, —$C_1$-$C_3$alkylene-HetA, AryA, —$C_1$-$C_3$ alkylene-AryA, or —$C_1$-$C_3$alkylene-HetA, wherein each $R^c$ and $R^d$ is optionally substituted with one to three $R^f$;

or, alternatively, $R^c$ and $R^d$ together with the nitrogen atom to which they are attached, come together to form a 4- to 7-membered cycloheteroalkyl optionally containing one or two additional heteroatoms independently selected from O, S and —$NR^g$;

each occurrence of $R^e$ is independently: hydrogen, —$C_1$-$C_6$alkyl, —$C_2$-$C_6$ alkenyl, —OH, —$OC_1$-$C_6$ alkyl, —$C_3$-$C_6$ cycloalkyl, —$C_1$-$C_3$ alkylene-$C_3$-$C_6$ cycloalkyl, HetA, AryA, —$C_1$-$C_3$ alkylene-AryA, or —$C_1$-$C_3$ alkylene-HetA; wherein each $R^e$ is optionally substituted with one to three $R^h$;

each occurrence of $R^f$ is independently: halogen, —$C_1$-$C_6$alkyl, —OH, —$OC_1$-$C_4$ alkyl, —$S(O)_mC_1$-$C_4$ alkyl, —CN, —$CF_3$, —$OCHF_2$, or —$OCF_3$; wherein said —$C_1$-$C_6$ alkyl, —$OC_1$-$C_4$ alkyl and —$S(O)_mC_1$-$C_4$ alkyl are optionally substituted with one to three substituents independently selected from: —OH, halogen, cyano, and —S(O)$_2$CH$_3$;

each occurrence of R is independently: hydrogen, —C(O)R$^e$, or —C$_1$-C$_6$ alkyl, wherein said —C$_1$-C$_6$alkyl is optionally substituted with one to five fluorines;

each occurrence of R$^h$ is independently: halogen, —C$_1$-C$_6$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_6$ alkyl, —OC$_1$-C$_4$ alkyl, and —S(O)$_m$C$_1$-C$_4$ alkyl are optionally substituted with one to three substituents independently selected from: —OH, halogen, cyano, and —S(O)$_2$CH$_3$;

each n is independently 0, 1, 2, 3 or 4;

each m is independently 0, 1 or 2, and each p is 1 or 2.

The present invention also relates to a pharmaceutical composition for treating a bacterial infection in a subject, including infection with multidrug resistant Gram-negative bacterial strains, comprising a bicyclic aryl monobactam compound of the invention and a pharmaceutically acceptable carrier, diluent or excipient.

The Compounds of Formula (I) (also referred to herein as the "bicyclic aryl monobactam compounds") and pharmaceutically acceptable salts thereof can be useful, for example, for inhibiting the growth of Gram-negative bacterial strains, including but not limited to, *Pseudomonas* and *Acinetobacter* strains, and/or for treating or preventing the clinical manifestations thereof in a patient.

The present invention is also directed to methods of treating Gram-negative bacterial infections in a subject in need of treatment thereof, comprising administering to the subject an effective amount of a bicyclic aryl monobactam compound of the invention. In specific embodiments of the invention, the method includes administration of one or more beta lactamase inhibitor compound(s).

Embodiments, sub-embodiments and features of the present invention are either further described in or will be apparent from the ensuing description, examples and appended claims.

DETAILED DESCRIPTION OF THE INVENTION

The invention relates to novel bicyclic aryl monobactam analogs, a class of highly potent antibiotics effective against a broad range of Gram-negative bacteria. These compounds have utility as therapeutic agents for the clinical treatment of various infections caused by Gram-negative bacteria, including strains that are multidrug resistant, and for the treatment or prevention of the clinical pathologies associated therewith.

In each of the various embodiments of the compounds of the invention described herein, each variable including those of Formulas I, IA, and IB, and the various embodiments thereof, each variable is selected independently of the others unless otherwise indicated.

The present invention encompasses all compounds of Formulas I, IA, and IB, and the various embodiments described herein, for example, any solvates, hydrates, stereoisomers, and tautomers of said compounds and of any pharmaceutically acceptable salts thereof.

The Compounds of Formula (I)

In one aspect, the present invention includes compounds of Formula I:

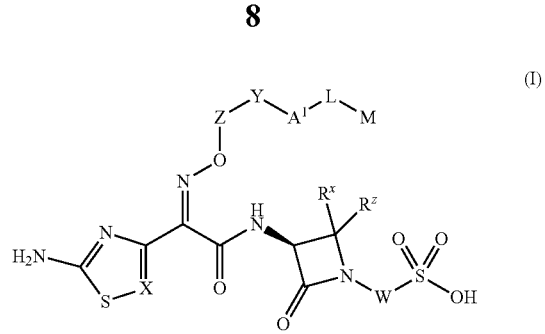

or a pharmaceutically acceptable salt thereof, wherein A$^1$, L, M, W, X, Y, Z, R$^X$ and R$^z$ are as defined herein for the Compounds of Formula (I); wherein the compounds may be suitable for use for the treatment of bacterial infections.

A first embodiment of the invention (Embodiment E1) is a compound of Formula I, or a pharmaceutically acceptable salt thereof, wherein A$^1$, L, M, W, X, Y, Z, R$^X$ and R$^z$ are as defined in Formula I in the Summary of the Invention.

A second embodiment (Embodiment E2) is a compound of Formula I, or a pharmaceutically acceptable salt thereof, wherein W is a bond, and all other variables are as defined in Embodiment E1.

A third embodiment (Embodiment E3) is a compound of Formula I, or a pharmaceutically acceptable salt thereof, wherein W is O, and all other variables are as defined in Embodiment E1.

A fourth embodiment (Embodiment E4) is a compound of Formula I, or a pharmaceutically acceptable salt thereof, wherein W is defined in Embodiment E2 or E3, X is N, and all other variables are as defined in Embodiment E1.

A fifth embodiment (Embodiment E5) is a compound of Formula I, or a pharmaceutically acceptable salt thereof, wherein W is defined in Embodiment E2 or E3, X is CR$^1$, and R$^1$ is hydrogen, halogen or C$_1$-C$_3$ alkyl optionally substituted with one to three R$^a$, and all other variables are as defined in Embodiment E1. In a sub-embodiment of Embodiment E5 (Embodiment E5-A), R$^1$ is hydrogen. In another sub-embodiment of Embodiment E5 (Embodiment E5-B), R$^1$ is halogen. In a further sub-embodiment of Embodiment E5 (Embodiment E5-C), R$^1$ is chlorine. In yet another sub-embodiment of Embodiment E5 (Embodiment E5-D), R$^1$ is fluorine. In another sub-embodiment of Embodiment E5 (Embodiment E5-D), R$^1$ is bromine. In a further sub-embodiment of Embodiment E5 (Embodiment E5-E), R$^1$ is C$_1$-C$_3$ alkyl optionally substituted with one to three R$^a$, wherein each occurrence of R$^a$ is independently hydrogen, halogen, C$_1$-C$_3$alkyl, —NR$^c$R$^d$ or —OR$^e$.

A sixth embodiment (Embodiment E6) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is C$_1$-C$_3$ alkylene optionally substituted with one to three R$^b$, wherein each occurrence of R$^b$ is independently C$_1$-C$_6$alkyl, C$_3$-C$_7$ cycloalkyl, —C(O)OR$^e$, —C(O)NR$^c$R$^d$, tetrazolyl, oxadiazolonyl, HetA, AryA, —S(O)$_m$R$^e$, —S(O)$_m$NR$^c$R$^d$, or —P(O)(R$^e$)$_p$, wherein said C$_1$-C$_6$ alkyl and said C$_3$-C$_7$ cycloalkyl are optionally substituted with one to three R$^a$; and all other variables are as defined in Embodiment E1. In a sub-embodiment of Embodiment E6, Z is C$_1$-C$_3$ alkylene substituted with one occurrence of R$^b$. In another sub-embodiment of Embodiment E6, Z is C$_1$-C$_3$ alkylene substituted with two occurrences of R$^b$.

In a further sub-embodiment of Embodiment E6, Z is C$_1$-C$_3$ alkylene substituted with three occurrences of R$^b$.

A seventh embodiment (Embodiment E7) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with —C(O)O$R^e$; and all other variables are as defined in Embodiment E1.

An eighth embodiment (Embodiment E8) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with —C(O)OH; and all other variables are as defined in Embodiment E1.

A ninth embodiment (Embodiment E9) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with tetrazolyl; and all other variables are as defined in Embodiment E1.

A tenth embodiment (Embodiment E10) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with $C_1$-$C_6$ alkyl, optionally substituted with one to three $R^a$, and all other variables are as defined in Embodiment E1.

An eleventh embodiment (Embodiment E11) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with methyl; and all other variables are as defined in Embodiment E1.

A twelfth embodiment (Embodiment E12) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with methyl and —C(O)OH; and all other variables are as defined in Embodiment E1.

A thirteenth embodiment (Embodiment E13) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is —CH(C(O)OH)$CH_2$— and all other variables are as defined in Embodiment E1.

A fourteenth embodiment (Embodiment E14) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is $C_1$-$C_3$ alkylene substituted with oxadiazolonyl, and all other variables are as defined in Embodiment E1.

A fifteenth embodiment (Embodiment E15) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is a bond, and all other variables are as defined in Embodiment E1.

A sixteenth embodiment (Embodiment E16) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is O, and all other variables are as defined in Embodiment E1.

A seventeenth embodiment (Embodiment E17) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is $NR^2$, and all other variables are as defined in Embodiment E1. In a sub-embodiment of Embodiment E17, $R^2$ is hydrogen. In another sub-embodiment of Embodiment E17, $R^2$ is $C_1$-$C_3$ alkyl optionally substituted with one to three $R^a$. In a further sub-embodiment of Embodiment E17, $R^2$ is C(O)$R^e$. In yet another sub-embodiment of Embodiment E17, $R^2$ is —C(O)N$R^c R^d$. In still another sub-embodiment of Embodiment E17, $R^2$ is —S(O)$_m R^e$. In a further sub-embodiment of Embodiment E17, $R^2$ is —S(O)$_m$N$R^c R^d$.

An eighteenth embodiment (Embodiment E18) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is S, and all other variables are as defined in Embodiment E1.

A nineteenth embodiment (Embodiment E19) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is $CH_2$, and all other variables are as defined in Embodiment E1.

A twentieth embodiment (Embodiment E20) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ a 9- to 11-membered bicyclic aromatic ring with 0, 1, 2, 3, or 4 heteroatom ring atoms independently selected from N, N as a quaternary salt, O and S, optionally substituted with one to four $R^4$; and all other variables are as defined in Embodiment E1.

A twenty-first embodiment (Embodiment E21) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is a 9-membered bicyclic aromatic ring with 0, 1, 2, 3, or 4 heteroatom ring atoms independently selected from N, N as a quaternary salt, O and S, optionally substituted with one to four $R^4$, and all other variables are as defined in Embodiment E1.

A twenty-second embodiment (Embodiment E22) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is a 10-membered bicyclic aromatic ring with 0, 1, 2, 3, or 4 heteroatom ring atoms independently selected from N, N as a quaternary salt, O and S, optionally substituted with one to four $R^4$, and all other variables are as defined in Embodiment E1.

A twenty-third embodiment (Embodiment E23) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is an 11-membered bicyclic aromatic ring with 0, 1, 2, 3, or 4 heteroatom ring atoms independently selected from N, N as a quaternary salt, O and S, optionally substituted with one to four $R^4$, and all other variables are as defined in Embodiment E1. In a sub-embodiment of Embodiment E21, E22 or E23, $A^1$ has 1 ring atom independently selected from N, N as a quaternary salt, O and S. In a further sub-embodiment of Embodiment E21, E22 or E23, $A^1$ has 2 ring atoms independently selected from N, N as a quaternary salt, O and S. In another sub-embodiment of Embodiment E21, E22 or E23, $A^1$ has 2 ring atoms independently selected from N, N as a quaternary salt, O and S. In yet another sub-embodiment of Embodiment E21, E22 or E23, $A^1$ has 3 ring atoms independently selected from N, N as a quaternary salt, O and S. In a further sub-embodiment of Embodiment E21, E22 or E23, $A^1$ has 4 ring atoms independently selected from N, N as a quaternary salt, O and S.

A twenty-fourth embodiment (Embodiment E24) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is a 9- to 11-membered bicyclic aromatic ring containing one heteroatom ring atom selected from N and N as a quaternary salt, and containing 0, 1, 2, or 3, additional heteroatoms independently selected from N, O and S, optionally substituted with one to four $R^4$, and all other variables are as defined in Embodiment E1.

A twenty-fifth embodiment (Embodiment E25) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

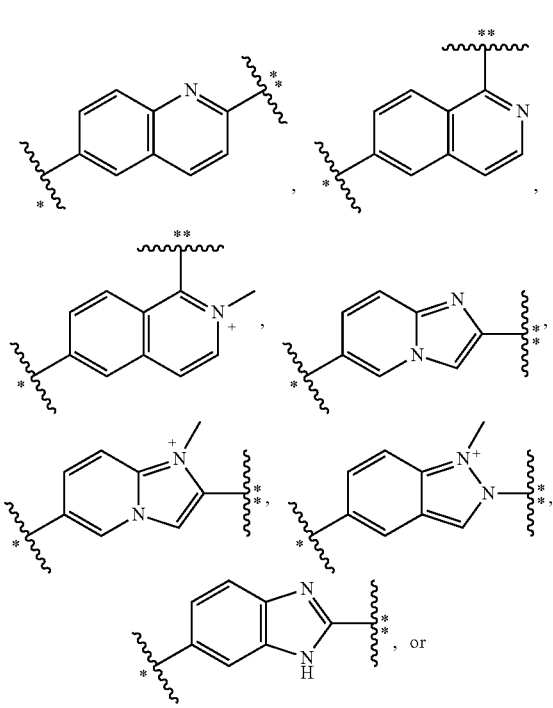

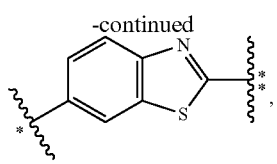

wherein ** indicates the point of attachment to L and * indicates the point of attachment to the rest of the compound, and all other variables are as defined in Embodiment E1.

A twenty-sixth embodiment (Embodiment E26) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

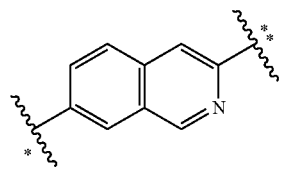

and all other variables are as defined in Embodiment E1.

A twenty-seventh embodiment (Embodiment E27) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

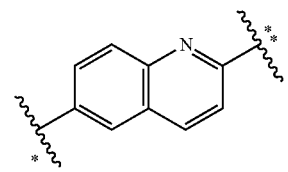 [SMILES: *c1ccc2nc(*)ccc2c1]

and all other variables are as defined in Embodiment E1.

A twenty-eighth embodiment (Embodiment E28) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

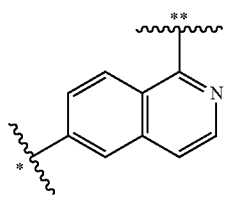 [SMILES: *c1ccc2c(*)nccc2c1]

and all other variables are as defined in Embodiment E1.

A twenty-ninth embodiment (Embodiment E29) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

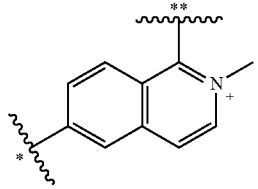

and all other variables are as defined in Embodiment E1.

A thirtieth embodiment (Embodiment E30) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

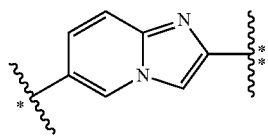 [SMILES: *c1ccc2nc(*)cn2c1]

and all other variables are as defined in Embodiment E1.

A thirty-first embodiment (Embodiment E31) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

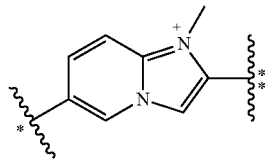

and all other variables are as defined in Embodiment E1.

A thirty-second embodiment (Embodiment E32) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

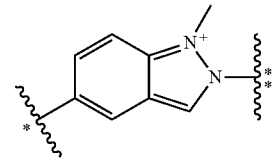

and all other variables are as defined in Embodiment E1.

A thirty-third embodiment (Embodiment E33) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

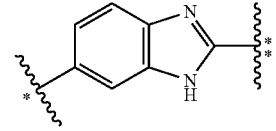

and all other variables are as defined in Embodiment E1.

A thirty-fourth embodiment (Embodiment E34) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is:

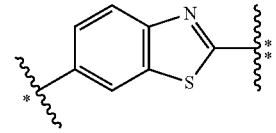 [SMILES: *c1ccc2nc(*)sc2c1]

and all other variables are as defined in Embodiment E1.

A thirty-fifth embodiment (Embodiment E35) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$CH_2$—; and all other variables are as defined in Embodiment E1.

A thirty-sixth embodiment (Embodiment E36) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is a bond; and all other variables are as defined in Embodiment E1.

A thirty-seventh embodiment (Embodiment E37) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —O—; and all other variables are as defined in Embodiment E1.

A thirty-eighth embodiment (Embodiment E38) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$C_1$-$C_6$alkylene-; and all other variables are as defined in Embodiment E1.

A thirty-ninth embodiment (Embodiment E39) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —NHC(O)—; and all other variables are as defined in Embodiment E1.

A fortieth embodiment (Embodiment E40) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —C(O)—; and all other variables are as defined in Embodiment E1.

A forty-first embodiment (Embodiment E41) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —C(=NH)—; and all other variables are as defined in Embodiment E1.

A forty-second embodiment (Embodiment E42) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$S(O)_m$—; m is 0, 1, or 2; and all other variables are as defined in Embodiment E1.

A forty-third embodiment (Embodiment E43) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$SC_1$-$C_6$alkylene-; and all other variables are as defined in Embodiment E1.

A forty-fourth embodiment (Embodiment E44) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$NR^3$$(CH_2)_n$—; n is 0, 1, 2, 3, or 4; and all other variables are as defined in Embodiment E1. In a sub-embodiment of Embodiment E44, $R^3$ is hydrogen. In another sub-embodiment of Embodiment E44, $R^3$ is —$C_1$-$C_3$ alkyl.

In a further sub-embodiment of Embodiment E44, $R^3$ is methyl.

A forty-fifth embodiment (Embodiment E45) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —NHC(=NH)—; and all other variables are as defined in Embodiment E1.

A forty-sixth embodiment (Embodiment E46) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is —$NHS(O)_m$—; m is 0, 1, or 2; and all other variables are as defined in Embodiment E1.

A forty-seventh embodiment (Embodiment E47) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is $N(R^3)_2$; and all other variables are as defined in Embodiment E1.

A forty-eighth embodiment (Embodiment E48) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is $N^+(C_1$-$C_3$alkyl$)_3$; and all other variables are as defined in Embodiment E1.

A forty-ninth embodiment (Embodiment E49) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is $C_2$-$C_6$alkyl, optionally substituted with one to four $R^6$; and all other variables are as defined in Embodiment E1.

A fiftieth embodiment (Embodiment E50) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is $C_3$-$C_7$ cycloalkyl, optionally substituted with one to four $R^6$; and all other variables are as defined in Embodiment E1.

A fifty-first embodiment (Embodiment E51) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is HetA, optionally substituted with one to four $R^6$; and all other variables are as defined in Embodiment E1.

A fifty-second embodiment (Embodiment E52) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is AryA, optionally substituted with one to four $R^6$; and all other variables are as defined in Embodiment E1.

A fifty-third embodiment (Embodiment E53) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is $C_3$-$C_7$ cycloalkyl, substituted with $N(R^3)_2$, and optionally substituted with one to three additional substituents, independently selected from halogen, $C_1$-$C_3$alkyl, —$NR^cR^d$ and —$OR^e$; and all other variables are as defined in Embodiment E1.

A fifty-fourth embodiment (Embodiment E54) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is a 5- or 6-membered monocyclic aromatic ring containing one heteroatom ring atom selected from N and N as a quaternary salt, and containing 0, 1, or 2 additional heteroatom ring atoms independently selected from N, O and S, optionally substituted with one to four $R^6$; and all other variables are as defined in Embodiment E1.

A fifty-fifth embodiment (Embodiment E55) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is a 4- to 6-membered saturated or monounsaturated monocyclic ring containing one heteroatom ring atom selected from N and N as a quaternary salt, and containing 0, 1, or 2, additional heteroatom ring atoms independently selected from N, O and S, optionally substituted with one to four $R^6$; and all other variables are as defined in Embodiment E1.

A fifty-sixth embodiment (Embodiment E56) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E35, L is defined in any of Embodiments E36-E46; M is —$NH_2$; and all other variables are as defined in Embodiment E1.

A fifty-seventh embodiment (Embodiment E57) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is —$NHCH_3$; and all other variables are as defined in Embodiment E1.

A fifty-eighth embodiment (Embodiment E58) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is a 5- or 6-membered monocyclic aromatic ring containing one heteroatom ring atom selected from N and N as a quaternary salt, and containing 0, 1, or 2 additional heteroatom ring atoms independently selected from N, O and S, optionally substituted with one or two $C_1$-$C_6$alkyl; and all other variables are as defined in Embodiment E1.

A fifty-ninth embodiment (Embodiment E59) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is a 4- to 6-membered saturated or monounsaturated monocyclic ring containing one heteroatom ring atom selected from N and N as a quaternary salt, and containing 0, 1, or 2, additional heteroatom ring atoms independently selected from N, O and S, optionally substituted with one or two $C_1$-$C_6$alkyl; and all other variables are as defined in Embodiment E1.

A sixtieth embodiment (Embodiment E60) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

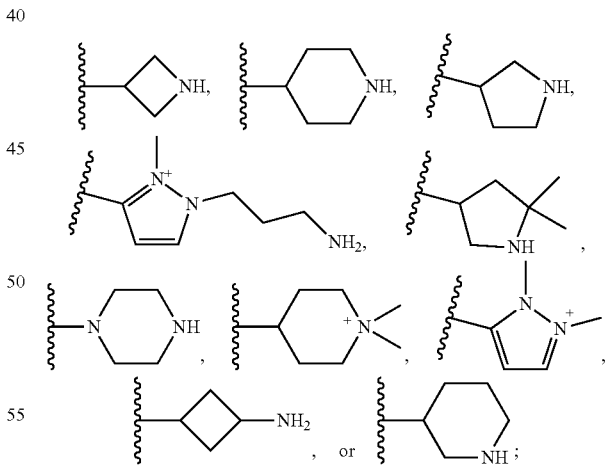

and all other variables are as defined in Embodiment E1.

A sixty-first embodiment (Embodiment E61) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

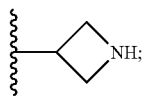 [SMILES: *C1CNC1]

and all other variables are as defined in Embodiment E1.

A sixty-second embodiment (Embodiment E62) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

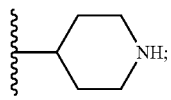

and all other variables are as defined in Embodiment E1.

A sixty-third embodiment (Embodiment E63) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

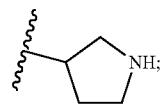 [SMILES: *C1CCNC1]

and all other variables are as defined in Embodiment E1.

A sixty-fourth embodiment (Embodiment E64) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

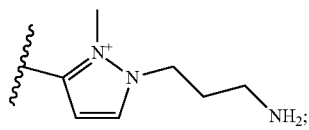 [SMILES: *c1ccn(CCCN)[n+]1C]

and all other variables are as defined in Embodiment E1.

A sixty-fifth embodiment (Embodiment E65) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

and all other variables are as defined in Embodiment E1.

A sixty-sixth embodiment (Embodiment E66) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

and all other variables are as defined in Embodiment E1.

A sixty-seventh embodiment (Embodiment E67) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

and all other variables are as defined in Embodiment E1.

A sixty-eighth embodiment (Embodiment E68) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

and all other variables are as defined in Embodiment E1.

A sixty-ninth embodiment (Embodiment E69) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

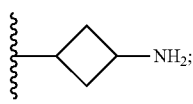

and all other variables are as defined in Embodiment E1.

A seventieth embodiment (Embodiment E70) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is:

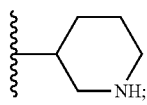

and all other variables are as defined in Embodiment E1.

A seventy-first embodiment (Embodiment E71) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70, $R^X$ and $R^Z$ are methyl; and all other variables are as defined in Embodiment E1.

A seventy-second embodiment (Embodiment E72) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; $R^X$ is hydrogen and $R^Z$ is methyl; and all other variables are as defined in Embodiment E1.

A seventy-third embodiment (Embodiment E73) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; at least one of $R^X$ and $R^Z$ is $SCH_3$, optionally substituted with one to three fluorines; and all other variables are as defined in Embodiment E1.

A seventy-fourth embodiment (Embodiment E74) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; at least one of $R^X$ and $R^Z$ is $SC_1$-$C_3$ alkyl, optionally substituted with one to seven fluorines; and all other variables are as defined in Embodiment E1.

A seventy-fifth embodiment (Embodiment E75) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; at least one of $R^X$ and $R^Z$ is $C_1$-$C_3$ alkyl, optionally substituted with one to seven fluorines; and all other variables are as defined in Embodiment E1.

A seventy-sixth embodiment (Embodiment E76) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; at least one of $R^X$ and $R^Z$ is ($C_1$-$C_3$alkylene)$_n$O$C_1$-$C_3$alkyl, optionally substituted with one to seven fluorines; and all other variables are as defined in Embodiment E1.

A seventy-seventh embodiment (Embodiment E77) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; at least one of $R^X$ and $R^Z$ is ($C_1$-$C_3$alkylene)$_n$N$C_1$-$C_3$alkyl, optionally substituted with one to seven fluorines; and all other variables are as defined in Embodiment E1.

A seventy-eighth embodiment (Embodiment E78) is a compound of Formula I, or a pharmaceutically acceptable salt thereof, wherein W is defined in Embodiment E2 or E3, X is defined in any of Embodiments E4, E5, E5-A, E5-B, E5-C, E5-D, or E5-E, Z is defined in any of Embodiments E6-E14, Y is defined in any of Embodiments E15-E19, $A^1$ is defined in any of Embodiments E20-E34, L is defined in any of Embodiments E35-E46; M is defined in any of Embodiments E47-E70; $R^X$ and $R^Z$, together with the carbon to which they are attached, come together to form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and $C_4$-$C_7$ heterocycloalkyl are optionally substituted with one to three substituents independently selected from —F, —OH and —O$C_1$-$C_3$alkyl; and all other variables are as defined in Embodiment E1.

A seventy-ninth embodiment (Embodiment E79) is a compound of Formula IA, or IB, or a pharmaceutically acceptable salt thereof,

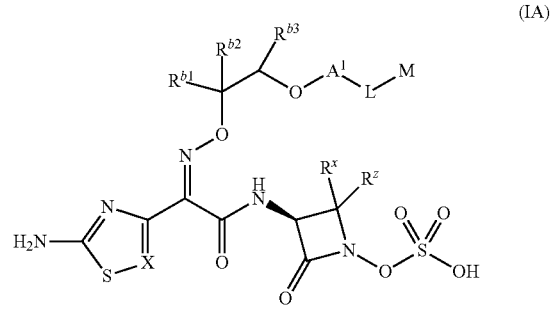

-continued

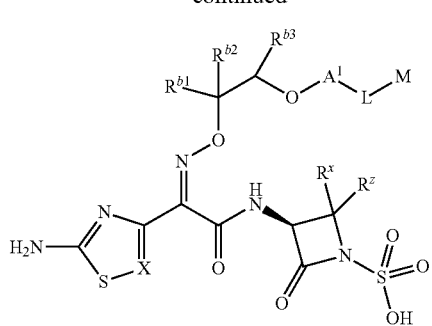

(IB)

wherein X is defined in any of Embodiments E1, E4, E5, E5-A, E5-B, E5-C, E5-D, or E5-E;

$R^x$ and $R^z$ are independently hydrogen, —S$C_1$-$C_3$alkyl, $C_1$-$C_3$ alkyl, —($C_1$-$C_3$alkylene)$_n$O$C_1$-$C_3$alkyl, or —($C_1$-$C_3$alkylene)$_n$N$C_1$-$C_3$alkyl, wherein said —S$C_1$-$C_3$alkyl, $C_1$-$C_3$ alkyl, —($C_1$-$C_3$alkylene)O$C_1$-$C_3$alkyl and —($C_1$-$C_3$alkylene)$_n$N$C_1$-$C_3$alkyl are optionally substituted with one to seven fluorines;

$R^{b1}$, $R^{b2}$, and $R^{b3}$ are independently hydrogen, $C_1$-$C_6$ alkyl, $C_3$-$C_7$ cycloalkyl, —C(O)O$R^e$, —C(O)N$R^c R^d$, tetrazolyl, oxadiazolonyl, HetA, AryA, —S(O)$_m R^e$, —S(O)$_m$N$R^c R^d$, or —P(O)($R^e$)$_p$, wherein said $C_1$-$C_6$ alkyl and $C_3$-$C_7$ cycloalkyl are optionally substituted with one to three $R^a$ and wherein said AryA and HetA are optionally substituted with one to four $R^4$;

$A^1$ is a 9- to 11-membered bicyclic aromatic ring containing one heteroatom ring atom selected from N and N as a quaternary salt, and containing 0, 1, 2, or 3, additional heteroatoms independently selected from N, O and S, optionally substituted with one to four $R^4$;

M is selected from the group consisting of:
(a) N($R^3$)$_2$,
(b) N$^+$($C_1$-$C_3$alkyl)$_3$,
(c) $C_3$-$C_7$ cycloalkyl, substituted with N($R^3$)$_2$, and optionally substituted with one to three additional substituents, independently selected from halogen, $C_1$-$C_3$alkyl, —N$R^c R^d$ and —O$R^e$,
(d) a 5- or 6-membered monocyclic aromatic ring containing one heteroatom ring atom selected from N and N as a quaternary salt, and containing 0, 1, or 2 additional heteroatom ring atoms independently selected from N, O and S, optionally substituted with one to four $R^6$; and
(e) a 4- to 6-membered saturated or monounsaturated monocyclic ring containing one heteroatom ring atom selected from N and N as a quaternary salt, and containing 0, 1, or 2, additional heteroatom ring atoms independently selected from N, O and S, optionally substituted with one to four $R^6$;

L is defined in any of Embodiments E35-E46; and all other variables are as defined in Embodiment E1.

An eightieth embodiment (Embodiment E80) is a compound of Formula IA or IB, or a pharmaceutically acceptable salt thereof, wherein $R^{b1}$ and $R^{b2}$ are independently hydrogen, $C_1$-$C_3$ alkyl, tetrazolyl, oxadiazolonyl or —C(O)O$R^e$; and $R^{b3}$ is hydrogen, and all other variables are as defined in Embodiment E79.

An eighty-first embodiment (Embodiment E81) is a compound of Formula IA or IB, or a pharmaceutically acceptable salt thereof, wherein $R^{b1}$ is —C(O)OH, $R^{b2}$ is hydrogen, and $R^{b3}$ is hydrogen, and all other variables are as defined in Embodiment E79.

An eighty-second embodiment (Embodiment E82) is a compound of Formula IA or IB, or a pharmaceutically acceptable salt thereof, wherein $R^{b1}$ is tetrazolyl, $R^{b2}$ is hydrogen, and $R^{b3}$ is hydrogen, and all other variables are as defined in Embodiment E79.

An eighty-third embodiment (Embodiment E83) is a compound of Formula IA or IB, or a pharmaceutically acceptable salt thereof, wherein $R^{b1}$ is oxadiazolonyl, $R^{b2}$ is hydrogen, and $R^{b3}$ is hydrogen, and all other variables are as defined in Embodiment E79.

An eighty-fourth embodiment (Embodiment E84) is a compound having the structure:

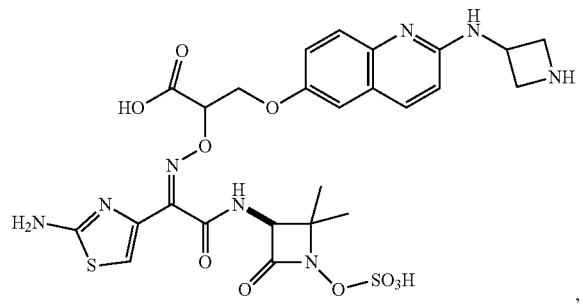

,

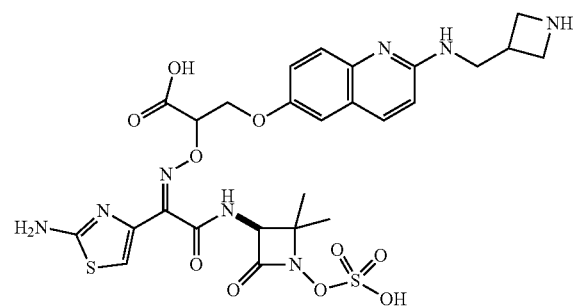

,

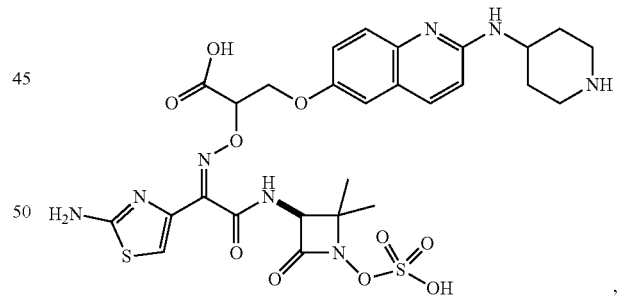

,

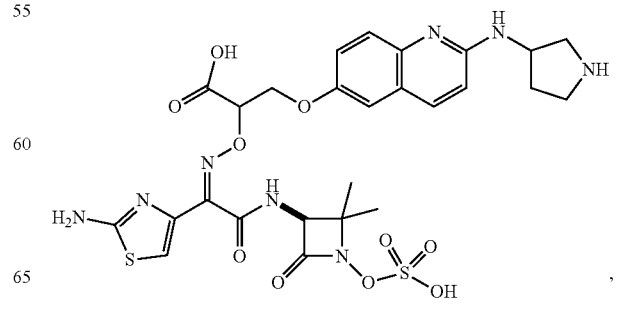

,

25
-continued
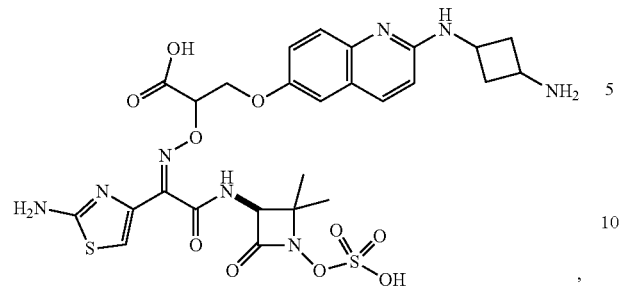
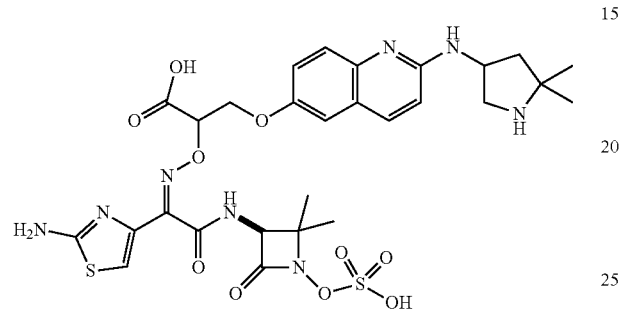
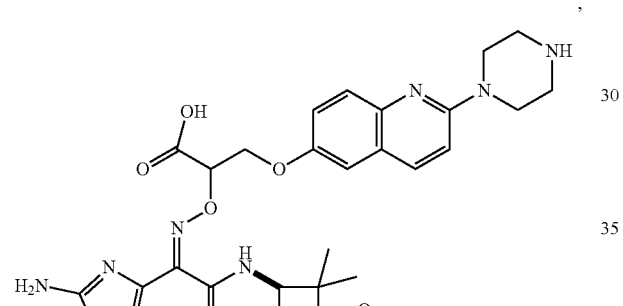
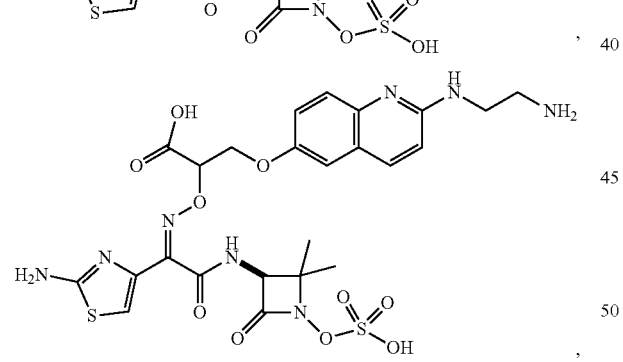
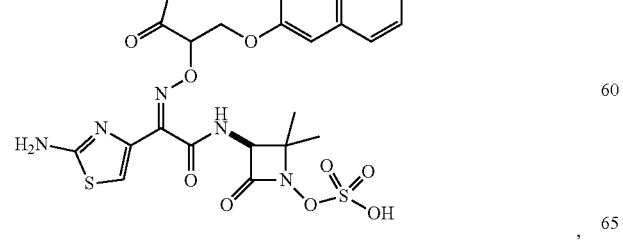
,
26
-continued
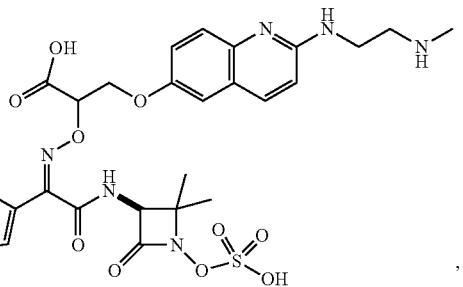
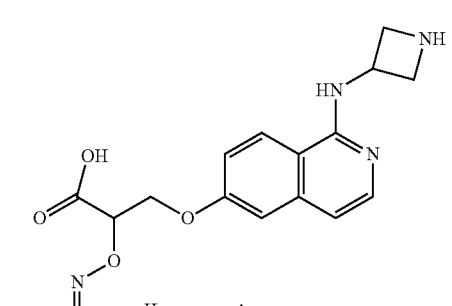
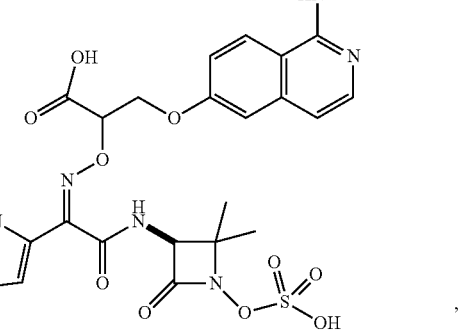
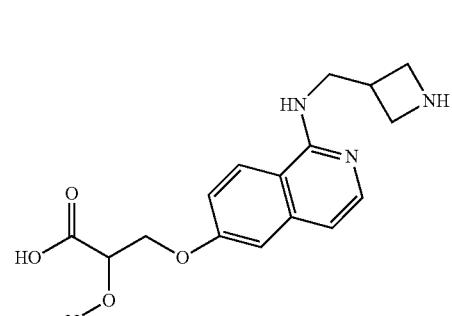
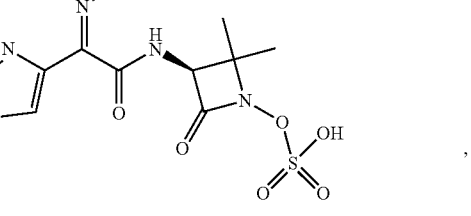
, 27
-continued
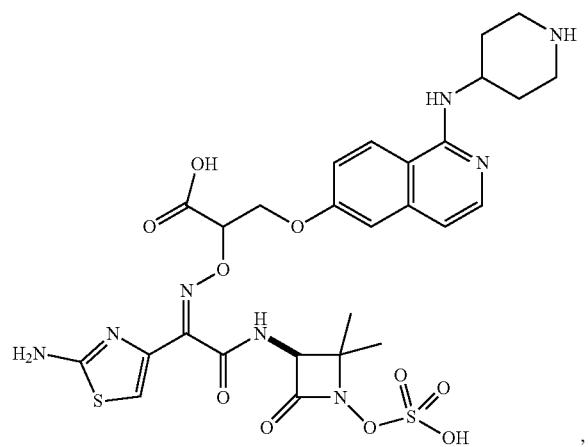
,
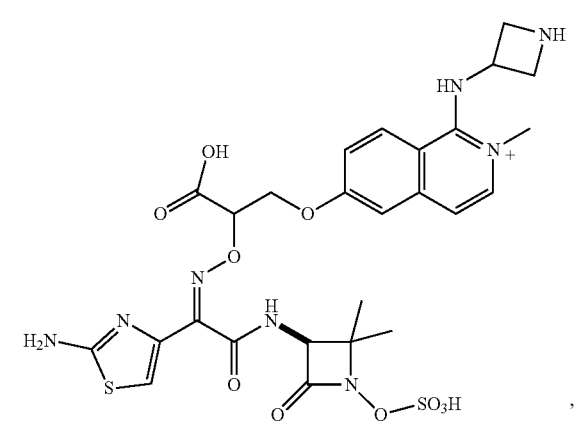
,
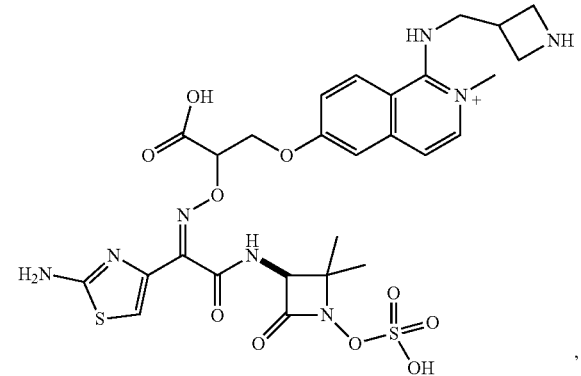
,
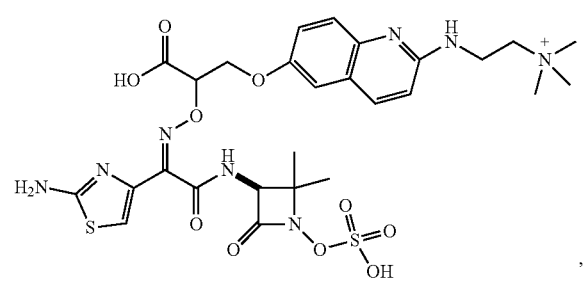
,
28
-continued
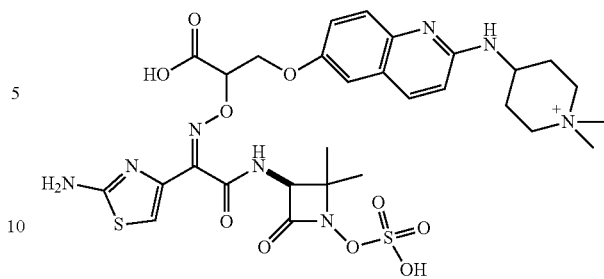
,
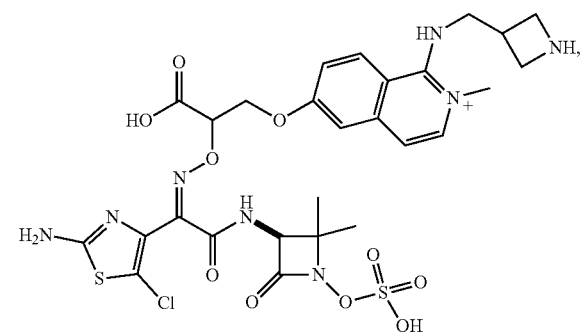
,
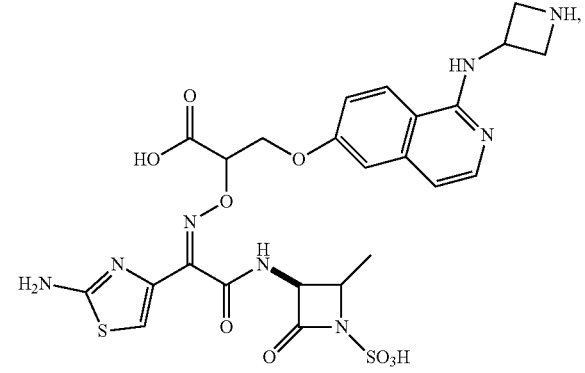
,
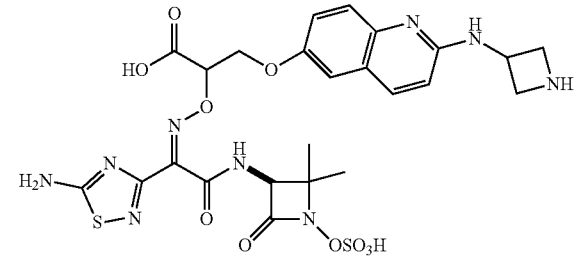
,
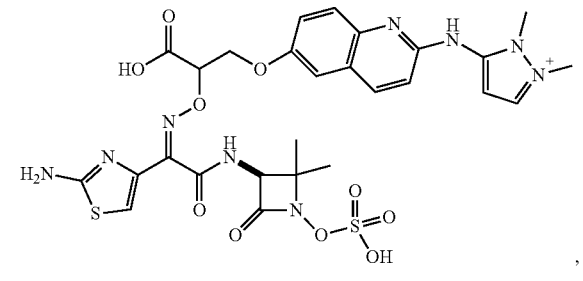
, 29
-continued
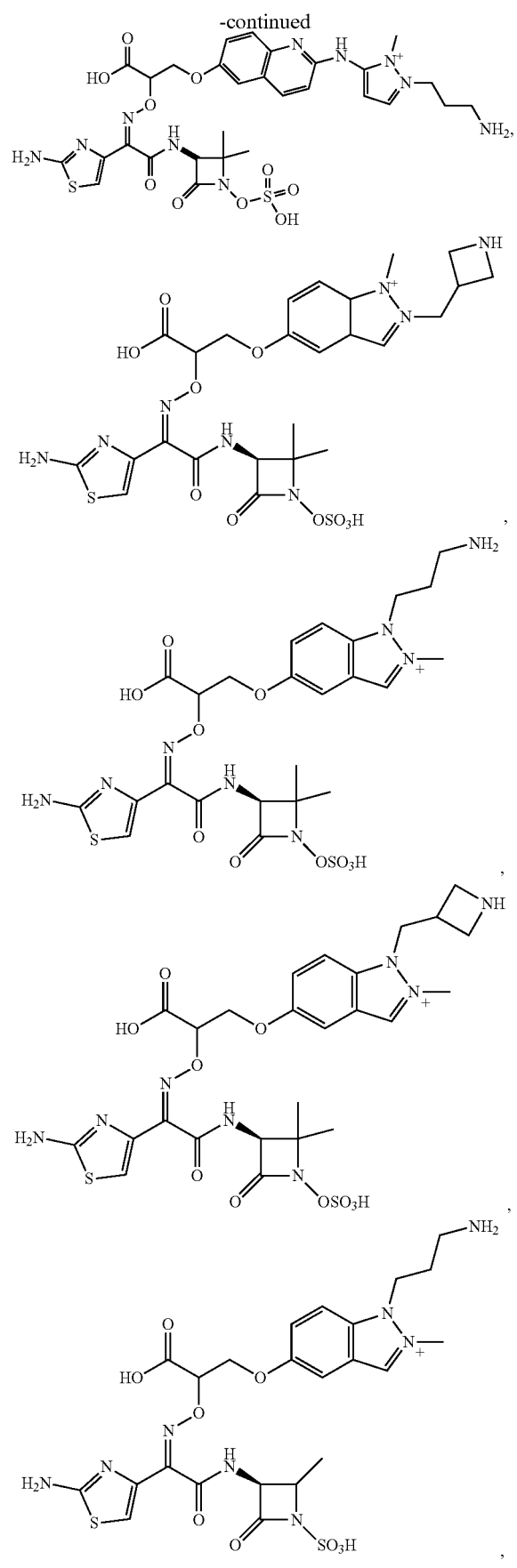
30
-continued
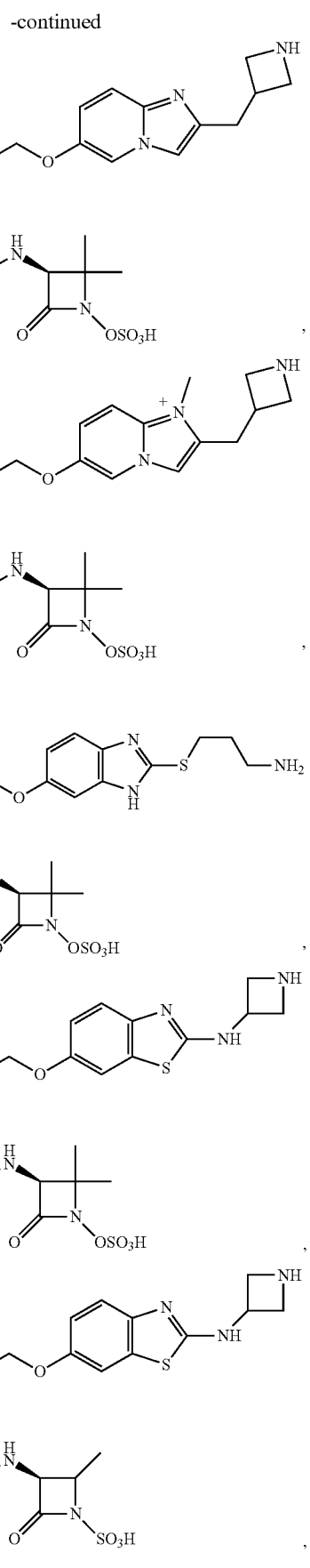

31
-continued
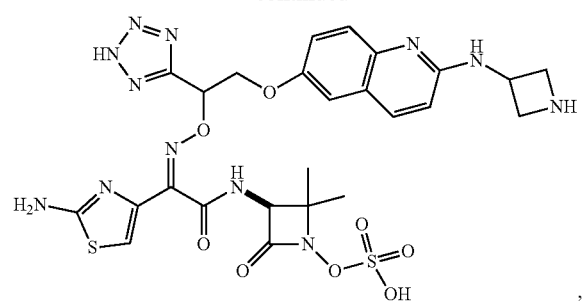
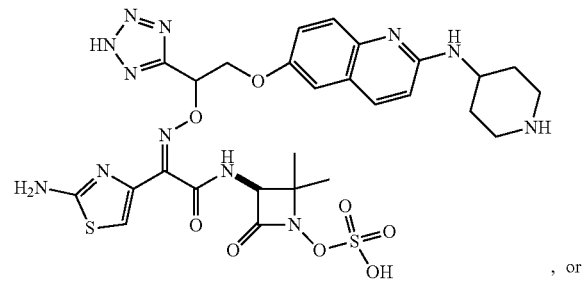
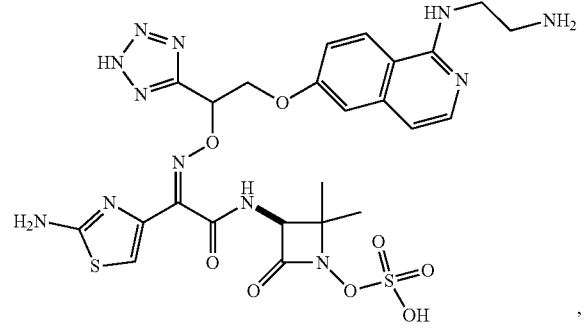
or a pharmaceutically acceptable salt thereof.
An eighty-fifth embodiment (Embodiment E85) is a compound having the structure:
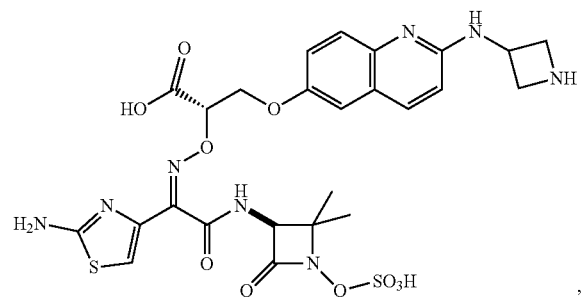
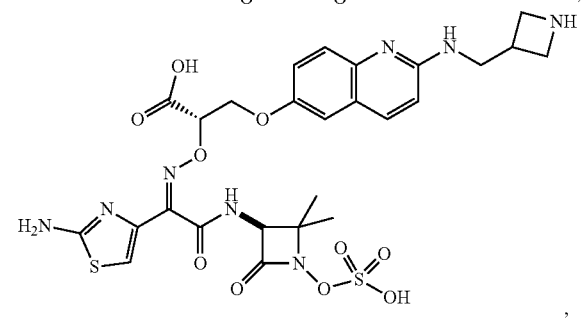
32
-continued
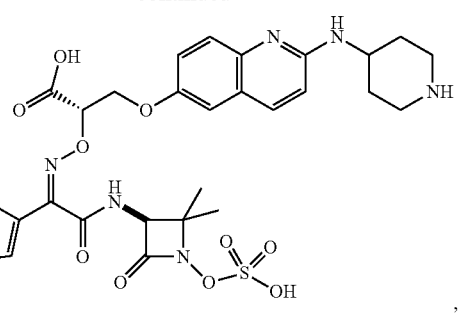
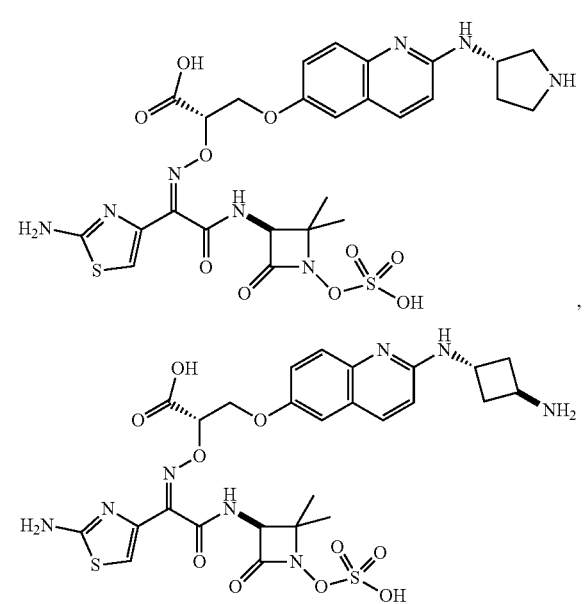
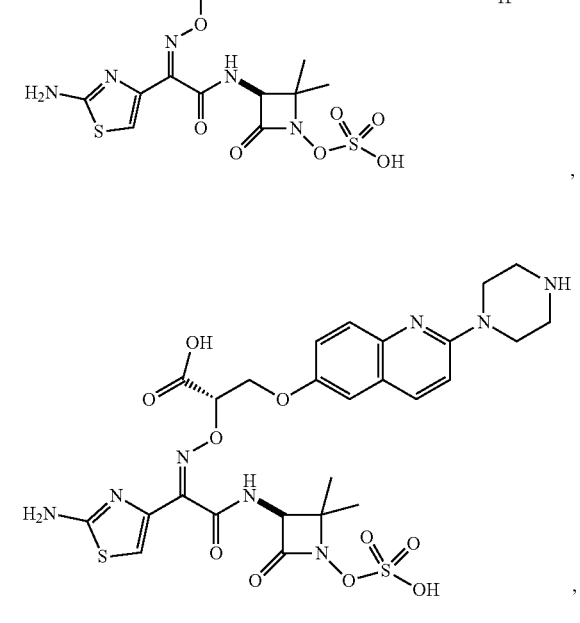
,

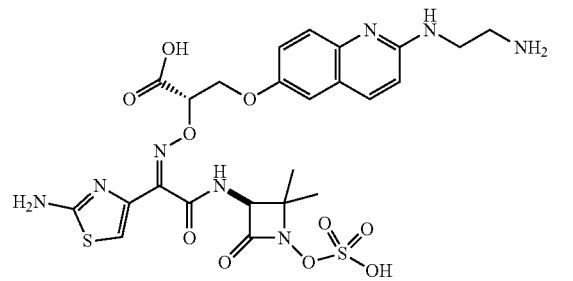,
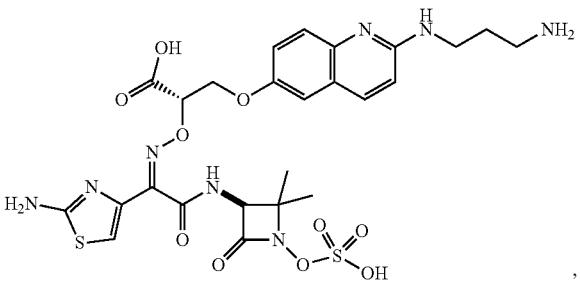,
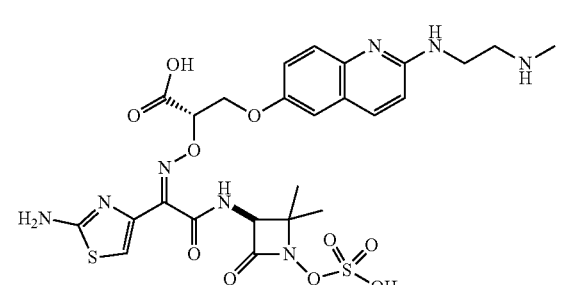,
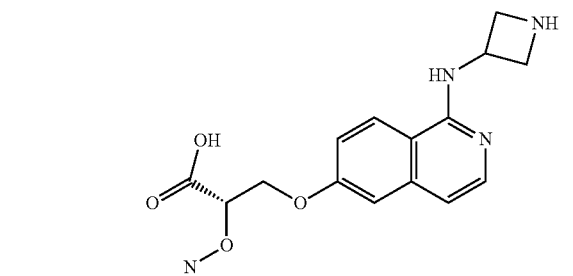,
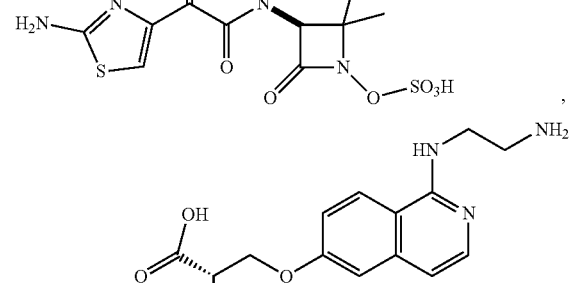,
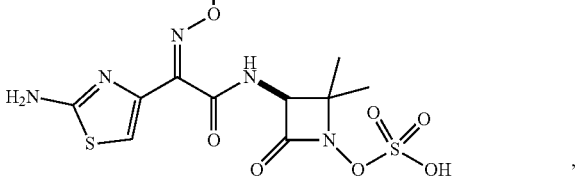,
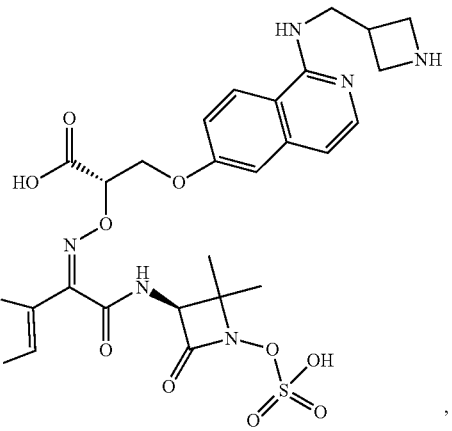,
,
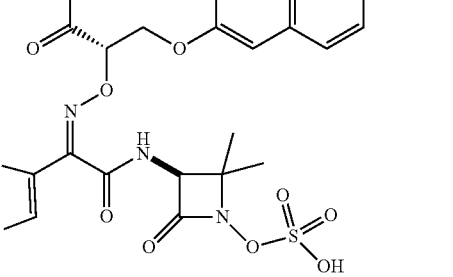,
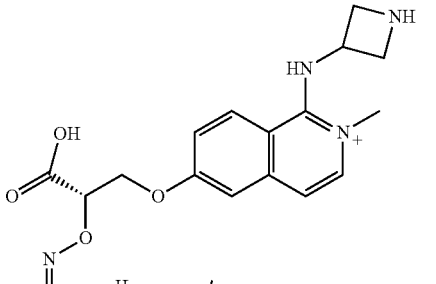,
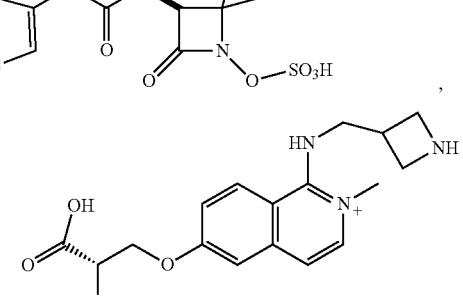,
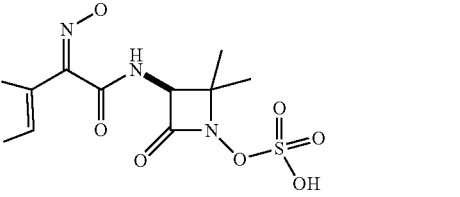, 35
-continued
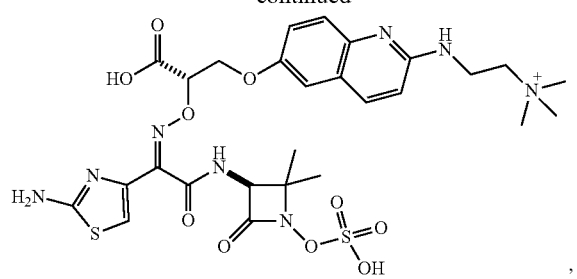
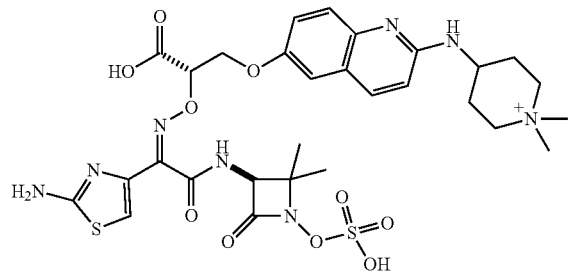
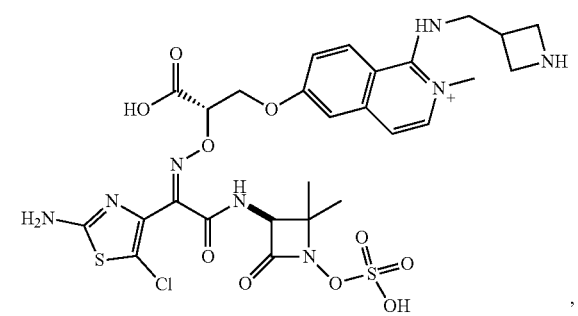
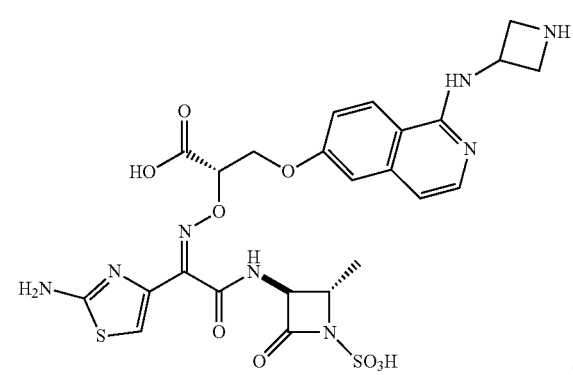
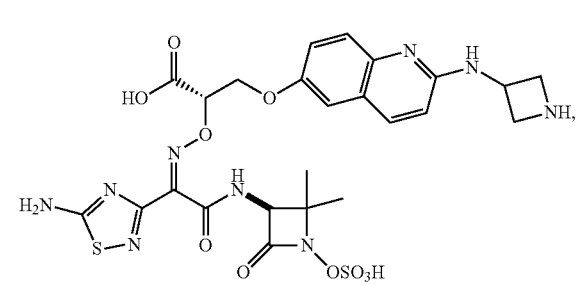
36
-continued
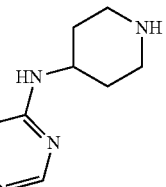
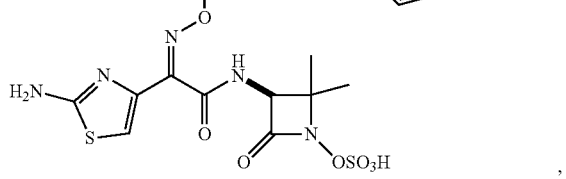
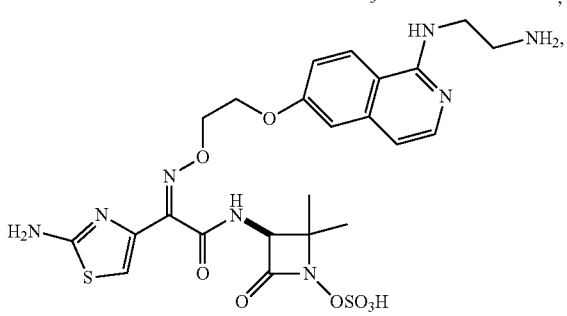
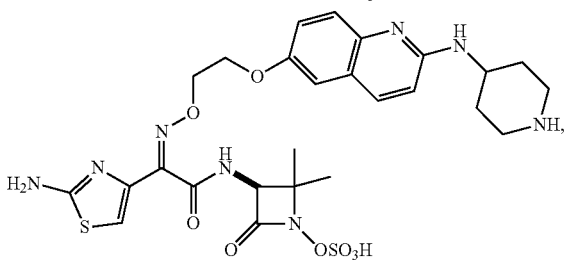
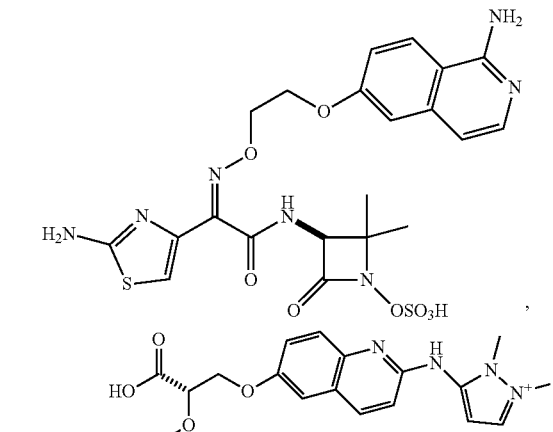
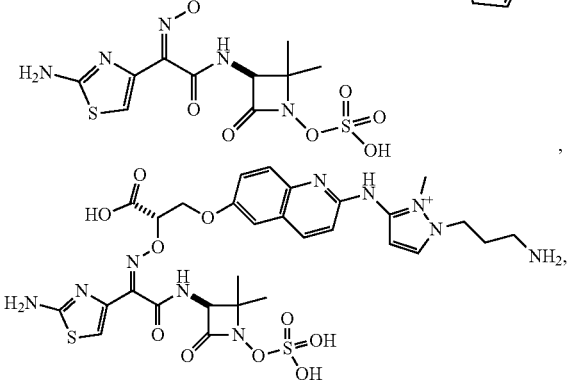

37
-continued
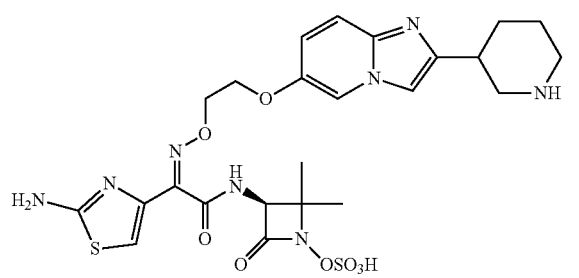
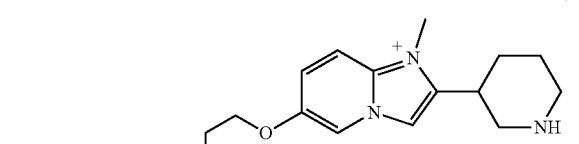
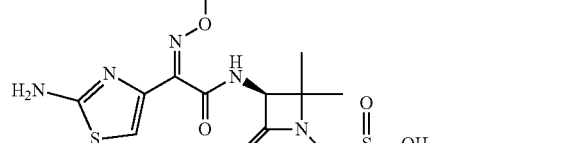
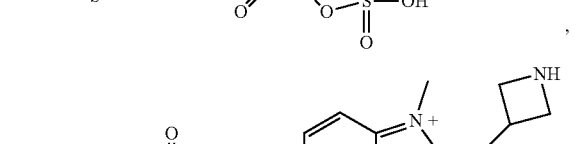
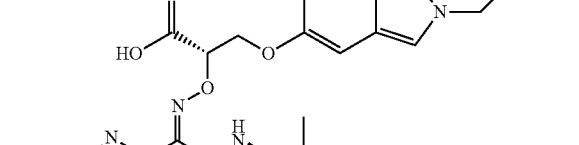
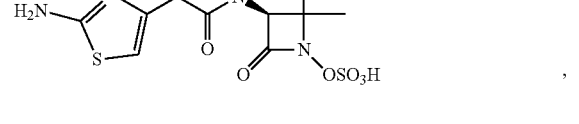
38
-continued
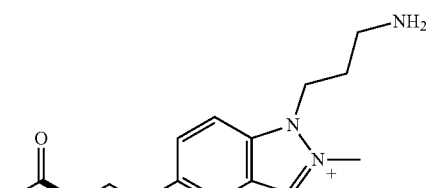
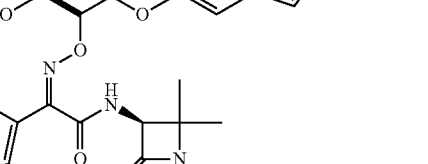
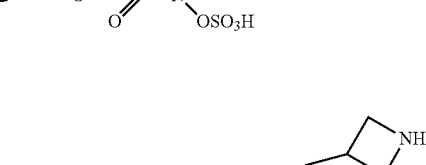
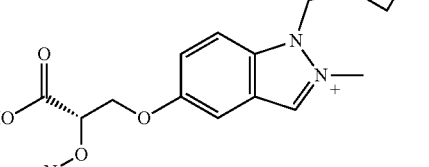
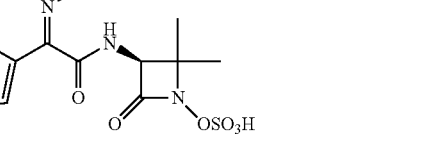

-continued

-continued

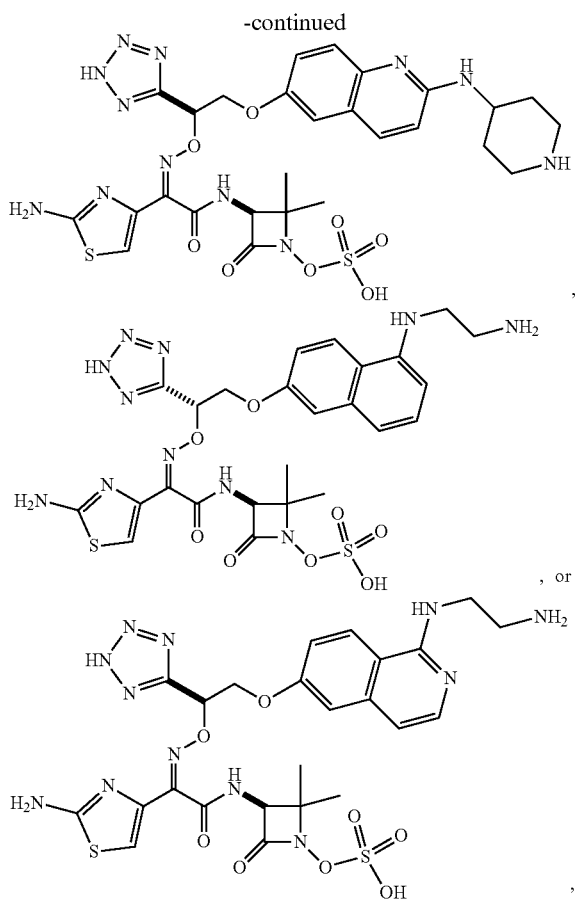

, or

, or a pharmaceutically acceptable salt thereof.

In another embodiment of the present invention, W is O.

In another embodiment of this invention, $R^X$ and $R^Z$ are independently hydrogen, and $C_1$-$C_3$ alkyl, wherein $C_1$-$C_3$ alkyl is optionally substituted with one to seven fluorines. In another embodiment of this invention, $R^X$ and $R^Z$ are independently $C_1$-$C_3$ alkyl, wherein $C_1$-$C_3$ alkyl is optionally substituted with one to seven fluorines. In another embodiment of this invention, $R^X$ and $R^Z$ are $CH_3$.

In another embodiment of the present invention, X is CH.

In another embodiment of this invention, $R^1$ is hydrogen.

In another embodiment of this invention, each occurrence of $R^a$ is independently —$OR^e$, or —$C(O)NR^cR^d$. In another embodiment of this invention, each occurrence of $R^a$ is independently —OH or $C(O)NH_2$.

In another embodiment of this invention, Z is $CH_2CHR^b$ or CH. In another embodiment of this invention, Z is $CH_2CHR^b$. In another embodiment of this invention, Z is $CH_2CHR^b$.

In another embodiment of this invention, each occurrence of $R^b$ is independently —$C(O)OR^e$, or tetrazolyl. In another embodiment of this invention, each occurrence of $R^b$ is independently —$CO_2H$ or tetrazolyl. In another embodiment of this invention, each occurrence of $R^b$ is —$CO_2H$. In another embodiment of this invention, each occurrence of $R^b$ is tetrazolyl.

In another embodiment of this invention, Y is O.

In another embodiment of this invention, each occurrence of $R^4$ is independently: —$C_1$-$C_6$ alkyl, halogen, or —$NR^cR^d$, wherein said $C_1$-$C_6$ alkyl is optionally substituted with one to three $R^a$. In another embodiment of this invention, each occurrence of $R^4$ is independently: —$CH_3$, halogen, or —$NH_2$.

In another embodiment of the present invention, $A^1$ is quinoline, isoquinoline, imidazo[1,2-a]pyridine, indazole, benzo[d]imidazole, benzo[d]thiazole, or naphthalene, optionally substituted with one to four $R^4$.

In another embodiment of the present invention, $A^1$ is:

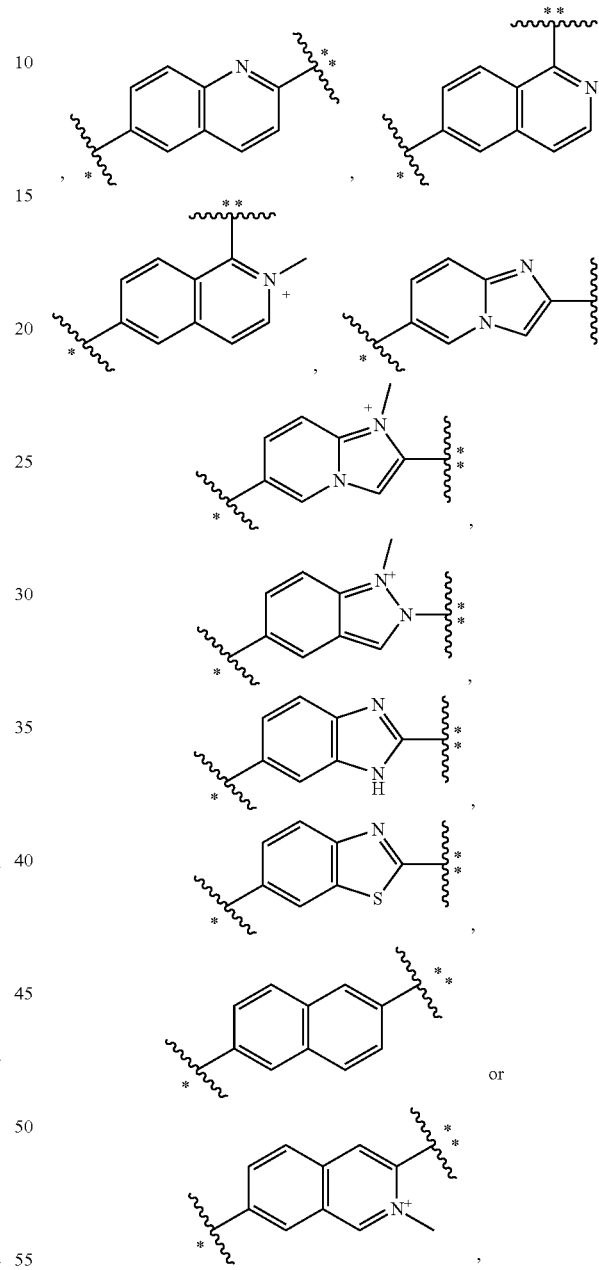

wherein ** indicates the point of attachment to L and * indicates the point of attachment to the rest of the compound.

In another embodiment, L is a bond, —O—, —$C_1$-$C_6$alkylene-, —NHC(O)—, —C(O)—, —C(=NH)—, —S(O)$_m$—, —S$C_1$-$C_6$alkylene-, —$NR^3(CH_2)_n$—, —NHC(=NH)—, or —NHS(O)$_m$—, wherein —$C_1$-$C_6$alkylene-, —NHC(O)—, —C(=NH)—, —S$C_1$-$C_6$alkylene-, —$NR^3$ $(CH_2)_n$—, —NHC(=NH)—, and —NHS(O)$_m$— are optionally substituted with one to four $R^7$.

In another embodiment, L is a bond.

In another embodiment, L is —C₁-C₆alkylene- or —NR³(CH₂)ᵣ—, wherein —C₁-C₆alkylene- and —NR³(CH₂)ₙ— are optionally substituted with one to four R⁷.

In another embodiment, L is —C₁-C₆alkylene-, wherein —C₁-C₆alkylene- is optionally substituted with one to four R⁷.

In another embodiment, L is —NR³(CH₂)ₙ—, wherein —NR³(CH₂)— is optionally substituted with one to four R⁷.

In another embodiment, R³ is hydrogen. In another embodiment, R³ is —C₁-C₃ alkyl.

In another embodiment, M is: —CH₂OH, —NH₂, —NHCH₃, or —N⁺(CH₃)₃, wherein M is optionally substituted with one or two R⁶.

In another embodiment, M is —CH₂OH, —NH₂, —NHCH₃, or —N⁺(CH₃)₃.

In another embodiment, M is —CH₂OH.

In another embodiment, M is N(R³)₂, N⁺(C₁-C₃alkyl)₃, C₂-C₆alkyl, C₃-C₇ cycloalkyl, HetA, or AryA, wherein said C₂-C₆alkyl, C₃-C₇ cycloalkyl, HetA, and AryA are optionally substituted with one to four R⁶.

In another embodiment, M is N(R³)₂, N⁺(C₁-C₃alkyl)₃, C₂-C₆alkyl, C₃-C₇ cycloalkyl, HetA, or AryA, wherein said C₂-C₆alkyl, C₃-C₇ cycloalkyl, HetA, and AryA are optionally substituted with one to four R⁶.

In another embodiment, M is N(R³)₂, N⁺(C₁-C₃alkyl)₃, C₂-C₆alkyl, C₃-C₇ cycloalkyl, or HetA, wherein said C₂-C₆alkyl, C₃-C₇ cycloalkyl, and HetA are optionally substituted with one to four R⁶.

In another embodiment of the present invention, M is:

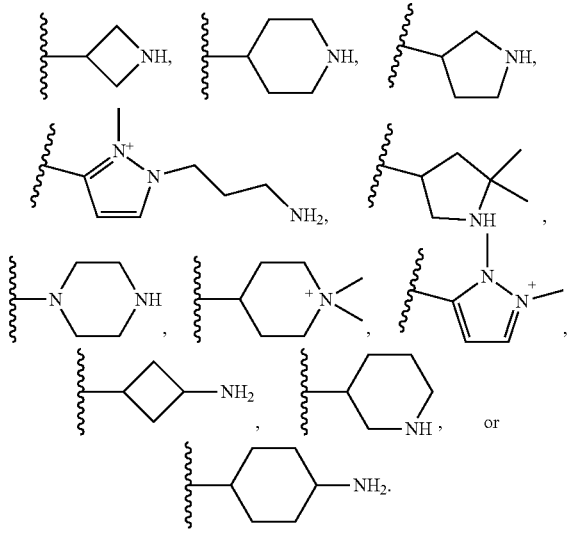

In another embodiment, each occurrence of R⁶ is independently selected from the group consisting of: halogen, —C₁-C₆alkyl, —(CH₂)ₙNRᶜRᵈ, —(CH₂)qORᵉ, —S(O)ₘRᵉ, —S(O)ₘNRᶜRᵈ, —C(O)Rᵉ, —OC(O)Rᵉ, —C(O)ORᵉ, —CN, —C(O)NRᶜRᵈ, —C(NH)NRᶜRᵈ, —NRᶜRᵈ, —N(Rᶜ)(C(O)Rᵉ), —N(Rᶜ)(C(O)ORᵉ), —N(Rᶜ)(C(O)NRᶜRᵈ), —N(Rᶜ)(S(O)ₘRᵉ), and —C₁-C₃alkylene-HetA. In another embodiment, each occurrence of R⁶ is independently selected from the group consisting of: —(CH₂)qORᵉ, and —C₁-C₃alkylene-HetA. In another embodiment, each occurrence of R⁶ is —C₁-C₃alkylene-HetA.

In another embodiment, each occurrence of R⁷ is independently selected from the group consisting of: halogen, —C₁-C₆alkyl, —(CH₂)ₙNRᶜRᵈ, —(CH₂)q—ORᵉ, —S(O)ₘRᵉ, —S(O)ₘNRᶜRᵈ, —C(O)Rᵉ, —OC(O)Rᵉ, —C(O)ORᵉ, —CN, —C(O)NRᶜRᵈ, —C(NH)NRᶜRᵈ, —NRᶜRᵈ, —N(Rᶜ)(C(O)Rᵉ), —N(Rᶜ)(C(O)ORᵉ), —N(Rᶜ)(C(O)NRᶜRᵈ), —N(Rᶜ)(S(O)ₘRᵉ), and —C₁-C₃alkylene-HetA.

In another embodiment, each occurrence of R⁷ is independently selected from the group consisting of: halogen, —C₁-C₆alkyl, —(CH₂)ₙNRᶜRᵈ, —(CH₂)q—ORᵉ, —C(O)NRᶜRᵈ and —C₁-C₃alkylene-HetA.

In another embodiment, each occurrence of R and Rᵈ is independently: hydrogen, —C₁-C₆ alkyl, —C₂-C₆ alkenyl, —C₃-C₆ cycloalkyl, —C₁-C₃ alkylene-C₃-C₆ cycloalkyl, HetA, —C₁-C₃alkylene-HetA, AryA, —C₁-C₃ alkylene-AryA, or —C₁-C₃alkylene-HetA, wherein each R and Rᵈ is optionally substituted with one to three Rᶠ.

In another embodiment, each occurrence of R is independently: hydrogen, or —C₁-C₆ alkyl.

In another embodiment, each occurrence of Rᵈ is independently: hydrogen, or —C₁-C₆ alkyl.

In another embodiment, each occurrence of Rᵉ is independently: hydrogen, —C₁-C₆alkyl, —C₂-C₆ alkenyl, —OH, or —OC₁-C₆ alkyl. In another embodiment, each occurrence of Rᵉ is independently: hydrogen, or —C₁-C₆alkyl. In another embodiment, Rᵉ is hydrogen. In another embodiment, Rᵉ is —C₁-C₆alkyl.

In another embodiment of the present invention, the compound of formula I is selected from:

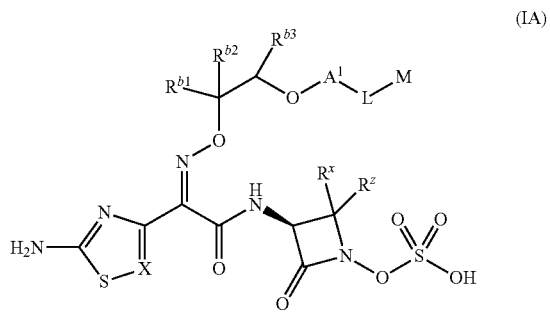

(IA)

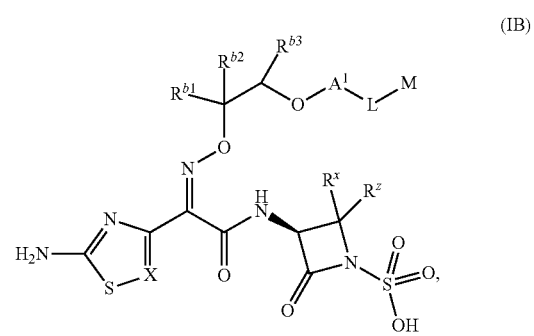

(IB)

or a pharmaceutically acceptable salt thereof.

In another embodiment of the present invention, the compound of formula I is selected from:

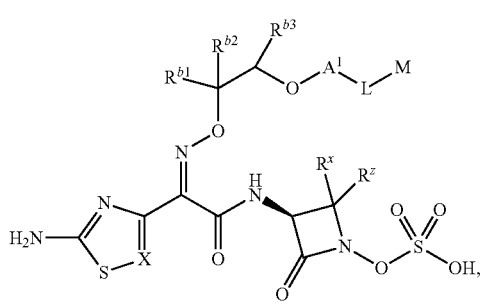
(IA)
or a pharmaceutically acceptable salt thereof.
In another embodiment of the present invention, the compound of formula I is selected from:
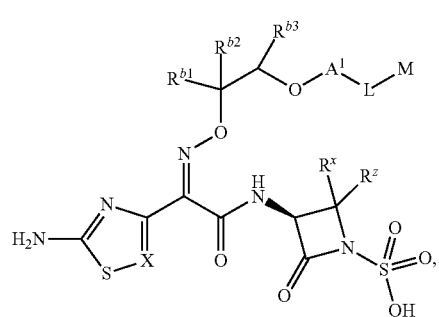
(IB)
or a pharmaceutically acceptable salt thereof.
In another embodiment of the present invention, the compound of formula (I) is selected from:
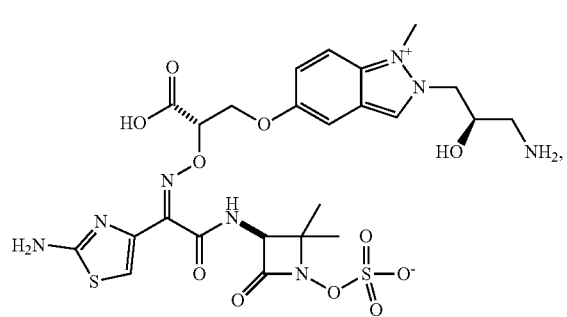
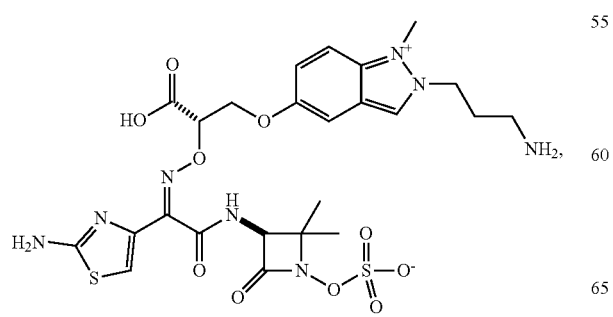
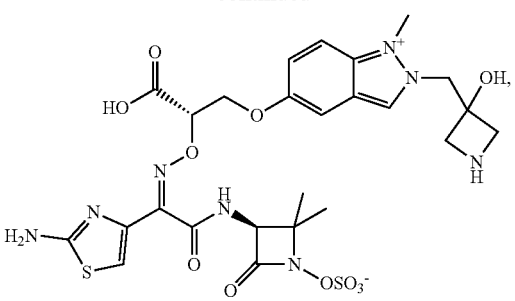
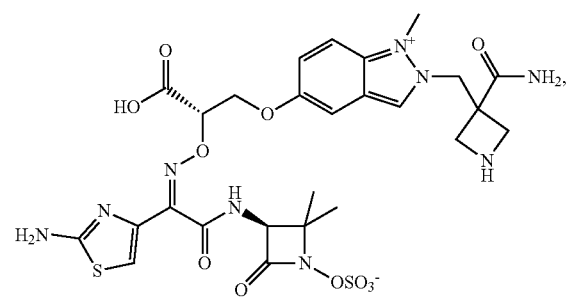
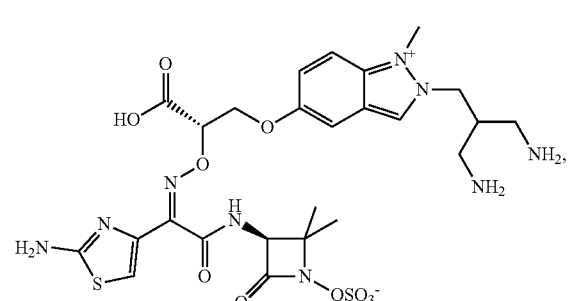
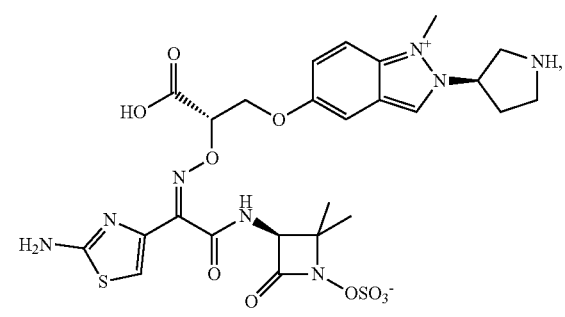
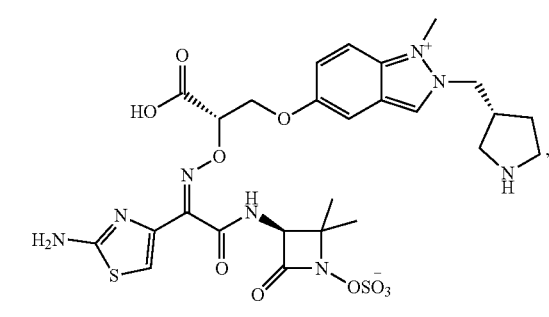

47
-continued
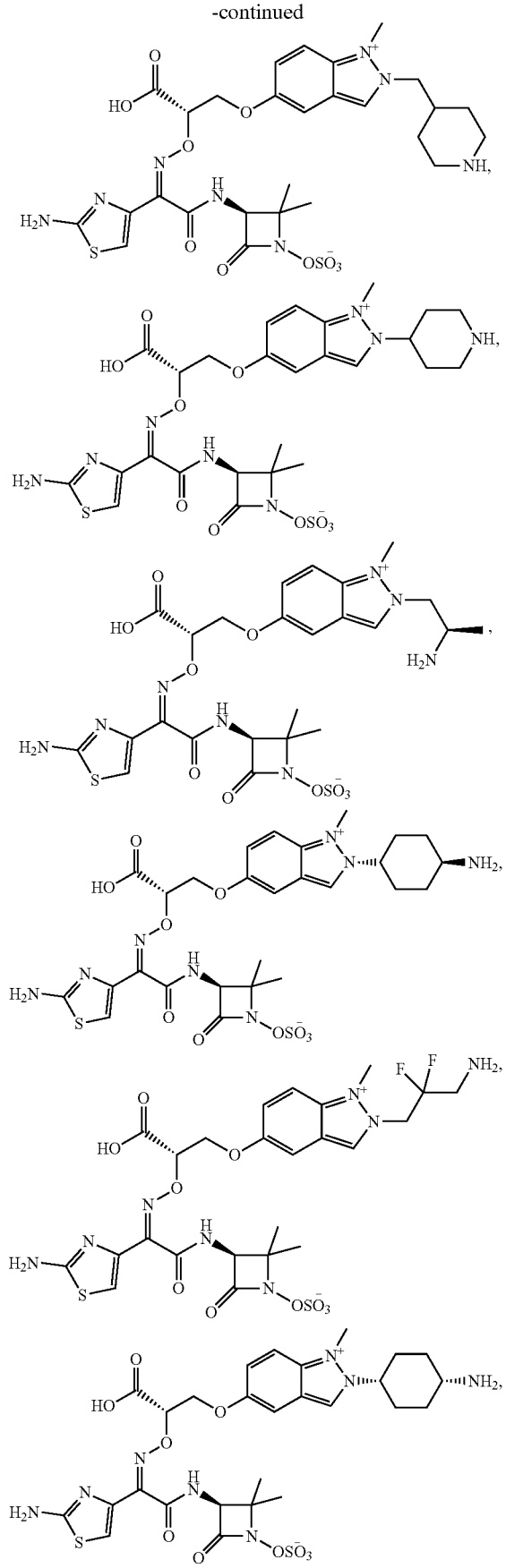
48
-continued
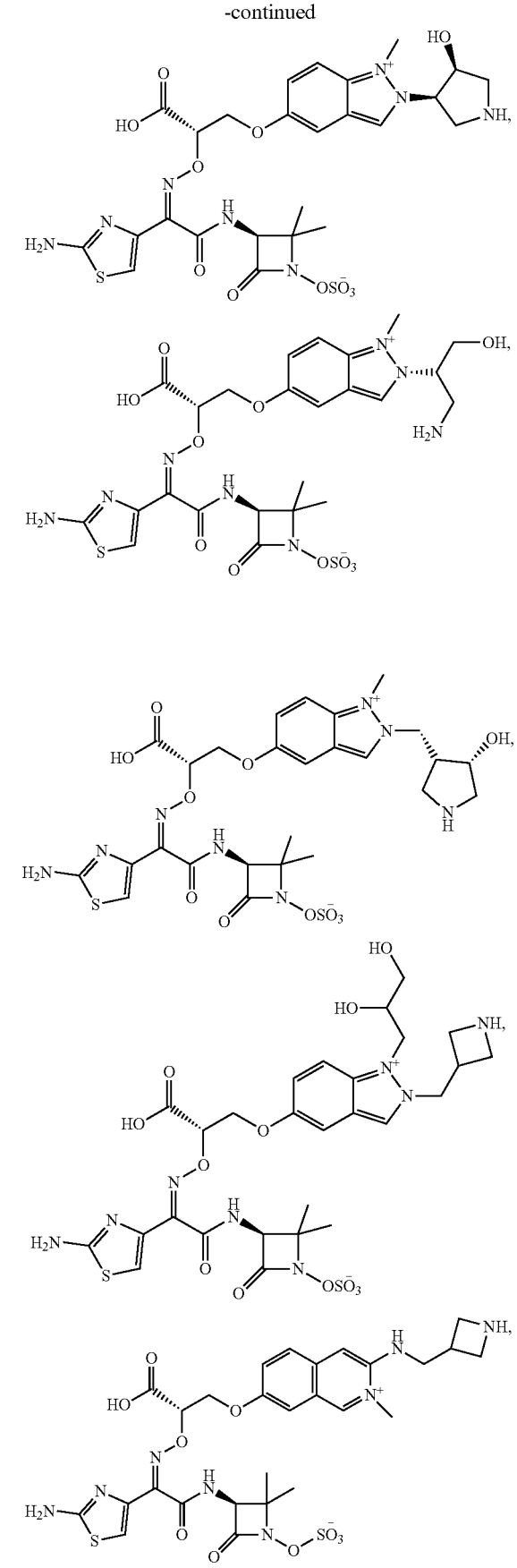

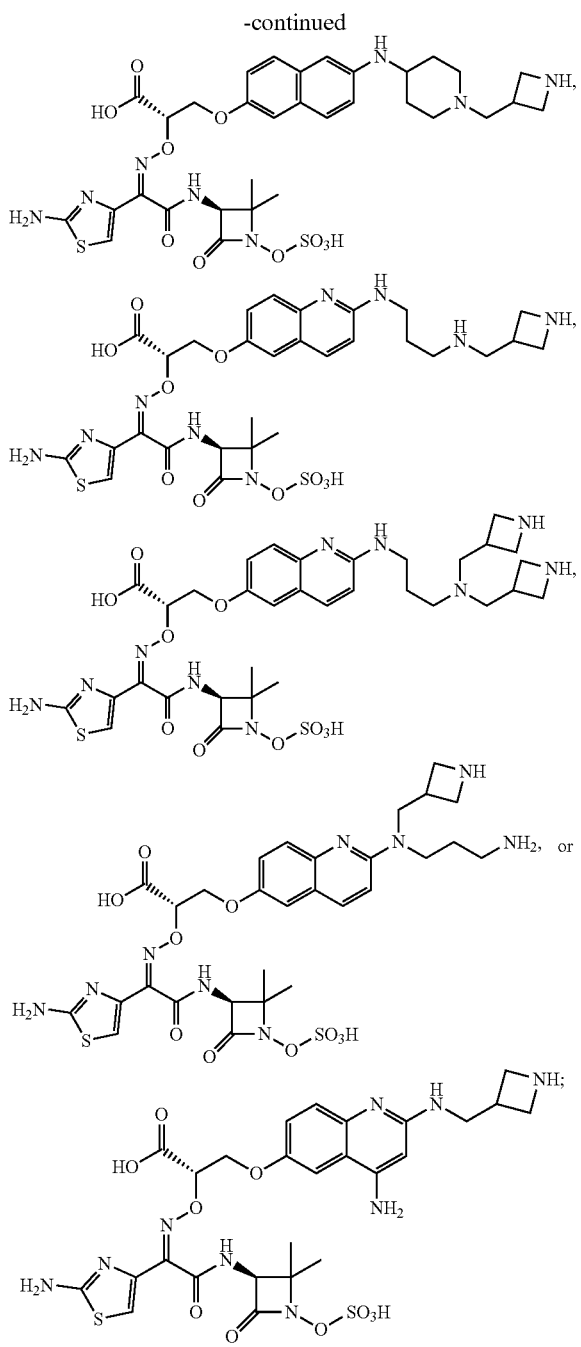

or a pharmaceutically acceptable salt thereof.

Other embodiments of the present invention include the following:

(a) A pharmaceutical composition comprising an effective amount of a compound of Formula I, IA, or IB, as defined herein, or a pharmaceutically acceptable salt thereof, and a pharmaceutically acceptable carrier.

(b) The pharmaceutical composition of (a), further comprising one or more beta-lactamase inhibitor compounds.

(c) The pharmaceutical composition of (b), wherein at least one of the one or more beta-lactamase inhibitor compounds is selected from the group consisting of: relebactam, tazobactam, clavulanic acid, sulbactam, and avibactam.

(d) A pharmaceutical composition comprising (i) a compound of Formula I, IA or IB, or a pharmaceutically acceptable salt thereof, and (ii) one or more additional compounds, wherein the one or more additional compounds are beta-lactamase inhibitor compounds, wherein the compound of Formula I, IA or IB, or pharmaceutically acceptable salt thereof, and the one or more additional compounds, are each employed in an amount that renders the combination effective for treating or preventing bacterial infection.

(e) The combination of (d), wherein one or more of the additional compounds is selected from the group consisting of: relebactam, tazobactam, clavulanic acid, sulbactam, and avibactam.

(f) A method for treating a bacterial infection in a subject which comprises administering to a subject in need of such treatment an effective amount of a compound of Formula I, IA or IB, or a pharmaceutically acceptable salt thereof.

(g) A method for preventing and/or treating a bacterial infection which comprises administering to a subject in need of such treatment a pharmaceutical composition comprising a pharmaceutically effective amount of a compound of Formula I, IA or IB, or a pharmaceutically acceptable salt thereof, and a pharmaceutically acceptable carrier.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to Gram negative bacteria.

(j) The method of treating a bacterial infection as set forth in (f), (g), (h), or (i), wherein the bacterial infection is due to *Pseudomonas aeruginosa* or *Acinetobacter baumannii*.

The present invention also includes a compound of Formula I, IA or IB, or a pharmaceutically acceptable salt thereof, (i) for use in, (ii) for use as a medicament for, or (iii) for use in the preparation (or manufacture) of a medicament for, medicine or treating bacterial infection, including infection with a multidrug resistant bacterial strain. In these uses, the compounds of the present invention can optionally be employed in combination with one or more second therapeutic agents including relebactam, tazobactam, clavulanic acid, sulbactam, and avibactam.

Additional embodiments of the invention include the pharmaceutical compositions, combinations and methods set forth in (a)-(j) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (j) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, IA or IB or its salt and a pharmaceutically acceptable carrier and optionally one or more excipients, it is understood that the term "substantially pure" is in reference to a compound of Formula I, IA or IB or its salt per se; i.e., the purity of this active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "β-lactamase inhibitor" refers to a compound which is capable of inhibiting enzyme activity from β-lactamases. As used herein, inhibiting β-lactamase activity means inhibiting the activity of a class A, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include metallo-β-lactamases of *Escherichia coli* (such as New Delhi Metallo-J-lactamase, NDM), *Serratia marcescens* (such as IMP), and *Klebsiella* spp. (such as Verona integron-encoded metallo-β-lactamase, VIM).). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics include penicillins, cephalosporins and carbapenems.

The term "β-lactam antibiotic" refers to a compound with antibiotic properties that contains a β-lactam functionality. Non-limiting examples of β-lactam antibiotics include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of +0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

Another embodiment of the present invention is a compound of Formula I, IA or IB, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, IA or IB or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I, IA and IB. Unless a specific stereochemistry is indicated, the present invention is meant to comprehend all such isomeric forms of these compounds. Centers of asymmetry that are present in the compounds of Formula I, IA and IB can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, IA and IB or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention.

Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In one embodiment, an alkylene group has from 1 to about 3 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Aromatic ring system" or "aromatic" in reference to a ring means monocyclic, bicyclic or tricyclic aromatic ring or ring system containing 5-14 ring atoms, wherein at least one of the rings is aromatic. The term may be used to describe a saturated or monounsaturated carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quaternary amine. In certain embodiments, an N ring atom can be in the form of an N-oxide.

"9- to 11-membered bicyclic aromatic ring" means a bicyclic ring system wherein at least one of the rings is aromatic. The term may be used to describe a cycloalkyl ring or a cycloalkenyl ring fused to an aryl or heteroaryl ring. The term may also be used to describe a heterocycloalkyl ring or a heterocycloalkenyl ring fused to an aryl or heteroaryl ring. For example, a 5-7-membered cycloalkyl can be fused through two adjacent ring atoms to a 5-6-membered heteroaryl containing 1, 2, or 3 heteroatom ring atoms selected from N, NH, O, and S, or aryl. In other example, a heterocycloalkyl ring is fused through two ring atoms to an aryl or 5-6-membered heteroaryl ring containing 1, 2, or 3 heteroatoms selected from N, NH, O, and S. In the case of a heterocycloalkyl ring containing one or more N atoms, the N can be in the form of quaternary amine. In certain embodiments, an N ring atom can be in the form of an N-oxide. Examples of a 9-11 membered bicyclic aromatic ring include, but are not limited to, quinoline, isoquinoline, imidazo[1,2-a]pyridine, indazole, benzo[d]imidazole, benzo[d]thiazole, and naphthalene.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, and the like. In one embodiment of the present invention, cycloalkyl is selected from: cyclopropane, cyclobutane, cyclopentane, and cyclohexane.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like.

"Heterocycloalkyl" as used herein, refers to a non-aromatic saturated monocyclic or multicyclic ring system comprising 3 to 11 ring atoms, wherein from 1 to 4 of the ring atoms are independently N, NH, S (including SO and $SO_2$) and O, and the remainder of the ring atoms are carbon atoms. A heterocycloalkyl group can be joined via a ring carbon or ring nitrogen atom (if present). Where the ring or ring system contains one or more N atoms, the N can be in the form of quaternary amine. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. When a heterocycloalkyl contains two rings, the rings may be fused or spirocyclic. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The nitrogen or sulfur atom of the heterocycloalkyl (if present) can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, delta-lactam, delta-lactone, silacyclopentane, silapyrrolidine and the like, and all isomers thereof.

"Heterocycloalkenyl" means a nonaromatic monocyclic, bicyclic or bridged carbocyclic ring or ring system containing at least one double bond and containing at least one heteroatom selected from N, NH, S and O. In one embodiment, heterocycloalkenyl refers to a non-aromatic saturated monocyclic or multicyclic ring system comprising 3 to 11 ring atoms containing at least one double bond, wherein from 1 to 4 of the ring atoms are independently N, NH, S (including SO and SO$_2$) and O, and the remainder of the ring atoms are carbon atoms.

"Heteroaryl" means monocyclic, bicyclic or tricyclic ring or ring system containing 5-14 carbon atoms and containing at least one ring heteroatom selected from N, NH, S (including SO and SO$_2$) and O, wherein at least one of the heteroatom containing rings is aromatic. In the case of a heteroaryl ring system where one or more of the rings are saturated and contain one or more N atoms, the N can be in the form of quaternary amine. In one embodiment, a heteroaryl group has 5 to 10 ring atoms. In another embodiment, a heteroaryl group is monocyclic and has 5 or 6 ring atoms. In another embodiment, a heteroaryl group is bicyclic. Any nitrogen atom of a heteroaryl can be optionally oxidized to the corresponding N-oxide. The term "heteroaryl" also encompasses a heteroaryl group, as defined above, which is fused to a benzene ring. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is pyridine. Examples of bicyclic rings include:

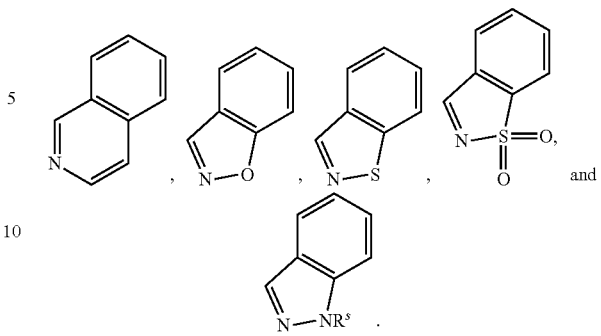

"Heterocycle" means a monocyclic or bicyclic saturated, partially unsaturated, or unsaturated ring system containing 5-10 atoms and containing at least one ring heteroatom selected from N, S and O. In select embodiments, the ring system contains 1-4 heteroatoms selected from N, S and O. When a heterocycle contains two rings, the rings may be fused, bridged or spirocyclic. Examples of monocyclic heterocycle rings include piperazine, piperidine, and morpholine. Examples of bicyclic heterocycle rings include 1,4-diazabicyclo[2,2,2]octane and 2,6-diazaspiroheptane.

"Halogen" includes fluorine, chlorine, bromine and iodine.

"Oxo" means an oxygen atom connected to another atom by a double bond and is can be represented "=O".

When any variable (e.g., $R^1$, $R^a$, etc.) occurs more than one time in any constituent or in Formula I, IA and IB, its definition on each occurrence is independent of its definition at every other occurrence. Also, combinations of substituents and/or variables are permissible only if such combinations result in stable compounds. A squiggly line across a bond in a substituent variable represents the point of attachment.

"Drug resistant" means, in connection with a Gram-negative bacterial strain, a strain which is no longer susceptible to at least one previously effective drug; which has developed the ability to withstand antibiotic attack by at least one previously effective drug. "Multi-drug resistant" means a strain that is no longer susceptible to two or more previously effective drugs; which has developed the ability to withstand antibiotic attack by two or more previously effective drugs. A drug resistant strain may relay that ability to withstand to its progeny. Said resistance may be due to random genetic mutations in the bacterial cell that alters its sensitivity to a single drug or to different drugs.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I, IA and IB.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. When a group, e.g., $C_1$-$C_6$ alkyl, is indicated as being substituted, such substitutions can also occur where such group is part of a larger substituent, e.g., —$C_1$-$C_6$alkyl-$C_3$-$C_7$cycloalkyl and —$C_1$-$C_6$alkyl-aryl.

In the compounds of Formula I, IA and IB, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, IA and IB. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, IA and IB can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

It should also be noted that any carbon as well as heteroatom with unsatisfied valences in the text, schemes, examples and tables herein is assumed to have the sufficient number of hydrogen atom(s) to satisfy the valences.

The compounds of the present invention have at least one asymmetric center and can have one or more additional centers as a result of the presence of certain substituents and/or substituent patterns. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfonate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quatemized with such agents as lower alkyl halides, such as methyl, ethyl, propyl, and butyl chloride, bromides and iodides;

dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The compound of the invention can also be employed in the form of a prodrug. Any prodrug precursor known in the art can be used to form a prodrug of the invention. In certain aspects of this embodiment, the hydrogen in —COOH in formula I can be replaced with any the following groups: $C_{1-6}$ alkyl, $C_{3-6}$ cycloalkyl, —$C_{1-6}$ alkylene-$C_{3-6}$ cycloalkyl, $C_{3-7}$ cycloheteroalkyl, —$C_{1-6}$ alkylene-$C_{3-7}$ cycloheteroalkyl, aryl, —$C_{1-10}$ alkylene-aryl, heteroaryl, and —$C_{1-10}$ alkylene-heteroaryl. In certain aspects of this embodiment, the $C_{1-6}$alkyl, $C_{3-6}$ cycloalkyl, or $C_{3-7}$cycloheteroalkyl can be substituted. In other aspects of this embodiment, each aryl and heteroaryl can be substituted.

As set forth above, the present invention includes pharmaceutical compositions comprising a compound of Formula I of the present invention, optionally including one or more other active components (e.g., a β-lactamase inhibitor), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, IA and IB, or a pharmaceutically acceptable salt thereof, optionally in combination with one or more β-lactamase inhibitors. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I, IA and IB mean providing the compound, or a pharmaceutically acceptable salt thereof, to the individual in need of treatment. When a compound or a salt thereof is provided in combination with one or more other active agents (e.g., a β-lactamase inhibitor), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein means the amount of active compound sufficient to inhibit bacterial growth and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, $21^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 microgram/mL, and in additional embodiment at least about 10 micrograms/mL, and at least about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I, IA and IB. Additional embodiments of the invention include the bacterial growth inhibiting method just described, wherein the compound of the present invention employed therein is a compound of one of the embodiments, sub-embodiments or classes described above.

The compound may optionally be used in the form of a pharmaceutically acceptable salt in these embodiments. The method can involve administration of a compound of Formula I, IA and IB to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula I, IA and IB is typically co-administered with one or more β-lactamase inhibitor compounds.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Compounds of the invention can be employed for the treatment, prophylaxis or inhibition of bacterial growth or infections due to bacteria that are resistant to β-lactam antibiotics. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 µg/mL, and bacterial strains which are slightly resistant to imipenem are those against which the MIC of imipenem is >4 µg/mL.

Compounds of the invention can be used in combination with one or more β-lactamase inhibitors for the treatment of infections caused by β-lactamase producing strains, in addition to those infections which are subsumed within the antibacterial spectrum of the antibiotic agent. Examples of β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus mirabilis, Morganella morganii, Providencia rettgeri, Stenotrophomonas maltophilia* and *Acinetobacter baumannii*.

It is generally advantageous to use a compound of Formula I, IA and IB in admixture or conjunction with one or more β-lactamase inhibitors, or a prodrug thereof. It is advantageous to use a compound of Formula I in combination with a class A and C β-lactamase inhibitor because of the class B β-lactamase resistant properties of the compounds. It is also advantageous to use a compound of Formula I in combination with one or more Class A, C, or D β-lactamase inhibitors to further limit β-lactam susceptibility. As already noted, the compound of Formula I and the one or more β-lactamase inhibitor can be administered separately (at the same time or as different times) or in the form of a single composition containing both active ingredients.

Relebactam, tazobactam, clavulanic acid, sulbactam, avibactam and other β-lactamase and metallo-β-lactamase inhibitors suitable for use in the present invention include those known to show inhibitory activity to β-lactamases.

Abbreviations employed herein include the following: aq.=aqueous; ACN=acetonitrile; BLI=β-lactamase inhibitor; Bn=benzyl; BOC (or Boc)=t-butyloxycarbonyl; $BOC_2O$=di-tert-butyl dicarbonate; CAN=ceric ammonium nitrate; CELITE=diatomaceous earth; CBZ (or Cbz)=carbobenzoxy (alternatively, benzyloxycarbonyl); $CDCl_3$=deuterated chloroform; $CH_3CN$=acetonitrile; DBU=1,8-diazabicyclo[5.4.0]undec-7-ene; DCC=dicyclohexyl carbodiimide; DCE=1,2-dichloroethane; DCM=dichloromethane; DEAD=diethyl azodicarboxylate; DIAD=diisopropyl azodicarboxylate; DIBAL-H=diisobutyl-aluminum hydride; DIEA=diisopropylethylamine; DMA=dimethylacetamide; DMAP=4-dimethylaminopyridine or N,N-dimethylaminopyridine; DMF=N,N-dimethylformamide; DMSO=dimethyl sulfoxide; EA is ethyl acetate; EDC=1-ethyl-3-(3-dimethylaminopropyl) carbodiimide; eq. or equiv.=equivalent(s); Et=ethyl; $Et_2O$=ethylene oxide; EtOAc=ethyl acetate; EtOH=ethanol; HOBT=1-hydroxy benzotriazole; HPLC=high-performance liquid chromatography; IPA=isopropyl alcohol; LC/MS or LC-MS=liquid chromatography/mass spectrometry; LDA=lithium diisopropylamide; m-CPBA=m-chloroperoxybenzoic acid; MBL=metallo β-lactamase; Me=methyl; MeOH=methanol; MeI=methyl iodide; MITC=minimum inhibitory threshold concentration; MPLC=medium pressure liquid chromatography; MTBE=methyl tert-butyl ether; NBS=N-bromosuccinimide; NCS=N-chlorosuccinimide; NMR=nuclear magnetic resonance; MS=mass spectrometry; MW=molecular weight; PE is petroleum ether; Pd/c=palladium on carbon; $PdCl_2$ (dppf)=[1,2'-bis(diphenylphosphino)ferrocene]dichloropalladium(II); PG=protective group; Ph=phenyl; RP-HPLC=reverse-phase high-performance liquid chromatography; r.t. and RT=room temperature; sat'd=saturated; 2nd generation RuPhos precatalyst is Chloro(2-dicyclohexylphosphino-2',6'-diisopropoxy-1,1'-biphenyl)[2-(2'-amino-1,1'-biphenyl)]palladium(II) (or RuPhos-Pd-G2); SEM-Cl=2-(trimethylsilyl)-ethoxymethyl chloride; tBu=tert butyl; TBAF=tetrabutylammonium fluoride; TBME=tert-butyl methyl ether; TBS=tert-butyldimethylsilyl; t-BuOH=tert-butanol; TBSO=tert-butyldimethylsilyl; TEA=triethylamine; TFA=trifluoroacetic acid; THF=tetrahydrofuran; TLC=thin layer chromatography; and TMS=trimethylsilyl.

Methods for Making the Compounds of Formula (I):

The compounds disclosed herein can be prepared and tested according to the following reaction schemes and Examples, or modifications thereof, using readily available starting materials, reagents and conventional synthesis procedures. In these reactions, it is also possible to make use of variations which are themselves known to those of ordinary skill in this art, but are not mentioned here in greater detail. Furthermore, other methods for preparing compounds disclosed herein will be readily apparent to the person of ordinary skill in the art in light of the following reaction scheme and Examples. Unless otherwise indicated, all variables are as defined above.

Scheme 1

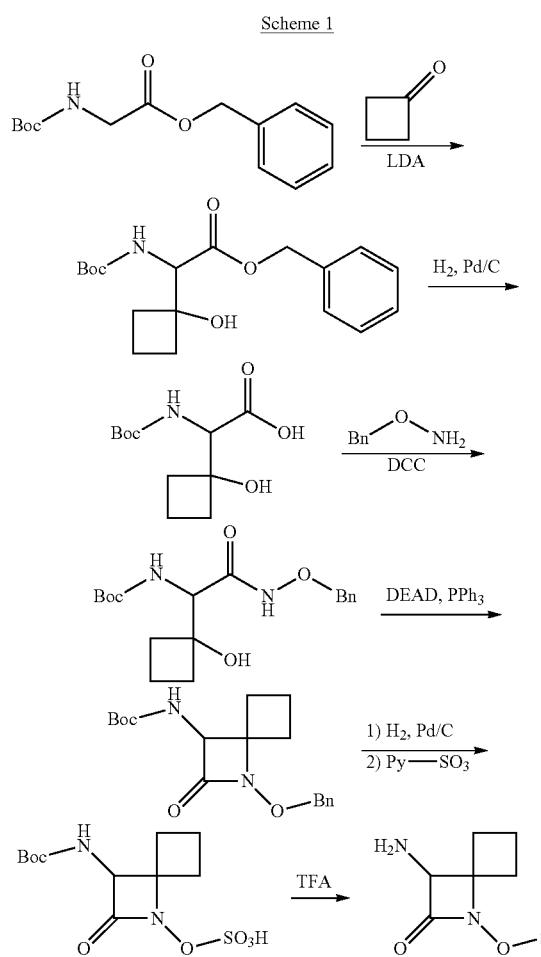

Monobactam compounds comprising a spirocycle at $R^x$ and $R^x$ can be synthesized following the scheme above, which shows the synthesis of a β-lactam intermediate wherein $R^x$ and $R^z$ come together to form a 4-membered spirocyclic ring. The final β-lactam intermediate shown in the scheme can alternatively be purchased from commercial sources. A synthetic scheme has also been discussed in detail in the literature. (See EP 0229012). This amine can be converted to the final monobactam compounds using procedures similar to those demonstrated in the following Examples.

Intermediate 1

Tert-Butyl oxirane-2-carboxylate

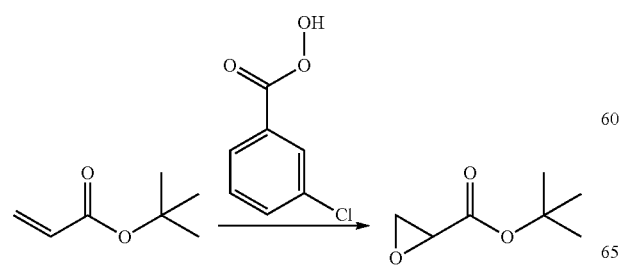

To a 1 L 2-neck round bottom flask fitted with a condenser, m-CPBA was added portion wise to a solution of tert-butyl acrylate (20 g, 156 mmol) in DCM (200 ml) (48.5 g, 281 mmol). The resulting solution was heated to 58-60° C. with an oil bath and refluxed for 2½ days. The mixture was checked by NMR to make sure the reaction was complete. The mixture was then cooled to room temperature and small portions of saturated sodium thiosulfate solution was added (about 40 mL, exotherm, added in small portions until no more heat was generated). After stirring the mixture for about 1 hr, a large amount of precipitate occurred. About 60-100 mL of water and 100-200 mL of DCM was added to dissipate the emulsion and generate a two-phase system. The aqueous layer was separated and the organic phase was washed with saturated NaHCO$_3$ (2×200 mL) and brine (100 mL), dried over MgSO$_2$ and concentrated to dryness (water bath temperature at 35° C.). The residue was suspended in 150 mL of hexane and let stand at room temperature for 1 hour. The mixture was then filtered, and the filtrate was concentrated to remove hexane in a ROTAVAPOR (BUCHI Labortechnik AG, Flawil, Switzerland) (<35° C.), resulting in the desired product. $^1$HNMR (500 MHz, CDCl$_3$) δ 3.35 (m, 1H), 2.86 (m, 2H), 1.52 (s, 9H).

Intermediate 2

(R, R)—Co Catalyst

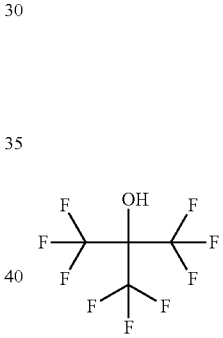

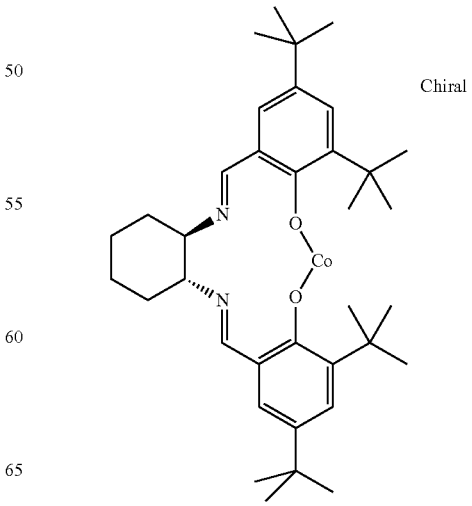

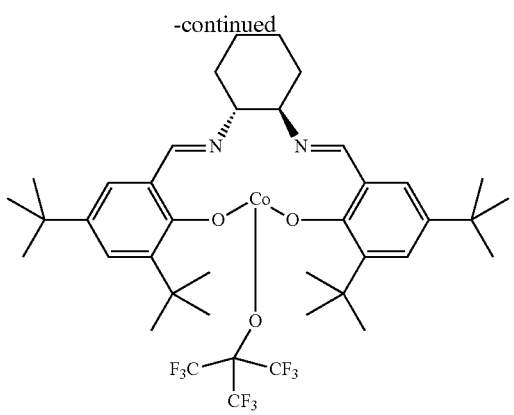

Reference: *J. Am. Chem. Soc.* 1999, 121, 6086-6087. To a solution of perfluoro-tert-butanol (1.96 g, 8.28 mmol) in DCM (97 ml) was added (R,R)-(−)-N,N'-bis(3,5-di-tert-butylsalicylidene)-1,2-cyclohexanediaminocobalt(II) (5 g, 8.28 mmol). The mixture was then stirred at 30° C. for 45 minutes open to air. The reaction was then concentrated and HiVac-dried to give the solid product.

Intermediate 3

2-(2-((tert-Butoxycarbonyl)amino)thiazol-4-yl)-2-oxoacetic Acid

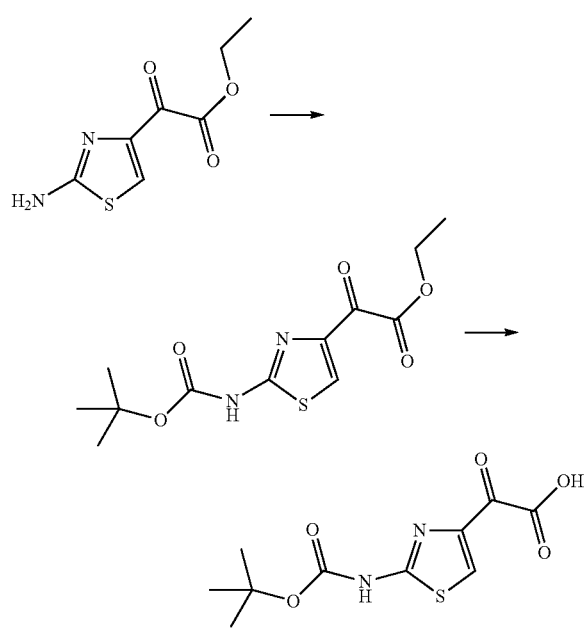

Step A: Preparation of Ethyl 2-(2-((tert-butoxycarbonyl)amino)thiazol-4-yl)-2-oxoacetate To a solution of ethyl 2-(2-aminothiazol-4-yl)-2-oxoacetate (10 g, 49.9 mmol) in acetonitrile (250 ml) was added BOC-anhydride (23.2 ml, 100 mmol) followed by N,N,N',N'-tetramethylethylenediamine (9.80 ml, 64.9 mmol). The mixture was stirred at room temperature for 3 hours. Solvent was removed, and the residue was partitioned between EtOAc and 1N HCl. The organic layer was washed with NaHCO$_3$ (Sat'd aq. solution) and brine, and dried over Na$_2$SO$_4$. Solvent was removed under vacuum. The residue was purified by column chromatography on silica gel (redi flash 220 g), and eluted with EtOAc/hexane (0-30%, 5 cv; 30%, 10 cv) to give the desired product as a solid. LC-MS [M+H]: m/z 301.

Step B: Preparation of 2-(2-((tert-butoxycarbonyl)amino)thiazol-4-yl)-2-oxoacetic Acid Ethyl 2-(2-((tert-butoxycarbonyl)amino)thiazol-4-yl)-2-oxoacetate (10.2 g, 34.1 mmol) was dissolved in THF (140 ml)/MeOH (50 ml), and sodium hydroxide (68.3 ml, 68.3 mmol, 1M) was added. The solution was stirred at room temperature for 4 hours. The reaction mixture was poured into water (1 L) and extracted with EtOAc (3×200 ml). The aqueous layer was acidified with HCl (1N) solution and re-extracted with EtOAc (3×200 ml). The organic layer was washed with brine and dried over Na$_2$SO$_4$, and concentrated to give the desired product as a solid. LC-MS [M+H]: m/z 273. $^1$HNMR (500 MHz, CDCl$_3$) δ 8.35 (s, 1H), 1.55 (s, 9H).

Intermediate 4

2-(2-((tert-Butoxycarbonyl)amino)-5-chlorothiazol-4-yl)-2-oxoacetic Acid

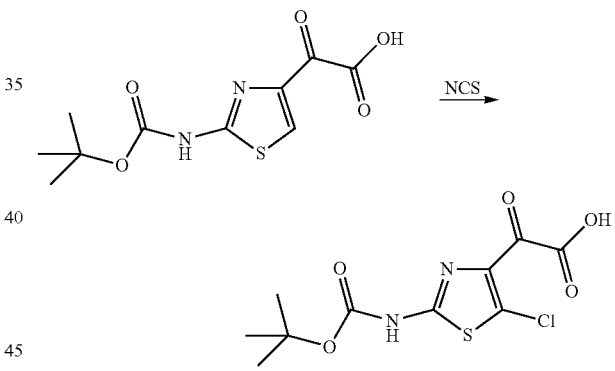

NCS (0.589 g, 4.41 mmol) was added to a suspension of 2-(2-((tert-butoxycarbonyl)-amino)thiazol-4-yl)-2-oxoacetic acid (intermediate 3) (1 g, 3.67 mmol) in DMF (10.0 ml). The mixture was heated to 50° C. overnight. It was then diluted with EtOAc (100 ml), and washed with water (3×30 ml) and brine. The organic layer was dried over Na$_2$SO$_4$. Solvent was removed under vacuum to give the desired product as a gum. LC-MS [M+H]: m/z 307.

Intermediate 5

2-(5-((tert-Butoxycarbonyl)amino)-1,2,4-thiadiazol-3-yl)-2-oxoacetic Acid

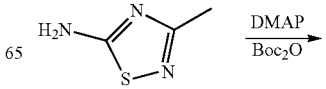

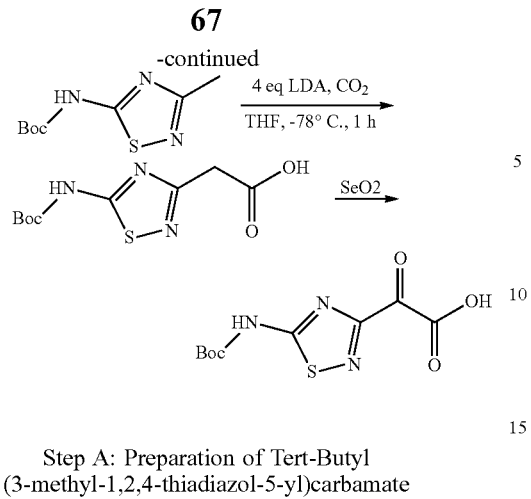

Step A: Preparation of Tert-Butyl (3-methyl-1,2,4-thiadiazol-5-yl)carbamate

Into a 5-L 4-necked round-bottom flask purged and maintained with an inert atmosphere of nitrogen, was placed 3-methyl-1,2,4-thiadiazol-5-amine (167 g, 1.45 mol, 1.00 equiv), 4-dimethylamino-pyridine (17.7 g, 144.88 mmol, 0.10 equiv), di-tert-butyl dicarbonate (348 g, 1.59 mol, 1.10 equiv), and butan-1-ol (1670 mL). The resulting solution was stirred for 1 hour at 40° C. The resulting mixture was concentrated under vacuum. The residue was washed with hexane. This resulted in tert-butyl N-(3-methyl-1,2,4-thiadiazol-5-yl)carbamate as a solid.

Step B: Preparation of 2-(5-((tert-butoxycarbonyl)amino)-1,2,4-thiadiazol-3-yl)acetic Acid Into a 5000-mL 4-necked round-bottom flask purged and maintained with an inert atmosphere of nitrogen, was placed a solution of tert-butyl N-(3-methyl-1,2,4-thiadiazol-5-yl)carbamate (128 g, 595 mmol, 1.00 equiv) in tetrahydrofuran (640 mL). The resulting solution was stirred at −78° C. and LDA (1190.69 mL, 4.00 equiv.) was added. 30 minutes later, $CO_2$ (g) was introduced to the solution over 30 minutes at −30° C. The reaction was then quenched by the addition of 1280 mL of water. The resulting solution was extracted with 640 mL of ethyl acetate and the aqueous layers were combined. The pH value of the solution was adjusted to 2 with HCl (2M mol/L). The resulting solution was extracted with 2.5 L of ethyl acetate and the organic layers were combined. The resulting mixture was washed with 2000 mL of brine. The mixture was dried over anhydrous sodium sulfate and concentrated under vacuum. This resulted in 2-(5-[[(tert-butoxy)carbonyl]amino]-1,2,4-thiadiazol-3-yl) acetic acid as a solid.

Step C: Preparation of 2-(5-((tert-Butoxycarbonyl)amino)-1,2,4-thiadiazol-3-yl)-2-oxoacetic Acid Into a 2000-mL 4-necked round-bottom flask, purged and maintained with an inert atmosphere of nitrogen, was placed a solution of 2-(5-[[(tert-butoxy)carbonyl]amino]-1,2,4-thiadiazol-3-yl)acetic acid (76 g, 293.12 mmol, 1.00 equiv) in dioxane (1520 mL) and $SeO_2$ (65.14 g, 587 mmol, 2.00 equiv). The resulting solution was stirred for 3 hours at 80° C. in an oil bath and then concentrated. The crude product was purified by Flash-Prep-HPLC with the following conditions (IntelFlash-1): Column, silica gel; mobile phase, ACN/$H_2O$ (0.5% HCl)=10/90-30/70 increasing to ACN/$H_2O$ (0.5% HCl)=90/10 to 70/30 within 20 min; Detector, UV 254 nm. This resulted in 2-(5-[[(tert-butoxy)carbonyl]amino]-1,2,4-thiadiazol-3-yl)-2-oxoacetic acid as a solid. LC-M: (ES, m/z): (M+H)=274. H-NMR (300 MHz, DMSO, ppm): δ 1.523-1.502 (s, 9H), 12.806 (s, 1H).

Intermediate 6

Tert-Butyl 3-((6-bromoimidazo[1,2-a]pyridin-2-yl)methyl)azetidine-1-carboxylate

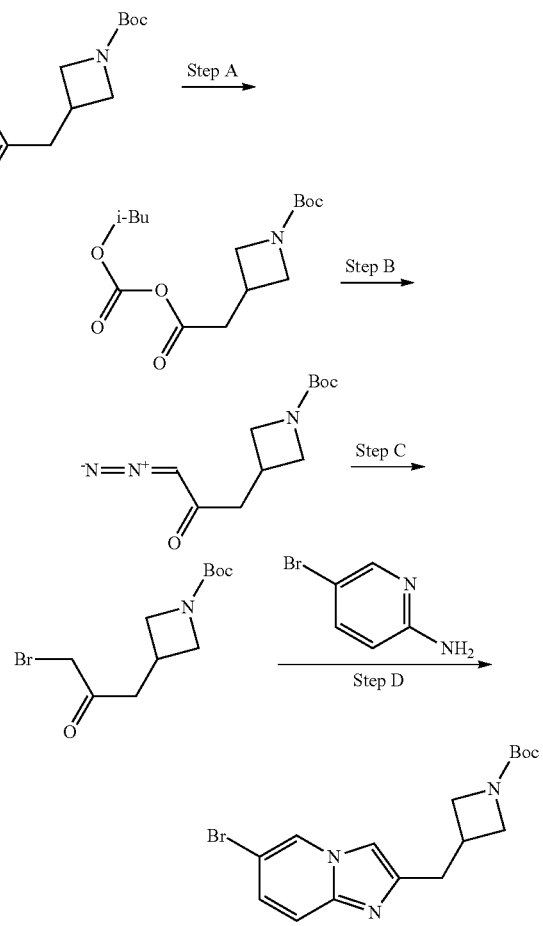

Step A: 2-(1-(tert-butoxycarbonyl)azetidin-3-yl)acetic (Isobutyl Carbonic) Anhydride Isobutyl carbonochloridate (3.2 g, 23 mmol) was added to a 0° C. cooled mixture of 2-(1-(tert-butoxycarbonyl)azetidin-3-yl)acetic acid (5 g, 23 mmol) and 4-methylmorpholine (2.6 g, 26 mmol) in THF (80 ml) under nitrogen. The mixture was stirred at 26° C. for 30 minutes. LCMS indicated the reaction was completed. The mixture was quickly filtered through a CELITE bed (about 5 mm thickness), which was directly used in the next step without purification. LCMS m/z [M+Na]$^+$: 338.1

Step B: Tert-Butyl 3-(3-diazo-2-oxopropyl)azetidine-1-carboxylate

To a solution of freshly generated diazomethane (9.8 g, 230 mmol) in $Et_2O$ (540 ml) was added dropwise 2-(1-(tert-butoxycarbonyl)azetidin-3-yl)acetic (isobutyl carbonic) anhydride (8.8 g, 28 mmol) in THF (100 ml) at 0° C. The reaction mixture was stirred at 0° C. for 0.5 hour and then warmed to 25° C. for 1 hour. A slow stream of nitrogen was bubbled through the mixture for 5 minutes to remove the excess diazomethane. The solvent was then carefully removed on a rotary evaporator (<35° C.) and dried on a vacuum pump to afford tert-butyl 3-(3-diazo-2-oxopropyl)azetidine-1-carboxylate, which was directly used next step without purification.

Step C: Tert-Butyl 3-(3-bromo-2-oxopropyl)azetidine-1-carboxylate

To a solution of tert-butyl 3-(3-diazo-2-oxopropyl)azetidine-1-carboxylate (6.7 g, 28 mmol) in THF (120 ml) was added aq. 48% HBr (3.2 ml, 28 mmol) at 0° C. The reaction mixture was stirred at 0° C. for 60 minutes. The resulting mixture was quenched with saturated aq. NaHCO₃ (60 mL), and the solvent was removed in vacuo. The reaction was then diluted with EtOAc (50 mL) and water (100 mL). The aqueous layer was extracted with EtOAc (3×60 mL). The combined organic phase was dried over Na₂SO₄, filtered and concentrated in vacuo to afford tert-butyl 3-(3-bromo-2-oxopropyl)azetidine-1-carboxylate, which was used directly for next step without purification. LCMS m/z [M−55+41]⁺: 279

Step D: Tert-Butyl 3-((6-bromoimidazo[1,2-a]pyridin-2-yl)methyl)azetidine-1-carboxylate To a mixture of tert-butyl 3-(3-bromo-2-oxopropyl)azetidine-1-carboxylate (6 g, 12 mmol) and 5-bromopyridin-2-amine (2.7 g, 15 mmol) in EtOH (90 ml) was added sodium bicarbonate (2.0 g, 24 mmol). The reaction mixture was stirred at 80° C. for 12 hours. Ethanol was removed in vacuo and the resulting material was mixed with water (50 mL) and ethyl acetate (50 mL). The aqueous layer was extracted with EtOAc (3×30 mL). The combined organic phase was dried over Na₂SO₄, filtered and concentrated in vacuo. The residue was purified by column chromatography (SiO₂, PE:EtOAc=20:1 to 1:1) to give tert-butyl 3-((6-bromoimidazo[1,2-a]pyridin-2-yl)methyl)azetidine-1-carboxylate. LCMS m/z [M+H]⁺: 366 ¹H NMR (400 MHz, CHCl₃-d) δ7.44-7.39 (m, 1H), 7.33-7.31 (m, 1H), 7.23-7.18 (m, 1H), 4.07-4.01 (m, 2H), 3.71-3.66 (m, 2H), 3.06-2.99 (m, 3H), 1.43 (s, 9H).

Intermediate 7

Tert-Butyl (R)-3-(3-formyl-4-nitrophenoxy)-2-hydroxypropanoate

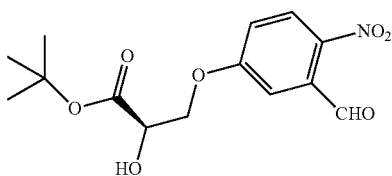 [SMILES: CC(C)(C)OC(=O)[C@H](O)COc1ccc([N+](=O)[O-])c(C=O)c1]

The mixture of tert-butyl oxirane-2-carboxylate (4.42 g, 30.7 mmol), 5-hydroxy-2-nitrobenzaldehyde (2.33 g, 13.94 mmol), molecular sieves (1 g), and Cobalt catalyst (R,R) (0.585 g, 0.697 mmol, Reference: J. Am. Chem. Soc. 1999, 121, 6086-6087) in t-BuOMe (20 ml) was stirred at rt for 3 days. After filtration through Celite™, the filtrate was concentrated and the residue was purified on silica gel column using EtOAc/hexane as eluting solvents to give the title compound. LC/MS: [M+H]⁺: 311.2; (2M+23)⁺: 645.2. ¹H NMR (500 MHz, CDCl₃): δ 10.49 (s, 1H), 8.19-8.17 (d, J=9.0 Hz, 1H), 7.38-7.37 (d, J=4.1 Hz, 1H), 7.22-7.20 (dd, J=9.8 and 3.3 Hz, 1H), 4.46-4.37 (m, 3H), 3.29 (s, 1H), 1.51 (s, 9H).

Intermediate 8

Tert-Butyl (S)-(3-amino-2-((tert-butyldimethylsilyl)oxy)propyl)carbamate

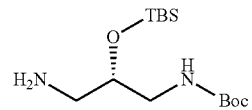

Step A: (S)-Benzyl Tert-Butyl (2-hydroxypropane-1,3-diyl)dicarbamate

To a solution of (S)-tert-butyl (3-amino-2-hydroxypropyl)carbamate (2.38 g, 12.5 mmol) in DCM (50 ml) at 0° C. was added TEA (4.53 ml, 32.5 mmol) and CBZ-Cl (2.32 ml, 16.3 mmol). The resulting solution was stirred from 0° C. to rt overnight. The mixture was concentrated and the residue was purified on silica gel column using EtOAc/hexane as eluting solvents to give the title compound. LC/MS: [M+1]⁺=325.2.

Step B: (S)-Benzyl Tert-Butyl (2-((tert-butyldimethylsilyl)oxy)propane-1,3-diyl)dicarbamate To a solution of (S)-benzyl tert-butyl (2-hydroxypropane-1,3-diyl)dicarbamate (2.94 g, 9.06 mmol) in DMF (20 ml) was added imidazole (3.09 g, 45.3 mmol), TBS-Cl (2.73 g, 18.1 mmol), and DMAP (0.111 g, 0.906 mmol). The resulting solution was stirred at rt for 2 h. Then the mixture was partitioned between EtOAc (300 ML) and water (200 mL). The organic phase was washed with water (200 mL×2), and brine (200 mL), dried over Na₂SO₄, and concentrated. The resulting residue was purified on silica gel column using EtOAc/hexane as eluting solvents to give the title compound. LC/MS: [M+1]⁺=439.4.

Step C: (S)-Tert-Butyl (3-amino-2-((tert-butyldimethylsilyl)oxy)propyl)carbamate To a solution of (S)-benzyl tert-butyl (2-((tert-butyldimethylsilyl)oxy)propane-1,3-diyl)dicarbamate (3.99 g, 9.10 mmol) in MeOH (100 ml) was added 10% Pd/C (0.968 g, 0.910 mmol). The resulting mixture was hydrogenated via H₂ balloon at rt for 1 h. Then the mixture was filtered through Celite™, and the filtrate was concentrated to give the title compound. LC/MS: [M+1]⁺=305.3.

Intermediate 9

Di-Tert-Butyl (2-(aminomethyl)propane-1,3-diyl)dicarbamate

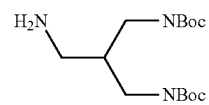

Step A: Methyl 3-((tert-butoxycarbonyl)amino)-2-(((tert-butoxycarbonyl)amino)methyl) propanoate To a solution of methyl 3-amino-2-(aminomethyl)propanoate dihydrochloride (1.01 g, 4.92 mmol) in dioxane (50 ml), water (10 ml), and THF (20 ml) at 0° C. was added di-tert-butyl dicarbonate (2.36 g, 10.8 mmol) and di-isopropylethylamine (1.89 mL, 10.8 mmol). The resulting solution was stirred at rt overnight. The volatiles were removed. The resulting residue was dissolved in EtOAc (200 mL), and washed with ice-cold HCl (0.5 N, 3×100 mL), followed by saturated NaHCO$_3$ (2×100 mL), then dried over Na$_2$SO$_4$, and concentrated to give the title compound. LC/MS: [M+1]$^+$=333.3.

Step B: Di-Tert-Butyl (2-(hydroxymethyl)propane-1,3-diyl)dicarbamate

To a mixture of methyl 3-((tert-butoxycarbonyl)amino)-2-(((tert-butoxycarbonyl)amino)methyl) propanoate (1.66 g, 4.99 mmol), lithium borohydride (0.544 g, 25.0 mmol), and lithium chloride (1.06 g, 25.0 mmol) in THF (anhydrous, 40 ml) at 0° C. was added MeOH (6 mL) dropwise over 10 min. The ice bath was removed and the reaction was stirred at rt for approx. 50 min. Then the reaction was cooled to 0° C. and quenched with 16 mL of saturated NaCl (16 mL); additional solid NaCl was added to ensure saturation, and then diluted with EtOAc (200 mL). The organic layer was collected. The aqueous layer was back-extracted with DCM (100 mL×3). The organic layers were combined, dried over Na$_2$SO$_4$, and concentrated in vacuo to give the title compound. LC/MS: [M+1]$^+$: 305.3.

Step C: 3-((tert-butoxycarbonyl)amino)-2-(((tert-butoxycarbonyl)amino)methyl)propyl methanesulfonate To a solution of di-tert-butyl (2-(hydroxymethyl)propane-1,3-diyl)dicarbamate (283 mg, 0.93 mmol) in DCM (anhydrous, 8 mL) at 0° C. was added TEA (0.259 mL, 1.86 mmol) and MsCl (0.087 mL, 1.12 mmol). The resulting solution was stirred at 0° C. for 1 h, then the reaction solution was partitioned between DCM (100 mL) and 0.2 M KHSO$_4$. The organic phase was separated, washed with 0.2 M KHSO$_4$, dried over Na$_2$SO$_4$, and concentrated to give the title compound. LC/MS: [M+1]$^+$: 383.3.

Step D: Di-Tert-Butyl (2-(azidomethyl)propane-1,3-diyl)dicarbamate

To a solution of 3-((tert-butoxycarbonyl)amino)-2-(((tert-butoxycarbonyl)amino)methyl)propyl methanesulfonate (1.57 g, 4.10 mmol) in DMSO (6 ml) was added sodium azide (0.801 g, 12.3 mmol). The resulting mixture was heated at 90° C. overnight. Then the mixture was diluted with EtOAc (200 ML) and washed with water (3×100 mL), dried over Na$_2$SO$_4$, and concentrated. The resulting residue was purified on silica gel column using EtOAc/hexane as eluting solvents to give the title compound. LC/MS: [M+1]$^+$=330.4.

Step E: Di-Tert-Butyl (2-(aminomethyl)propane-1,3-diyl)dicarbamate

To a solution of di-tert-butyl (2-(azidomethyl)propane-1, 3-diyl)dicarbamate (1.4 g, 4.25 mmol) in MeOH (50 ml) was added Pd/C (4.52 g, 4.25 mmol). The resulting mixture was hydrogenated via H$_2$ balloon at rt for 3 h. Then the mixture was filtered through Celite™, and the filtrate was concentrated to give the title compound. LC/MS: [M+1]$^+$: 304.3.

Intermediate 10

Tert-Butyl (R)-2-((tert-butyldimethylsilyl)oxy)-3-((3-chloroisoquinolin-7-yl)oxy)propanoate

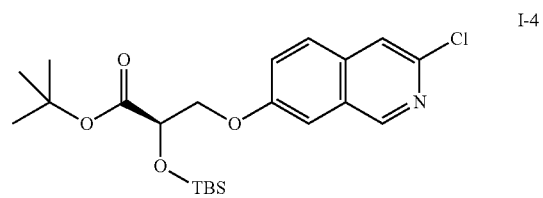

I-4

Step A: (Z)-2-(hydroxyimino)-6-methoxy-2,3-dihydro-1H-inden-1-one 6-methoxy-2,3-dihydro-1H-inden-1-one (30 g, 185 mmol) was dissolved in MeOH (400 mL). The mixture was heated to 40° C., then isoamyl nitrite (52.3 mL, 388 mmol) and concentrated HCl (30.4 ml, 370 mmol) were added. The reaction mixture was stirred at 40° C. for 2 h, and then cooled to room temperature. The resulting precipitate was collected by filtration and dried under high vacuum to obtain the title compound, which was used directly without further purification. LCMS (ESI) calc'd for C$_{10}$H$_9$NO$_3$, [M+Na]$^+$: 192.0, found: 192.0.

Step B: 1,3-dichloro-7-methoxyisoquinoline

To a suspension of (Z)-2-(hydroxyimino)-6-methoxy-2,3-dihydro-1H-inden-1-one (10 g, 52.3 mmol) in POCl$_3$ (91 mL, 978 mmol), and PCl$_5$ (17.10 g, 82 mmol) was added at 0° C., then HCl (excess) gas was bubbled through the solution until the solution was saturated with HCl. The reaction mixture was stirred at 30° C. for 18 h, then the solvent was removed in vacuo and ice water (50 mL) was added to the resulting residue. The resulting precipitate was collected by filtration, washed with water (5 mL), and dried under high vacuum to give the title compound, which was used directly without further purification. LCMS (ESI) calc'd for C$_{10}$H$_7$Cl$_2$NO [M+H]$^+$: 228.0, 230.0, found: 228.0.

Step C: 3-chloro-7-methoxyisoquinoline 1,3-dichloro-7-methoxyisoquinoline (11 g, 48.2 mmol) was suspended in acetic acid (90 mL) and concentrated HCl (30 mL), and then treated with Sn (17.18 g, 144.7 mmol), and then stirred at 60° C. for 24 h. The resulting mixture was basified to pH=9 with concentrated NH$_4$OH and then extracted with ethyl acetate (150 mL×3). The combined organic layers were washed with saturated NaHCO$_3$ solution (400 mL), dried over Na$_2$SO$_4$, filtered and concentrated in vacuo. The resulting residue was purified by silica gel column (SiO$_2$; EtOAc/PE=1:20 to 2:1) to give the title compound. LC-MS (ESI) calc'd for C$_{10}$H$_8$ClNO [M+H]$^+$: 194.0, found: 194.0.

Step D: 3-chloroisoquinolin-7-ol 3-chloro-7-methoxyisoquinoline (4.7 g, 24.3 mmol) was dissolved in DCM (80 mL). Then BBr$_3$ (6.20 ml, 65.5 mmol)

was added slowly at 25° C. and solution was stirred at 25° C. for 18 h. After cooling to 0° C., methanol (40 mL) was added slowly to quench the reaction. The solution was stirred for an additional 10 minutes, then concentrated under reduced pressure. The resulting residue was treated with methanol (40 mL) and concentrated under reduced pressure. The resulting oil was treated with saturated aqueous sodium bicarbonate slowly with stirring until a pH~7-8 was achieved. The resulting solid was collected using vacuum filtration and was washed with water (10 mL) and methylene chloride (10 mL) to give the title compound, which was used directly without further purification. LCMS (ESI) calc'd for $C_9H_6C_1NO$ [M+H]$^+$: 180.0, found: 180.0.

Step E: (R)-Tert-Butyl 3-((3-chloroisoquinolin-7-yl)oxy)-2-hydroxypropanoate

To a mixture of Co-catalyst (1.31 g, 1.56 mmol), 3-chloroisoquinolin-7-ol (3.5 g, 19.5 mmol) and molecular sieves (200 mg) in TBME (10 mL) was added tert-butyl oxirane-2-carboxylate (10 g, 55.5 mmol). The resulting suspension was stirred at 25° C. under $N_2$ for 72 h. Then the reaction was filtered and purified by silica-gel chromatography ($SiO_2$, EA: PE=0% to 40%) to give the title compound. LC-MS (ESI) calc'd for $C_{16}H_{18}C_1NO_4$, [M+H]$^+$: 324.0, found: 324.1.

Step F: (R)-Tert-Butyl 2-((tert-butyldimethylsilyl)oxy)-3-((3-chloroisoquinolin-7-yl)oxy) propanoate To the mixture of (R)-tert-butyl 3-((3-chloroisoquinolin-7-yl)oxy)-2-hydroxypropanoate (1.9 g, 5.87 mmol), imidazole (1.2 g, 17.6 mmol) in DMF (20 mL) was added TBS-Cl (1.77 g, 11.7 mmol), The resulting suspension was stirred at 25° C. for 18 hrs. LCMS showed the desired product formed. The reaction mixture was filtered and diluted with EtOAc (200 mL), washed with saturated brine (3*180 mL). The organic layer was dried over $Na_2SO_4$, filtered and concentrated. The residue mixture was purified by silica-gel chromatography ($SiO_2$, EA: PE=0% to 30%) to give the title compound. LCMS (ESI) calc'd for $C_{22}H_{32}C_1NO_4Si$ [M+H]$^+$: 438.1, found: 438.2. $^1$H NMR (400 MHz, CHLOROFORM-d) δ=8.92-8.88 (m, 1H), 8.84 (s, 1H), 7.60-7.51 (m, 2H), 7.27 (dd, J=2.3, 9.0 Hz, 1H), 7.13 (d, J=2.3 Hz, 1H), 4.45-4.40 (m, 1H), 4.24 (br d, J=3.3 Hz, 1H), 4.15 (br d, J=7.0 Hz, 1H), 1.40 (s, 9H), 0.81 (s, 9H), 0.05 (s, 3H), 0.00 (s, 3H).

Intermediate 11

Tert-Butyl 3-(((3-((tert-butoxycarbonyl)amino)propyl)amino)methyl)azetidine-1-carboxylate

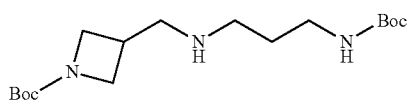

I-5

To a solution of tert-butyl (3-aminopropyl)carbamate (1.6 g, 9.18 mmol) in MeOH (50 ml) was added tert-butyl 3-formylazetidine-1-carboxylate (1.70 g, 9.18 mmol). It was stirred at RT for 1 hr. Sodium triacetoxyborohydride (3.89 g, 18.4 mmol) and AcOH (1.05 ml, 18.4 mmol) was added. The reaction mixture was stirred at RT for 5 hrs and quenched with water. MeOH was removed under vacuum. The solution was diluted with EtOAc, washed with aq. $NaHCO_3$ solution, water and brine. The organic solution was dried with $Na_2SO_4$ and concentrated to give the title compound. LC-MS [M+H]: m/z 344.41.

Intermediate 12

Tert-Butyl (R)-3-((4-(N,N-bis(tert-butoxycarbonyl)amino)-2-chloroquinolin-6-yl)oxy)-2-((tert-butyldimethylsilyl)oxy)propanoate

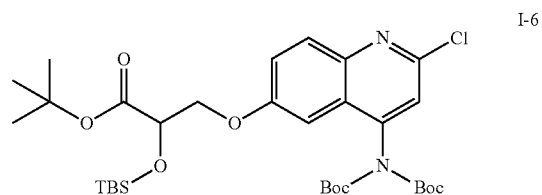

I-6

Step A: 2,4-dichloro-6-methoxyquinoline $POCl_3$ (80 ml) was added through a condenser into a 250 mL round bottom flask containing malonic acid (25.3 g, 244 mmol) at 20° C. While stirring, 4-methoxyaniline (20 g, 162 mmol) was added in small portions over a period of 15 minutes. The reaction mixture was heated and stirred at 105° C. for 3 h. Then the reaction mixture was cooled to 20° C. and concentrated in vacuo to remove $POCl_3$. The resulting residue was dissolved in DCM (200 mL). Then the mixture was poured into concentrated ammonium hydroxide and the final pH of the aqueous layer was about 10. The aqueous layer was extracted with DCM (3×100 mL). The combined organic layers were dried over $Na_2SO_4$, filtered and concentrated in vacuo. The resulting residue was purified by column chromatography ($SiO_2$, PE:EtOAc=100:1 to 10:1) to give the title compound.

Step B: 2-chloro-6-methoxy-N-(4-methoxybenzyl)quinolin-4-amine

To a mixture of 2,4-dichloro-6-methoxyquinoline (6.0 g, 26.3 mmol) and (2,4-dimethoxyphenyl)methanamine (6.60 g, 39.5 mmol) in DMSO (80 ml) was added $Et_3N$ (11.00 ml, 79 mmol). The reaction mixture was stirred at 90° C. for 48 h. Then the reaction was cooled to 20° C., and diluted with EtOAc (100 mL) and water (100 mL). The aqueous layer was extracted with EtOAc (3×100 mL). The combined organic layers were dried over $Na_2SO_4$, filtered and concentrated in vacuo. The resulting residue was purified by column chromatography ($SiO_2$, PE:EtOAc=10:1 to 1:1) to give the title compound.

Step C: 4-amino-2-chloroquinolin-6-ol

To a mixture of 2-chloro-N-(2,4-dimethoxybenzyl)-6-methoxyquinolin-4-amine (5 g, 13.9 mmol) in DCM (150 ml) was added $BBr_3$ (6.59 ml, 69.7 mmol). The reaction mixture was stirred at 25° C. for 16 h. Then MeOH (10 mL) was added dropwise to the mixture to quench the reaction. The resulting mixture was concentrated in vacuo. The resulting residue was washed with PE/EtOAc (1:1; 20 ml×3), and then dried under vacuum to give the title compound, which was used for next step without further purification. LCMS (ESI) calc'd for $C_9H_7ClN_2O$ [M+H]$^+$: 195, found: 195.0.

Step D: Tert-Butyl 3-((4-amino-2-chloroquinolin-6-yl)oxy)-2-hydroxypropanoate

To a mixture of 4-amino-2-chloroquinolin-6-ol (1.5 g, 7.71 mmol) and tert-butyl oxirane-2-carboxylate (4.44 g, 30.8 mmol) in N,N-Dimethylformamide (5 ml) was added $Cs_2CO_3$ (5.02 g, 15.41 mmol). The resulting suspension was stirred at 40° C. under $N_2$ for 16 h. Then the mixture was filtered and the filtrate was purified by column chromatography on silica gel ($SiO_2$, EtOAc:PE=0-50%), followed by preparative HPLC (Waters Xbridge Prep OBD C18 150*30 5u; mobile phase A: water (0.05% ammonia hydroxide v/v) mobile phase B: acetonitrile; Gradient: 24-54% B, 10.0 min; 100% B, 2 min; FlowRate: 25 mL/min) to give the title compound. LCMS (ESI) calc'd for $C_{16}H_{19}ClN_2O_4$[M+H]$^+$: 339, found: 339.0. $^1$H NMR (400 MHz, CHLOROFORM-d) δ 7.85 (d, J=9.2 Hz, 1H), 7.33 (br dd, J=2.6, 9.1 Hz, 1H), 7.00 (d, J=2.5 Hz, 1H), 6.61 (s, 1H), 4.71 (br s, 2H), 4.45 (br s, 1H), 1.50 (s, 9H)

Step E: Tert-Butyl 3-((4-amino-2-chloroquinolin-6-yl)oxy)-2-((tert-butyldimethylsilyl)oxy) propanoate To a mixture of tert-butyl 3-((4-amino-2-chloroquinolin-6-yl)oxy)-2-hydroxypropanoate (450 mg, 1.33 mmol) and imidazole (136 mg, 1.99 mmol) in N,N-dimethylformamide (8 ml) was added TBS-Cl (240 mg, 1.59 mmol). The resulting suspension was stirred at 25° C. under $N_2$ for 16 h. Then the mixture was diluted with EtOAc (30 ml), washed with brine (10 ml×3), dried over $Na_2SO_4$, filtered and concentrated in vacuo. The resulting residue was purified by column chromatography on silica gel (SiO2, EtOAc/Pentane=0~30%) to give the title compound. LCMS (ESI) calc'd for $C_{22}H_{33}ClN_2O_4Si$ [M+H]$^+$: 453, found: 453.2.

Step F: Tert-Butyl (R)-3-((4-(N,N-bis(tert-butoxycarbonyl)amino)-2-chloroquinolin-6-yl)oxy)-2-((tert-butyldimethylsilyl)oxy)propanoate To a mixture of tert-butyl 3-((4-amino-2-chloroquinolin-6-yl)oxy)-2-((tert-butyldimethylsilyl)oxy)propanoate (750 mg, 1.655 mmol) and TEA (0.346 ml, 2.483 mmol) in dichloromethane (10 ml) were added $BOC_2O$ (0.461 ml, 1.987 mmol) and DMAP (20.22 mg, 0.166 mmol). The resulting suspension was stirred at 20° C. under $N_2$ for 16 h. Then the mixture was evaporated under vacuum, the resulting residue was purified by column chromatography on silica gel (SiO2, EtOAc:PE=0-20) to give the title compound. LC-MS (ESI) calc'd for $C_{32}H_{49}ClN_2O_8Si$ [M+H]$^+$: 653, found: 653.3. $^1$H NMR (400 MHz, CHLOROFORM-d) δ 7.96 (d, J=9.2 Hz, 1H), 7.45-7.37 (m, 1H), 7.23 (s, 1H), 6.98 (d, J=2.7 Hz, 1H), 4.52 (dd, J=3.5, 6.7 Hz, 1H), 4.32-4.11 (m, 2H), 1.53-1.49 (m, 9H), 1.36 (s, 18H), 0.93 (s, 9H), 0.20-0.10 (m, 6H).

The below Examples describe the synthesis of compounds of the invention in the form of particular salts. The free base form of these salts may be obtained by purifying the final product with reverse-phase HPLC using formic acid as the modifier. Formic acid can be removed from the sample by lyophilization, which can be repeated one or more times if desired to remove any residual TFA salt and enhance the free base content.

Example 1

3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)azetidin-1-ium 2,2,2-trifluoroacetate (C1)

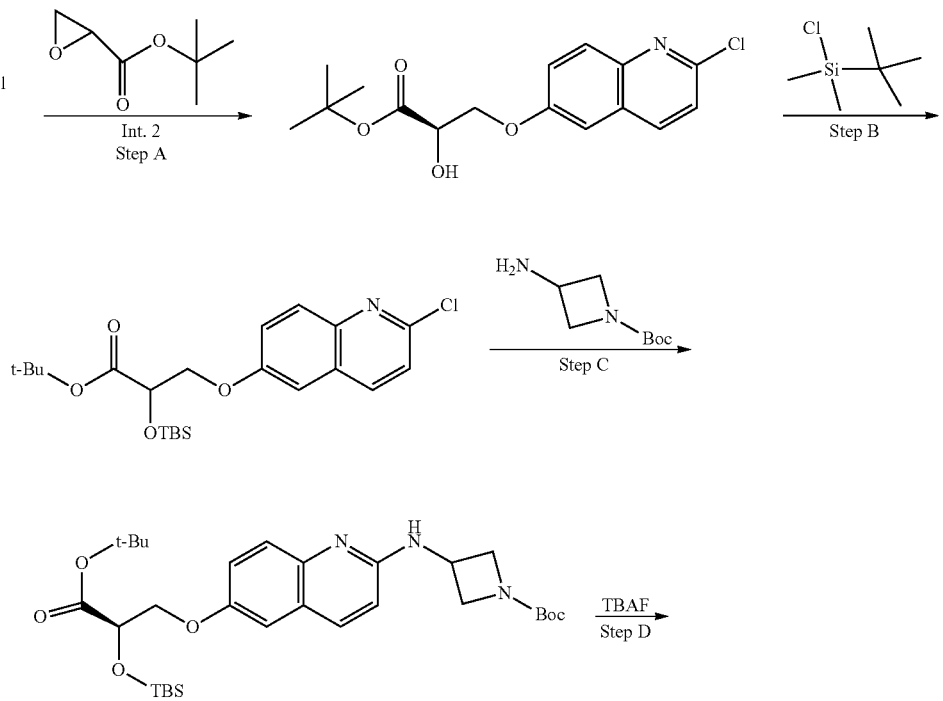

-continued
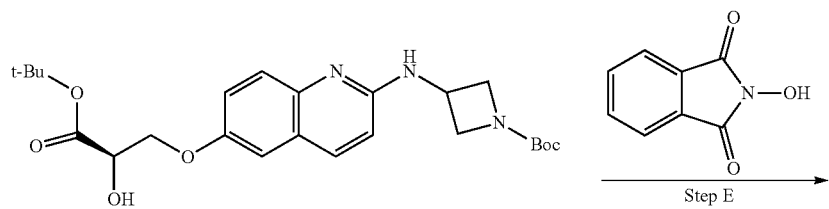
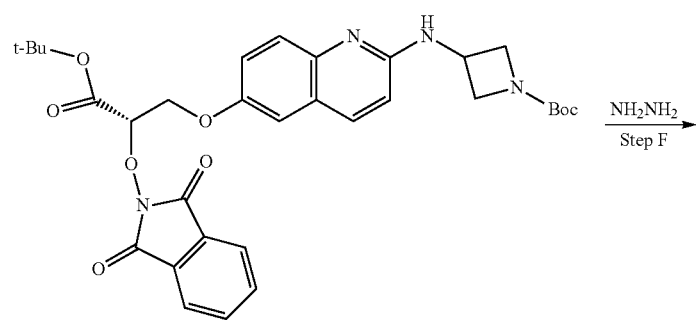
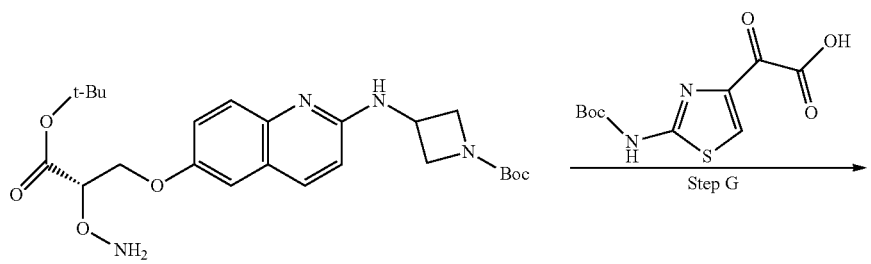
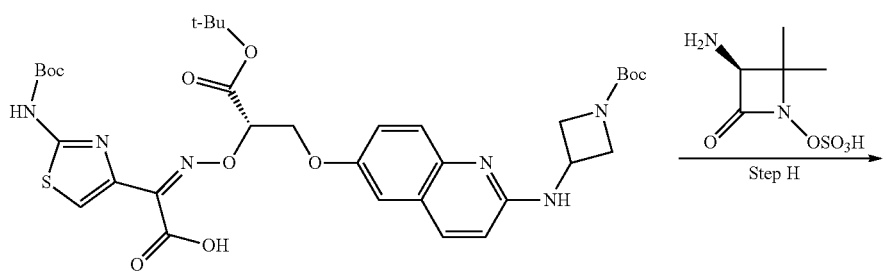
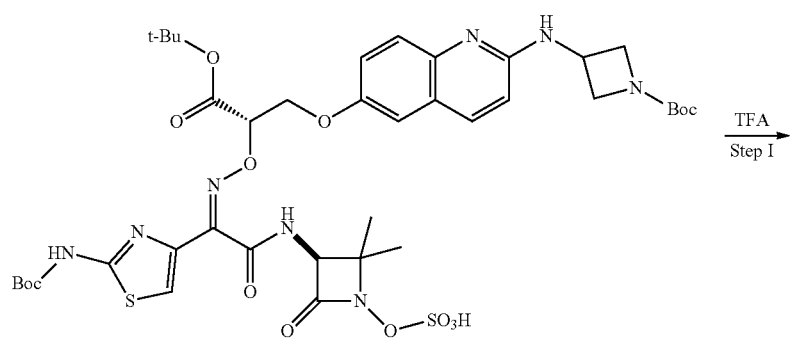

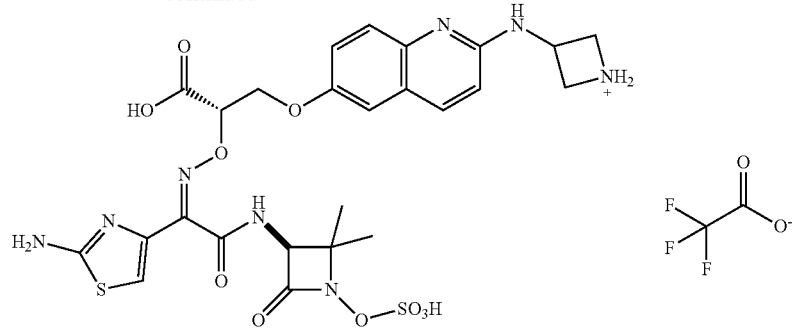

C.1

Step A. Preparation of Tert-Butyl (R)-3-((2-chloro-quinolin-6-yl)oxy)-2-hydroxypropanoate A mixture of 2-chloroquinolin-6-ol (1.0 g, 5.6 mmol), cobalt catalyst (Int. 2) (0.93 g, 1.1 mmol), molecular sieves (1 g, powder), and tert-butyl oxirane-2-carboxylate (1.8 g, 12 mmol) in TBME (5 ml) was stirred at room temperature under $N_2$ over the weekend. More cobalt catalyst (0.5 g) and tert-butyl oxirane-2-carboxylate (0.8 mL) were added. The mixture was stirred at room temperature for 2 more days. The reaction mixture was diluted with EtOAc to dissolve most of the reagents and product. The solid was filtered off and solvent was removed. The residue was purified by column chromatography on silica gel, eluting with EtOAc/hexane (35%) to give the desired product as a solid. LC-MS [M+H]+: m/z 324.18

Step B. Preparation of Tert-Butyl (R)-2-((tert-butyldimethylsilyl)oxy)-3-((2-chloroquinolin-6-yl)oxy) propanoate To a solution of tert-butyl 3-((2-chloroquinolin-6-yl)oxy)-2-hydroxypropanoate (0.5 g, 1.5 mmol), imidazole (0.53 g, 7.7 mmol), and TBS-Cl (3.9 ml, 3.9 mmol) in acetonitrile (10 ml) was added DMAP (0.019 g, 0.154 mmol). The resulting solution was stirred at room temperature for 3 hours. After concentration, the residue was dissolved in EtOAc, washed with saturated $NaHCO_3$, water and brine. The solvent was removed. The residue was purified on silica gel column (24 g) using 0-20% EtOAc/hexane as gradient to give tert-butyl 2-((tert-butyldimethylsilyl)oxy)-3-((2-chloroquinolin-6-yl)oxy)propanoate as a solid. LC-MS [M+H]+: m/z 440.24

Step C. Preparation of Tert-Butyl (R)-3-((6-(3-(tert-butoxy)-2-((tert-butyldimethylsilyl)oxy)-3-oxopropoxy)quinolin-2-yl)amino)azetidine-1-carboxylate To a solution of tert-butyl (R)-2-((tert-butyldimethylsilyl)oxy)-3-((2-chloroquinolin-6-yl)oxy)propanoate (150 mg, 0.34 mmol) in dioxane (2 ml) was added tert-butyl 3-amino-azetidine-1-carboxylate, 2nd generation RuPhos precatalyst (39.9 mg, 0.051 mmol) and $Cs_2CO_3$ (223 mg, 0.68 mmol). After the solution was degassed and refilled with $N_2$, it was heated at 70° C. overnight. The mixture was diluted with EtOAc, washed with $NH_4Cl$, water and brine. The solvent was removed. The residue was purified by column chromatography on silica gel (24 g), eluting with EtOAc/hexane (30%) to give the desired product as an oil. LC-MS [M+H]+: m/z 574.52

Step D. Preparation of Tert-Butyl (R)-3-((6-(3-(tert-butoxy)-2-hydroxy-3-oxopropoxy)-quinolin-2-yl)amino)azetidine-1-carboxylate To a solution of tert-butyl (R)-3-((6-(3-(tert-butoxy)-2-((tert-butyldimethylsilyl)oxy)-3-oxopropoxy)quinolin-2-yl)amino)azetidine-1-carboxylate (0.129 g, 0.225 mmol) in THF (3 ml) was added TBAF (0.225 ml, 0.225 mmol) at room temperature. The solution was stirred for hour and the solvent was removed. The residue was purified by column chromatography on silica gel (24 g), eluting with EtOAc/hexane (80%, 15 cv) to give the desired product. LC-MS [M+H]: m/z 460.43

Step E. Preparation of Tert-Butyl (S)-3-((6-(3-(tert-butoxy)-2-((1,3-dioxoisoindolin-2-yl)oxy)-3-oxopropoxy)quinolin-2-yl)amino)azetidine-1-carboxylate 2-hydroxyisoindoline-1,3-dione (0.039 g, 0.24 mmol) and triphenylphosphine (0.068 g, 0.26 mmol) were added to a solution of tert-butyl (R)-3-((6-(3-(tert-butoxy)-2-hydroxy-3-oxopropoxy)quinolin-2-yl)amino)azetidine-1-carboxylate (0.1 g, 0.22 mmol) in THF (3 ml), followed by DIAD (0.051 ml, 0.26 mmol) at room temperature. The solution was stirred overnight. Solvent was removed. The residue was purified by column chromatography on silica gel (12 g), eluting with EtOAc/hexane (70% 10 cv) to give the desired product as an oil. LC-MS [M+H]+: m/z 605.55

Step F. Preparation of Tert-Butyl (S)-3-((6-(2-(aminooxy)-3-(tert-butoxy)-3-oxopropoxy)-quinolin-2-yl)amino)azetidine-1-carboxylate To a solution of tert-butyl (S)-3-((6-(3-(tert-butoxy)-2-((1,3-dioxoisoindolin-2-yl)oxy)-3-oxopropoxy)quinolin-2-yl)amino)azetidine-1-carboxylate in EtOH (2 ml) was added hydrazine (6.75 µl, 0.215 mmol). The solution was stirred at room temperature for 1 hour. Solvent was removed. DCM (3 ml) was added to the residue and stirred at room temperature for 1 hour. The solid was then filtered off. The solution was concentrated to give the desired product as a film. LC-MS [M+H]+: m/z 475.38

Step G. Preparation of (S,Z)-2-(((1-(tert-butoxy)-3-((2-((1-(tert-butoxycarbonyl)azetidin-3-yl)amino)quinolin-6-yl)oxy)-1-oxopropan-2-yl)oxy)imino)-2-(2-((tert-butoxycarbonyl)-amino)thiazol-4-yl)acetic Acid A solution of 2-(2-((tert-butoxycarbonyl)amino)thiazol-4-yl)-2-oxoacetic acid (intermediate 3) (0.048 g, 0.18 mmol) and tert-butyl (S)-3-((6-(2-(aminooxy)-3-(tert-butoxy)-3-oxopropoxy)quinolin-2-yl)amino)azetidine-1-carboxylate (0.1 g, 0.166 mmol) in EtOH (2 ml) and DCE (1 ml) was stirred at room temperature overnight. The mixture was concentrated and used as is in next step. LC-MS [M+H]$^+$: m/z 729.63

Step H. Preparation of Tert-Butyl 3-((6-((S)-3-(tert-butoxy)-2-((((Z)-1-(2-((tert-butoxycarbonyl) amino)thiazol-4-yl)-2-(((S)-2,2-dimethyl-4-oxo-1-(sulfooxy)azetidin-3-yl)amino)-2-oxoethylidene)-amino)oxy)-3-oxopropoxy)quinolin-2-yl)amino)azetidine-1-carboxylate To the solution of (S,Z)-2-(((1-(tert-butoxy)-3-((2-((1-(tert-butoxy-carbonyl)azetidin-3-yl)amino)quinolin-6-yl)oxy)-1-oxopropan-2-yl)oxy)imino)-2-(2-((tert-butoxycarbonyl)amino)thiazol-4-yl)acetic acid (0.14 g, 0.164 mmol) in DMF (1 ml) was added DCC (0.084 g, 0.41 mmol) and HOBT (0.063 g, 0.41 mmol). The resulting solution was stirred at room temperature for 30 minutes before addition of (S)-3-amino-2,2-dimethyl-4-oxoazetidin-1-yl hydrogen sulfate (0.069 g, 0.33 mmol) and sodium bicarbonate (0.069 g, 0.82 mmol). The resulting mixture was stirred at room temperature overnight. The mixture was filtered. The solution was purified on RP-HPLC (Gilson) (C-18 column) eluting with 20-100% ACN/Water with 0.05% TFA. The product fraction was lyophilized to give the desired product as a solid. LC-MS [M+H]$^+$: m/z 921.67

Step I. Preparation of (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylamino)quinolin-6-yl)oxy)propanoic acid compound with 2,2,2-trifluoroacetic Acid (1:1)

To a solution of tert-butyl 3-((6-((S)-3-(tert-butoxy)-2-(((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-quinolin-2-yl)amino)azetidine-1-carboxylate, TFA (86 mg, 0.083 mmol) in CH$_2$Cl$_2$ (1 ml) was added TFA (2 ml, 26.0 mmol). The solution was stirred at room temperature for 0.5 hour. Solvent was removed under vacuum. The residue was washed with Et$_2$O twice. Solid crude product was collected and dried. The residue was dissolved in DMSO and purified on RP-HPLC (Gilson) (C-18 column), eluting with 2-40% ACN/water with 0.05% TFA. The product fraction was lyophilized to give the desired product as a solid. LC-MS [M+H]$^+$: m/z 665.34. $^1$HNMR (500 MHz, CDCl$_3$) δ: 8.33 (1H, d, J=9.8 Hz), 7.81 (1H, d, J=9.5 Hz), 7.44-7.51 (2H, m), 7.13 (2H, t, J=8.4 Hz), 5.28 (1H, s), 5.15 (1H, d, J=8.0 Hz), 4.55-4.70 (5H, m), 4.31 (2H, d, J=9.4 Hz), 1.46-1.50 (3H, s), 1.16 (3H, s).

TABLE 1

By using the same general procedures described in Example 1, substituting the appropriate reactants and reagents, the following compounds were synthesized and characterized by LC/MS.

| Example | Name | Structure | LCMS |
|---|---|---|---|
| 2 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-((azetidin-3-ylmethyl)amino)quinolin-6-yl)oxy)propanoic acid | 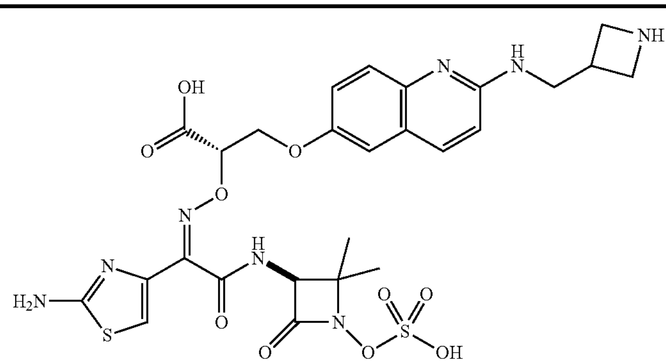 | 679.32 |
| 3 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(piperidin-4-ylamino)quinolin-6-yl)oxy)propanoic acid | 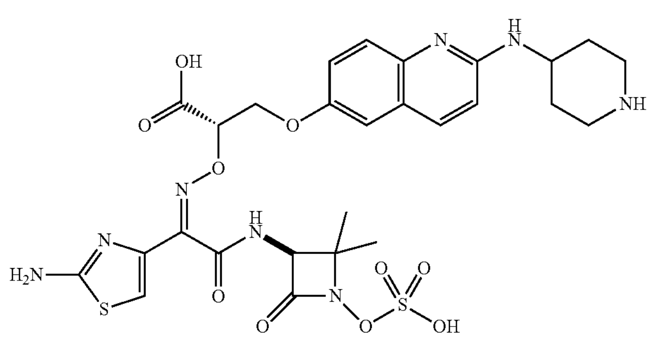 | 693.44 |

TABLE 1-continued

By using the same general procedures described in Example 1, substituting the appropriate reactants and reagents, the following compounds were synthesized and characterized by LC/MS.

| Example | Name | Structure | LCMS |
|---|---|---|---|
| 4 | (S)-3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)pyrrolidin-1-ium 2,2,2-trifluoroacetate | 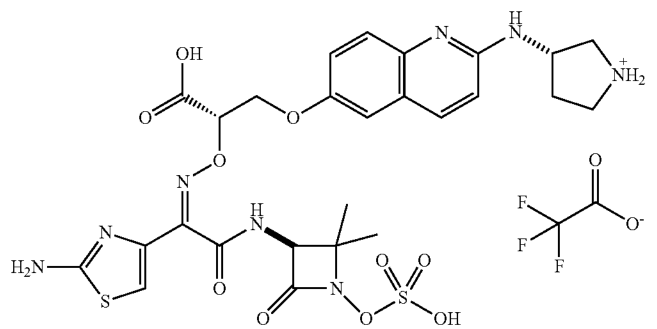 | 679.42 |
| 5 | (S)-3-((2-(((1r,3S)-3-aminocyclobutyl)amino)quinolin-6-yl)oxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid | 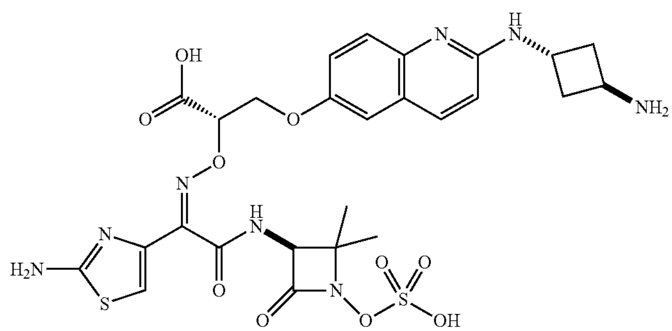 | 679.49 |
| 6 | 4-((6-((S)-2-((((Z)-1-(2-aminothiazol-4-yl)-2-(((S)-2,2-dimethyl-4-oxo-1-(sufooxy)azetidin-3-yl)amino)-2-oxoethylidene)amino)oxy)-2-carboxyethoxy)quinolin-2-yl)amino)-2,2-dimethylpyrrolidin-1-ium 2,2,2-trifluoroacetate | 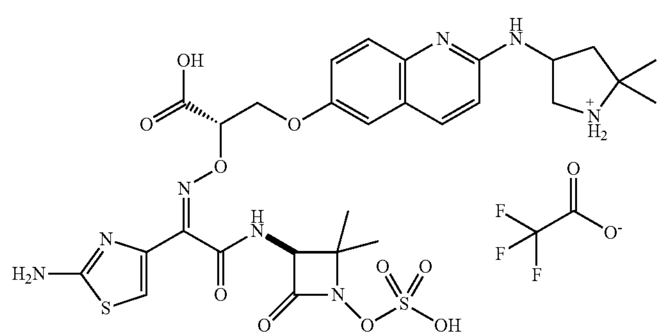 | 707.45 |
| 7 | 4-(6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)piperazin-1-ium 2,2,2-trifluoroacetate | 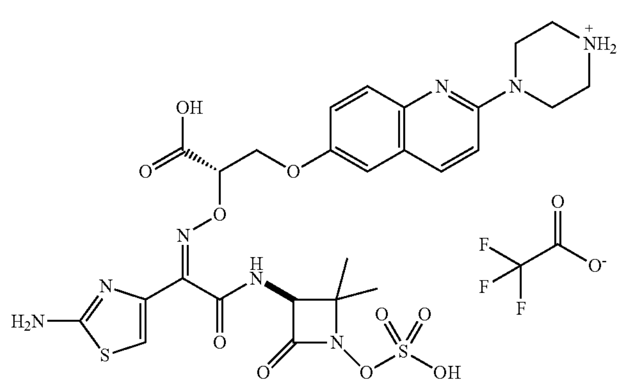 | 679.42 |

Example 8

(S)-3-((2-((2-aminoethyl)amino)quinolin-6-yl)oxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic Acid (C8)

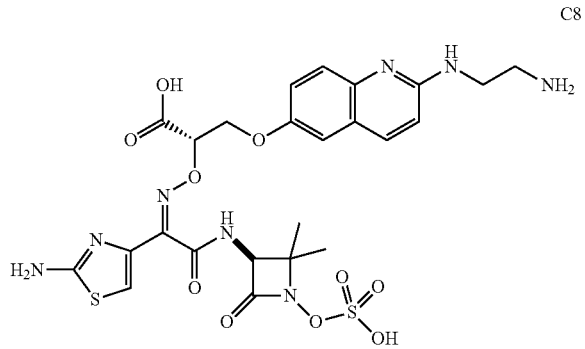 [SMILES: CC1(C)[C@H](NC(=O)/C(=N\O[C@@H](COc2ccc3nc(NCCN)ccc3c2)C(=O)O)c2csc(N)n2)C(=O)N1OS(=O)(=O)O]

Compound 8 was prepared by using the same procedures as in Example 1 except using the conditions described below for step C. To a solution of tert-butyl (R)-2-((tert-butyldimethylsilyl)oxy)-3-((2-chloroquinolin-6-yl)oxy)propanoate (0.25 g, 0.57 mmol) in dioxane (1 ml) was added tert-butyl (2-aminoethyl)-carbamate (0.18 g, 1.14 mmol), MorDalphos—G3-palladacycle (0.095 g, 0.114 mmol) and $Cs_2CO_3$ (0.46 g, 1.43 mmol). The mixture was degassed and refilled with $N_2$. It was heated at 75° C. overnight. The solid was filtered off and solvent was removed in vacuum. The residue was purified by column chromatography on silica gel (24 g), eluting with EtOAc/hexane to give the desired product as a gum.

The rest of the steps were the same as in Example 1. The title compound 8 was characterized by LC/MS and NMR. LC-MS [M+H]$^+$: m/z 653.47. $^1$HNMR (500 MHz, D$_2$O) δ 8.10-8.12 (1H, m), 7.62 (1H, d, J=9.4 Hz), 7.25-7.37 (2H, m), 6.96-6.99 (1H, m), 6.87 (1H, s), 4.90-4.93 (1H, m), 4.35-4.46 (2H, m), 3.80 (2H, dd, J=6.5, 5.7 Hz), 3.25-3.31 (2H, m), 1.31 (3H, s), 0.92 (3H, s).

TABLE 2

By using the same general procedures as described in Example 8, substituting the appropriate reactants and reagents, the following compounds were synthesized and characterized by LC/MS.

| Example | Name | Structure | LCMS |
|---|---|---|---|
| 9 | (S)-3-((2-((3-aminopropyl)amino)quinolin-6-yl)oxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid | 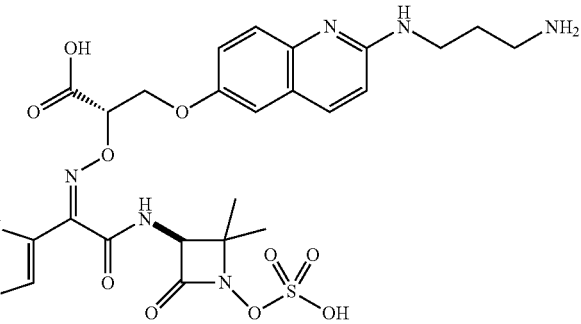 | 667.36 |
| 10 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-((2-(methylamino)ethyl)amino)quinolin-6-yl)oxy)propanoic acid | 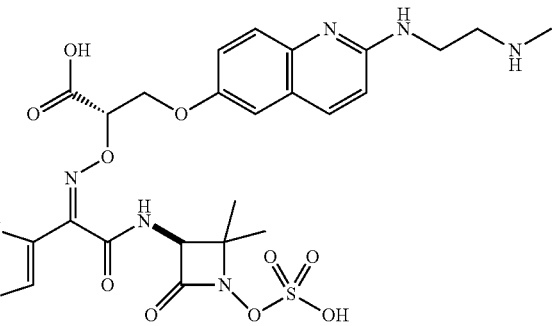 | 667.36 |

Example 11
(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((1-((1-(tert-butoxycarbonyl)azetidin-3-yl)amino)isoquinolin-6-yl)oxy) propanoic Acid (C11)
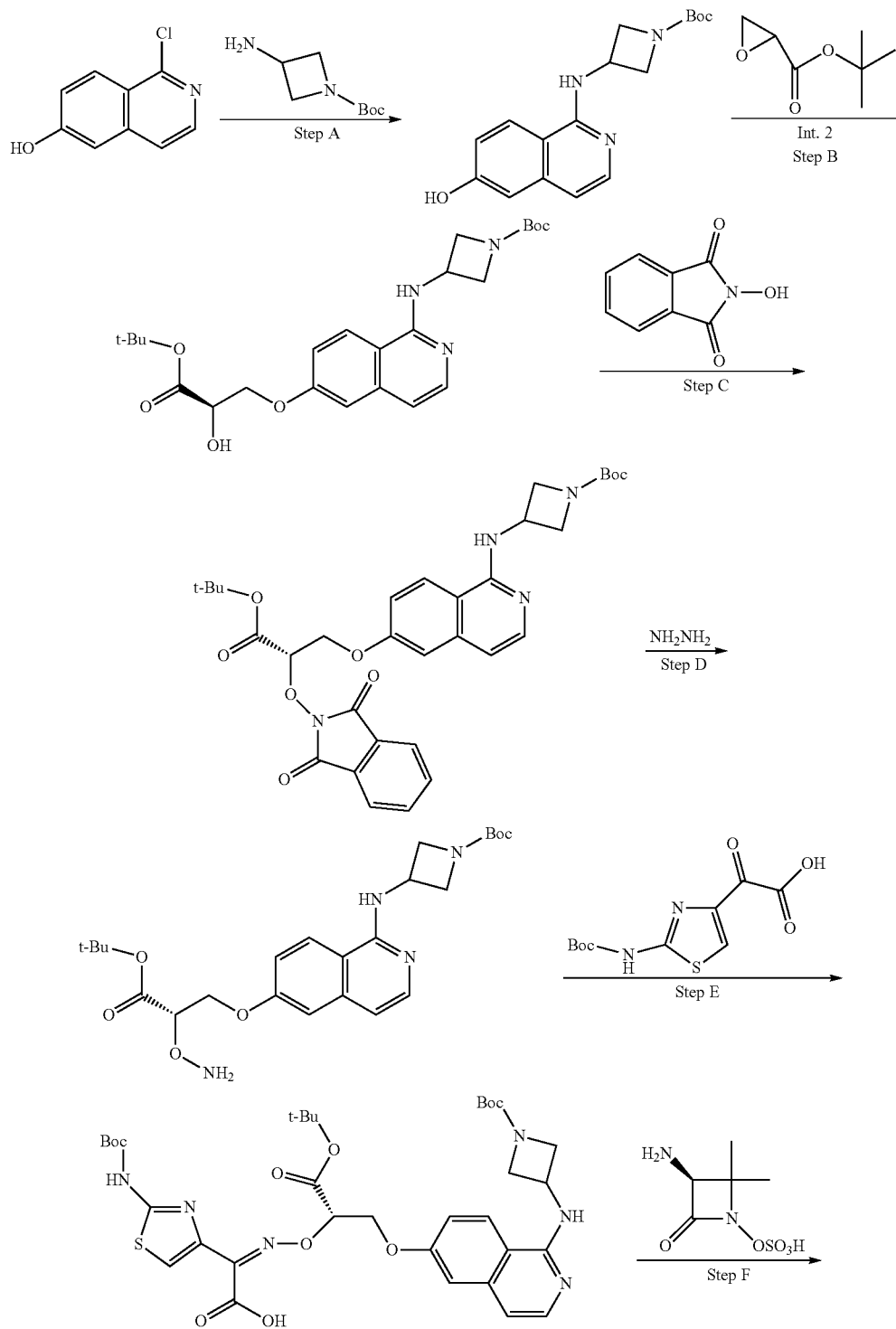

-continued

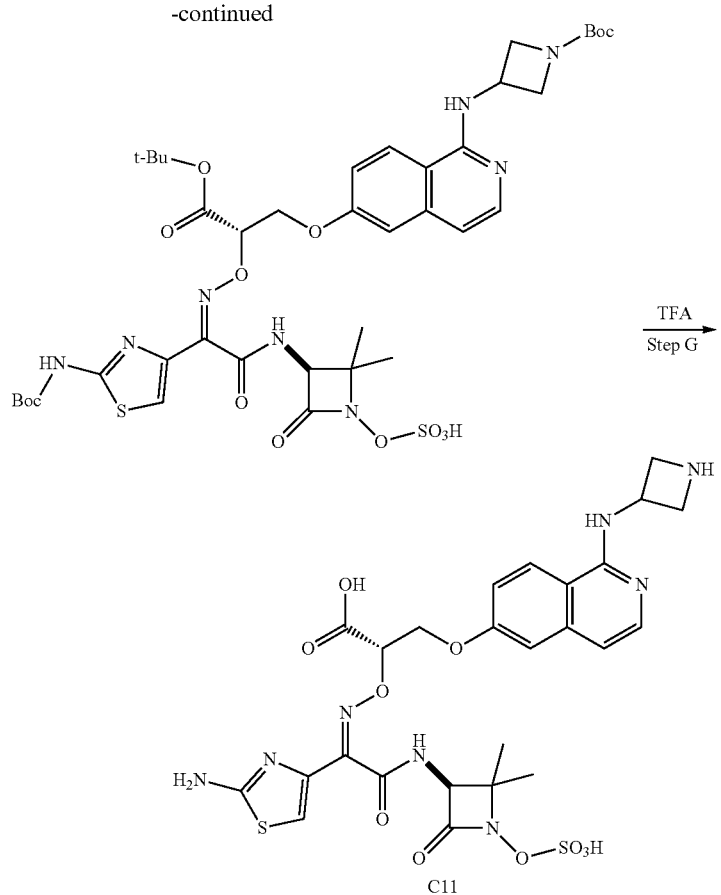

Step A. Preparation of Tert-Butyl 3-((6-hydroxyisoquinolin-1-yl)amino)azetidine-1-carboxylate To a solution of 1-chloroisoquinolin-6-ol (0.2 g, 1.1 mmol) in dioxane (3 ml) was added tert-butyl 3-aminoazetidine-1-carboxylate (0.29 g, 1.7 mmol), 2nd generation RuPhos precatalyst (0.13 g, 0.17 mmol) and $Cs_2CO_3$ (1.1 g, 3.3 mmol). The sealed vial was degassed and refilled with $N_2$ and heated at 80° C. overnight. Solid was filtered off and solvent was removed. The residue was purified by column chromatography on silica gel, eluting with EtOAc/hexane to give the desired product as a gum. LC-MS [M+H]$^+$: m/z 316.33.

Step B. Preparation of Tert-Butyl (R)-3-((6-(3-(tert-butoxy)-2-hydroxy-3-oxopropoxy) isoquinolin-1-yl)amino)azetidine-1-carboxylate A solution of tert-butyl 3-((6-hydroxy-isoquinolin-1-yl)amino)azetidine-1-carboxylate (0.21 g, 0.67 mmol) in MTBE (1 ml) was added tert-butyl oxirane-2-carboxylate (0.21 g, 1.5 mmol) and cobalt catalyst (Int. 2) (0.11 g, 0.13 mmol). The mixture was degassed and refilled with $N_2$ and stirred at room temperature over the weekend. Solid was filtered off and solvent was removed. The residue was purified by column chromatography on silica gel, eluting with EtOAc/hexane to give the desired product as a gum. LC-MS [M+H]$^+$: m/z 460.40.

Step C. Preparation of Tert-Butyl (S)-3-((6-(3-(tert-butoxy)-2-((1,3-dioxoisoindolin-2-yl)oxy)-3-oxopropoxy)isoquinolin-1-yl)amino)azetidine-1-carboxylate 2-hydroxy-isoindoline-1,3-dione (0.070 g, 0.43 mmol) and triphenylphosphine (0.12 g, 0.47 mmol) were added to a solution of tert-butyl (R)-3-((6-(3-(tert-butoxy)-2-hydroxy-3-oxopropoxy)-isoquinolin-1-yl)amino)azetidine-1-carboxylate (0.18 g, 0.39 mmol) in THF (4 ml) followed by DIAD (0.091 ml, 0.47 mmol) at room temperature. The mixture was stirred for 1 hour and concentrated. The residue was purified by column chromatography on silica gel, eluting with EtOAc/hexane to give the desired product as an oil. LC-MS [M+H]$^+$: m/z 605.45. The rest of the procedure from step D to step G was the same as described in step F to step I in Example 1 with the corresponding isoquinoline intermediates. The title compound 11 (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((1-((1-(tert-butoxycarbonyl)azetidin-3-yl)amino)isoquinolin-6-yl)oxy) propanoic acid was characterized by LC/MS and NMR. LC-MS [M+H]$^+$: m/z 665.29. $^1$HNMR (500 MHz, $D_2O$) δ 8.17 (1H, d), 7.32 (1H, d), 7.20 (1H, d), 7.16 (1H, s), 7.08 (1H, d), 7.02 (1H, s), 5.12 (1H, s), 5.00 (1H, m), 4.40-4.54 (5H, m), 4.26-4.32 (2H, m), 1.23 (3H, s), 0.90 (3H, s).

TABLE 3

By using the same general procedures described in Example 11, substituting the appropriate reactants and reagents, the following compounds were synthesized and characterized by LC/MS.

| Example | Name | Structure | LCMS |
|---|---|---|---|
| 12 | 2-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)isoquinolin-1-yl)amino)ethan-1-aminium 2,2,2-trifluoroacetate | 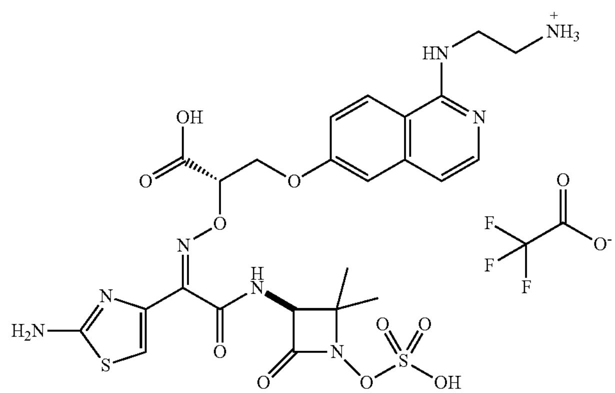 | 653.15 |
| 13 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((1-((azetidin-3-ylmethyl)amino)isoquinolin-6-yl)oxy)propanoic acid | 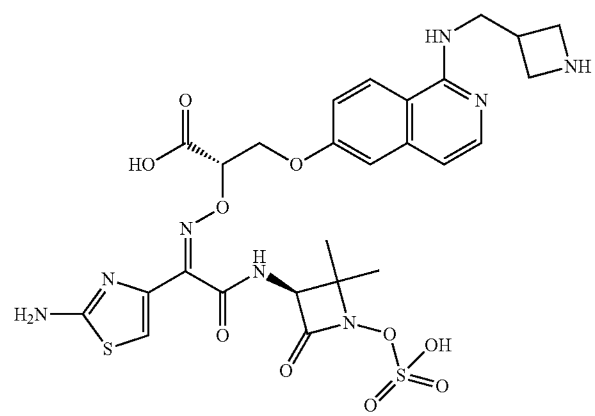 [SMILES: CC1(C)[C@H](NC(=O)/C(=N\O[C@@H](COc2ccc3c(NCC4CNC4)nccc3c2)C(=O)O)c2csc(N)n2)C(=O)N1OS(=O)(=O)O] | 679.19 |
| 14 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((1-(piperidin-4-ylamino)isoquinolin-6-yl)oxy)propanoic acid | 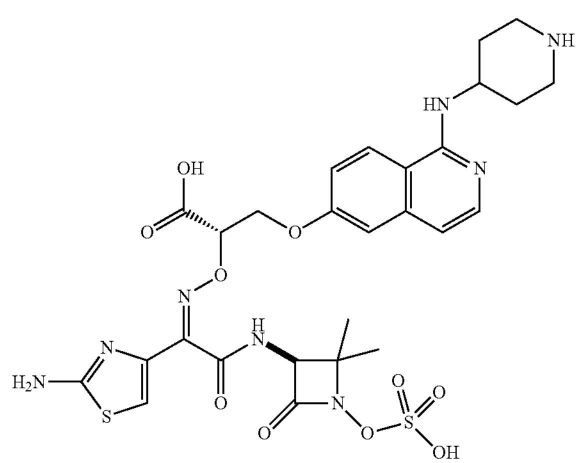 | 693.36 |

Example 15
6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxy ethoxy)-1-(azetidin-3-ylamino)-2-methylquinolin-2-ium 2,2,2-trifluoroacetate (C15)
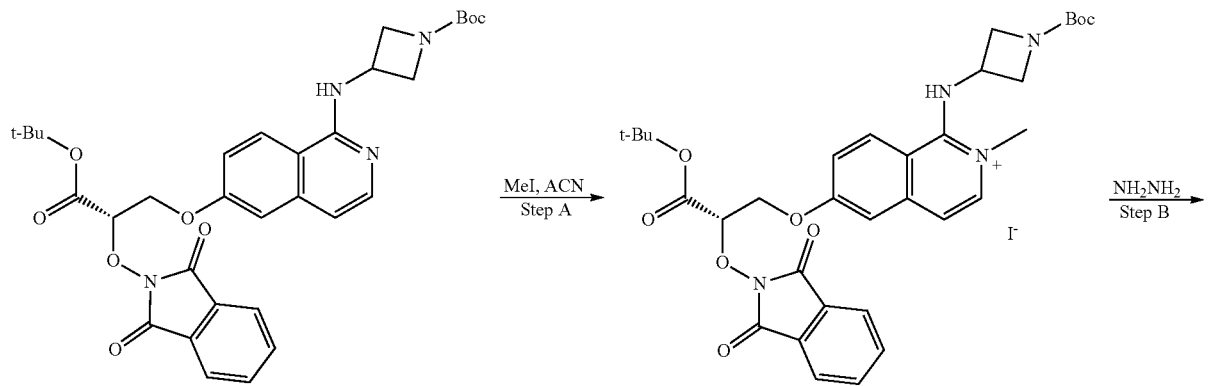
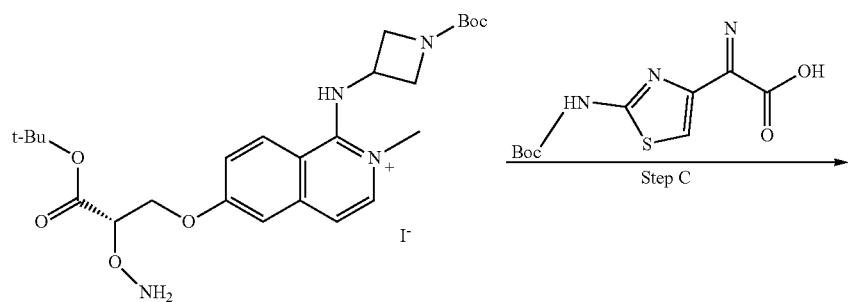
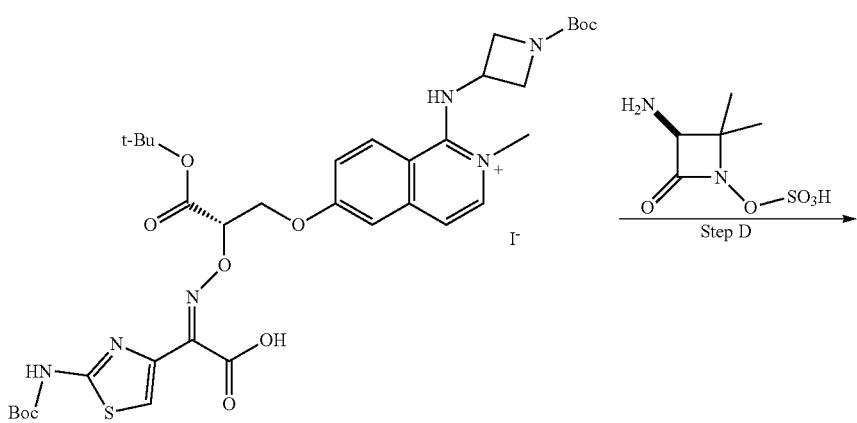

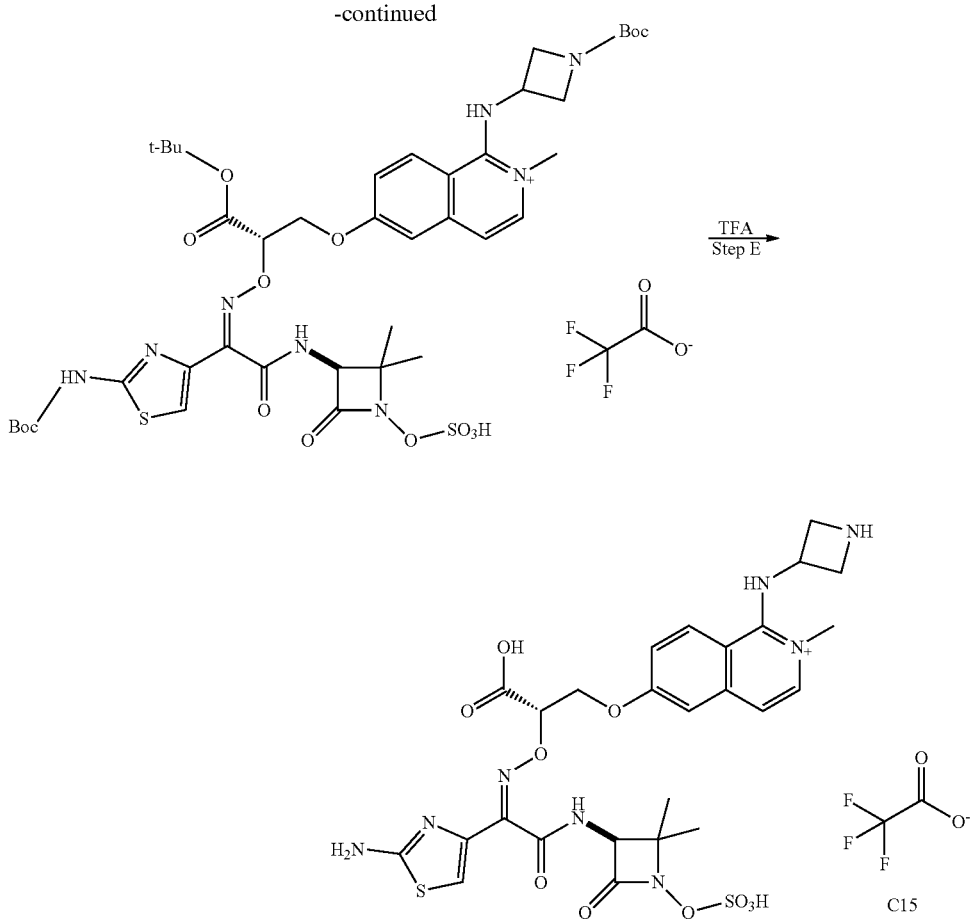

Step A. Preparation of (S)-6-(3-(tert-butoxy)-2-((1,3-dioxoisoindolin-2-yl)oxy)-3-oxopropoxy)-1-((1-(tert-butoxycarbonyl)azetidin-3-yl)amino)-2-methyl-isoquinolin-2-ium MeI (0.052 ml, 0.83 mmol) was added to the intermediate from step C in Example 11 tert-butyl (S)-3-((6-(3-(tert-butoxy)-2-((1,3-dioxoisoindolin-2-yl)oxy)-3-oxopropoxy)-isoquinolin-1-yl)amino)azetidine-1-carboxylate (50 mg, 0.083 mmol) in acetonitrile (1 ml) in a sealed microwave vial. The solution was heated at 90° C. overnight. The solvent was removed under vacuum and the crude the product was used in next step. LC-MS [M+H]: m/z 619.41. The rest of procedure from step B to step E followed the same procedure as described in step F to step I in Example 1 with the corresponding intermediates. The title compound 15, 6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1-(azetidin-3-ylamino)-2-methylisoquinolin-2-ium 2,2,2-trifluoroacetate, was characterized by LC/MS and NMR. LC-MS [M+H]$^+$: m/z 679.66. $^1$H NMR (CH$_3$OH-d$_4$, 500 MHz): δ 7.99 (1H, d, J=9.3 Hz), 7.85 (1H, d, J=7.1 Hz), 7.44-7.50 (3H, m), 7.10 (1H, s), 5.30-5.37 (2H, m), 4.84 (1H, dd, J=11.5, 2.3 Hz), 4.61-4.73 (3H, m), 4.54-4.54 (1H, m), 4.49 (2H, t, J=9.3 Hz), 4.06 (3H, s), 1.51 (3H, s), 1.19 (3H, s).

Example 16
(S)-3-((Z)-2-(2-aminothiazol-4-yl)-2-(((S)-2-((1-((azetidin-3-ylmethyl)amino)-2-methylisoquinolin-2-ium-6-yl)oxy)-1-carboxyethoxy)imino)acetamido)-2,2-dimethyl-4-oxoazetidin-1-yl Sulfate (C16)
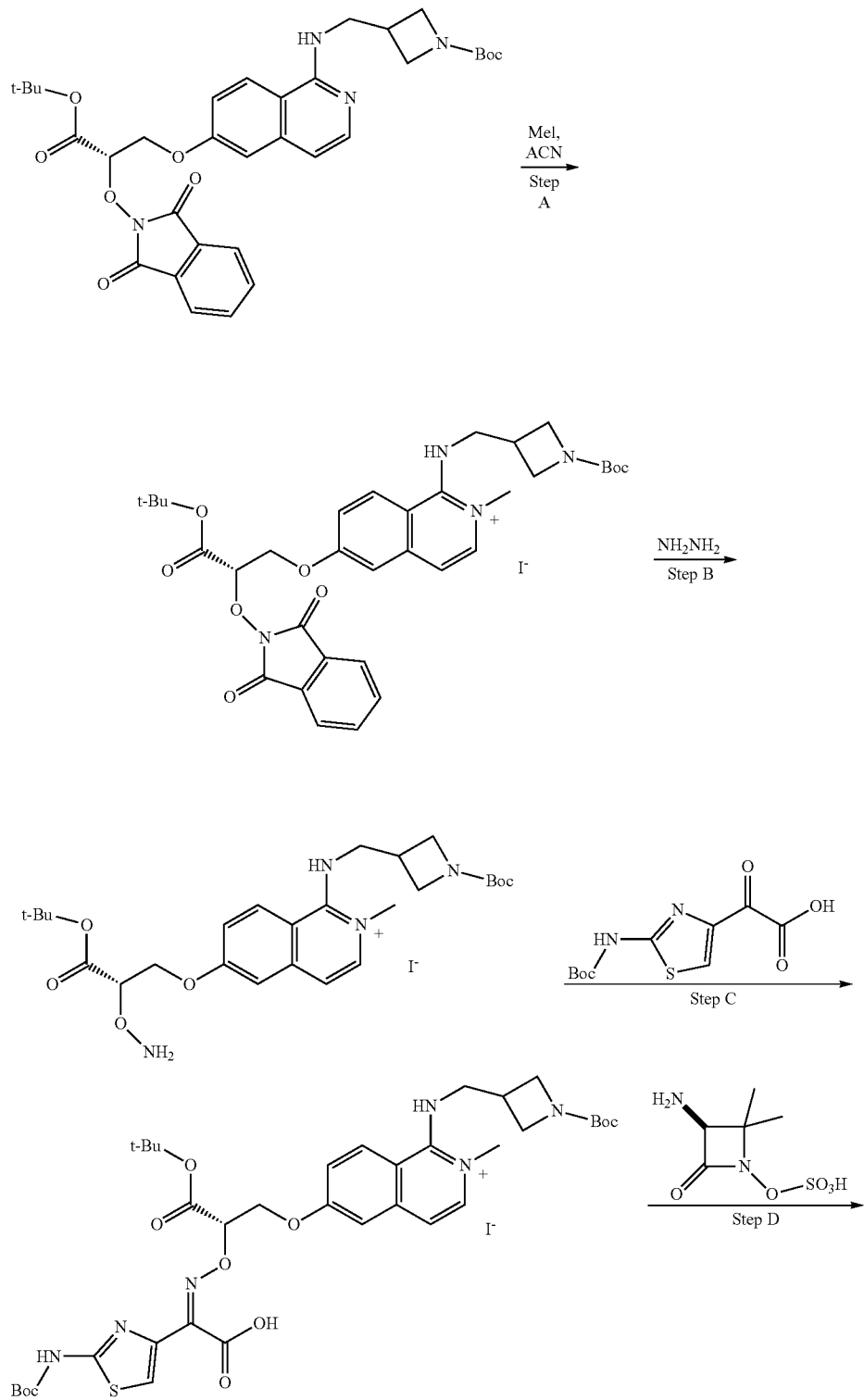

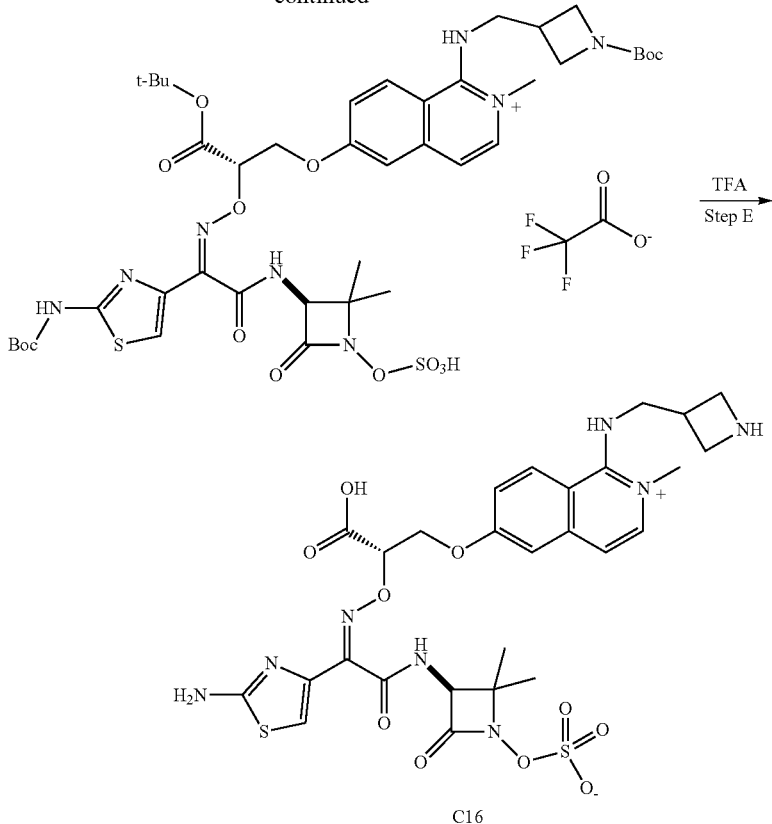

C16

The method for preparing Compound 16 was the same as that described in Example 15 with the starting intermediate tert-butyl (S)-3-(((6-(3-(tert-butoxy)-2-((1,3-dioxoisoindolin-2-yl)oxy)-3-oxopropoxy)isoquinolin-1-yl)amino)methyl)azetidine-1-carboxylate (intermediate used to prepare compound 13, prepared following steps A-C of Example 11 using 1-chloroisoquinolin-6-ol and tert-butyl 3-(aminomethyl)azetidine-1-carboxylate). The title compound 16 was characterized by LC/MS and NMR. LC-MS [M+H]$^+$: m z 693.29. $^1$HNMR (500 MHz, D$_2$O) $\delta_H$ 8.33 (1H, m), 7.62 (1H, d, J=7.2 Hz), 7.37-7.29 (3H, m), 6.99 (1H, s), 5.07 (1H, s), 4.26 (2H, t, J=10.0 Hz), 4.10 (2H, m), 4.06-3.98 (3H, m), 3.92 (3H, s), 1.40 (3H, s), 1.05 (3H, s).

Example 17

2-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)-N,N,N-trimethylethane-1-aminium 2,2,2-trifluoroacetate (C17)

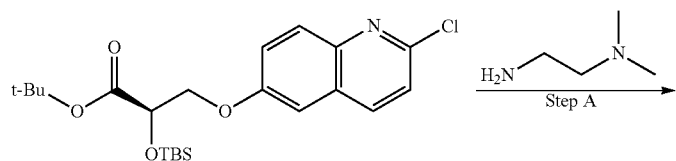

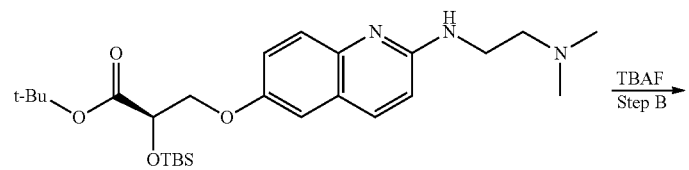

-continued
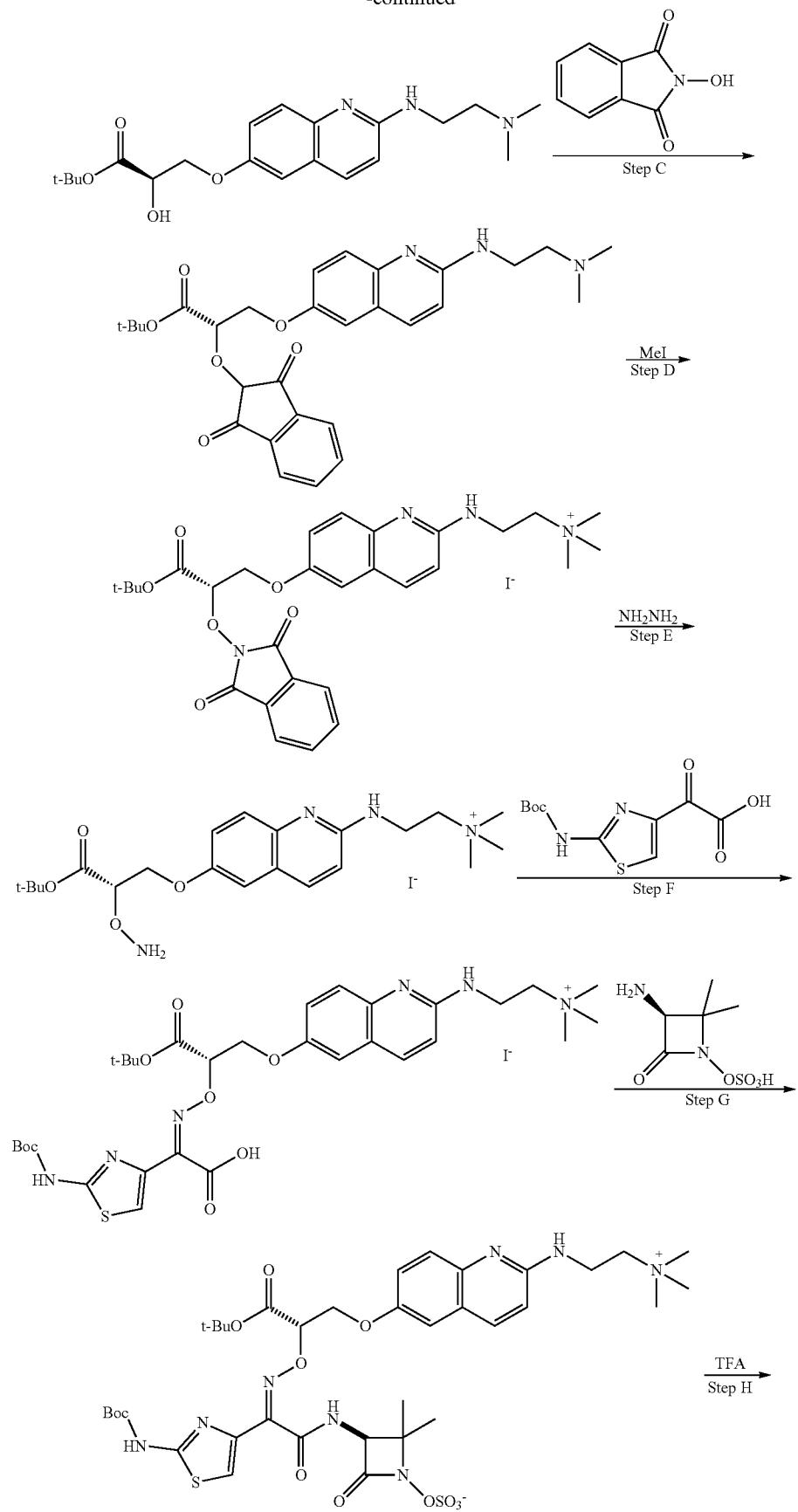

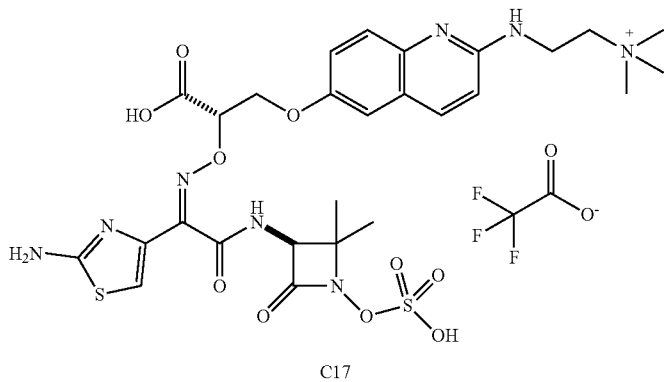

C17

Step A. Preparation of Tert-Butyl (R)-2-((tert-butyldimethylsilyl)oxy)-3-((2-((2-(dimethylamino)-ethyl)amino)quinolin-6-yl)oxy)propanoate To a solution of the intermediate tert-butyl (R)-2-((tert-butyldimethylsilyl)oxy)-3-((2-chloroquinolin-6-yl)oxy)propanoate (from step B in Example 1) (0.3 g, 0.68 mmol) in dioxane (1 ml) was added N1,N1-dimethylethane-1,2-diamine (0.12 g, 1.4 mmol), MorDalphos-G3-palladacycle (0.057 g, 0.068 mmol) and $Cs_2CO_3$ (0.56 g, 1.7 mmol). The mixture was degassed and refilled with $N_2$. It was then heated at 75° C. overnight and concentrated. The mixture was purified by column chromatography on silica gel, eluting with EtOAc/10% of 7N $NH_3$ in MeOH to give the desired product as an oil. LC-MS [M+H]: m/z 490.44.

Step B. Preparation of Tert-Butyl (R)-3-((2-((2-(dimethylamino)ethyl)amino)quinolin-6-yl)oxy)-2-hydroxypropanoate To a solution of tert-butyl (R)-2-((tert-butyldimethylsilyl)oxy)-3-((2-((2-(dimethylamino)ethyl)amino)quinolin-6-yl)oxy)propanoate (0.25 g, 0.51 mmol) in THF (10 ml) was added TBAF (0.51 ml, 0.51 mmol) at room temperature. The solution was stirred for 1 hour and concentrated. The residue was purified by column chromatography on silica gel, eluting with EtOAc and 7N $NH_3$ in MeOH to give the desired product as an oil. LC-MS [M+H]: m/z 376.34.

Step C. Preparation of Tert-Butyl (S)-3-((2-((2-(dimethylamino)ethyl)amino)quinolin-6-yl)oxy)-2-((1,3-dioxoisoindolin-2-yl)oxy)propanoate 2-hydroxyisoindoline-1,3-dione (0.081 g, 0.50 mmol) and triphenylphosphine (0.14 g, 0.54 mmol) were added to a solution of tert-butyl (R)-3-((2-((2-(dimethylamino)ethyl) amino)quinolin-6-yl)oxy)-2-hydroxy-propanoate (0.17 g, 0.45 mmol) in THF (3 ml) followed by DIAD (0.11 ml, 0.54 mmol) at RT. The solution was stirred for 4 hours and concentrated. The residue was purified by column chromatography on silica gel, eluting with EtOAc for 10 column volumes and then $Et_3N$/acetone 5%/95% to give the desired product as an oil. LC-MS [M+H]: m/z 521.39.

Step D. Preparation of (S)-2-((6-(3-(tert-butoxy)-2-(((1,3-dioxoisoindolin-2-yl)oxy)-3-oxopropoxy)quinolin-2-yl)amino)-N,N,N-trimethylethane-1-aminium To a solution of tert-butyl (S)-3-((2-((2-(dimethylamino) ethyl)amino)quinolin-6-yl)oxy)-2-((((1,3-dioxoisoindolin-2-yl)oxy)-propanoate (75 mg, 0.14 mmol) in ACN (1 ml) was added MeI (0.036 ml, 0.58 mmol) in a sealed vial. The mixture was stirred at room temperature for 3 hours and concentrated under high vacuum to give the crude product, which was used as is in the next step. LC-MS [M+H]: m/z 535.49.

The rest of the procedure from step E to step H followed the same procedure as in step F to step I of Example 1 with the corresponding intermediates. The title compound 17, 2-((6-((S)-2-(((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl) amino)-N,N,N-trimethylethane-1-aminium 2,2,2-trifluoroacetate, was characterized by LC/MS and NMR. LC-MS [M+H]: m/z 695.34. $^1$H NMR ($CH_3OH$-$d_4$, 500 MHz): $\delta_H$ 8.27 (1H, d, J=9.5 Hz), 7.81 (1H, d, J=9.2 Hz), 7.49 (1H, d, J=9.4 Hz), 7.42 (1H, s), 7.11 (1H, d, J=9.7 Hz), 7.02 (1H, s), 5.23 (1H, d, J=5.5 Hz), 4.58 (1H, dd, J=11.8, 5.8 Hz), 4.47 (1H, s), 4.13 (2H, d, J=6.9 Hz), 3.82 (2H, t, J=6.8 Hz), 3.30 (9H, s), 1.48 (3H, s), 1.11 (3H, s).

TABLE 4

By using generally the same procedure as in Example 17, substituting the appropriate reactants and reagents, the following compound was synthesized and characterized by LC/MS.

| Example | Name | Structure | LCMS |
|---|---|---|---|
| 18 | 4-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)-1,1-dimethylpiperidin-1-ium 2,2,2-trifluoroacetate | 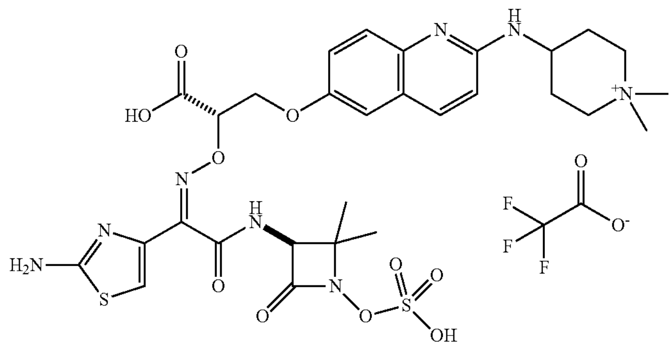 | 721.49 |

Example 19

(S)-3-((Z)-2-(2-amino-5-chlorothiazol-4-yl)-2-(((S)-2-((1-((azetidin-3-ylmethyl)amino)-2-methylisoquinolin-2-ium-6-yl)oxy)-1-carboxyethoxy)imino)acetamido)-2,2-dimethyl-4-oxoazetidin-1-yl sulfate, 2,2,2-trifluoroacetate Salt ($C_{19}$)

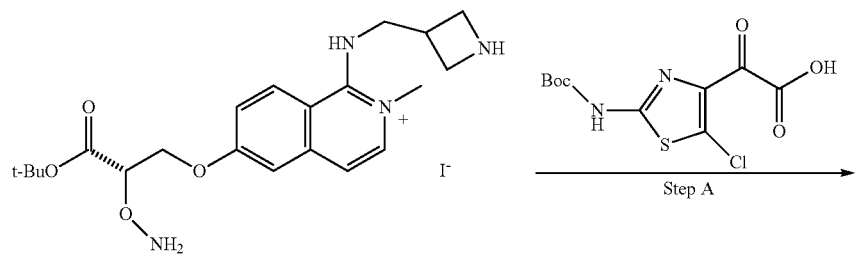

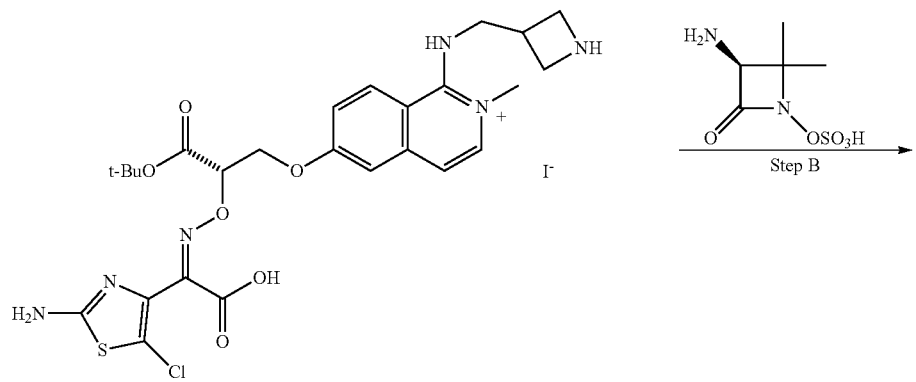

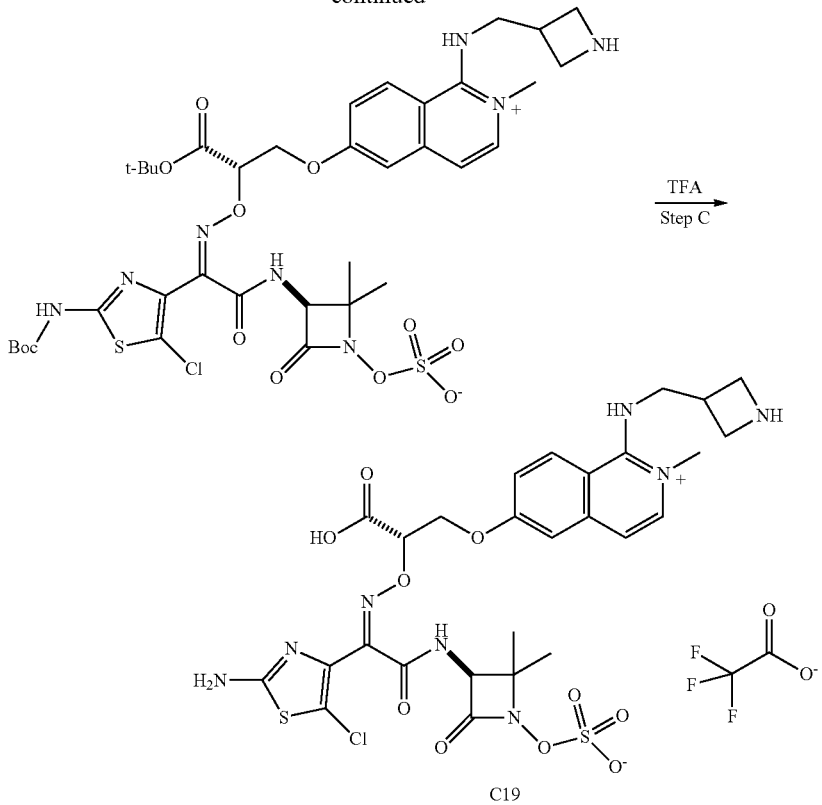

Step A. Preparation of (S,Z)-6-(3-(tert-butoxy)-2-((((1-(2-((tert-butoxycarbonyl)amino)-5-chlorothiazol-4-yl)-2-carboxy-2-oxoethylidene)amino)oxy)-3-oxopropoxy)-1-(((1-(tert-butoxycarbonyl)azetidin-3-yl)methyl)amino)-2-methylisoquinolin-2-ium A solution of (S)-6-(2-(aminooxy)-3-(tert-butoxy)-3-oxopropoxy)-1-(((1-(tert-butoxycarbonyl)azetidin-3-yl)methyl)amino)-2-methylisoquinolin-2-ium, iodide (Intermediate from step B in Example 16) (40 mg, 0.063 mmol) and 2-(2-((tert-butoxycarbonyl)amino)-5-chlorothiazol-4-yl)-2-oxoacetic acid (Int. 4) (21.4 mg, 0.070 mmol) in EtOH (2 ml) and DCE (1 ml) was stirred at room temperature overnight and then concentrated under vacuum. The resultant mixture was used as crude in the next step. LC-MS [M+H]: m/z 791.37.

Step B and Step C followed the same procedure as step H and step I in Example 1. The title compound 19 (S)-3-((Z)-2-(2-amino-5-chlorothiazol-4-yl)-2-(((S)-2-((1-((azetidin-3-ylmethyl)amino)-2-methylisoquinolin-2-ium-6-yl)oxy)-1-carboxyethoxy)imino)acetamido)-2,2-dimethyl-4-oxoazetidin-1-yl sulfate, 2,2,2-trifluoroacetate salt was characterized by LC/MS and NMR. LC-MS [M+H]: m/z 727.30. $^1$H NMR (H$_2$O-d$_2$, 500 MHz): δ$_H$ 8.24-8.26 (1H, m), 7.59-7.61 (1H, m), 7.25-7.37 (3H, m), 5.15-5.20 (2H, m), 4.19-4.24 (2H, m), 4.16 (2H, d, J=7.5 Hz), 3.98 (2H, dd, J=11.0, 7.4 Hz), 3.89 (3H, s), 3.84-3.88 (1H, m), 3.44 (1H, t, J=7.9 Hz), 3.16-3.19 (1H, m), 1.39 (3H, s), 1.00 (3H, s).

Example 20

3-((6-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)isoquinolin-1-yl)amino)azetidin-1-ium (C20)

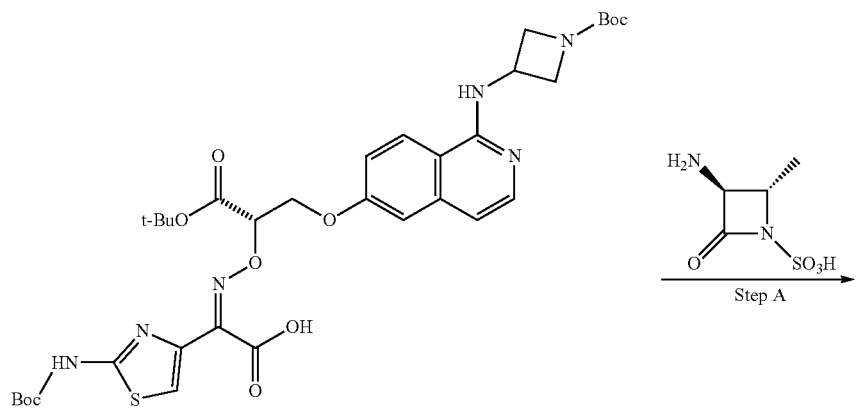

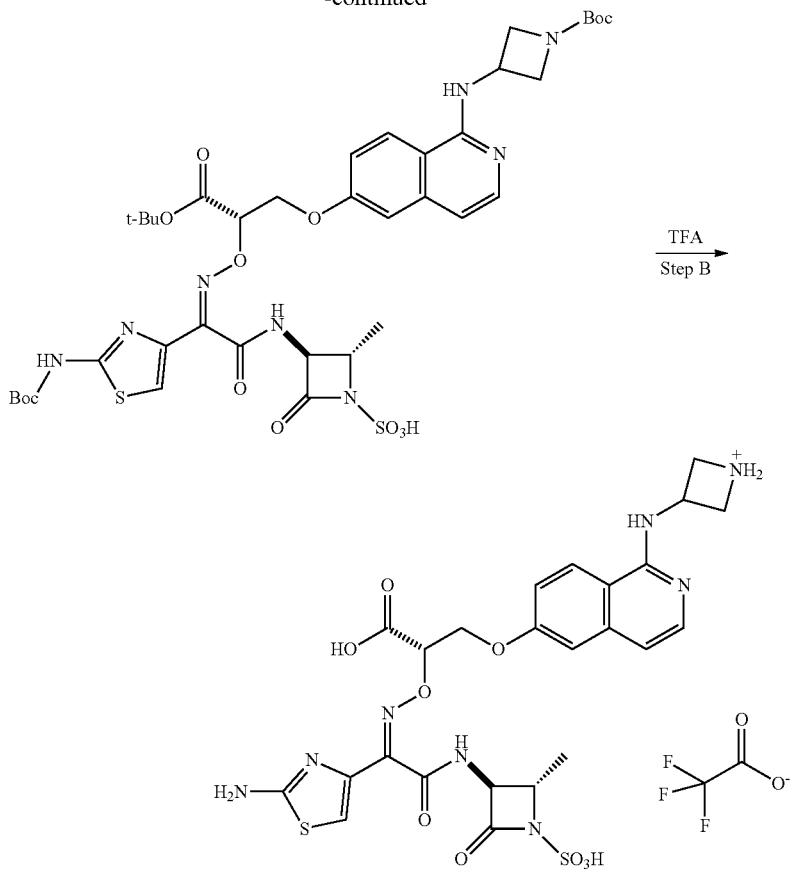

C20

Step A. Preparation of (2S,3S)-3-((Z)-2-((((S)-1-(tert-butoxy)-3-((1-(((1-(tert-butoxy-carbonyl)azetidin-3-yl)amino)isoquinolin-6-yl)oxy)-1-oxopropan-2-yl)oxy)imino)-2-(2-((tert-butoxycarbonyl)amino)thiazol-4-yl)acetamido)-2-methyl-4-oxoazetidine-1-sulfonic Acid To a solution of (S,Z)-2-(((1-(tert-butoxy)-3-((1-((1-(tert-butoxycarbonyl)azetidin-3-yl)amino)isoquinolin-6-yl)oxy)-1-oxopropan-2-yl)oxy)imino)-2-(2-((tert-butoxycarbonyl)amino)thiazol-4-yl)acetic acid (from Step E in Example 11) (60 mg, 0.082 mmol) in DMF (3 ml) was added DCC (42 mg, 0.21 mmol) and HOBT (32 mg, 0.21 mmol). The resulting solution was stirred at room temperature for 30 minutes before addition of (2S,3S)-3-amino-2-methyl-4-oxoazetidine-1-sulfonic acid (29.7 mg, 0.165 mmol) and sodium bicarbonate (34.6 mg, 0.412 mmol). The resulting mixture was stirred at room temperature overnight and filtered. The solution was purified on RP-HPLC (Gilson C-18 column) eluting with 20-100% ACN/water with 0.05% TFA. The product fraction was lyophilized to give the desired product as a solid. LC-MS [M+H]: m/z 891.75.

Step B. Preparation of (S)-2-(((((Z)-1-(2-aminothiazol-4-yl)-2-(((2S,3S)-2-methyl-4-oxo-1-sulfoazetidin-3-yl)amino)-2-oxoethylidene)amino)oxy)-3-((1-(azetidin-3-ylamino)-isoquinolin-6-yl)oxy)propanoic acid compound with 2,2,2-trifluoroacetic Acid (1:1)

To a solution of (2S,3S)-3-((Z)-2-((((S)-1-(tert-butoxy)-3-((1-(((1-(tert-butoxycarbonyl)-azetidin-3-yl)amino)isoquinolin-6-yl)oxy)-1-oxopropan-2-yl)oxy)imino)-2-(2-((tert-butoxycarbonyl)-amino)thiazol-4-yl)acetamido)-2-methyl-4-oxoazetidine-1-sulfonic acid (41 mg, 0.046 mmol) in $CH_2Cl_2$ (0.5 ml) was added TFA (0.5 ml, 6.5 mmol). The mixture was stirred at room temperature for 0.5 hour and concentrated. The residue was washed with $Et_2O$ twice and air-dried to give the crude solid. The residue was purified on RP-HPLC (Gilson C-18 column) eluting with 0-40% ACN/water with 0.05% TFA. The product fraction was lyophilized to give the desired product as a solid. LC-MS [M+H]: m/z 635.29. $^1$H NMR ($H_2O$-$d_2$, 500 MHz): $δ_H$ 8.25 (1H, d, J=9.2 Hz), 7.40 (1H, d, J=7.1 Hz), 7.31 (1H, d, J=9.5 Hz), 7.26 (1H, d, J=2.7 Hz), 7.08-7.10 (1H, m), 6.98 (1H, s), 5.10 (1H, d, J=5.0 Hz), 5.00 (1H, t, J=7.5 Hz), 4.60-4.64 (2H, m), 4.51 (2H, t, J=9.7 Hz), 4.36-4.41 (2H, m), 3.36 (1H, dd, J=6.4, 2.9 Hz), 1.05 (3H, d, J=6.2 Hz).

111

Example 21

3-((6-((S)-2-((((Z)-1-(5-amino-1,2,4-thiadiazol-3-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)azetidin-1-ium 2,2,2-trifluoroacetate (C21)

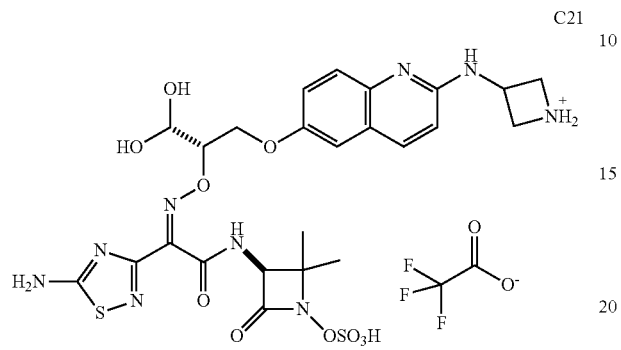

112

Compound 21 was prepared following the same procedure as in Example 1 except in step G reagent 2-(5-((tert-butoxycarbonyl)amino)-1,2,4-thiadiazol-3-yl)-2-oxoacetic acid was used. LC-MS [M+H]: m/z 666.20

Example 22

(S,Z)-4-((6-(2-(((1-(2-aminothiazol-4-yl)-2-((2,2-dimethyl-4-oxo-1-(sulfooxy)azetidin-3-yl)amino)-2-oxoethylidene)amino)oxy)ethoxy)isoquinolin-1-yl)amino)piperidin-1-ium (C22)

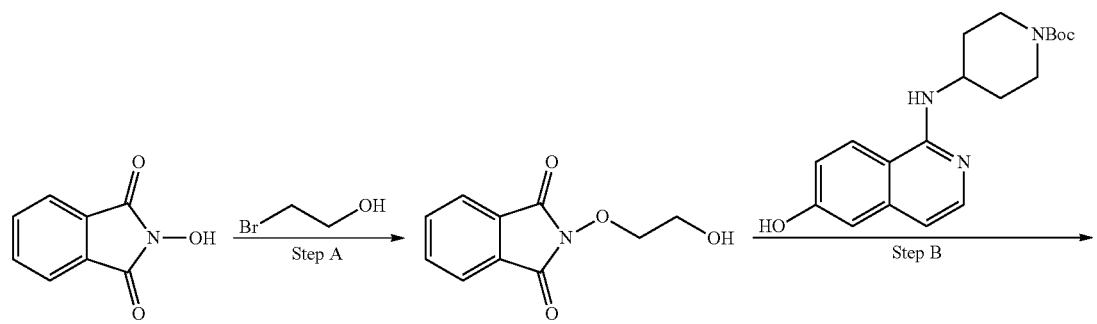

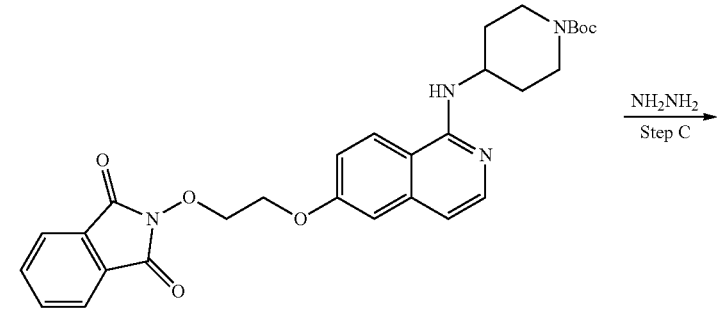

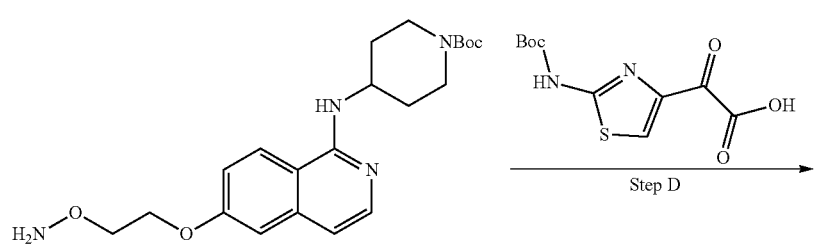

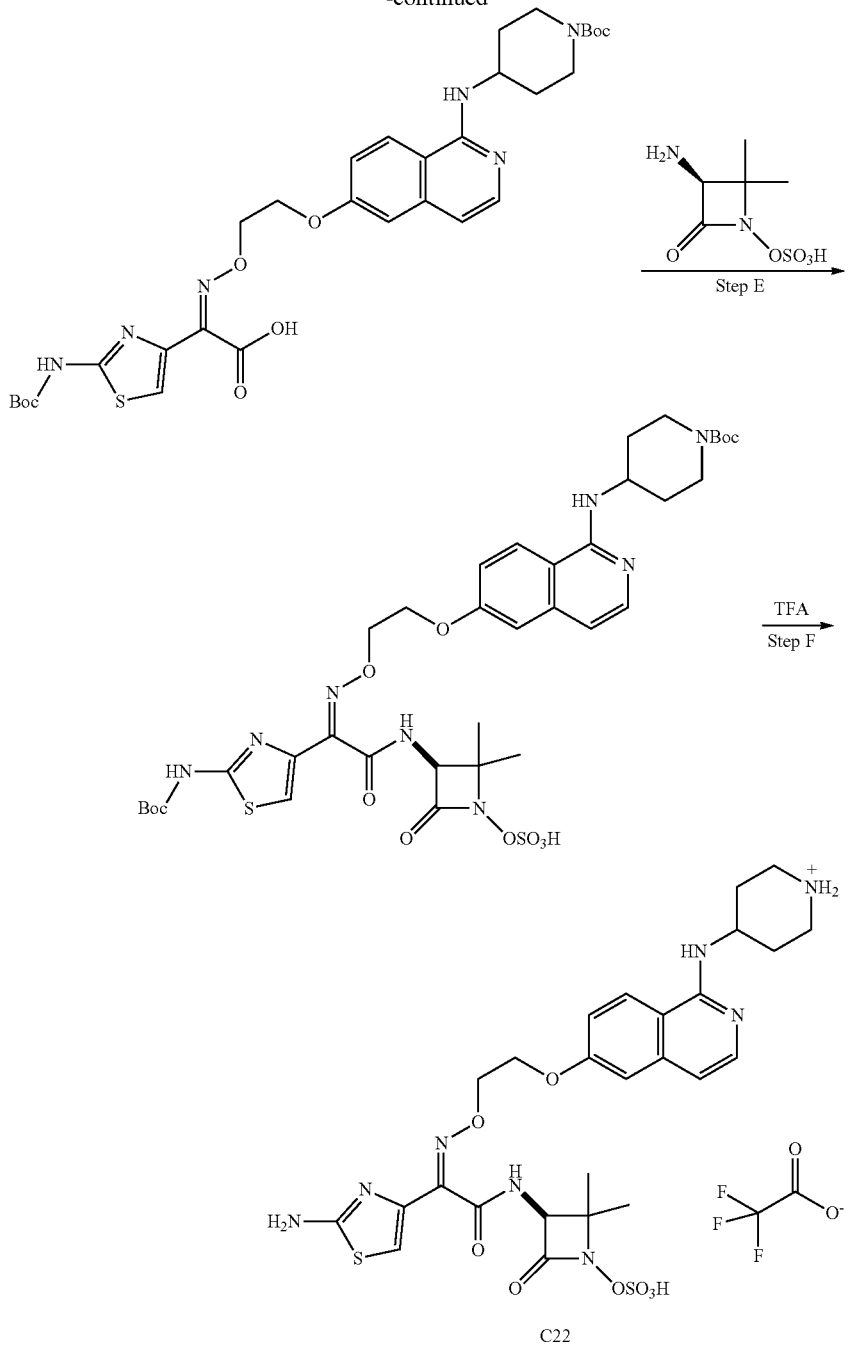

Step A. Preparation of 2-(2-hydroxyethoxy)isoindoline-1,3-dione

A solution of N-hydroxyphthalimide (5.0 g, 31 mmol), bromoethanol (6.5 ml, 92 mmol) and DBU (4.6 ml, 31 mmol) in DMF (60 ml) was heated to 50° C. and stirred overnight. The mixture was diluted with water and extracted with EtOAc. The organic layer was washed with water and brine, and dried over $Na_2SO_4$. The solution was concentrated. The residue was purified by column chromatography on silica gel, eluting with EtOAc/hexane to give the desired product as a solid. LC-MS [M+H]: m/z 208.48.

Step B. Preparation of Tert-Butyl 4-((6-(2-((1,3-dioxoisoindolin-2-yl)oxy)ethoxy)isoquinolin-1-yl)amino)piperidine-1-carboxylate To a solution of tert-butyl 4-((6-hydroxyisoquinoline-1-yl)amino)piperidine-1-carboxylate (Common intermediate from preparation of Example 14, produced following step A of Example 11 using 1-chloroisoquinolin-6-ol and tert-butyl 4-aminopiperidine-1-carboxylate) (50 mg, 0.15 mmol) in DCM (2 mL) was added 2-(2-hydroxyethoxy)isoindoline-1,3-dione (30 mg, 0.15 mmol) and triphenylphosphine (42 mg, 0.16 mmol) followed by DIAD (0.084 mL, 0.16 mmol). The mixture was stirred at room temperature for 2 hours and the solvent was removed. The residue was purified by column chromatography on silica gel, eluting with EtOAc/hexane to give the desired product as a gum. LC-MS [M+H]: m/z 533.38.

Step C. Preparation of Tert-Butyl 4-((6-(2-(aminooxy)ethoxy)isoquinolin-1-yl)amino)-piperidine-1-carboxylate To a solution of tert-butyl 4-((6-(2-(((1,3-dioxoisoindolin-2-yl)oxy)ethoxy)isoquinolin-1-yl)amino)piperidine-1-carboxylate (40 mg, 0.075 mmol) in ethanol (5 ml) was added hydrazine (2.8 µl, 0.090 mmol). The mixture was stirred at room temperature for 30 minutes. Solvent was removed. The residue was dissolved in 5 ml DCM and stirred at room temperature for 15 minutes. Solid was filtered off. The solvent was removed to give the crude product and used in the next step. LC-MS [M+H]: m/z 403.30. The procedures of step D to step F were the same as step G to step I in Example 1. The title compound 22 was characterized by LC/MS and NMR. LC-MS [M+H]: m/z 649.26. ¹H NMR (CH$_3$OH-d$_4$, 500 MHz): δ$_H$ 8.48 (1H, d, J=9.3 Hz), 7.57 (1H, d, J=7.0 Hz), 7.44 (1H, dd, J=9.3, 2.5 Hz), 7.38 (1H, d, J=2.6 Hz), 7.21 (1H, d, J=7.1 Hz), 7.01 (1H, s), 4.64-4.67 (2H, m), 4.58-4.62 (1H, m), 4.48-4.51 (1H, m), 4.13-4.17 (1H, m), 3.62 (2H, d, J=13.1 Hz), 3.20 (2H, t, J=12.8 Hz), 2.37 (2H, d, J=13.9 Hz), 2.06-2.14 (2H, m), 1.51 (3H, s), 1.27 (3H, s).

Example 25

(S,Z)-1-amino-6-(2-(((1-(2-aminothiazol-4-yl)-2-((2,2-dimethyl-4-oxo-1-(sulfooxy)azetidin-3-yl)amino)-2-oxoethylidene)amino)oxy)ethoxy)isoquinolin-2-ium 2,2,2-trifluoroacetate (C25)

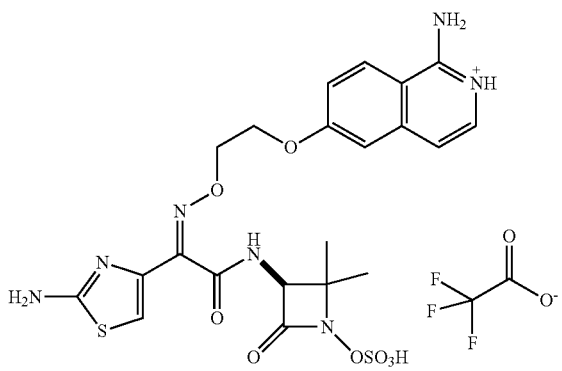

C25

Compound 25 was prepared by using generally the same procedure in Example 22, with reagent 1-aminoisoquinolin-

TABLE 5

By using generally the same procedure as described in Example 22, substituting the appropriate reactants and reagents, the following compounds were synthesized and characterized by LC/MS.

| Example | Name | Structure | LCMS |
|---|---|---|---|
| 23 | (S,Z)-2-((6-(2-(((1-(2-aminothiazol-4-yl)-2-((2,2-dimethyl-4-oxo-1-(sulfooxy)azetidin-3-yl)amino)-2-oxoethylidene)amino)oxy)ethoxy)isoquinolin-1-yl)amino)ethan-1-aminium 2,2,2-trifluoroacetate | 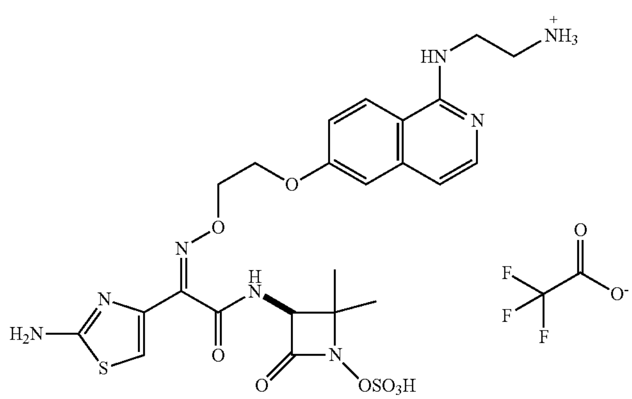 | 609.28 |
| 24 | (S,Z)-4-((6-(2-(((1-(2-aminothiazol-4-yl)-2-((2,2-dimethyl-4-oxo-1-(sulfooxy)azetidin-3-yl)amino)-2-oxoethylidene)amino)oxy)ethoxy)quinolin-2-yl)amino)piperidin-1-ium 2,2,2-trifluoroacetate | 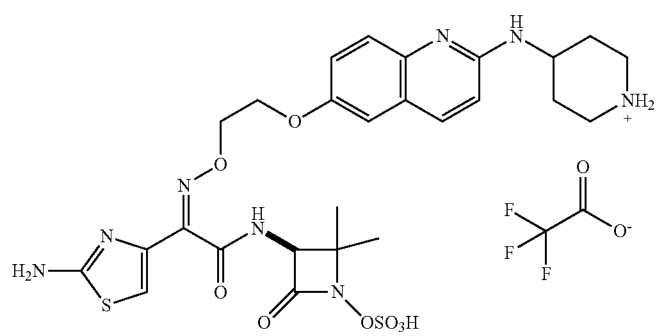 | 649.26 |

6-ol in step B. The title compound 25 was characterized by LC/MS. LC-MS [M+H]: m/z 566.36.

Example 26

5-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)quinolin-2-yl)amino)-1,2-dimethyl-1H-pyrazol-2-ium 2,2,2-trifluoroacetate (C26)

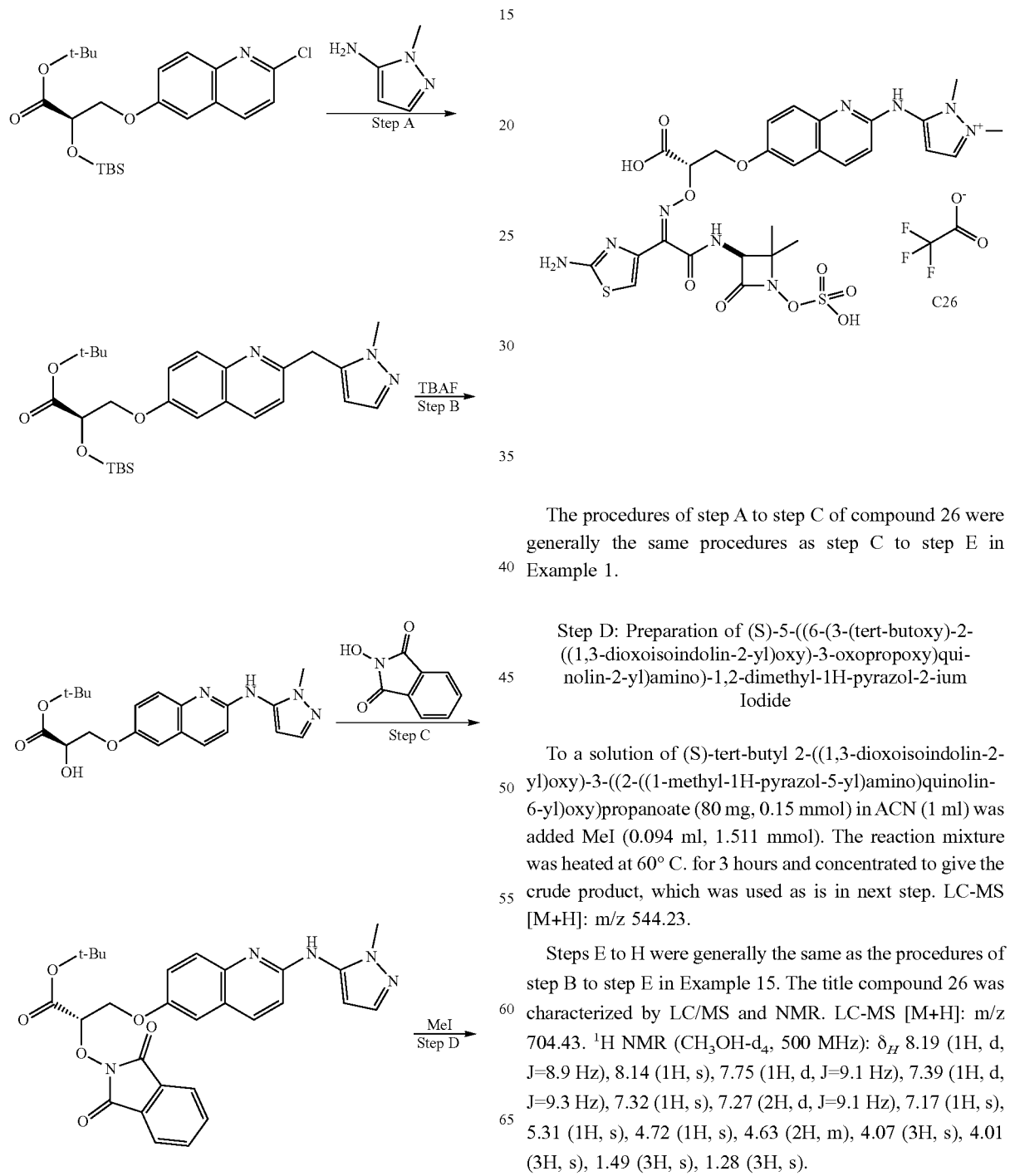

The procedures of step A to step C of compound 26 were generally the same procedures as step C to step E in Example 1.

Step D: Preparation of (S)-5-((6-(3-(tert-butoxy)-2-((1,3-dioxoisoindolin-2-yl)oxy)-3-oxopropoxy)quinolin-2-yl)amino)-1,2-dimethyl-1H-pyrazol-2-ium Iodide To a solution of (S)-tert-butyl 2-((1,3-dioxoisoindolin-2-yl)oxy)-3-((2-((1-methyl-1H-pyrazol-5-yl)amino)quinolin-6-yl)oxy)propanoate (80 mg, 0.15 mmol) in ACN (1 ml) was added MeI (0.094 ml, 1.511 mmol). The reaction mixture was heated at 60° C. for 3 hours and concentrated to give the crude product, which was used as is in next step. LC-MS [M+H]: m/z 544.23.

Steps E to H were generally the same as the procedures of step B to step E in Example 15. The title compound 26 was characterized by LC/MS and NMR. LC-MS [M+H]: m/z 704.43. $^1$H NMR (CH$_3$OH-d$_4$, 500 MHz): δ$_H$ 8.19 (1H, d, J=8.9 Hz), 8.14 (1H, s), 7.75 (1H, d, J=9.1 Hz), 7.39 (1H, d, J=9.3 Hz), 7.32 (1H, s), 7.27 (2H, d, J=9.1 Hz), 7.17 (1H, s), 5.31 (1H, s), 4.72 (1H, s), 4.63 (2H, m), 4.07 (3H, s), 4.01 (3H, s), 1.49 (3H, s), 1.28 (3H, s).

Example 27

(S)-3-((Z)-2-(((S)-2-((2-((1-(3-aminopropyl)-2-methyl-1H-pyrazol-2-ium-3-yl)amino)quinolin-6-yl)oxy)-1-carboxyethoxy)imino)-2-(2-aminothiazol-4-yl)acetamido)-2,2-dimethyl-4-oxoazetidin-1-yl Sulfate (C27)

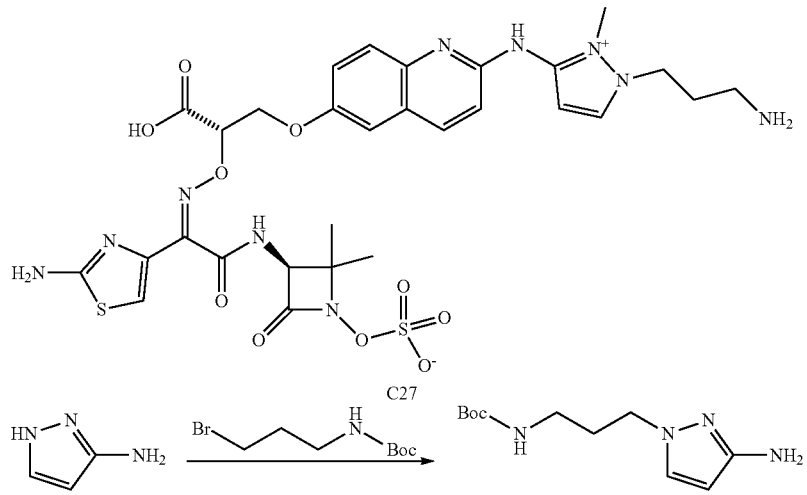

Step A. Preparation of Tert-Butyl (3-(3-amino-1H-pyrazol-1-yl)propyl)carbamate To a solution of 1H-pyrazol-3-amine (0.5 g, 6.0 mmol) in DMF (5 ml) was added NaH (0.26 g, 6.6 mmol). The resulting mixture was stirred at room temperature for 10 minutes. tert-butyl (3-bromopropyl)carbamate (1.6 g, 6.6 mmol) was added. The mixture was stirred at room temperature for 3 hours. The reaction mixture was quenched and diluted with water, extracted with EtOAc. The combined organic layer was washed with water and brine, dried over $Na_2SO_4$ and concentrated. The residue was purified by column chromatography on silica gel, eluting with EtOAc to give the desired product as an oil. LC-MS [M+H]: m/z 241.22. By using generally the same procedure in Example 26, compound 27 was synthesized with the above intermediate, and characterized by LC/MS. LC-MS [M+H]: m/z 747.39.

Example 28

3-(6-(2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)ethoxy)imidazo[1,2-a]pyridin-2-yl)piperidin-1-ium 2,2,2-trifluoroacetate (C28)

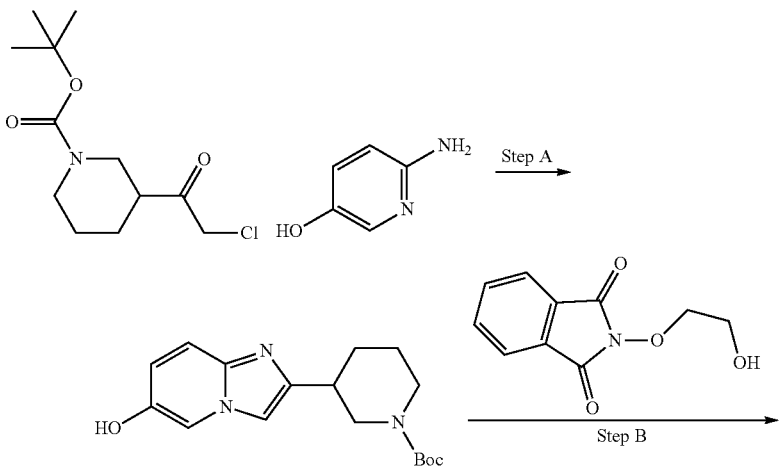

-continued
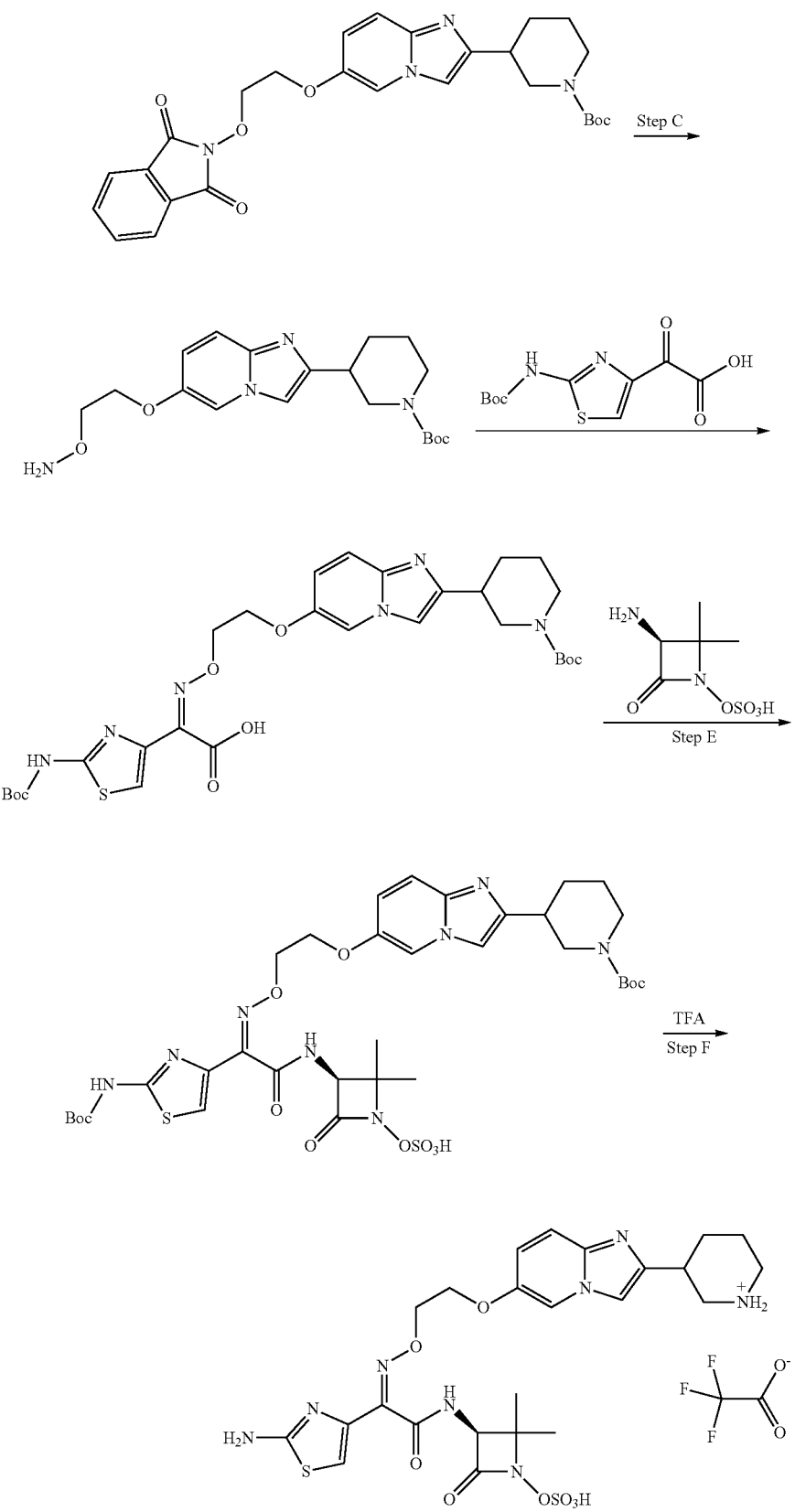

Step A: Preparation of Tert-Butyl 3-(6-hydroxyimidazo[1,2-a]pyridin-2-yl)piperidine-1-carboxylate In a 250 ml round bottom flask, 6-aminopyridin-3-ol and HCl salt (2.0 g, 13 mmol) were suspended in EtOH (40 ml), and then sodium bicarbonate (1100 mg, 13 mmol) was added and stirred for 5 minutes. After all went into solution, tert-butyl 3-(2-chloroacetyl)piperidine-1-carboxylate (5 g, 19 mmol) was added and the mixture was heated to 90° C. for 16 hours. The reaction was concentrated and the residue was purified by reverse phase MPLC with ACN and water buffered with 0.05% TFA to give solid TFA salt of product. The salt was dissolved in water (15 ml), the pH was adjusted to ~7-8 with sat'd aqueous NaHCO$_3$ solution, and then the resultant product was extracted with a mixture of IPA:CHCl3 (1:3). The organic layer was washed the brine (1×), dried (Na$_2$SO$_4$), filtered and concentrated. The residue was re-crystallized from THF to yield tert-butyl 3-(6-hydroxy-imidazo[1,2-a]pyridin-2-yl)piperidine-1-carboxylate. LC-MS m/z [M+H]$^+$: 318.08.

Step B: Tert-butyl 3-(6-(2-((1,3-dioxoisoindolin-2-yl)oxy)ethoxy)imidazo[1,2-a]pyridin-2-yl)piperidine-1-carboxylate 2-(2-hydroxyethoxy)isoindoline-1,3-dione (118 mg, 0.57 mmol), tert-butyl 3-(6-hydroxyimidazo[1,2-a]pyridin-2-yl)piperidine-1-carboxylate (120 mg, 0.38 mmol), and triphenylphosphine (150 mg, 0.57 mmol) were dissolved in THF (4 mL) and cooled to −70° C. and then DEAD was added (0.093 mL, 0.57 mmol). The reaction was warmed up to room temperature for 1 hour. The reaction was concentrated and the residue was purified by MPLC with 0-50% EtOAc/ethanol 1:3 to give tert-butyl 3-(6-(2-((1,3-dioxoisoindolin-2-yl)oxy)ethoxy)imidazo[1,2-a]pyridin-2-yl)piperidine-1-carboxylate. LC-MS m/z [M+H]$^+$: 507.78.

Step C: Tert-Butyl 3-(6-(2-(aminooxy)ethoxy)imidazo[1,2-a]pyridin-2-yl)piperidine-1-carboxylate Tert-butyl 3-(6-(2-((1,3-dioxoisoindolin-2-yl)oxy)ethoxy)imidazo[1,2-a]pyridin-2-yl)piperidine-1-carboxylate (112 mg, 0.22 mmol) was dissolved in ethanol (7 mL) and cooled to 0° C., then hydrazine (8.5 µl, 0.26 mmol) was added. The mixture was stirred at room temperature for 1 hour. The reaction was concentrated and stirred in DCM (20 ml) for 15 minutes. The DCM suspension was filtered and concentrated to give tert-butyl 3-(6-(2-(aminooxy)ethoxy)imidazo[1,2-a]pyridin-2-yl)piperidine-1-carboxylate. LC-MS m/z [M+H]$^+$: 377.12

Step D: (Z)-2-(2-((tert-butoxycarbonyl)amino)thiazol-4-yl)-2-((2-((2-(1-(tert-butoxycarbonyl)piperidin-3-yl)imidazo[1,2-a]pyridin-6-yl)oxy)ethoxy)imino)acetic Acid Tert-butyl 3-(6-(2-(aminooxy)ethoxy)imidazo[1,2-a]pyridin-2-yl)piperidine-1-carboxylate (85 mg, 0.23 mmol) was dissolved in a mixture of ethanol (5.6 ml) and chloroform (1.9 ml), and then 2-(2-((tert-butoxycarbonyl)amino)thiazol-4-yl)-2-oxoacetic acid (intermediate 3) (62 mg, 0.226 mmol) was added. The reaction was stirred at room temperature for 3 hours. The reaction was concentrated to yield (Z)-2-(2-((tert-butoxycarbonyl)amino) thiazol-4-yl)-2-((2-((2-(1-(tert-butoxycarbonyl)piperidin-3-yl)imidazo[1,2-a]pyridin-6-yl)oxy)ethoxy)imino)acetic acid. LC-MS m/z [M+H]$^+$: 631.51.

Step E: Preparation of Tert-Butyl 3-(6-(2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)-oxy) ethoxy) imidazo[1,2-a]pyridin-2-yl)piperidine-1-carboxylate (Z)-2-(2-((tert-butoxycarbonyl)amino)thiazol-4-yl)-2-((2-((2-(1-(tert-butoxycarbonyl)piperidin-3-yl)imidazo[1,2-a]pyridin-6-yl)oxy-)ethoxy)-imino)acetic acid (0.14 g, 0.22 mmol) was dissolved in DMF (4 ml), 1H-benzo[d][1,2,3]triazol-1-ol hydrate (0.071 g, 0.450 mmol) and N,N'-methanediylidenedicyclohexanamine (0.094 g, 0.450 mmol) were added, and then the mixture was stirred at room temperature for 0.5 hour. (S)-3-amino-2,2-dimethyl-4-oxoazetidin-1-yl hydrogen sulfate (0.095 g, 0.45 mmol) was added followed by sodium hydrogencarbonate (0.076 g, 0.90 mmol). The reaction was stirred at room temperature for 16 hours. The reaction was filtered and purified by reverse phase HPLC with ACN and water buffered with 0.05% TFA to yield tert-butyl 3-(6-(2-(((Z)-1-(2-((tert-butoxy-carbonyl)amino)thiazol-4-yl)-2-(((S)-2,2-dimethyl-4-oxo-1-(sulfooxy)azetidin-3-yl)amino)-2-oxoethylidene) amino)oxy)-ethoxy)imidazo[1,2-a]pyridin-2-yl)piperidine-1-carboxylate. LC-MS m/z [M+H]$^+$: 823.59

Step F: Preparation of 3-(6-(2-((((Z)-1-(2-aminothiazol-4-yl)-2-(((S)-2,2-dimethyl-4-oxo-1-(sulfooxy)azetidin-3-yl)amino)-2-oxoethylidene)amino)oxy) ethoxy)imidazo[1,2-a]pyridin-2-yl)piperidin-1-ium 2,2,2-trifluoroacetate Tert-butyl 3-(6-(2-(((Z)-(1-(2-((tert-butoxy-carbonyl)-amino)thiazol-4-yl)-2-(((S)-2,2-dimethyl-4-oxo-1-(sulfooxy)azetidin-3-yl)amino)-2-oxo-ethylidene)amino)oxy) ethoxy)imidazo[1,2-a]pyridin-2-yl)piperidine-1-carboxylate (5 mg, 6.1 µmol) was dissolved in DCM (1 mL), TFA (0.47 µl, 6.1 µmol) was added, and then the mixture was stirred at room temperature for 0.5 hour. The reaction was concentrated without heating. The residue was purified by reverse phase HPLC with ACN and water buffered with 0.05% TFA to yield product 3-(6-(2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-ethoxy)imidazo[1,2-a]pyridin-2-yl)piperidin-1-ium 2,2,2-trifluoro-acetate. LC-MS m/z [M+H]$^+$: 623.32. $^1$H NMR (CD3OD-d$_1$, 500 MHz): 1.29 (3H, s), 1.50 (3H, s), 1.94-1.90 (2H, m), 2.13-2.08 (1H, m), 2.31-2.28 (1H, m), 3.14-3.06 (1H, m), 3.47-3.39 (2H, m), 3.73-3.71 (1H, m), 4.42-4.39 (1H, m), 4.49-4.46 (1H, m), 4.60 (4H, m), 6.94 (1H, s), 7.74 (2H, s), 8.05 (1H, s), 8.45 (1H, s).

Example 29

(3S)-3-((Z)-2-(2-aminothiazol-4-yl)-2-((2-((1-methyl-2-(piperidin-1-ium-3-yl)imidazo[1,2-a]pyridin-1-ium-6-yl)oxy)ethoxy)imino)acetamido)-2,2-dimethyl-4-oxoazetidin-1-yl sulfate 2,2,2-trifluoroacetate (C29)

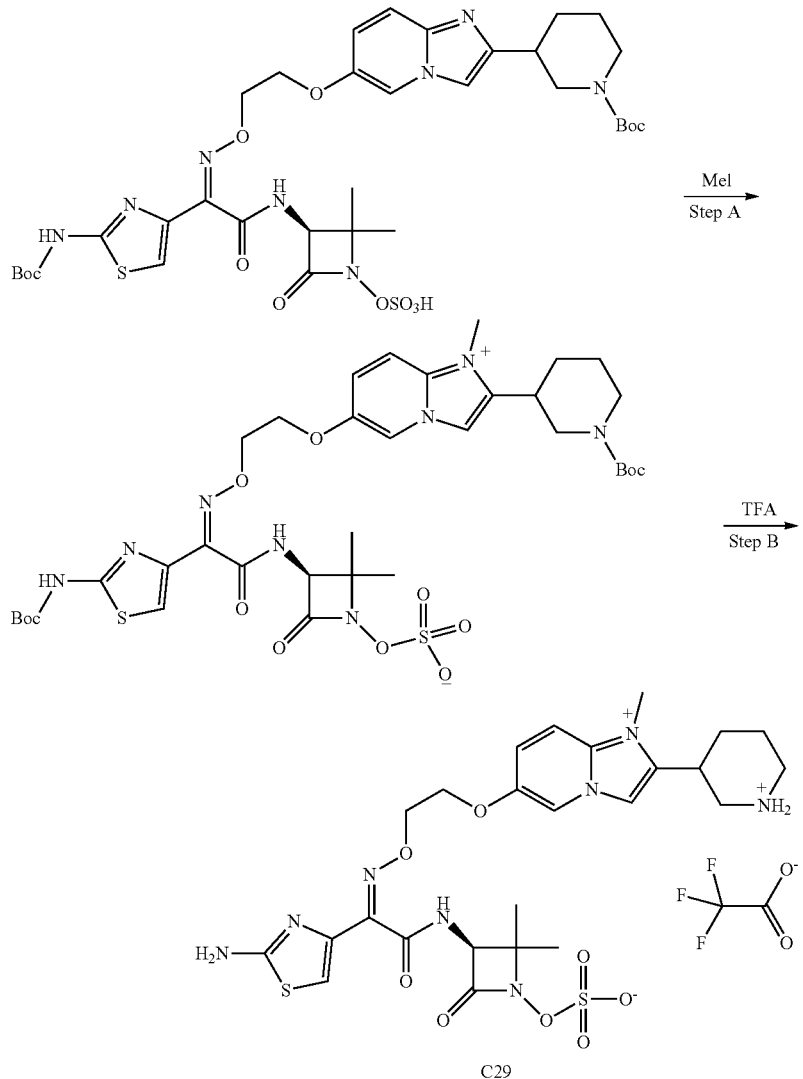

Step A: Preparation of (3S)-3-((Z)-2-(2-((tert-butoxycarbonyl)amino)thiazol-4-yl)-2-((2-((2-(1-(tert-butoxycarbonyl)piperidin-3-yl)-1-methylimidazo[1,2-a]pyridin-1-ium-6-yl)oxy)-ethoxy)imino)-acetamido)-2,2-dimethyl-4-oxoazetidin-1-yl Sulfate Tert-butyl 3-(6-(2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)ethoxy)imidazo[1,2-a]pyridin-2-yl)piperidine-1-carboxylate (step E, Example 28) (10 mg, 0.012 mmol) was dissolved in acetonitrile (1 ml) in a microwave tube then iodomethane (7.6 µl, 0.122 mmol) was added and the tube was sealed. The reaction was stirred at room temperature for 16 hours. Sodium bicarbonate (2.04 mg, 0.024 mmol) was added to the reaction, which was heated at 43° C. for 16 hours. The reaction was filtered and the residue was purified by reverse phase HPLC with ACN and water buffered with 0.05% TFA to yield the product. LC-MS m/z [M+H]$^+$: 838

Step B: Preparation of (3S)-3-((Z)-2-(2-aminothiazol-4-yl)-2-((2-((1-methyl-2-(piperidin-1-ium-3-yl)imidazo[1,2-a]pyridin-1-ium-6-yl)oxy)ethoxy)imino)acetamido)-2,2-dimethyl-4-oxoazetidin-1-yl sulfate 2,2,2-trifluoroacetate (3S)-3-((Z)-2-(2-((tert-butoxycarbonyl)-amino)thiazol-4-yl)-2-((2-((2-(1-(tert-butoxycarbonyl)piperidin-3-yl)-1-methylimidazo[1,2-a]pyridin-1-ium-6-yl)oxy)-ethoxy)imino)acetamido)-2,2-dimethyl-4-oxoazetidin-1-yl sulfate (8 mg, 9.6 μmol) was dissolved in DCM (1 mL), and then TFA (0.74 μl, 9.6 μmol) was added. The reaction was stirred at room temperature for 0.5 hour. The reaction was concentrated and the residue was purified by reverse phase HPLC with ACN and water buffered with 0.05% TFA to give (3S)-3-(((Z)-2-(2-aminothiazol-4-yl)-2-((2-((1-methyl-2-(piperidin-3-yl)imidazo[1,2-a]pyridin-1-ium-6-yl)oxy)ethoxy)-imino)acetamido)-2,2-dimethyl-4-oxoazetidin-1-yl sulfate 2,2,2-trifluoroacetate. LC-MS m/z [M+H]$^+$: 637.41. $^1$H NMR (CH$_3$OH-d$_4$, 500 MHz): 1.31-1.23 (3H, m), 1.50 (3H, d, J=5.4 Hz), 1.97-1.90 (2H, m), 2.14-2.11 (1H, m), 2.30-2.28 (1H, m), 3.17-3.05 (1H, m), 3.30-3.28 (1H, m), 3.51-3.38 (1H, m), 3.76-3.66 (1H, m), 4.0 (3H, s), 4.45-4.37 (1H, m), 4.51-4.47 (1H, m), 4.63-4.59 (3H, m), 6.98-6.97 (1H, m), 7.75 (1H, s), 7.79 (1H, ddd, J=9.9, 5.3, 2.2 Hz), 7.94 (1H, d, J=9.9 Hz), 8.05 (1H, s), 8.12 (1H, s), 8.45-8.44 (1H, m).

Examples 30 and 31

5-(((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate (C30) and 5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate

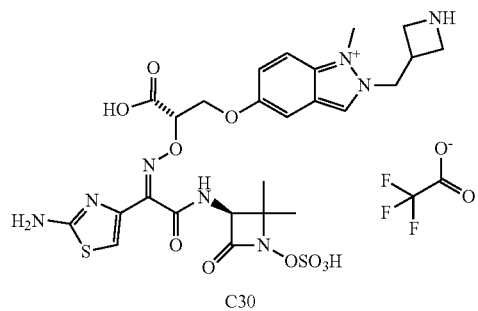

C30

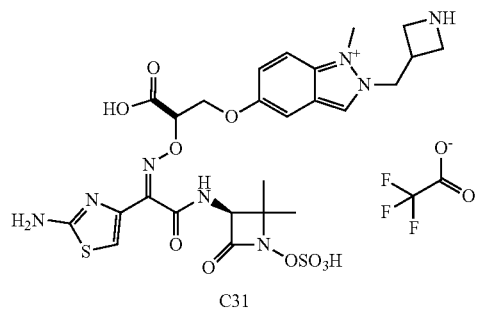

C31

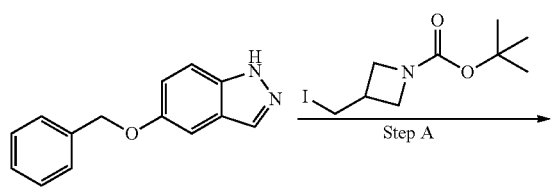

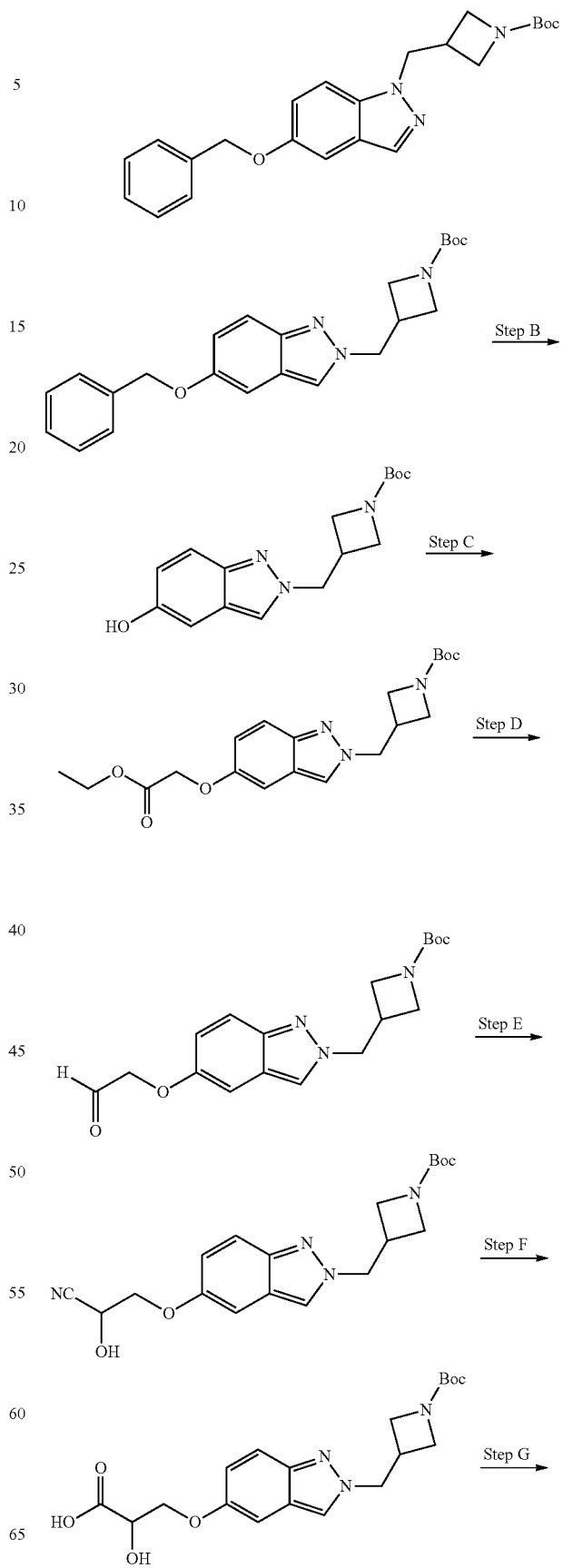

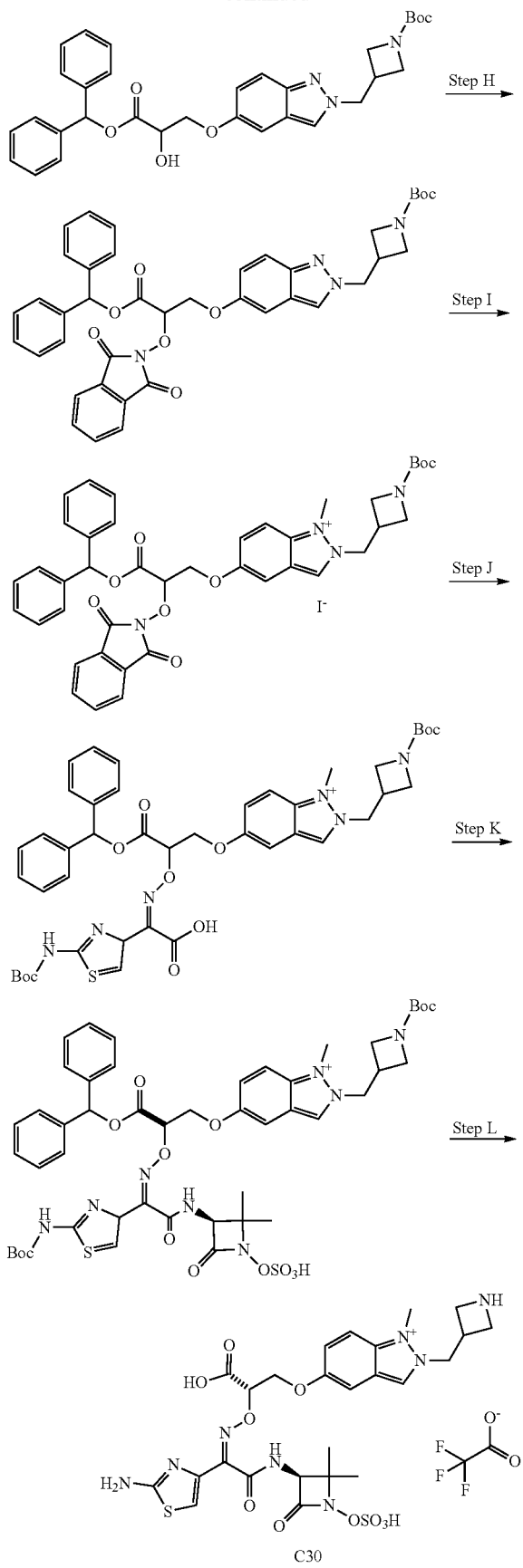

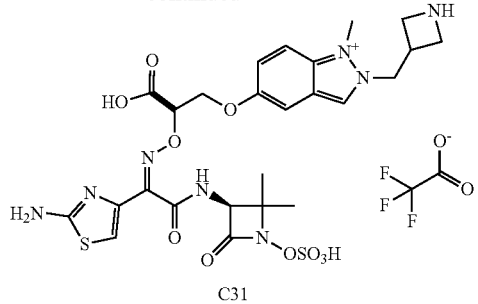

C31

Step A: Preparation of Tert-Butyl 3-((5-(benzyloxy)-2H-indazol-2-yl)methyl)azetidine-1-carboxylate and tert-butyl 3-((5-(benzyloxy)-1H-indazol-1-yl)methyl)azetidine-1-carboxylate To a solution of 5-(benzyloxy)-1H-indazole (1 g, 4.5 mmol) in DMF (16 ml) at 0° C. was added NaH (60%, 0.27 g, 6.7 mmol). The resulting solution was stirred at 0° C. for 30 minutes before addition of tert-butyl 3-(iodomethyl)azetidine-1-carboxylate (1.3 g, 4.5 mmol). The resulting solution was stirred at room temperature for 5 hours. After quenching by addition of water, the mixture was partitioned between EtOAc (200 mL) and water (100 mL), and the organic phase was washed with saturated NaHCO$_3$ (3×100 mL), dried over Na$_2$SO$_4$, concentrated and the residue was purified on silica gel column using EtOAc/hexane as eluting solvents to give tert-butyl 3-((5-(benzyloxy)-2H-indazol-2-yl)methyl)-azetidine-1-carboxylate. LC/MS: (M+1)$^+$=394.4. $^1$H NMR (CDCl$_3$, 500 MHz): δ 7.79 (s, 1H), 7.64-7.62 (d, J 9.5 Hz, 1H), 7.50-7.48 (d, J 7.2 Hz, 2H), 7.44-7.41 (t, J 7.2 Hz, 2H), 7.37-7.36 (d, J 7.2 Hz, 1H), 7.12-7.10 (dd, J 2.1 Hz and 9.3 Hz, 1H), 6.96-6.95 (d, J 2.1 Hz, 1H), 5.10 (s, 2H), 4.59-4.58 (d, J 6.1 Hz, 2H), 4.09-4.05 (t, J 8.2 Hz, 2H), 3.81-3.77 (m, 2H), 3.25-3.20 (m, 1H), 1.45 (s, 9H); and tert-butyl 3-((5-(benzyloxy)-1H-indazol-1-yl)-methyl)azetidine-1-carboxylate. LC/MS: (M+1)$^+$=394.4, $^1$H NMR (CDCl$_3$, 500 MHz): δ 7.9 (s, 1H), 7.50-7.49 (d, J 7.5 Hz, 2H), 7.44-7.41 (t, J 8.0 Hz, 2H), 7.38-7.35 (m, 2H), 5.13 (s, 2H), 4.55-4.53 (d, J 7.6 Hz, 2H), 4.06-4.03 (t, J 8.6 Hz, 2H), 3.83-3.80 (m, 2H), 3.20-3.15 (m, 1H), 1.46 (s, 9H).

Step B: Preparation of Tert-Butyl 3-((5-hydroxy-2H-indazol-2-yl)methyl)azetidine-1-carboxylate To the solution of tert-butyl 3-((5-(benzyloxy)-2H-indazol-2-yl)methyl)-azetidine-1-carboxylate (1.03 g, 2.6 mmol) in MeOH (50 ml) was added 10% Pd/C (0.28 g, 0.26 mmol). The resulting mixture was hydrogenated at 50 psi for 40 hours. The mixture was filtered through CELITE, and the filtrate was concentrated to give tert-butyl 3-((5-hydroxy-2H-indazol-2-yl)methyl)azetidine-1-carboxylate. LC/MS: (M+1)$^+$=304.2

Step C: Preparation of Tert-Butyl 3-((5-(2-ethoxy-2-oxoethoxy)-2H-indazol-2-yl)methyl)-azetidine-1-carboxylate To the solution of tert-butyl 3-((5-hydroxy-2H-indazol-2-yl)methyl)azetidine-1-carboxylate (0.89 g, 2.9 mmol) in ethyl acetate (100 ml) was added K$_2$CO$_3$ (0.81 g, 5.9 mmol) and ethyl 2-bromoacetate (0.39 ml, 3.5 mmol). The resulting mixture was heated at reflux overnight. After filtration through CELITE, the filtrate was concentrated and the residue was purified on silica gel column using EtOAc/hexane as eluting solvents to give tert-butyl 3-((5-(2-ethoxy-2-oxoethoxy)-2H-indazol-2-yl)methyl)-azetidine-1-carboxylate. LC/MS: (M+1)=390.3

Step D: Preparation of Tert-Butyl 3-((5-(2-oxoethoxy)-2H-indazol-2-yl)methyl)azetidine-1-carboxylate To the solution of tert-butyl 3-((5-(2-ethoxy-2-oxoethoxy)-2H-indazol-2-yl)methyl)azetidine-1-carboxylate (0.31 g, 0.80 mmol) in $CH_2Cl_2$ (14 ml) at −78° C. was added DIBAL-H (1.6 ml, 1.6 mmol) dropwise. The resulting solution was stirred at −78° C. for 4 hours. The reaction was quenched by addition of MeOH (3 mL) followed by addition of saturated potassium tartrate (100 mL). The resulting mixture was stirred at room temperature for 8 hours, and the mixture was extracted with DCM (3×100 mL). The combined organic phase was dried over $Na_2SO_4$, and concentrated to give tert-butyl 3-((5-(2-oxoethoxy)-2H-indazol-2-yl)methyl)azetidine-1-carboxylate. LC/MS: $(M+1+18)^+=364.3$ Step E: Preparation of Tert-Butyl 3-((5-(2-cyano-2-hydroxyethoxy)-2H-indazol-2-yl)methyl)azetidine-1-carboxylate To the mixture of tert-butyl 3-((5-(2-oxoethoxy)-2H-indazol-2-yl)methyl)azetidine-1-carboxylate (0.47 g, 1.4 mmol) in t-BuOMe (10 ml) and water (2 ml) was added acetic acid (3 ml) dropwise and sodium cyanide (0.10 g, 2.04 mmol).

The resulting solution was stirred at room temperature overnight. The solution was added to saturated $Na_2CO_3$ (100 mL) at 0° C. The mixture was extracted with EtOAc (2×150 mL), and the combined organic phase was washed with saturated $NaHCO_3$ (2×100 mL), dried over $Na_2SO_4$, and concentrated. The residue was purified on silica gel column using EtOAc/hexane as eluting solvents to give tert-butyl 3-((5-(2-cyano-2-hydroxyethoxy)-2H-indazol-2-yl)methyl)azetidine-1-carboxylate. LC/MS: $(M+1)^+=373.3$ Step F: Preparation of 3-((2-((1-(tert-butoxycarbonyl)azetidin-3-yl)methyl)-2H-indazol-5-yl)oxy)-2-hydroxypropanoic acid To the solution of tert-butyl 3-((5-(2-cyano-2-hydroxyethoxy)-2H-indazol-2-yl)methyl)azetidine-1-carboxylate (0.21 g, 0.56 mmol) in MeOH (20 ml) at 0° C. was bubbled HCl (g) for 20 minutes, and then the resulting solution was stirred from 0° C. to room temperature overnight. After concentration, the residue was dissolved in dioxane (10 mL) and water (2 mL). To the resulting solution was added NaOH (5 ml, 5.00 mmol) and $Boc_2O$ (0.16 ml, 0.68 mmol). The resulting solution was stirred at room temperature for 1 hour. After removing the volatile, the aqueous phase was extracted with DCM (2×10 mL), and then acidified to pH 3, and the precipitate was extracted with DCM (3×50 mL). The combined organic phase was dried over $Na_2SO_4$, and concentrated to give 3-((2-((1-(tert-butoxycarbonyl)azetidin-3-yl)methyl)-2H-indazol-5-yl)oxy)-2-hydroxypropanoic acid. LC/MS: $(M+1)^+=392.3$ Step G: Preparation of Tert-Butyl 3-((5-(3-(benzhydryloxy)-2-hydroxy-3-oxopropoxy)-2H-indazol-2-yl)methyl)azetidine-1-carboxylate To the solution of 3-((2-((1-(tert-butoxycarbonyl)azetidin-3-yl)methyl)-2H-indazol-5-yl)oxy)-2-hydroxypropanoic acid (190 mg, 0.48 mmol) in MeOH (10 ml) was added diphenyl diazomethane (470 mg, 2.4 mmol). The resulting solution was stirred at room temperature for 1 hour. After concentration, the residue was purified on silica gel column using EtOAc/hexane as eluting solvents to give tert-butyl 3-((5-(3-(benzhydryloxy)-2-hydroxy-3-oxopropoxy)-2H-indazol-2-yl)methyl)azetidine-1-carboxylate. LC/MS: $(M+1)^+=558.4$ Step H: Preparation of Tert-Butyl 3-((5-(3-(benzhydryloxy)-2-((1,3-dioxoisoindolin-2-yl)oxy)-3-oxopropoxy)-2H-indazol-2-yl)methyl)azetidine-1-carboxylate To the solution of tert-butyl 3-((5-(3-(benzhydryloxy)-2-hydroxy-3-oxopropoxy)-2H-indazol-2-yl)methyl)azetidine-1-carboxylate (200 mg, 0.36 mmol) in THF (4 ml) was added 2-hydroxyisoindoline-1,3-dione (70 mg, 0.43 mmol), triphenylphosphine (141 mg, 0.54 mmol) and DEAD (0.085 ml, 0.54 mmol). The resulting solution was stirred at room temperature for 2 hours. After concentration, the residue was purified on silica gel column using EtOAc/hexane as eluting solvents to give tert-butyl 3-((5-(3-(benzhydryloxy)-2-((1,3-dioxoisoindolin-2-yl)oxy)-3-oxopropoxy)-2H-indazol-2-yl)methyl)azetidine-1-carboxylate. LC/MS: $(M+1)^+=703.5$ Step I: Preparation of 5-(3-(benzhydryloxy)-2-((1,3-dioxoisoindolin-2-yl)oxy)-3-oxopropoxy)-2-((1-(tert-butoxycarbonyl)azetidin-3-yl)methyl)-1-methyl-2H-indazol-1-ium Iodide To the solution of tert-butyl 3-((5-(3-(benzhydryloxy)-2-((1,3-dioxoisoindolin-2-yl)oxy)-3-oxopropoxy)-2H-indazol-2-yl)methyl)azetidine-1-carboxylate (230 mg, 0.33 mmol) in acetonitrile (5 ml) was added MeI (0.20 ml, 3.3 mmol). The resulting solution was heated at 70° C. for 4 days. Additional MeI (0.20 ml, 3.3 mmol) was then added and the resulting solution was heated at 80° C. for 24 hours. The solution was then concentrated to give 5-(3-(benzhydryloxy)-2-((1,3-dioxoisoindolin-2-yl)oxy)-3-oxopropoxy)-2-((1-(tert-butoxycarbonyl)azetidin-3-yl)methyl)-1-methyl-2H-indazol-1-ium iodide. LC/MS: $M^+=717.6$ Step J: Preparation of (Z)-5-(3-(benzhydryloxy)-2-(((((2-((tert-butoxycarbonyl)amino)-thiazol-4-yl)(carboxy)methylene)amino)oxy)-3-oxopropoxy)-2-((1-(tert-butoxycarbonyl)-azetidin-3-yl)methyl)-1-methyl-2H-indazol-1-ium To the solution of 5-(3-(benzhydryloxy)-2-((1,3-dioxoisoindolin-2-yl)oxy)-3-oxopropoxy)-2-((1-(tert-butoxycarbonyl)azetidin-3-yl)methyl)-1-methyl-2H-indazol-1-ium iodide (240 mg, 0.33 mmol) in ethanol (5 ml) and $CH_2Cl_2$ (5.00 ml) at 0° C. was added hydrazine (10 µl, 0.33 mmol). The resulting solution was stirred at 0° C. for 1 hour. Then 2-(2-((tert-butoxycarbonyl)amino)thiazol-4-yl)-2-oxoacetic acid (intermediate 3) (134 mg, 0.49 mmol) was added to the above solution, and the resulting solution was stirred at 0° C. to room temperature for 2 hours. The reaction was concentrated and the residue was purified on reverse phase MPLC column using acetonitrile (0.05% TFA)/water (0.0%% TFA) as eluting solvents to give (Z)-5-(3-(benzhydryloxy)-2-((((2-((tert-butoxycarbonyl)amino)thiazol-4-yl)(carboxy)methylene)amino)oxy)-3-oxopropoxy)-2-((1-(tert-butoxycarbonyl)azetidin-3-yl)methyl)-1-methyl-2H-indazol-1-ium. LC/MS: $M^+=841.5$ Step K: Preparation of 5-(3-(benzhydryloxy)-2-(((Z)-(1-(2-((tert-butoxycarbonyl)amino)-thiazol-4-yl)-2-(((S)-2,2-dimethyl-4-oxo-1-(sulfooxy)azetidin-3-yl)amino)-2-oxo-ethylidene)amino)oxy)-3-oxopropoxy)-2-((1-(tert-butoxycarbonyl)azetidin-3-yl)methyl)-1-methyl-2H-indazol-1-ium To the solution of (Z)-5-(3-(benzhydryloxy)-2-((((2-((tert-butoxycarbonyl)amino)thiazol-4-yl)(carboxy)methylene)amino)oxy)-3-oxopropoxy)-2-((1-(tert-butoxycarbonyl)azetidin-3-yl)methyl)-1-methyl-2H-indazol-1-ium (64 mg, 0.076 mmol) in DMF (2 ml) was added DCC (125 mg, 0.61 mmol) and HOBT (47 mg, 0.30 mmol). The resulting solution was stirred at room temperature for 30 minutes before addition of (S)-3-amino-2,2-dimethyl-4-oxoazetidin-1-yl hydrogen sulfate (64 mg, 0.30 mmol) and sodium bicarbonate (77 mg, 0.91 mmol). The resulting mixture was stirred at room temperature overnight. After filtration, the filtrate was purified on reverse phase MPLC using acetonitrile (0.05% TFA)/water (0.05% TFA) as eluting solvents to give 5-(3-(benzhydryloxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)azetidin-3-yl)methyl)-1-methyl-2H-indazol-1-ium. LC/MS: $M^+=1033.6$ Step L: Preparation of 5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate (C30) and 5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate (C31)

To the solution of 5-(3-(benzhydryloxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-azetidin-3-yl)methyl)-1-methyl-2H-indazol-1-ium (70 mg, 0.068 mmol) in $CH_2Cl_2$ (2 ml) was added TFA (2 mL, 26 mmol). The resulting solution was stirred at room temperature for 40 minutes, concentrated, and then the residue was treated with $Et_2O$ and concentrated again. The residue was purified on reverse phase HPLC using acetonitrile (0.05% TFA)/water (0.05% TFA) to give 5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate (C30, the fast eluting diastereomer). LC/MS: $(M+1)^+=667.1$, $^1H$ NMR (500 MHz, $D_2O$): δ 8.68 (s, 1H), 7.62-7.60 (d, J 8.0 Hz, 1H), 7.45-7.43 (d, J 8.6 Hz, 1H), 7.23 (s, 1H), 7.03 (s, 1H), 5.07 (s, 1H), 4.97-4.95 (d, J 7.5 Hz, 2H), 4.65 (s, 1H), 4.49-4.44 (m, 2H), 4.24-4.20 (t, J 9.8 Hz, 2H), 4.13 (s, 3H), 4.10-4.06 (t, J 9.5 Hz, 2H), 3.68-3.61 (m, 1H), 1.32 (s, 3H), 0.89 (s, 3H); and 5-((R)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-carboxyethoxy)-2-(azetidin-3-ylmethyl)-1-methyl-2H-indazol-1-ium 2,2,2-trifluoroacetate (C31, the slow eluting diastereomer). LC/MS: $(M+1)^+=667.1$, $^1H$ NMR (500 MHz, $D_2O$): δ 8.68 (s, 1H), 7.63-7.61 (d, J 10.0 Hz, 1H), 7.45-7.43 (dd, J 10.0 Hz and 1.5 Hz, 1H), 7.24 (d, J 1.5 Hz, 1H), 7.02 (s, 1H), 5.02-4.99 (m, 1H), 4.97-4.95 (d, J 7.8 Hz, 2H), 4.65 (s, 1H), 4.46-4.41 (m, 2H), 4.24-4.20 (t, J 10.9 Hz, 2H), 4.13 (s, 3H), 4.10-4.06 (t, J 9.8 Hz, 2H), 3.68-3.61 (m, 1H), 1.32 (s, 3H), 0.95 (s, 3H).

Examples 32 and 33

1-(3-aminopropyl)-5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-methyl-1H-indazol-2-ium 2,2,2-trifluoroacetate (C32) and 1-(3-aminopropyl)-5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-methyl-1H-indazol-2-ium 2,2,2-trifluoroacetate (C33)

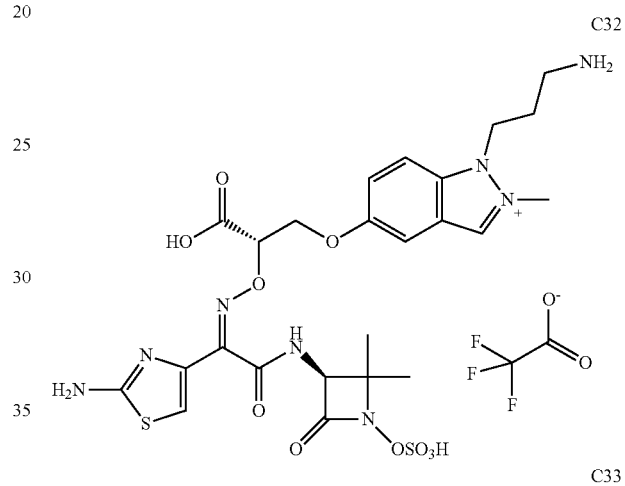

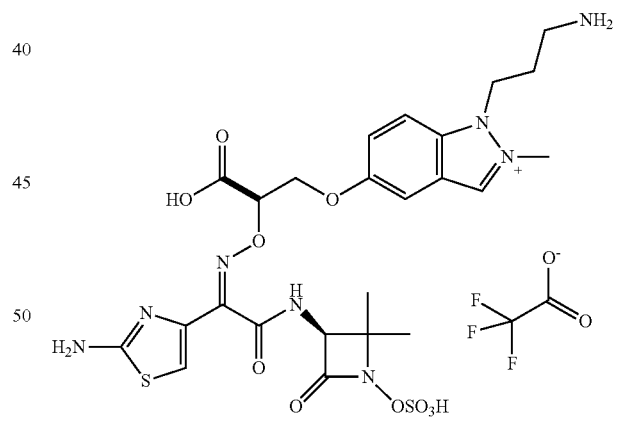

Compounds 32 and 33 were prepared following the same general procedure as Example 30 and 31.

Compound 32: 1-(3-aminopropyl)-5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-methyl-1H-indazol-2-ium 2,2,2-trifluoroacetate. LC/MS: $(M+1)^+=655.4$ $^1HNMR$ (500 MHz, $D_2O$): δ 8.66 (s, 1H), 7.65-7.63 (d, J 9.2 Hz, 1H), 7.47-7.44 (dd, J 1.6 Hz and 9.4 Hz, 1H), 7.47-7.44 (d, J 2.2 Hz, 1H), 7.03 (s, 1H), 5.06-5.04 (m, 1H), 4.67 (s, 1H), 4.46-4.39 (m, 2H), 4.28 (s, 3H), 3.05-3.02 (m, 2H), 2.21-2.17 (m, 2H), 1.34 (s, 3H), 0.95 (s, 3H).

Compound 33: 1-(3-aminopropyl)-5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-methyl-1H-indazol-2-ium 2,2,2-trifluoroacetate. LC/MS: (M+1)$^+$=655.4, $^1$HNMR (500 MHz, D$_2$O): δ 8.65 (s, 1H), 7.65-7.63 (d, J 9.6 Hz, 1H), 7.46-7.44 (dd, J 9.9 Hz and 2.4 Hz, 1H), 7.27 (d, J 2.4 Hz, 1H), 7.04 (s, 1H), 5.02-5.00 (m, 1H), 4.69 (s, 1H), 4.47-4.41 (m, 2H), 4.28 (s, 3H), 3.05-3.02 (t, J 7.6 Hz, 2H), 2.2-2.16 (m, 2H), 1.32 (s, 3H), 0.97 (s, 3H).

Examples 34 and 35

5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1-(azetidin-3-ylmethyl)-2-methyl-1H-indazol-2-ium 2,2,2-trifluoroacetate (C34) and 5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1-(azetidin-3-ylmethyl)-2-methyl-1H-indazol-2-ium 2,2,2-trifluoroacetate (C35)

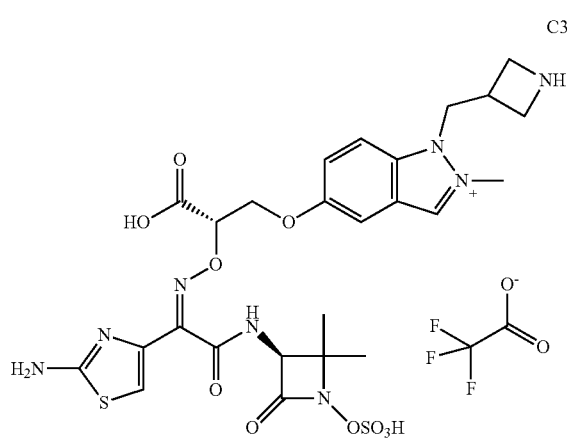

C34

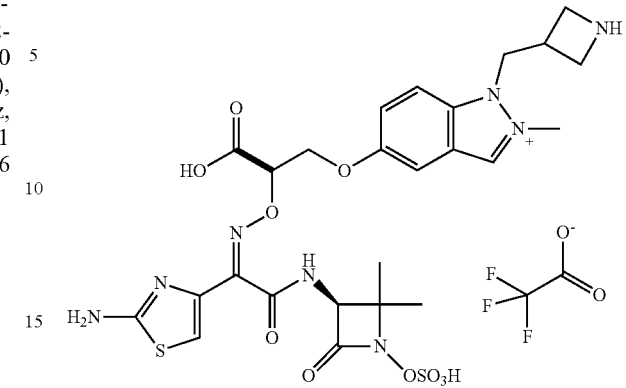

C35

Compounds 34 and 35 were prepared following the same general procedure as Example 30 and 31.

Compound 34: 5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1-(azetidin-3-ylmethyl)-2-methyl-1H-indazol-2-ium 2,2,2-trifluoroacetate. LC/MS: (M+1)$^+$=667.4. $^1$H NMR (500 MHz, D$_2$O): δ 8.68 (s, 1H), 7.76-7.74 (d, J 9.1 Hz, 1H), 7.48-7.46 (m, 1H), 7.28-7.27 (m, 1H), 7.05 (s, 1H), 5.11-5.10 (m, 1H), 4.99-4.97 (d, J 6.7 Hz, 2H), 4.68 (s, 1H), 4.48-4.40 (m, 2H), 4.26 (s, 3H), 4.12-4.02 (m, 4H), 3.56-3.50 (m, 1H), 1.34 (s, 3H), 0.93 (s, 3H).

Compound 35: 5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1-(azetidin-3-ylmethyl)-2-methyl-1H-indazol-2-ium 2,2,2-trifluoroacetate. LC/MS: (M+1)$^+$=667.1, $^1$H NMR (500 MHz, D$_2$O): δ 8.68 (s, 1H), 7.76-7.74 (d, J 9.0 Hz, 1H), 7.48-7.46 (dd, J 9.8 Hz and 2.3 Hz, 1H), 7.27-7.26 (d, J 2.3 Hz, 1H), 7.04 (s, 1H), 5.05 (m, 1H), 4.99-4.97 (d, J 9.2 Hz, 2H), 4.49-4.42 (m, 2H), 4.26 (s, 3H), 4.12-4.01 (m, 4H), 3.56-3.49 (m, 1H), 1.32 (s, 3H), 0.96 (s, 3H).

Example 36

1-(3-aminopropyl)-5-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)-2-methyl-1H-indazol-2-ium 2,2,2-trifluoroacetate (C36

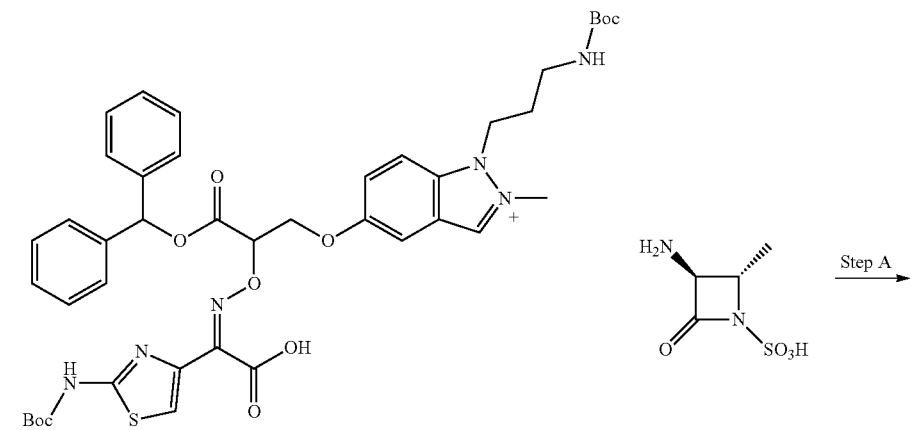

-continued

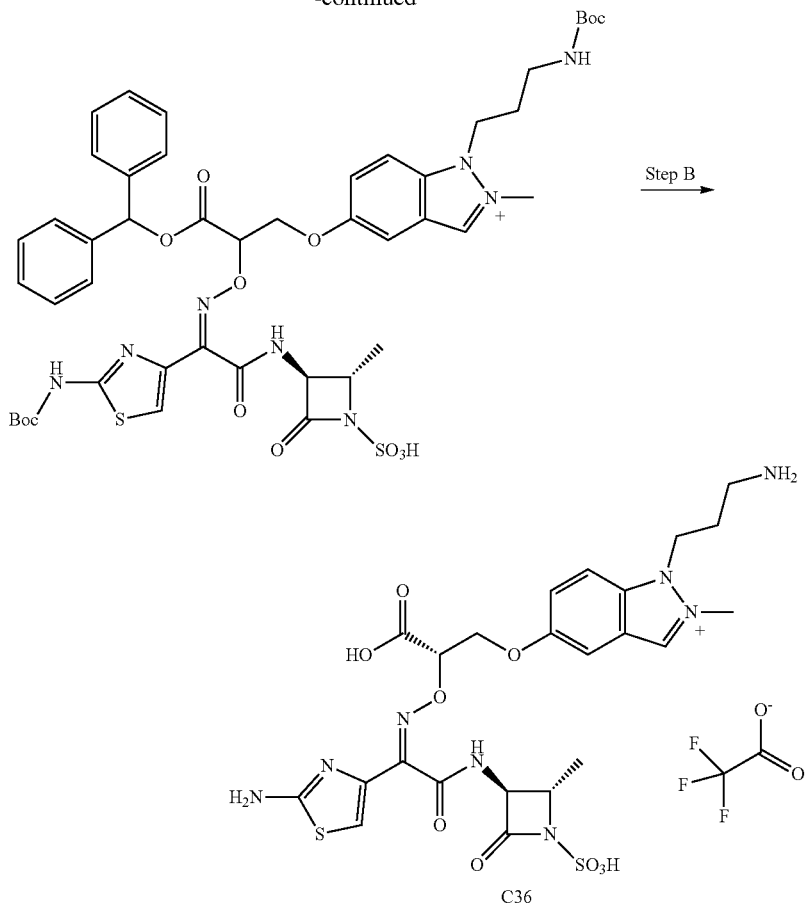

Step A: Preparation of 5-(3-(benzhydryloxy)-2-(((Z)-(1-(2-((tert-butoxycarbonyl)amino)-thiazol-4-yl)-2-(((2S,3S)-2-methyl-4-oxo-1-sulfoazetidin-3-yl)amino)-2-oxo-ethylidene)amino)oxy)-3-oxopropoxy)-1-(3-((tert-butoxycarbonyl)amino)propyl)-2-methyl-1H-indazol-2-ium (Z)-5-(3-(benzhydryloxy)-2-((((2-((tert-butoxycarbonyl)amino)thiazol-4-yl)(carboxy)methylene)-amino)oxy)-3-oxopropoxy)-1-(3-((tert-butoxycarbonyl)amino)-propyl)-2-methyl-1H-indazol-2-ium was prepared from 5-(benzyloxy)-1H-indazole and tert-butyl (3-iodopropyl)carbamate by following the same procedure from steps A-J in Examples 30 and 31. To the solution of (Z)-5-(3-(benzhydryloxy)-2-((((2-((tert-butoxycarbonyl)-amino)thiazol-4-yl)(carboxy)methylene)amino)oxy)-3-oxopropoxy)-1-(3-((tert-butoxy-carbonyl)amino)propyl)-2-methyl-1H-indazol-2-ium (54 mg, 0.065 mmol) in DMF (2 ml) was added DCC (67 mg, 0.32 mmol) and HOBT (40 mg, 0.26 mmol). The resulting mixture was stirred at room temperature for 30 minutes before addition of (2S,3S)-3-amino-2-methyl-4-oxoazetidine-1-sulfonic acid (47 mg, 0.26 mmol) and sodium bicarbonate (55 mg, 0.65 mmol). The resulting mixture was stirred at room temperature for 5 hours. The mixture was filtered and the filtrate was purified on reverse phase HPLC using acetonitrile (0.05% TFA)/water (0.05% TFA) as mobile phase to give 5-(3-(benzhydryloxy)-2-(((Z)-(1-(2-((tert-butoxycarbonyl)amino)thiazol-4-yl)-2-(((2S,3S)-2-methyl-4-oxo-1-sulfoazetidin-3-yl)amino)-2-oxoethylidene)amino)oxy)-3-oxopropoxy)-1-(3-((tertbutoxycarbonyl)-amino)propyl)-2-methyl-1H-indazol-2-ium. LC/MS: $M^+=991.6$ Step B: Preparation of 1-(3-aminopropyl)-5-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)-2-methyl-1H-indazol-2-ium 2,2,2-trifluoroacetate To the solution of 5-(3-(benzhydryloxy)-2-(((Z)-(1-(2-((tert-butoxycarbonyl)amino)thiazol-4-yl)-2-(((2S,3S)-2-methyl-4-oxo-1-sulfoazetidin-3-yl)amino)-2-oxoethylidene)amino)oxy)-3-oxopropoxy)-1-(3-((tert-butoxycarbonyl)amino)propyl)-2-methyl-1H-indazol-2-ium (42 mg, 0.042 mmol) in DCM (2 ml) was added TFA (2 mL, 26 mmol). The resulting solution was stirred at room temperature for 30 minutes. The solution was concentrated and the residue was purified on reverse phase HPLC using acetonitrile (0.05% TFA)/water (0.0-5% TFA) to give 1-(3-aminopropyl)-5-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)-2-methyl-1H-indazol-2-ium 2,2,2-trifluoroacetate (the more polar diastereomer). LC/MS: $(M+1)^+=625.4$, $^1$HNMR (500 MHz, CD$_3$OD): δ 8.86 (s, 1H), 7.82-7.80 (d, J 9.8 Hz, 1H), 7.57-7.55 (d, J 9.8 Hz, 1H), 7.48 (s, 1H), 6.90 (s, 1H), 5.20 (s, 1H), 4.81-4.66 (m, 2H), 4.42 (s, 3H), 4.16-4.15 (d, J 1.7 Hz, 1H), 3.81-3.77 (m, 1H), 3.13-3.10 (t, J 7.6 Hz, 2H), 2.32-2.22 (m, 2H), 1.43 (d, J 6.9 Hz, 3H).

Examples 37 and 38
(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylmethyl)imidazo[1,2-a]pyridin-6-yl)oxy)propanoic acid, 2,2,2-trifluoroacetate salt (C37) and (R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylmethyl)imidazo[1,2-a]pyridin-6-yl)oxy)propanoic acid, 2,2,2-trifluoroacetate salt (C38)
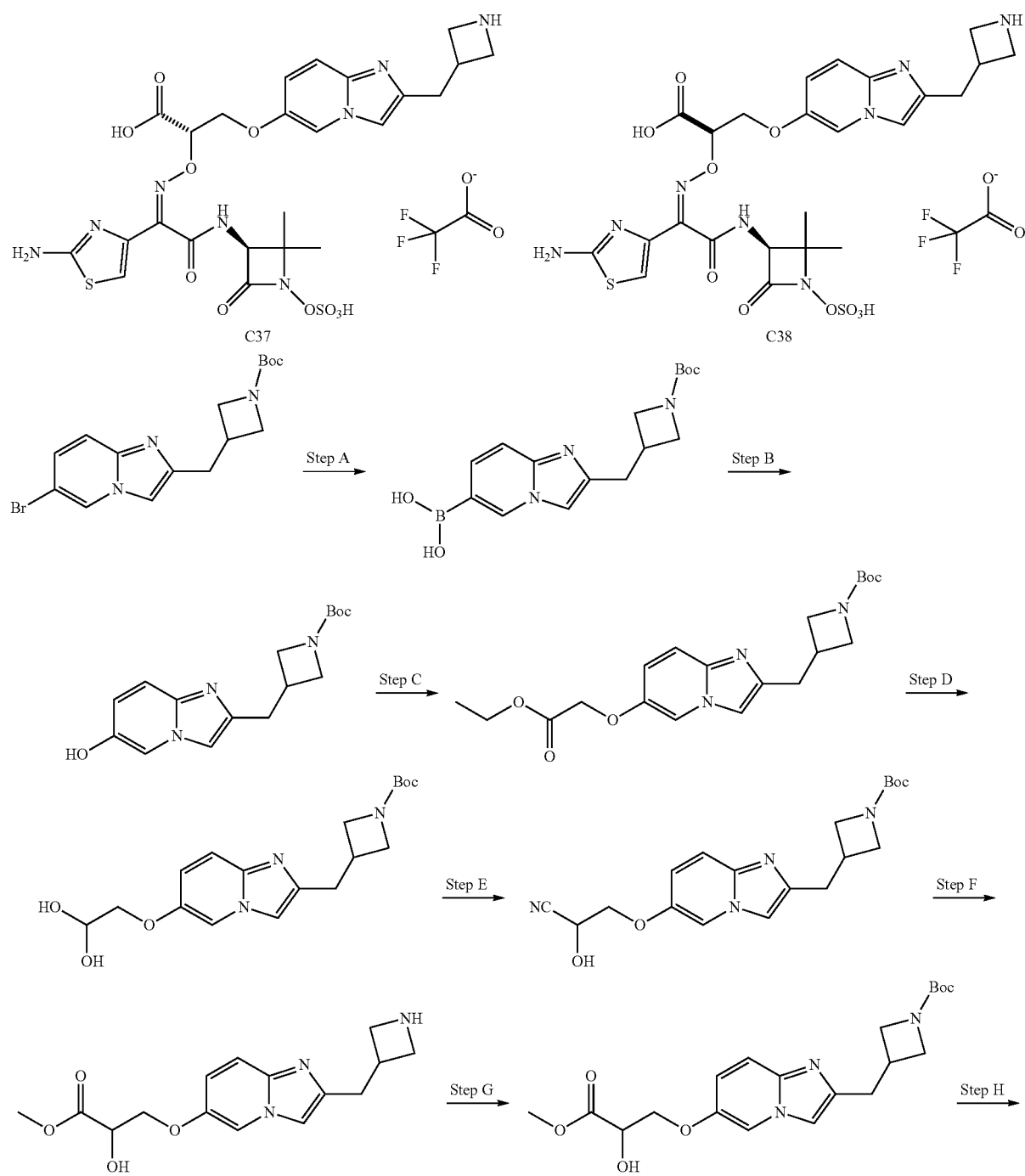

-continued
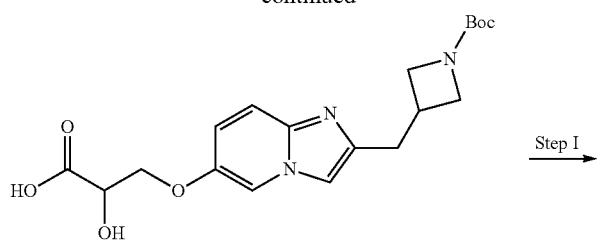
Step I
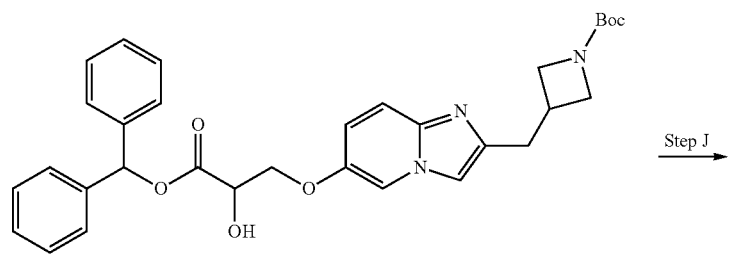
Step J
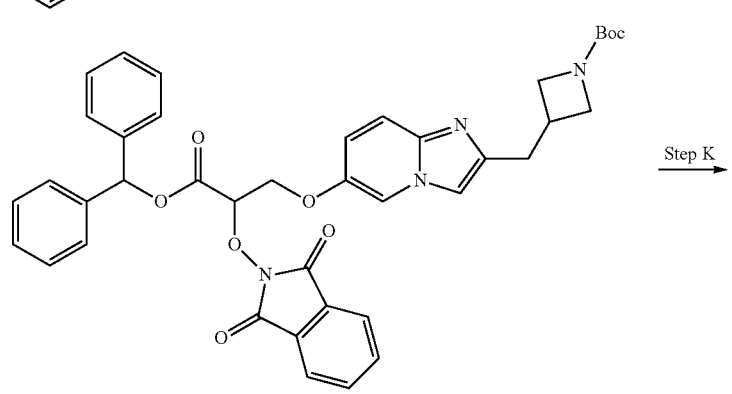
Step K
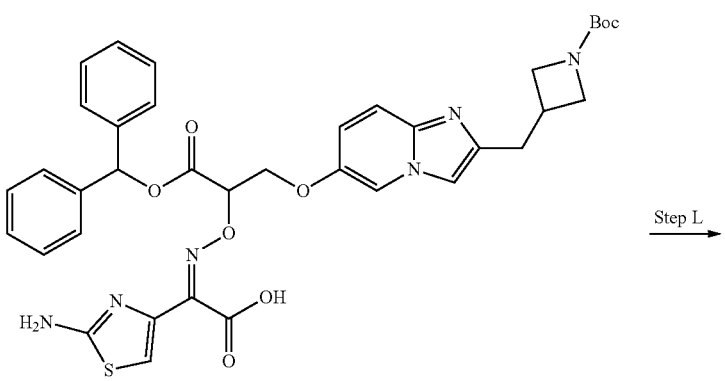
Step L
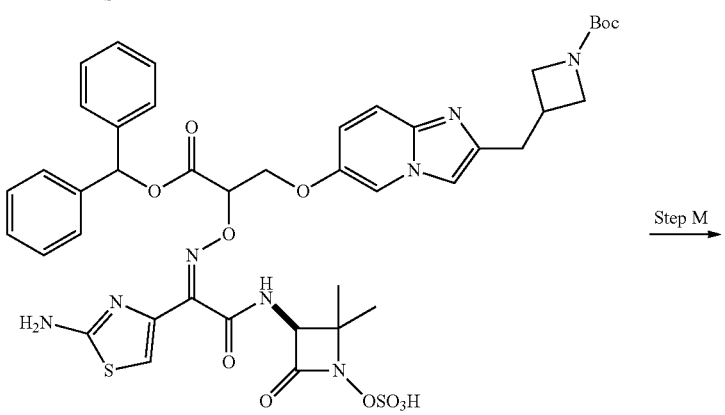
Step M

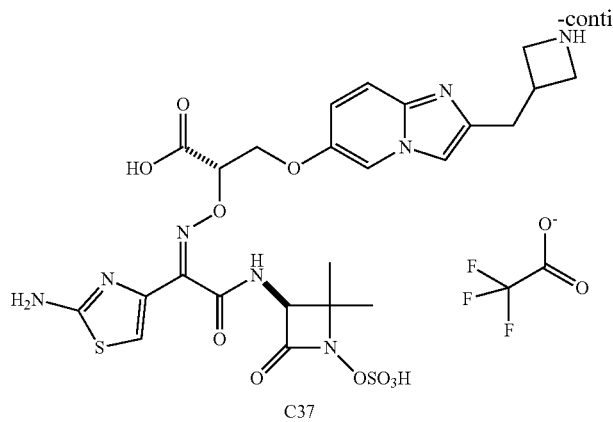

C37

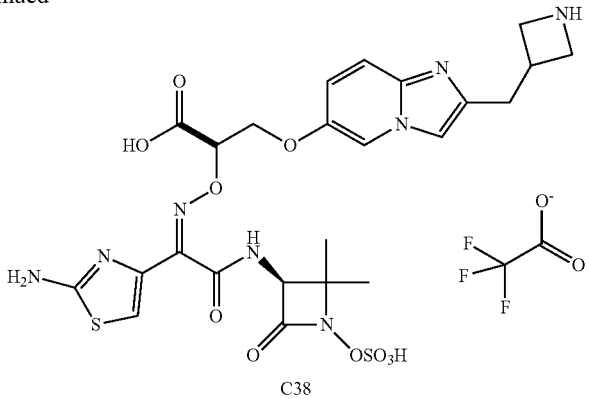

C38

Step A: Preparation of (2-((1-(tert-butoxycarbonyl) azetidin-3-yl)methyl)imidazo[1,2-a]pyridin-6-yl) boronic Acid A mixture of potassium acetate (178 mg, 1.8 mmol), PdCl$_2$ (dppf)-CH$_2$Cl$_2$ adduct (49 mg, 0.060 mmol), bis(pinacolato)diboron (184 mg, 0.72 mmol), and tert-butyl 3-((6-bromoimidazo[1,2-a]pyridin-2-yl)methyl)azetidine-1-carboxylate (Int. 6) (221 mg, 0.60 mmol) was degassed by vacuum/N$_2$ refill three times in a microwave vessel, followed by addition of dioxane (4 ml). The resulting mixture was further degassed by vacuum/N$_2$ refill three times, and then heated at 100° C. overnight. After filtration of the mixture through CELITE, the filtrate was concentrated and the residue was purified on reverse phase MPLC (150 g column) using acetonitrile (0.05% TFA)/water (0.05% TFA) as mobile phase to give (2-((1-(tert-butoxycarbonyl)azetidin-3-yl)methyl)-imidazo[1,2-a]pyridin-6-yl)boronic acid. LC/MS: (M+1)$^+$=332.2

Step B: Preparation of Tert-Butyl 3-((6-hydroxyimidazo[1,2-a]pyridin-2-yl)methyl)azetidine-1-carboxylate To the solution of (2-((1-(tert-butoxycarbonyl)azetidin-3-yl)methyl)imidazo-[1,2-a]pyridin-6-yl)boronic acid (950 mg, 2.9 mmol) in THF (40 ml) and ethanol (20 mL) at 0° C. was added sodium bicarbonate (1400 mg, 17 mmol) and hydrogen peroxide (1.2 ml, 11.5 mmol). The resulting mixture was stirred at 0° C. to room temperature overnight. The reaction was quenched by addition of saturated thiosulfate (100 mL), and then the volatile was evaporated and the aqueous phase was extracted with DCM (3×100 mL). The combined organic phase was dried over Na$_2$SO$_4$, concentrated and the residue was purified on silica gel column using MeOH/DCM as eluting solvents to give tert-butyl 3-((6-hydroxyimidazo[1,2-a]pyridin-2-yl)methyl)azetidine-1-carboxylate. LC/MS: (M+1)=304.2

Step C: Preparation of Tert-Butyl 3-((6-(2-ethoxy-2-oxoethoxy)imidazo[1,2-a]pyridin-2-yl)-methyl)azetidine-1-carboxylate To the solution of tert-butyl 3-((6-hydroxyimidazo[1,2-a]pyridin-2-yl)methyl)azetidine-1-carboxylate (0.5 g, 1.6 mmol) in ethyl acetate (20 ml) was added potassium carbonate (0.46 g, 3.3 mmol) and ethyl bromoacetate (0.18 ml, 1.6 mmol). The resulting mixture was heated at 60° C. overnight. After filtration through CELITE, the residue was purified on silica gel column using MeOH/DCM to give tert-butyl 3-((6-(2-ethoxy-2-oxoethoxy)imidazo[1,2-a]pyridin-2-yl)methyl)azetidine-1-carboxylate. LC/MS: (M+1)$^+$=390.3

Step D: Preparation of Tert-Butyl 3-((6-(2,2-dihydroxyethoxy)imidazo[1,2-a]pyridin-2-yl)methyl)azetidine-1-carboxylate To the solution of tert-butyl 3-((6-(2-ethoxy-2-oxoethoxy)imidazo[1,2-a]pyridin-2-yl)methyl)azetidine-1-carboxylate (405 mg, 1.04 mmol) in DCM (12 ml) at −78° C. was added DIBAL-H (1M in DCM) (2.1 ml, 2.1 mmol). The resulting solution was stirred at −78° C. for 5 hours. The reaction was quenched by addition of MeOH (4 mL) and saturated potassium tartrate (50 mL). The mixture was stirred at room temperature overnight. The solid was collected by filtration and the filtrate was extracted with 30% IPA in DCM (3×150 mL). The combined organic phase was dried over Na$_2$SO$_4$, concentrated to give tert-butyl 3-((6-(2,2-dihydroxyethoxy)imidazo[1,2-a]pyridin-2-yl)methyl)azetidine-1-carboxylate. LC/MS: (M+1)$^+$=364.3

Step E: Preparation of Tert-Butyl 3-((6-(2-cyano-2-hydroxyethoxy)imidazo[1,2-a]pyridin-2-yl)methyl)azetidine-1-carboxylate To the solution of tert-butyl 3-((6-(2,2-dihydroxy-ethoxy)imidazo[1,2-a]pyridin-2-yl)methyl)azetidine-1-carboxylate (0.52 g, 1.4 mmol) in methyl tert-butyl ether (10 ml), acetic acid (2 ml), and water (2 ml) was added sodium cyanide (0.10 g, 2.1 mmol). The resulting solution was stirred at room temperature overnight. The solution was added to ice, cooled saturated Na$_2$CO$_3$ (150 mL), and the mixture was extracted with EtOAc (100 mL) and 30% IPA in DCM (2×100 mL). The combined organic phase was dried over Na$_2$SO$_4$, concentrated and the residue was purified on a silica gel column using MeOH/DCM as eluting solvents to give tert-butyl 3-((6-(2-cyano-2-hydroxy-ethoxy)imidazo[1,2-a]pyridin-2-yl)methyl)azetidine-1-carboxylate. LC/MS: (M+1)$^+$=373.3

Step F: Preparation of Methyl 3-((2-(azetidin-3-ylmethyl)imidazo[1,2-a]pyridin-6-yl)oxy)-2-hydroxypropanoate A solution of tert-butyl 3-((6-(2-cyano-2-hydroxyethoxy)imidazo[1,2-a]pyridin-2-yl)methyl)azetidine-1-carboxylate (0.17 g, 0.46 mmol) in MeOH (10 ml) at 0° C. was bubbled with HCl (gas) for 10 minutes. The resulting solution was stirred from 0° C. to room temperature overnight. The solution was concentrated to give methyl 3-((2-(azetidin-3-ylmethyl)imidazo[1,2-a]pyridin-6-yl)oxy)-2-hydroxypropanoate. LC/MS: (M+1)=306.2

Step G: Preparation of Tert-Butyl 3-((6-(2-hydroxy-3-methoxy-3-oxopropoxy)imidazo[1,2-a]pyridin-2-yl)methyl)azetidine-1-carboxylate To the mixture of methyl 3-((2-(azetidin-3-ylmethyl)imidazo[1,2-a]pyridin-6-yl)oxy)-2-hydroxypropanoate (140 mg, 0.46 mmol) in $CH_2Cl_2$ (12 ml) was added $Boc_2O$ (0.14 ml, 0.59 mmol), water (24 ml), dioxane (12.00 ml), and triethylamine (0.317 mL, 2.276 mmol). The resulting mixture was stirred at room temperature for 2 hours. The mixture was concentrated to give tert-butyl 3-((6-(2-hydroxy-3-methoxy-3-oxopropoxy)imidazo[1,2-a]pyridin-2-yl)methyl)azetidine-1-carboxylate. LC/MS: (M+1)$^+$=406.3

Step H: 3-((2-((1-(tert-butoxycarbonyl)azetidin-3-yl)methyl)imidazo[1,2-a]pyridin-6-yl)oxy)-2-hydroxypropanoic Acid To the solution of tert-butyl 3-((6-(2-hydroxy-3-methoxy-3-oxopropoxy)imidazo[1,2-a]pyridin-2-yl)methyl)azetidine-1-carboxylate (185 mg, 0.46 mmol) in THF (20 ml), MeOH (20 ml), and water (10 ml) was added NaOH (6 ml, 6.00 mmol). The resulting solution was stirred at room temperature for 2 hours. After evaporating the volatiles, the aqueous phase was acidified to pH 3 by 1N HCl. The mixture was lyophilized, and the residue was then purified on reverse phase MPLC using acetonitrile (0.05% TFA)/water (0.05% TFA) as mobile phase to give 3-((2-((1-(tert-butoxycarbonyl)-azetidin-3-yl)methyl)imidazo[1,2-a]pyridin-6-yl)oxy)-2-hydroxypropanoic acid. LC/MS: (M+1)$^+$=392.3

Step I: Preparation of Tert-Butyl 3-((6-(3-(benzhydryloxy)-2-hydroxy-3-oxopropoxy)-imidazo[1,2-a]pyridin-2-yl)methyl)azetidine-1-carboxylate To the solution of 3-((2-((1-(tert-butoxycarbonyl)azetidin-3-yl)methyl)imidazo[1,2-a]pyridin-6-yl)oxy)-2-hydroxypropanoic acid (82 mg, 0.21 mmol) in MeOH (5 ml) was added diphenyl diazomethane (205 mg, 1.05 mmol). The resulting mixture was stirred at room temperature for 2 hours. The mixture was concentrated and the residue was purified on silica gel using MeOH/DCM as eluting solvents to give tert-butyl 3-((6-(3-(benzhydryloxy)-2-hydroxy-3-oxopropoxy)imidazo[1,2-a]pyridin-2-yl)methyl)azetidine-1-carboxylate. LC/MS: (M+1)$^+$=558.4

Step J: Preparation of Tert-Butyl 3-((6-(3-(benzhydryloxy)-2-((1,3-dioxoisoindolin-2-yl)oxy)-3-oxopropoxy)imidazo[1,2-a]pyridin-2-yl)methyl)azetidine-1-carboxylate To the solution of tert-butyl 3-((6-(3-(benzhydryloxy)-2-hydroxy-3-oxopropoxy)imidazo[1,2-a]pyridin-2-yl)methyl)azetidine-1-carboxylate (47 mg, 0.084 mmol) in THF (2 ml) was added 2-hydroxyisoindoline-1,3-dione (16.50 mg, 0.101 mmol), triphenylphosphine (33.2 mg, 0.126 mmol), and DEAD (0.020 ml, 0.126 mmol). The resulting solution was stirred at room temperature for 2 hours. The solution was concentrated and the residue was purified on silica gel column using MeOH/DCM as eluting solvents to give tert-butyl 3-((6-(3-(benzhydryloxy)-2-((1,3-dioxoisoindolin-2-yl)oxy)-3-oxopropoxy)imidazo[1,2-a]pyridin-2-yl)methyl)azetidine-1-carboxylate. LC/MS: (M+1)$^+$=703.4

Step K: Preparation of (Z)-2-(((1-(benzhydryloxy)-3-((2-((1-(tert-butoxycarbonyl)azetidin-3-yl)methyl)imidazo[1,2-a]pyridin-6-yl)oxy)-1-oxopropan-2-yl)oxy)imino)-2-(2-((tert-butoxycarbonyl)amino)thiazol-4-yl)acetic Acid To the solution of tert-butyl 3-((6-(3-(benzhydryloxy)-2-((1,3-dioxoisoindolin-2-yl)oxy)-3-oxopropoxy)imidazo[1,2-a]pyridin-2-yl)methyl)azetidine-1-carboxylate (29 mg, 0.041 mmol) in $CH_2Cl_2$ (2 ml) and EtOH (2 ml) was added hydrazine (2.6 µl, 0.081 mmol). The resulting solution was stirred at room temperature for 5 hours. Then 2-(2-((tert-butoxycarbonyl)amino)thiazol-4-yl)-2-oxoacetic acid (intermediate 3) (33 mg, 0.12 mmol) was added to the above solution and the resulting solution was stirred at room temperature for 1 hour. The solution was then concentrated and the residue was purified on reverse phase MPLC using acetonitrile (0.05% TFA)/water (0.05% TFA) to give (Z)-2-(((1-(benzhydryloxy)-3-((2-((1-(tert-butoxycarbonyl)azetidin-3-yl)methyl)imidazo[1,2-a]pyridin-6-yl)oxy)-1-oxopropan-2-yl)oxy)imino)-2-(2-((tert-butoxycarbonyl)amino)thiazol-4-yl)acetic acid. LC/MS: (M+1)$^+$=827.4

Step L: Preparation of Tert-Butyl 3-((6-(3-(benzhydryloxy)-2-(((Z)-(1-(2-((tert-butoxy-carbonyl)-amino)thiazol-4-yl)-2-(((S)-2,2-dimethyl-4-oxo-1-(sulfooxy)azetidin-3-yl)amino)-2-oxo-ethylidene)amino)oxy)-3-oxopropoxy)imidazo[1,2-a]pyridin-2-yl)methyl)azetidine-1-carboxylate To the solution of (Z)-2-(((1-(benzhydryloxy)-3-((2-((1-(tert-butoxycarbonyl)azetidin-3-yl)methyl)-imidazo[1,2-a]pyridin-6-yl)oxy)-1-oxopropan-2-yl)oxy)imino)-2-(2-((tert-butoxycarbonyl)-amino)thiazol-4-yl)acetic acid (36 mg, 0.043 mmol) in DMF (2 ml) was added DCC (71 mg, 0.34 mmol) and HOBt (26 mg, 0.17 mmol). The resulting mixture was stirred at room temperature for 30 minutes, and then (S)-3-amino-2,2-dimethyl-4-oxoazetidin-1-yl hydrogen sulfate (36 mg, 0.17 mmol) and sodium bicarbonate (72 mg, 0.86 mmol) were added. The resulting mixture was stirred at room temperature for 6 hours. After filtration the filtrate was purified on reverse phase HPLC using acetonitrile (0.05% TFA)/water (0.0% TFA) as mobile phase to give tert-butyl 3-((6-(3-(benzhydryloxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)imidazo[1,2-a]pyridin-2-yl)methyl)azetidine-1-carboxylate. LC/MS: (M+1)$^+$=1019.8

Step M: Preparation of (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-yl-methyl)-imidazo[1,2-a]pyridin-6-yl)oxy)propanoic acid, 2,2,2-trifluoroacetate salt and (R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylmethyl)imidazo[1,2-a]pyridin-6-yl)oxy)-propanoic acid, 2,2,2-trifluoroacetate Salt To the solution of tert-butyl 3-((6-(3-(benzhydryloxy)-2-((((Z)-(1-(2-((tert-butoxycarbonyl)amino)thiazol-4-yl)-2-

(((S)-2,2-dimethyl-4-oxo-1-(sulfooxy)azetidin-3-yl)amino)-2-oxoethylidene)amino)oxy)-3-oxopropoxy)imidazo-[1,2-a]pyridin-2-yl)methyl)azetidine-1-carboxylate (16 mg, 0.016 mmol) in CH$_2$Cl$_2$ (2 ml) was added TFA (2 mL, 26 mmol). The resulting solution was stirred at room temperature for 1 hour. After concentration, the residue was purified on reverse phase HPLC using acetonitrile (0.05% TFA)/water (0.05% TFA) to give:

Compound 37: (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylmethyl)imidazo[1,2-a]pyridin-6-yl)oxy)propanoic acid, 2,2,2-trifluoroacetate salt (the fast eluting diastereomer). LC/MS: (M+1)$^+$=653.16, $^1$NMR (D$_2$O, 500 MHz): δ 8.56 (s, 1H), 7.68 (s, 1H), 7.62-7.60 (d, J 10.0 Hz, 1H), 7.55-7.53 (d, J 10.0 Hz, 1H), 6.99 (s, 1H), 5.00 (s, 1H), 4.67 (s, 1H), 4.45-4.40 (m, 2H), 4.16-4.13 (t, J 10.3 Hz, 2H), 3.91-3.87 (t, J 9.3 Hz, 2H), 3.36-3.29 (m, 1H), 3.16-3.14 (d, J 7.9 Hz, 2H), 1.37 (s, 3H), 1.04 (s, 3H); and Compound 38: (R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(azetidin-3-ylmethyl)imidazo[1,2-a]pyridin-6-yl)oxy)propanoic acid, 2,2,2-trifluoroacetate salt (the slow eluting diastereomer). LC/MS: (M+1)$^+$=653.16, $^1$NMR (D$_2$O, 500 MHz): δ 8.19 (d, J 1.2 Hz, 1H), 7.72 (s, 1H), 7.63-7.61 (d, J 9.1 Hz, 1H), 7.57-7.54 (dd, J 9.1 Hz and 2.4 Hz, 1H), 6.98 (s, 1H), 4.96 (s, 1H), 4.68 (s, 1H), 4.43-4.42 (m, 2H), 4.16-4.13 (t, J 9.5 Hz, 2H), 3.91-3.87 (t, J 8.8 Hz, 2H), 3.36-3.14 (d, J 8.0 Hz, 2H), 1.36 (s, 3H), 1.07 (s, 3H).

Examples 39 and 40

6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate (C3 9) and 6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate (C40)

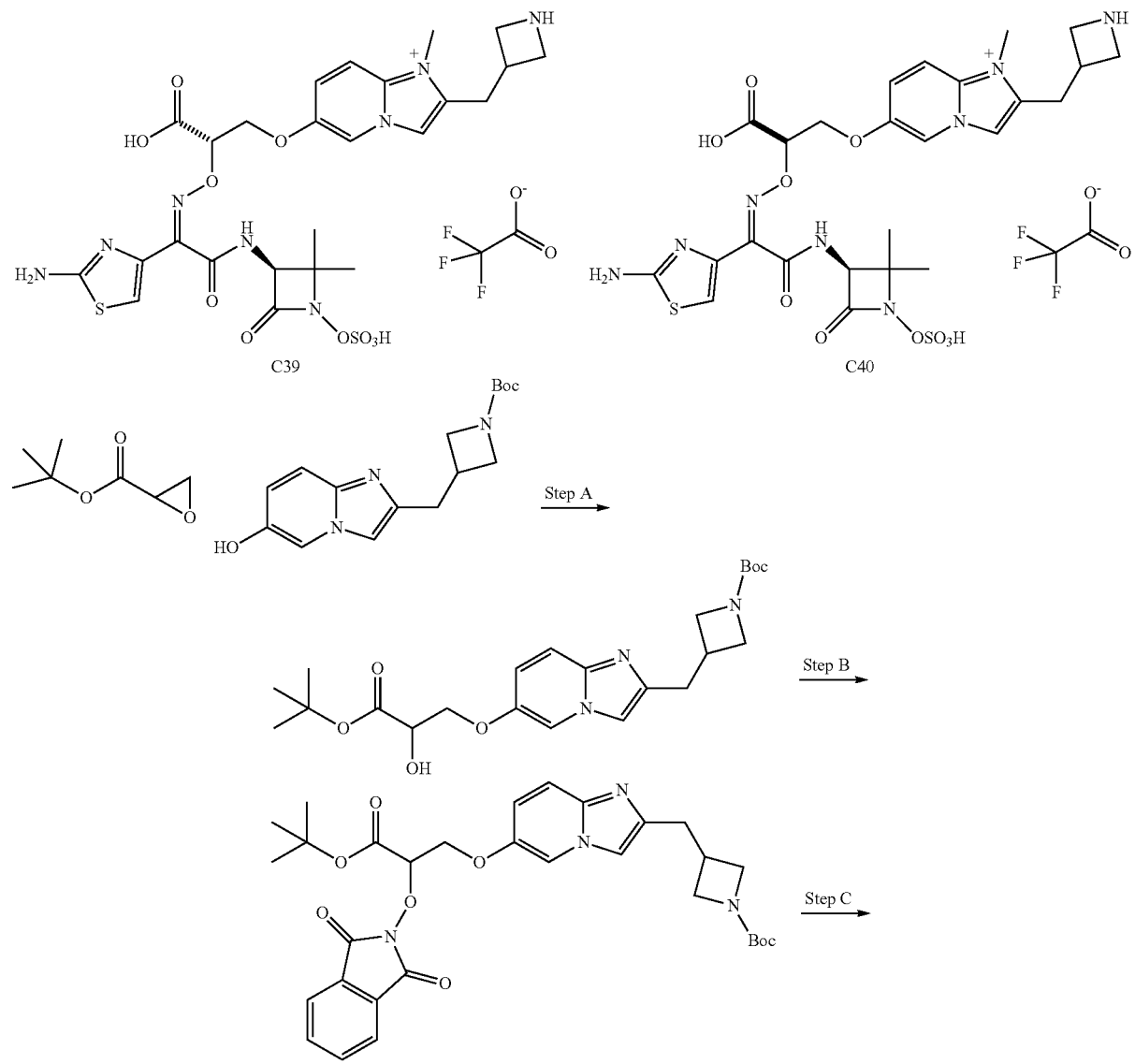

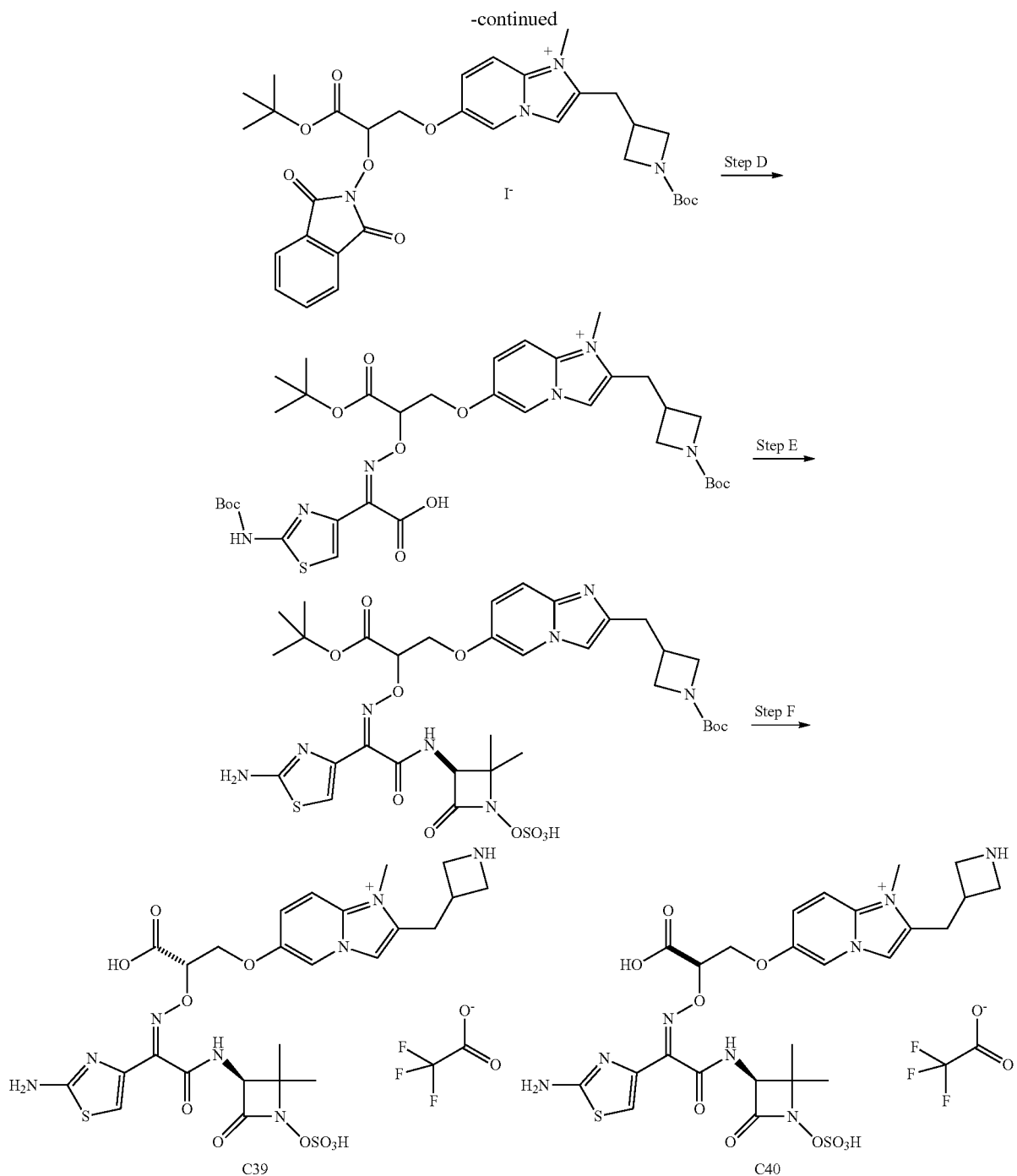

Step A: Preparation of Tert-Butyl 3-((6-(3-(tert-butoxy)-2-hydroxy-3-oxopropoxy)imidazo-[1,2-a]pyridin-2-yl)methyl)azetidine-1-carboxylate To a suspension of tert-butyl 3-((6-hydroxyimidazo[1,2-a]pyridin-2-yl)methyl)azetidine-1-carboxylate (step B of Examples 37 and 38) (1.1 g, 3.6 mmol) and tert-butyl oxirane-2-carboxylate (2.1 g, 14.5 mmol) in t-BuOMe (6 ml) was added lithium chloride (0.15 g, 3.6 mmol) and NaH (0.29 g, 7.2 mmol, 60%). The resulting mixture was heated at 50° C. overnight, and then additional sodium hydride (0.145 g) and tert-butyl oxirane-2-carboxylate (1.04 g) was added and the resulting mixture was heated at 50° C. for 3 days. The reaction mixture was quenched by addition of saturated $NaHCO_3$ (100 mL) dropwise. The mixture was then extracted with DCM (3×70 mL), and the combined organic phase was dried over $Na_2SO_4$ and concentrated. The residue was purified on silica gel column using MeOH/DCM as eluting solvents to give tert-butyl 3-((6-(3-(tert-butoxy)-2-hydroxy-3-oxopropoxy)imidazo[1,2-a]pyridin-2-yl)methyl)azetidine-1-carboxylate. LC/MS: $(M+1)^+$=448.3

Step B: Preparation of Tert-Butyl 3-((6-(3-(tert-butoxy)-2-((1,3-dioxoisoindolin-2-yl)oxy)-3-oxopropoxy)imidazo[1,2-a]pyridin-2-yl)methyl)azetidine-1-carboxylate To the solution of tert-butyl 3-((6-(3-(tert-butoxy)-2-hydroxy-3-oxopropoxy)imidazo[1,2-a]pyridin-2-yl)methyl)azetidine-1-carboxylate (310 mg, 0.69 mmol) in THF (4 ml) was added 2-hydroxyisoindoline-1,3-dione (136 mg, 0.83 mmol), triphenylphosphine (273 mg, 1.039 mmol), and DEAD (0.165 ml, 1.04 mmol). The resulting solution was stirred at room temperature for 2 hours. After concentration, the residue was purified on silica gel column using MeOH/DCM as eluting solvents to give tert-butyl 3-((6-(3-(tert-butoxy)-2-((1,3-dioxoisoindolin-2-yl)oxy)-3-oxopropoxy)imidazo[1,2-a]pyridin-2-yl)methyl)azetidine-1-carboxylate. LC/MS: $(M+1)^+=593.1$ Step C: Preparation of 6-(3-(tert-butoxy)-2-((1,3-dioxoisoindolin-2-yl)oxy)-3-oxopropoxy)-2-((1-(tert-butoxycarbonyl)azetidin-3-yl)methyl)-1-methylimidazo[1,2-a]pyridin-1-ium Iodide To the solution of tert-butyl 3-((6-(3-(tert-butoxy)-2-((1,3-dioxoisoindolin-2-yl)oxy)-3-oxopropoxy)imidazo[1,2-a]pyridin-2-yl)methyl)azetidine-1-carboxylate (0.37 g, 0.62 mmol) in acetonitrile (8 ml) was added MeI (0.12 ml, 1.9 mmol). The resulting solution was heated at 60° C. for 20 hours. The solution was concentrated to give 6-(3-(tert-butoxy)-2-((1,3-dioxoisoindolin-2-yl)oxy)-3-oxopropoxy)-2-((1-(tert-butoxycarbonyl)azetidin-3-yl)methyl)-1-methylimidazo[1,2-a]pyridin-1-ium iodide. LC/MS: $M^+=607.4$ Step D: Preparation of (Z)-6-(3-(tert-butoxy)-2-((((2-((tert-butoxycarbonyl)amino)thiazol-4-yl)(carboxy)methylene)amino)oxy)-3-oxopropoxy)-2-((1-(tert-butoxycarbonyl)azetidin-3-yl)methyl)-1-methylimidazo[1,2-a]pyridin-1-ium To the solution of 6-(3-(tert-butoxy)-2-((1,3-dioxoisoindolin-2-yl)oxy)-3-oxopropoxy)-2-((1-(tert-butoxycarbonyl)azetidin-3-yl)methyl)-1-methylimidazo[1,2-a]pyridin-1-ium iodide (0.47 g, 0.64 mmol) in ethanol (8 ml) and $CH_2Cl_2$ (8 ml) was added hydrazine (0.030 ml, 0.96 mmol). The resulting solution was stirred at room temperature for 2 hours. Then 2-(2-((tert-butoxycarbonyl)amino)thiazol-4-yl)-2-oxoacetic acid (intermediate 3) (0.26 g, 0.96 mmol) was added to the above mixture.

The resulting mixture was stirred at room temperature for 2 hours, and the solution was concentrated and the residue was purified on reverse phase MPLC using acetonitrile (0.05% TFA)/water (0.05% TFA) as mobile phase to give (Z)-6-(3-(tert-butoxy)-2-((((2-((tert-butoxycarbonyl)amino)thiazol-4-yl)(carboxy)methylene)amino)oxy)-3-oxopropoxy)-2-((1-(tert-butoxycarbonyl)azetidin-3-yl)methyl)-1-methylimidazo[1,2-a]pyridin-1-ium. LC/MS: $M+=731.3$ Step E: Preparation of 6-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)-oxy)-3-oxopropoxy)-2-((1-(tert-butoxycarbonyl)azetidin-3-yl)methyl)-1-methylimidazo[1,2-a]pyridin-1-ium To the solution of (Z)-6-(3-(tert-butoxy)-2-((((2-((tert-butoxycarbonyl)-amino)thiazol-4-yl)(carboxy)methylene)amino)oxy)-3-oxopropoxy)-2-((1-(tert-butoxy-carbonyl)azetidin-3-yl)methyl)-1-methylimidazo[1,2-a]pyridin-1-ium (120 mg, 0.16 mmol) in DMF (4 ml) was added DCC (270 mg, 1.3 mmol) and HOBt (100 mg, 0.66 mmol). The resulting mixture was stirred at room temperature for 30 minutes before addition of (S)-3-amino-2,2-dimethyl-4-oxoazetidin-1-yl hydrogen sulfate (138 mg, 0.66 mmol) and sodium bicarbonate (275 mg, 3.3 mmol). The resulting mixture was stirred at room temperature overnight. After filtration, the filtrate was purified on reverse MPLC using acetonitrile (0.05% TFA)/water (0.05% TFA) as mobile phase to give 6-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxy-carbonyl)-azetidin-3-yl)methyl)-1-methylimidazo[1,2-a]pyridin-1-ium. LC/MS: $(M+1)^+/2=462.4$ Step F: Preparation of 6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate and 6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate To the solution of 6-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-azetidin-3-yl)methyl)-1-methylimidazo[1,2-a]pyridin-1-ium (106 mg, 0.115 mmol) in $CH_2Cl_2$ (2 ml) was added TFA (4 mL, 51.9 mmol). The resulting solution was stirred at room temperature for 50 minutes. The solution was concentrated and the residue was treated with $Et_2O$. The solid was collected and dried over high vacuum. The residue was then dissolved in DMSO (2 mL) and purified on reverse phase HPLC using acetonitrile (0.05% TFA)/water (0.05% TFA) as mobile phase to give:

Compound 39: 6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate (the fast eluent), LC/MS: $(M+1)^+=667.1$, $^1$H-NMR (500 MHz, $D_2O$), δ 8.19-8.18 (d, J 2.1 Hz, 1H), 7.73-7.71 (d, J 11.0 Hz, 2H), 7.62-7.59 (dd, J 9.8 Hz and 3.0 Hz, 1H), 7.05 (s, 1H), 5.09-5.07 (m, 1H), 4.68 (s, 1H), 4.50-4.43 (m, 2H), 4.24-4.20 (t, J 11.6 Hz, 2H), 3.95-3.90 (m, 2H), 3.79 (s, 3H), 3.41-3.34 (m, 1H), 3.21-3.19 (d, J=6.2 Hz, 2H), 1.38 (s, 3H), 1.02 (s, 3H).

Compound 40: 6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-2-(azetidin-3-ylmethyl)-1-methylimidazo[1,2-a]pyridin-1-ium 2,2,2-trifluoroacetate (the slow eluent), LC/MS: $(M+1)^+=667.0$. $^1$H-NMR (500 MHz, $D_2O$), δ 8.21-8.20 (d, J 2.8 Hz, 1H), 7.75-7.73 (t, J 4.9 Hz, 2H), 7.64-7.61 (dd, J 10.3 Hz and 2.8 Hz, 2H), 7.05 (s, 1H), 5.04-5.02 (m, 1H), 4.48-4.44 (m, 2H), 4.25-4.20 (m, 2H), 3.95-3.91 (m, 2H), 3.80 (s, 3H), 3.41-3.34 (m, 1H), 3.21-3.19 (d, J=7.7 Hz, 2H), 1.38 (s, 3H), 1.06 (s, 3H).

Examples 41 and 42

3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1H-benzo[d]imidazol-2-yl)thio)propan-1-aminium 2,2,2-trifluoroacetate (C41) and 3-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1H-benzo[d]imidazol-2-yl)thio)propan-1-aminium 2,2,2-trifluoroacetate (C42)

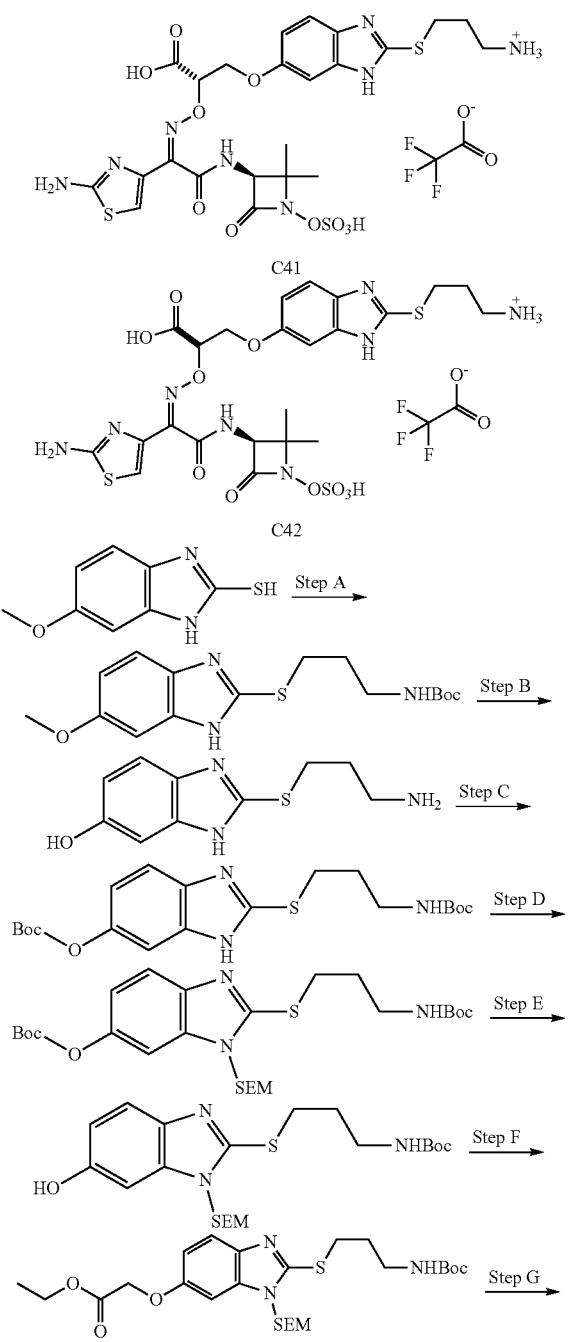

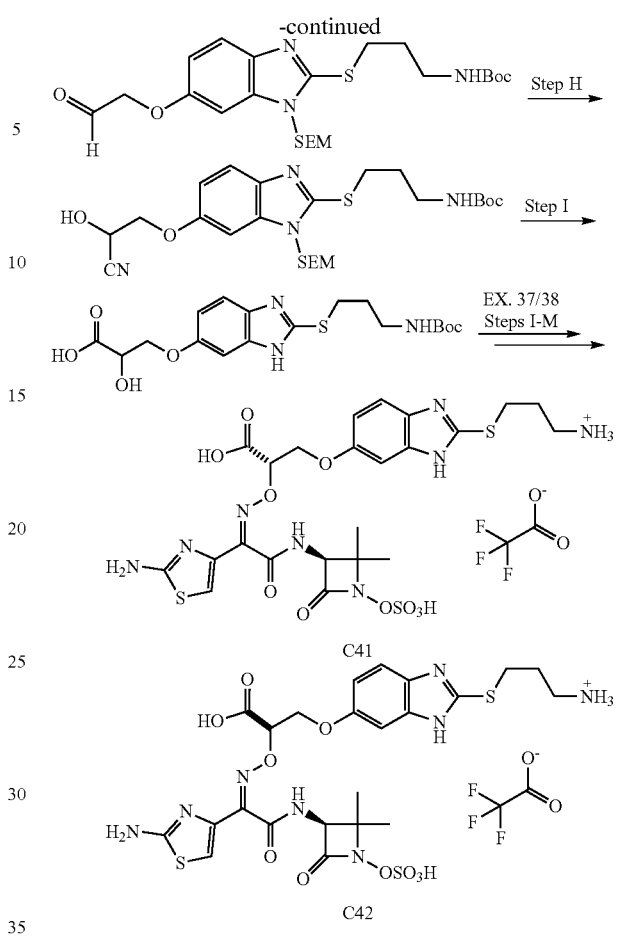

Step A: Preparation of Tert-Butyl (3-((5-methoxy-1H-benzo[d]imidazol-2-yl)thio)propyl)-carbamate To the solution of 5-methoxy-1H-benzo[d]imidazole-2-thiol (1.06 g, 5.9 mmol) in DMF (8 ml) at 0° C. was added sodium bicarbonate (0.49 g, 5.9 mmol), and a solution of tert-butyl (3-iodopropyl)-carbamate (1.7 g, 5.9 mmol) in DMF (6 mL) dropwise. The resulting solution was stirred at 0° C. overnight. The mixture was partitioned between EtOAc and saturated NaHCO$_3$. The organic phase was washed with saturated NaHCO$_3$ three times, dried over Na$_2$SO$_4$, concentrated and the residue was purified on silica gel column using EtOAc/hexane as eluting solvents to give tert-butyl (3-((5-methoxy-1H-benzo[d]imidazol-2-yl)thio)propyl)carbamate. LC/MS: (M+1)$^+$: 338.6

Step B: Preparation of 2-((3-aminopropyl)thio)-1H-benzo[d]imidazol-5-ol

To the solution of tert-butyl (3-((5-methoxy-1H-benzo[d]imidazol-2-yl)thio)propyl)carbamate (2.5 g, 7.3 mmol) in CH$_2$Cl$_2$ (30 ml) at 0° C. was added BBr$_3$ (22 ml, 22 mmol). The resulting solution was stirred at 0° C. for 4 hours, and the reaction was then quenched by addition of MeOH. The mixture was concentrated to give 2-((3-aminopropyl)thio)-1H-benzo[d]imidazol-5-ol. LC/MS: (M+1)$^+$: 224.2

Step C: Preparation of Tert-Butyl (3-((5-((tert-butoxycarbonyl)oxy)-1H-benzo[d]imidazol-2-yl)thio)propyl)carbamate To 2-((3-aminopropyl)thio)-1H-benzo[d]imidazol-5-ol (1.6 g, 7.3 mmol) in dioxane (50 ml) and water (50.0 ml) was added K₂CO₃ (5.1 g, 37 mmol) and Boc₂O (5.6 ml, 24 mmol). The resulting mixture was stirred at room temperature overnight. NaOH (20 ml, 20 mmol) and additional BOC₂O (5.61 ml, 24.16 mmol) was added and the resulting mixture was stirred at room temperature overnight. After removing the volatiles, to the aqueous phase was added MeOH (40 mL) and THF (80 mL) and NaOH (1N, 80 mL). The resulting solution was stirred at room temperature for 0.5 hour. After removing the volatile, the aqueous phase was extracted with DCM three times, and the combined organic phase was dried over Na₂SO₄ and concentrated. The residue was purified on silica gel column using EtOAc/hexane as eluting solvents to give tert-butyl (3-((5-((tert-butoxy-carbonyl)oxy)-1H-benzo[d]imidazol-2-yl)thio)propyl)carbamate. LC/MS: (M+1)⁺: 424.3

Step D: Preparation of Tert-Butyl (3-((5-((tert-butoxycarbonyl)oxy)-1-((2-(trimethylsilyl)-ethoxy)methyl)-1H-benzo[d]imidazol-2-yl)thio)propyl)carbamate To the solution of tert-butyl (3-((5-((tert-butoxycarbonyl)oxy)-1H-benzo[d]imidazol-2-yl)thio)propyl)carbamate (0.73 g, 1.7 mmol) in DCM (50 ml) at 0° C. was added DIEA (0.60 ml, 3.4 mmol), and SEM-Cl (0.37 ml, 2.1 mmol). The resulting solution was stirred from 0° C. to room temperature for 8 hours. The solution was partitioned between DCM and saturated NaHCO₃, and the aqueous phase was extracted with DCM. The combined organic phase was dried over Na₂SO₄ and concentrated. The residue was purified on a silica gel column using EtOAc/hexane as eluting solvents to give tert-butyl (3-((5-((tert-butoxycarbonyl)oxy)-1-((2-(trimethylsilyl)ethoxy)methyl)-1H-benzo[d]imidazol-2-yl)thio)propyl)carbamate. LC/MS: (M+1)⁺: 554.5

Step E: Preparation of Tert-Butyl (3-((5-hydroxy-1-((2-(trimethylsilyl)ethoxy)methyl)-1H-benzo[d]imidazol-2-yl)thio)propyl)carbamate To the solution of tert-butyl (3-((5-((tert-butoxycarbonyl)oxy)-1-((2-(trimethylsilyl)ethoxy)methyl)-1H-benzo[d]imidazol-2-yl)thio)propyl)carbamate (0.91 g, 1.6 mmol) in THF (10 ml) and MeOH (20 ml) was added NaOH (6.6 ml, 6.6 mmol). The resulting solution was stirred at room temperature for 4 hours. After concentration, the aqueous phase was acidified to pH 8, and then saturated NaHCO₃ (100 mL) was added. The mixture was extracted with DCM three times. The combined organic phase was dried over Na₂SO₄ and concentrated to give tert-butyl (3-((5-hydroxy-1-((2-(trimethylsilyl)ethoxy)methyl)-1H-benzo[d]imidazol-2-yl)thio)propyl)-carbamate. LC/MS: (M+1)⁺: 454.8

Step F: Preparation of Ethyl 2-((2-((3-((tert-butoxycarbonyl)amino)propyl)thio)-1-((2-(trimethylsilyl)ethoxy)methyl)-1H-benzo[d]imidazol-5-yl)oxy)acetate A mixture of K₂CO₃ (0.43 g, 3.1 mmol), ethyl bromoacetate (0.21 ml, 1.8 mmol), and tert-butyl (3-((5-hydroxy-1-((2-(trimethylsilyl)ethoxy)methyl)-1H-benzo[d]imidazol-2-yl)thio)propyl)carbamate (0.7 g, 1.5 mmol) was heated at 80° C. overnight. After filtration, the filtrate was concentrated and the residue was purified on silica gel column using EtOAc/hexane as eluting solvents to give ethyl 2-((2-((3-((tert-butoxycarbonyl)amino)propyl)thio)-1-((2-(trimethylsilyl)ethoxy)-methyl)-1H-benzo[d]imidazol-5-yl)oxy)acetate. LC/MS: (M+1)⁺: 540.5

Step G: Preparation of Tert-Butyl (3-((5-(2-oxoethoxy)-1-((2-(trimethylsilyl)ethoxy)methyl)-1H-benzo[d]imidazol-2-yl)thio)propyl)carbamate To the solution of ethyl 2-((2-((3-((tert-butoxycarbonyl)amino)propyl)thio)-1-((2-(trimethylsilyl)ethoxy)methyl)-1H-benzo[d]imidazol-5-yl)oxy)acetate (0.71 g, 1.3 mmol) in CH₂Cl₂ (30 ml) at −78° C. was added DIBAL-H (2.6 ml, 2.6 mmol) dropwise. The resulting solution was stirred at −78° C. for 3 hours. The reaction was quenched by addition of MeOH (5 mL) and stirred with saturated potassium tartrate (100 mL) for 3 hours. The mixture was extracted with DCM three times, and the combined organic phase was dried over Na₂SO₄, concentrated to give tert-butyl (3-((5-(2-oxoethoxy)-1-((2-(trimethylsilyl)ethoxy)methyl)-1H-benzo[d]imidazol-2-yl)thio)propyl)carbamate. LC/MS: (M+1+18)⁺: 514.4

Step H: Preparation of Tert-Butyl (3-((5-(2-cyano-2-hydroxyethoxy)-1-((2-(trimethyl-silyl)-ethoxy)methyl)-1H-benzo[d]imidazol-2-yl)thio)propyl)carbamate To a solution of tert-butyl (3-((5-(2-oxoethoxy)-1-((2-(trimethylsilyl)ethoxy)methyl)-1H-benzo[d]imidazol-2-yl)thio)-propyl)carbamate (0.96 g, 1.9 mmol) in t-BuOMe (16 ml) and water (3 ml) at 0° C. was added acetic acid (4 ml) and NaCN (0.19 g, 3.9 mmol). The resulting solution was stirred from 0° C. at room temperature overnight. The solution was added to saturated Na₂CO₃ (200 mL) at 0° C., and the mixture was extracted with EtOAc. The combined organic phase was washed with saturated NaHCO₃, dried over Na₂SO₄, and then concentrated to give tert-butyl (3-((5-(2-cyano-2-hydroxyethoxy)-1-((2-(trimethylsilyl)-ethoxy)methyl)-1H-benzo[d]imidazol-2-yl)thio)propyl)carbamate. LC/MS: (M+1)⁺: 523.4

Step I: Preparation of 3-((2-((3-((tert-butoxycarbonyl)amino)propyl)thio)-1H-benzo[d]imidazol-5-yl)oxy)-2-hydroxypropanoic Acid A solution of tert-butyl (3-((5-(2-cyano-2-hydroxyethoxy)-1-((2-(trimethylsilyl)ethoxy)methyl)-1H-benzo[d]imidazol-2-yl)thio)propyl)carbamate (0.83 g, 1.6 mmol) in MeOH (20 ml) at 0° C. was bubbled with HCl for 15 minutes. Then the resulting solution was stirred from 0° C. to room temperature overnight. Water (5 mL) was added dropwise, and the resulting solution was stirred at room temperature for 0.5 hour, and then heated at reflux for 0.5 hour. After removing the volatiles, the aqueous phase was basified to pH 10 by the addition of saturated NaOH at 0° C. Then dioxane (20 mL) and Boc₂O (0.92 ml, 4.0 mmol) were added and the resulting solution was stirred at room temperature for 2 hours. After removing the volatile, the aqueous phase was extracted with DCM, and then acidified to pH 4. The solution was then purified on reverse phase MPLC using acetonitrile (0.05% TFA)/water (0.05% TFA) to give 3-((2-((3-((tert-butoxycarbonyl)amino)propyl)thio)-1H-benzo[d]imidazol-5-yl)oxy)-2-hydroxypropanoic acid. LC/MS: (M+1)⁺: 412.3

Compounds 41/42 were prepared from 3-((2-((3-((tert-butoxycarbonyl)amino)propyl)thio)-1H-benzo[d]imidazol-5-yl)oxy)-2-hydroxypropanoic acid following steps I-M as described for Compounds 37/38.

Compound 41: 3-((6-((S)-2-(((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1H- benzo[d]imidazol-2-yl)thio)propan-1-aminium 2,2,2-trifluoroacetate (the fast eluting diastereomer). LC/MS: (M+1)$^+$=673.6, $^1$H-NMR (500 MHz, D$_2$O): δ 7.47-7.46 (d, J 8.8 Hz, 1H), 7.10-7.09 (d, J 2.5 Hz, 1H), 7.05-7.03 (dd, J 2.3 Hz and 9.2 Hz, 1H), 7.02 (s, 1H), 8.08-8.07 (m, 1H), 4.61 (s, 1H), 4.50-4.41 (m, 2H), 3.38-3.33 (t, J 7.9 Hz, 2H), 3.10-3.07 (t, J 7.7 Hz, 2H), 2.07-2.04 (m, 2H), 1.32 (s, 3H), 0.99 (s, 3H).

Compound 42: 3-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-1H-benzo[d]imidazol-2-yl)thio)propan-1-aminium 2,2,2-trifluoroacetate (the slow eluted diastereomer). LC/MS: (M+1)$^+$=673.6, $^1$H-NMR (500 MHz, D$_2$O): δ 7.47-7.46 (d, J 9.1 Hz, 1H), 7.11-7.10 (d, J 3.1 Hz, 1H), 7.05-7.03 (dd, J 8.4 Hz and 2.6 Hz, 1H), 7.02 (s, 1H), 5.02-5.00 (m, 1H), 4.62 (s, 1H), 4.47-4.40 (m, 2H), 3.36-3.33 (t, J 8.0 Hz, 2H), 3.10-3.07 (t, J=8.0 Hz, 2H), 2.08-2.02 (m, 2H), 1.31 (s, 3H), 0.93 (s, 3H).

Example 43

3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)benzo[d]thiazol-2-yl)amino)azetidin-1-ium 2,2,2-trifluoroacetate (C43)

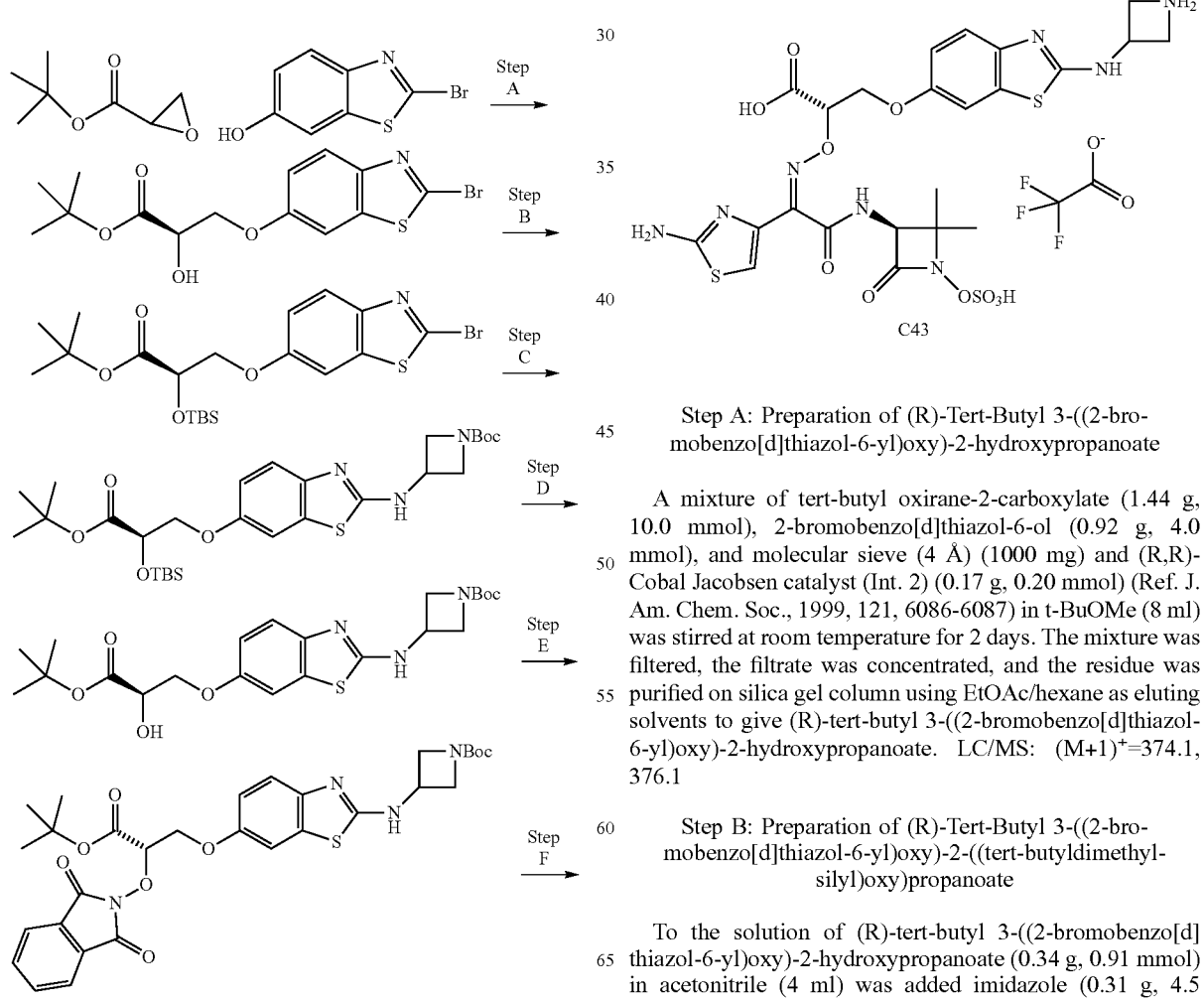

Step A: Preparation of (R)-Tert-Butyl 3-((2-bromobenzo[d]thiazol-6-yl)oxy)-2-hydroxypropanoate A mixture of tert-butyl oxirane-2-carboxylate (1.44 g, 10.0 mmol), 2-bromobenzo[d]thiazol-6-ol (0.92 g, 4.0 mmol), and molecular sieve (4 Å) (1000 mg) and (R,R)-Cobal Jacobsen catalyst (Int. 2) (0.17 g, 0.20 mmol) (Ref. J. Am. Chem. Soc., 1999, 121, 6086-6087) in t-BuOMe (8 ml) was stirred at room temperature for 2 days. The mixture was filtered, the filtrate was concentrated, and the residue was purified on silica gel column using EtOAc/hexane as eluting solvents to give (R)-tert-butyl 3-((2-bromobenzo[d]thiazol-6-yl)oxy)-2-hydroxypropanoate. LC/MS: (M+1)$^+$=374.1, 376.1

Step B: Preparation of (R)-Tert-Butyl 3-((2-bromobenzo[d]thiazol-6-yl)oxy)-2-((tert-butyldimethylsilyl)oxy)propanoate To the solution of (R)-tert-butyl 3-((2-bromobenzo[d]thiazol-6-yl)oxy)-2-hydroxypropanoate (0.34 g, 0.91 mmol) in acetonitrile (4 ml) was added imidazole (0.31 g, 4.5 mmol), TBS-Cl (0.20 g, 1.4 mmol), and DMAP (5.6 mg, 0.045 mmol). The resulting solution was stirred at room temperature for 2 hours. After concentration, the residue was purified on silica gel column using EtOAc/hexane as eluting solvents to give (R)-tert-butyl 3-((2-bromobenzo[d]thiazol-6-yl)oxy)-2-((tert-butyldimethyl-silyl)oxy)propanoate. LC/MS: (M+1)$^+$=488.3, 490.2

Step C: Preparation of (R)-Tert-Butyl 3-((6-(3-(tert-butoxy)-2-((tert-butyldimethylsilyl)oxy)-3-oxo-propoxy)benzo[d]thiazol-2-yl)amino)azetidine-1-carboxylate A mixture of tert-butyl 3-aminoazetidine-1-carboxylate (123 mg, 0.71 mmol), tert-butyl (R)-3-((2-bromobenzo[d]thiazol-6-yl)oxy)-2-((tert-butyldimethylsilyl)oxy) propanoate (290 mg, 0.59 mmol) and cesium carbonate (580 mg, 1.8 mmol) in dioxane (10 ml) was degassed by vacuum/$N_2$ refilled in a sealed tube three times, followed by addition of Ruthphos pre-catalyst G2 (92 mg, 0.12 mmol). The resulting mixture was further degassed by vacuum/$N_2$ refill three times, and then heated at 80° C. for 16 hours. The mixture was filtered through CELITE. The filtrate was concentrated and the residue was purified on silica gel column using EtOAc/hexane as eluting solvents to give (R)-tert-butyl 3-((6-(3-(tert-butoxy)-2-((tert-butyldimethylsilyl)oxy)-3-oxopropoxy)benzo[d]thiazol-2-yl)amino)azetidine-1-carboxylate. LC/MS: (M+1)$^+$=580.5

Step D: Preparation of (R)-Tert-Butyl 3-((6-(3-(tert-butoxy)-2-hydroxy-3-oxopropoxy)-benzo[d]-thiazol-2-yl)amino)azetidine-1-carboxylate To a solution of (R)-tert-butyl 3-((6-(3-(tert-butoxy)-2-((tert-butyldimethylsilyl)oxy)-3-oxopropoxy)benzo[d]thiazol-2-yl)amino)azetidine-1-carboxylate (240 mg, 0.40 mmol) in THF (5 ml) at 0° C. was added TBAF (0.40 ml, 0.40 mmol). The resulting solution was stirred at 0° C. for 30 minutes. After concentration, the residue was purified on silica gel column using EtOAc/hexane as eluting solvents to give (R)-tert-butyl 3-((6-(3-(tert-butoxy)-2-hydroxy-3-oxopropoxy)-benzo[d]thiazol-2-yl)amino)azetidine-1-carboxylate. LC/MS: (M+1)$^+$=466.3

Step E: Preparation of (S)-Tert-Butyl 3-((6-(3-(tert-butoxy)-2-((1,3-dioxoisoindolin-2-yl)oxy)-3-oxopropoxy)benzo[d]thiazol-2-yl)amino)azetidine-1-carboxylate To a solution of (R)-tert-butyl 3-((6-(3-(tert-butoxy)-2-hydroxy-3-oxopropoxy)benzo[d]thiazol-2-yl)amino)-azetidine-1-carboxylate (48 mg, 0.10 mmol) in THF (2 ml) was added 2-hydroxyisoindoline-1,3-dione (18 mg, 0.11 mmol), triphenylphosphine (38 mg, 0.14 mmol), and DEAD (0.023 ml, 0.14 mmol). The resulting solution was stirred at room temperature for 1.5 hours. After concentration, the residue was purified on silica gel column using EtOAc/hexane as eluting solvents to give (S)-tert-butyl 3-((6-(3-(tert-butoxy)-2-((1,3-dioxoisoindolin-2-yl)oxy)-3-oxopropoxy)benzo[d]thiazol-2-yl)amino)azetidine-1-carboxylate. LC/MS: (M+1)$^+$=611.4

Step F: Preparation of (S)-Tert-Butyl 3-((6-(2-(aminooxy)-3-(tert-butoxy)-3-oxopropoxy)-benzo[d]thiazol-2-yl)amino)azetidine-1-carboxylate To a solution of (S)-tert-butyl 3-((6-(3-(tert-butoxy)-2-((1,3-dioxoisoindolin-2-yl)oxy)-3-oxopropoxy)benzo[d]thiazol-2-yl)amino)-azetidine-1-carboxylate (53 mg, 0.087 mmol) in EtOH (4 ml) and DCM (2 ml) at 0° C. was added hydrazine (3.3 µl, 0.10 mmol). The resulting solution was stirred at 0° C. for 1 hour. The solution was concentrated to give (S)-tert-butyl 3-((6-(2-(aminooxy)-3-(tert-butoxy)-3-oxopropoxy)benzo[d]thiazol-2-yl)amino)azetidine-1-carboxylate. LC/MS: (M+1)$^+$=481.4

Step G: Preparation of (S,Z)-2-(((1-(tert-butoxy)-3-((2-((1-(tert-butoxycarbonyl)azetidin-3-yl)amino)benzo[d]thiazol-6-yl)oxy)-1-oxopropan-2-yl)oxy)imino)-2-(2-((tert-butoxy-carbonyl)amino)thiazol-4-yl)acetic Acid To a solution of (S)-tert-butyl 3-((6-(2-(aminooxy)-3-(tert-butoxy)-3-oxopropoxy)benzo[d]thiazol-2-yl)amino)azetidine-1-carboxylate (42 mg, 0.087 mmol) in EtOH (6 ml) and DCM (6 mL) was added 2-(2-((tert-butoxycarbonyl)-amino)thiazol-4-yl)-2-oxoacetic acid (intermediate 3) (36 mg, 0.13 mmol). The resulting solution was stirred at room temperature for 1 hour. After concentration, the residue was purified on reverse phase HPLC using acetonitrile and water (0.05% TFA) to give (S,Z)-2-(((1-(tert-butoxy)-3-((2-((1-(tert-butoxy-carbonyl)azetidin-3-yl)amino)benzo[d]thiazol-6-yl)oxy)-1-oxopropan-2-yl)oxy)imino)-2-(2-((tert-butoxycarbonyl)amino)thiazol-4-yl)acetic acid. LC/MS: (M+1)$^+$=735.4

Step H: Preparation of Tert-Butyl 3-((6-((S)-3-(tert-butoxy)-2-(((Z)-(1-(2-((tert-butoxy-carbonyl)-amino)thiazol-4-yl)-2-(((S)-2,2-dimethyl-4-oxo-1-(sulfooxy)azetidin-3-yl)amino)-2-oxoethylidene)amino)oxy)-3-oxopropoxy)benzo[d]thiazol-2-yl)amino)azetidine-1-carboxylate To a solution of (S,Z)-2-(((1-(tert-butoxy)-3-((2-((1-(tert-butoxycarbonyl)-azetidin-3-yl)amino)benzo[d]thiazol-6-yl)oxy)-1-oxopropan-2-yl)oxy)imino)-2-(2-((tert-butoxy-carbonyl)amino)thiazol-4-yl)acetic acid (24 mg, 0.033 mmol) in DMF (2 ml) was added DCC (34 mg, 0.16 mmol) and HOBt (20 mg, 0.13 mmol). The resulting mixture was stirred at room temperature for 30 minutes before addition of (S)-3-amino-2,2-dimethyl-4-oxoazetidin-1-yl hydrogen sulfate (27 mg, 0.13 mmol) and sodium bicarbonate (27 mg, 0.33 mmol). The resulting mixture was stirred at room temperature for 3 hours. Additional DCC (33.7 mg, 0.163 mmol) was added and the resulting mixture was continually stirred at room temperature overnight. After filtration the filtrate was purified on reverse phase HPLC using acetonitrile (0.05% TFA)/water (0.05% TFA) as mobile phase to give tert-butyl 3-((6-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)-amino)oxy)-3-oxopropoxy)-benzo[d]thiazol-2-yl)amino)azetidine-1-carboxylate. LC/MS: (M+1)$^+$=927.6

Step I: Preparation of 3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-benzo[d]thiazol-2-yl)amino)azetidin-1-ium 2,2,2-trifluoroacetate To the solution of tert-butyl 3-((6-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)benzo[d]thiazol-2-yl)amino)azetidine-1-carboxylate (17 mg, 0.018 mmol) in DCM (1 ml) was added TFA (2 ml, 26.0 mmol). The resulting solution was stirred at room temperature for 1 hour. After concentration the residue was purified on reverse phase HPLC using acetonitrile (0.05% TFA)/water (0.05% TFA) as the mobile phase to give the desired product. LC/MS: (M+1)$^+$=671.1, $^1$H-NMR (CD$_3$OD, 500 MHz): δ 7.46-7.44 (d, J 8.6 Hz, 1H), 7.35-7.34 (d, J 2.5 Hz, 1H), 7.14 (s, 1H), 7.00-6.98 (dd, J 8.8 Hz and 2.2 Hz, 1H), 5.22-5.20 (m, 1H), 4.82-4.76 (m, 1H), 4.54-4.29 (m, 2H), 4.47-4.43 (t, J 9.9 Hz, 2H), 4.33-4.29 (m, 2H), 3.53-3.49 (m, 1H), 1.54 (s, 3H), 1.31 (s, 3H).

Example 44

3-((6-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)benzo[d]thiazol-2-yl)amino)azetidin-1-ium 2,2,2-trifluoroacetate (C44)

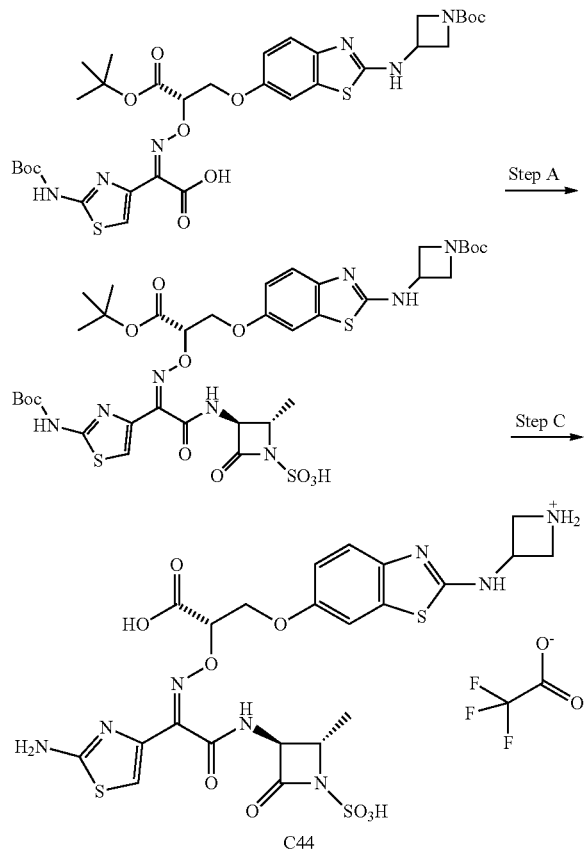

Step A: (2S,3S)-3-((Z)-2-((((S)-1-(tert-butoxy)-3-((2-((1-(tert-butoxycarbonyl)azetidin-3-yl)-amino)benzo[d]thiazol-6-yl)oxy)-1-oxopropan-2-yl)oxy)imino)-2-(2-((tert-butoxycarbonyl)-amino)thiazol-4-yl)acetamido)-2-methyl-4-oxoazetidine-1-sulfonic Acid To a solution of (S,Z)-2-(((1-(tert-butoxy)-3-((2-((1-(tert-butoxycarbonyl)azetidin-3-yl)amino)benzo[d]-thiazol-6-yl)oxy)-1-oxopropan-2-yl)oxy)imino)-2-(2-((tert-butoxycar-bonyl)amino)thiazol-4-yl)acetic acid (step G of Example 43) (24 mg, 0.033 mmol) in DMF (2 ml) was added DCC (34 mg, 0.16 mmol) and HOBt (20.01 mg, 0.131 mmol). The resulting mixture was stirred at room temperature for 30 minutes before addition of (2S,3S)-3-amino-2-methyl-4-oxoazetidine-1-sulfonic acid (23 mg, 0.13 mmol) and sodium bicarbonate (27 mg, 0.33 mmol). The resulting mixture was stirred at room temperature for 3 hours. Additional DCC (33.7 mg, 0.163 mmol) was added and the resulting mixture continued to be stirred at room temperature overnight. After filtration, the filtrate was purified on reverse phase HPLC using acetonitrile (0.05% TFA)/water (0.05% TFA) as mobile phase to give (2S,3S)-3-((Z)-2-((((S)-1-(tert-butoxy)-3-((2-((1-(tert-butoxy-carbonyl)azetidin-3-yl)amino)benzo[d]thiazol-6-yl)oxy)-1-oxopropan-2-yl)oxy)imino)-2-(2-((tert-butoxy-carbonyl)amino)thiazol-4-yl)acetamido)-2-methyl-4-oxoazetidine-1-sulfonic acid. LC/MS: (M+1)$^+$=897.5

Step B: Preparation of 3-((6-((S)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-carboxyethoxy)benzo-[d]thiazol-2-yl)amino)azetidin-1-ium 2,2,2-trifluoroacetate To the solution of (2S,3S)-3-((Z)-2-((((S)-1-(tert-butoxy)-3-((2-((1-(tert-butoxycarbonyl)azetidin-3-yl)amino)-benzo[d]thiazol-6-yl)oxy)-1-oxopropan-2-yl)oxy)imino)-2-(2-((tert-butoxycarbonyl)-amino)thiazol-4-yl)acetamido)-2-methyl-4-oxoazetidine-1-sulfonic acid (21 mg, 0.023 mmol) in CH$_2$Cl$_2$ (1 ml) was added TFA (2 mL, 26 mmol). The resulting solution was stirred at room temperature for 40 minutes. The reaction was concentrated and the residue was purified on reverse phase HPLC using acetonitrile (0.05% TFA)/water (0.05% TFA) as mobile phase to give the desired product. LC/MS: (M+1)$^+$=641.4, $^1$H-NMR (500 MHz, CD$_3$OD): δ 7.45-7.43 (d, J 9.1 Hz, 1H), 7.36-7.35 (d, J 2.5 Hz, 1H), 7.13 (s, 1H), 7.02-7.00 (dd, J=8.6 Hz, 2.5 Hz, 1H), 5.20-5.18 (m, 1H), 4.77-4.74 (m, 1H), 4.58-4.55 (m, 2H), 4.47-4.43 (t, J 9.8 Hz, 2H), 4.42-4.41 (d, J 3.2 Hz, 1H), 4.34-4.30 (m, 2H), 4.00-3.99 (m, 1H), 1.44-1.43 (d, J 6.3 Hz, 3H).

Examples 45 and 46

3-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)azetidin-1-ium 2,2,2-trifluoroacetate (C45) and 3-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)azetidin-1-ium 2,2,2-trifluoroacetate (C46)

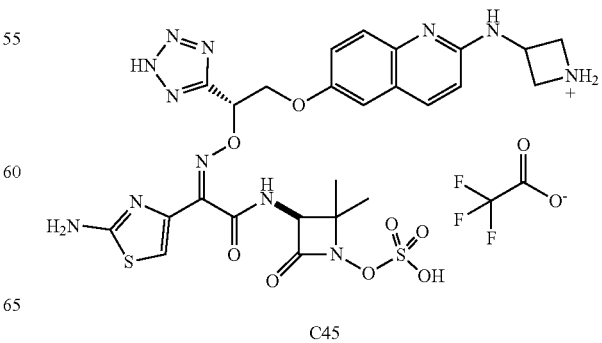

C45

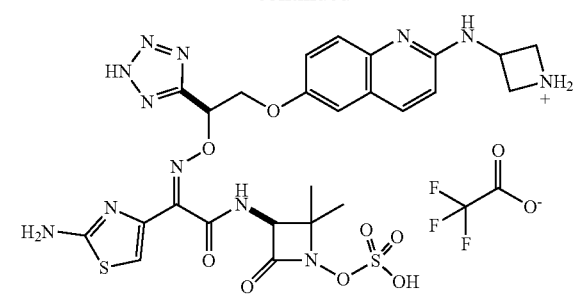
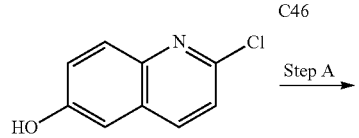 Step A →
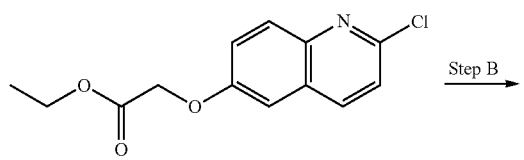 Step B →
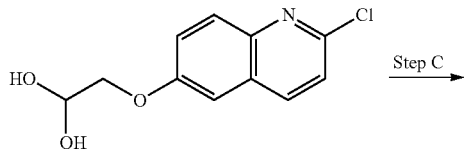 Step C →
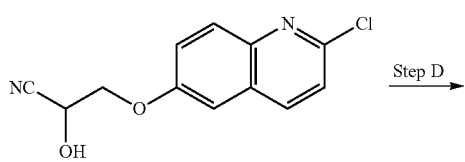 Step D →
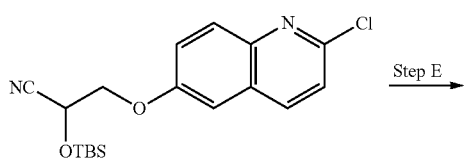 Step E →
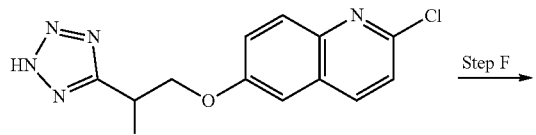 Step F →
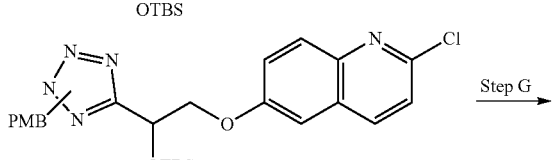 Step G →
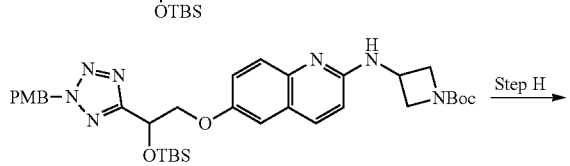 Step H →
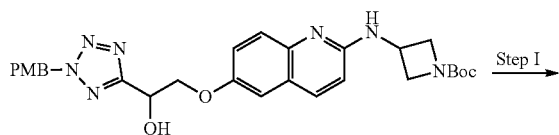 Step I →
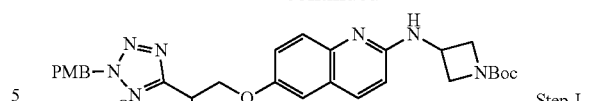 Step J →
 Step K →
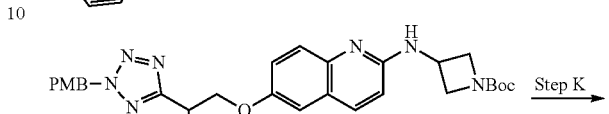 Step L →
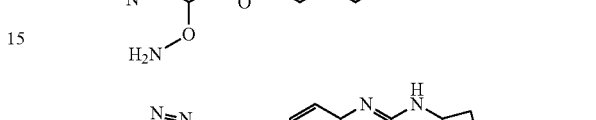 Step M →
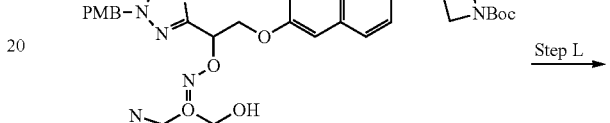 Step N →
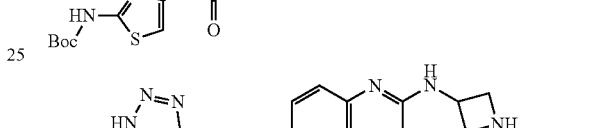 Step O →
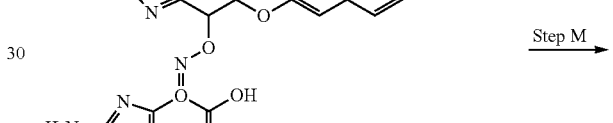
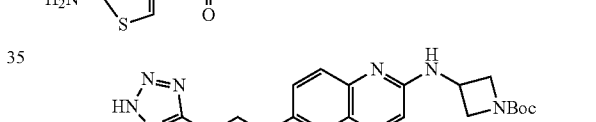
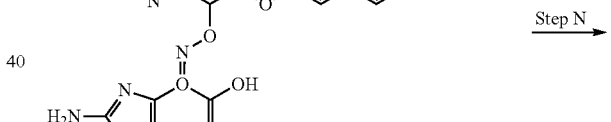
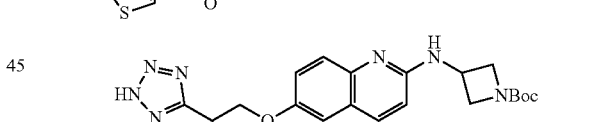
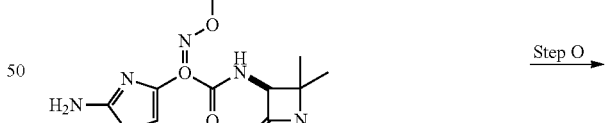
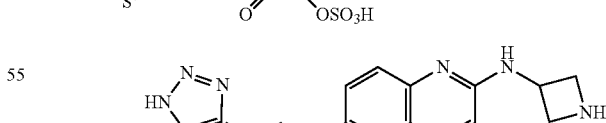
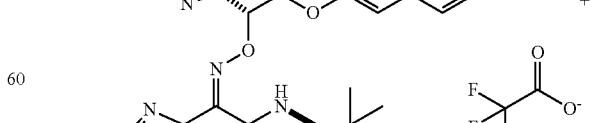

-continued

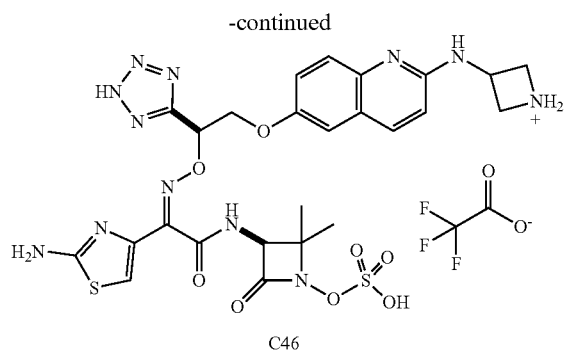

C46

Step A: Preparation of Ethyl 2-((2-chloroquinolin-6-yl)oxy)acetate

To a solution of 2-chloroquinolin-6-ol (5.3 g, 30 mmol) in EtOAc (100 ml) was added $K_2CO_3$ (6.1 g, 44 mmol) and ethyl bromoacetate (3.9 ml, 35 mmol). The resulting mixture was heated at 60° C. overnight. After cooling to room temperature, the mixture was filtered through CELITE and the filtrate was concentrated. The residue was purified on silica gel column using EtOAc/hexane as eluting solvents to give ethyl 2-((2-chloroquinolin-6-yl)oxy)acetate. LC/MS: $(M+1)^+=266.7$

Step B: Preparation of 2-((2-chloroquinolin-6-yl)oxy)ethane-1,1-diol

To a solution of ethyl 2-((2-chloroquinolin-6-yl)oxy)acetate (5.9 g, 22 mmol) in DCM (100 ml) at −78° C. was added DIBAL-H (25 ml, 25 mmol) dropwise. The resulting solution was stirred at −78° C. for 3 hours. The reaction was quenched by addition of methanol (5 mL). The mixture was then stirred at −78° C. for 10 minutes. Saturated potassium tartrate (500 mL) and DCM (200 mL) were added and the resulting mixture was stirred at room temperature overnight. The mixture was filtered, and the solid was washed with water, and dried under vacuum to give 2-((2-chloroquinolin-6-yl)oxy)ethane-1,1-diol. LC/MS: $(M+1)^+=239.9$

Step C: Preparation of 3-((2-chloroquinolin-6-yl)oxy)-2-hydroxypropanenitrile To a mixture of 2-((2-chloroquinolin-6-yl)oxy)ethane-1,1-diol (4.2 g, 18 mmol) in THF (60 ml), acetic acid (20 ml) and water (5 ml) was added sodium cyanide (1.7 g, 35 mmol). The resulting mixture was stirred at room temperature overnight. The reaction solution was then added to a solution of sodium carbonate (60 g) in 300 mL water at 0° C. dropwise. The volatiles were evaporated and the aqueous was extracted with EtOAc twice. The combined organic phase was washed with water two times, dried over $Na_2SO_4$, and concentrated to give 3-((2-chloroquinolin-6-yl)oxy)-2-hydroxypropanenitrile. LC/MS: $(M+1)^+=248.8$

Step D: Preparation of 2-((tert-butyldimethylsilyl)oxy)-3-((2-chloroquinolin-6-yl)oxy)propanenitrile To a solution of 3-((2-chloroquinolin-6-yl)oxy)-2-hydroxypropanenitrile (4.3 g, 17 mmol), imidazole (5.9 g, 87 mmol), and TBS-Cl (6.6 g, 43 mmol) in acetonitrile (20 ml) was added DMAP (0.212 g, 1.737 mmol). The resulting solution was stirred at room temperature for 1 hour. After concentration, the residue was diluted in DCM (50 mL). The solid was filtered off and the filtrate was purified on silica gel column using EtOAc/hexane as eluting solvents to give 2-((tert-butyldimethylsilyl)oxy)-3-((2-chloroquinolin-6-yl)oxy)propanenitrile. LC/MS: $(M+1)^+=363.1$

Step E: Preparation of 6-(2-((tert-butyldimethylsilyl)oxy)-2-(2H-tetrazol-5-yl)ethoxy)-2-chloroquinoline To a mixture of dibutyltin oxide (0.83 g, 3.4 mmol) and 2-((tert-butyldimethylsilyl)oxy)-3-((2-chloroquinolin-6-yl)oxy)propanenitrile (6.1 g, 17 mmol) in toluene (100 ml) was added TMS-$N_3$ (6.7 ml, 50 mmol). The resulting mixture was heated at 110° C. for 1 hour. The mixture was concentrated and the residue was partitioned between EtOAc (200 mL) and saturated $NH_4Cl$ (100 mL). The organic phase was washed with saturated $NH_4Cl$ twice, dried over $Na_2SO_4$, and concentrated and the residue was purified on silica gel column using MeOH/DCM as eluting solvents to give 6-(2-((tert-butyldimethylsilyl)oxy)-2-(2H-tetrazol-5-yl)ethoxy)-2-chloroquinoline. LC/MS: $(M+1)^+=406.1$

Step F: Preparation of 6-(2-((tert-butyldimethylsilyl)oxy)-2-(2-(4-methoxybenzyl)-2H-tetrazol-5-yl)ethoxy)-2-chloroquinoline and 6-(2-((tert-butyldimethylsilyl)oxy)-2-(1-(4-methoxybenzyl)-1H-tetrazol-5-yl)ethoxy)-2-chloroquinoline To a mixture of 6-(2-((tert-butyldimethylsilyl)oxy)-2-(2H-tetrazol-5-yl)ethoxy)-2-chloroquinoline (5.4 g, 11 mmol), tetrabutylammonium chloride hydrate (0.33 g, 1.1 mmol), $K_2CO_3$ (4.6 g, 33 mmol) in DCE (100 ml), water (50 ml) and acetonitrile (50 ml) was added 4-methoxybenzyl chloride (1.7 ml, 12.2 mmol). The resulting mixture was heated at 40° C. overnight. After evaporating the volatiles, the mixture was suspended in DCM (200 mL) and then filtered. The filtrate was extracted with DCM three times. The combined organic phase was dried over $Na_2SO_4$, concentrated and the residue was purified on silica gel column using EtOAc/hexane as eluting solvents to give two regioisomers 6-(2-((tert-butyldimethylsilyl)oxy)-2-(2-(4-methoxybenzyl)-2H-tetrazol-5-yl)ethoxy)-2-chloroquinoline, and 6-(2-((tert-butyldimethyl-silyl)oxy)-2-(1-(4-methoxybenzyl)-1H-tetrazol-5-yl)ethoxy)-2-chloroquinoline. LC/MS: $(M+1)^+=527.7$

Step G: Preparation of Tert-Butyl 3-((6-(2-((tert-butyldimethylsilyl)oxy)-2-(2-(4-methoxybenzyl)-2H-tetrazol-5-yl)ethoxy)quinolin-2-yl)-2-amino)azetidine-1-carboxylate A mixture of tert-butyl 3-aminoazetidine-1-carboxylate (290 mg, 1.7 mmol), 6-(2-((tert-butyldimethyl-silyl)oxy)-2-(2-(4-methoxybenzyl)-2H-tetrazol-5-yl)ethoxy)-2-chloroquinoline (810 mg, 1.54 mmol), cesium carbonate (1500 mg, 4.6 mmol) in dioxane (10 ml) was degassed by vacuum/$N_2$ refill three times, followed by addition of Ruthphos pre-cat G2 (240 mg, 0.31 mmol). The resulting mixture was further degassed by vacuum/$N_2$ refill three times, and then heated at 80° C. for 16 hours. The mixture was filtered through CELITE, and the filtrate was concentrated. The residue was purified on silica gel column using EtOAc/hexane to give tert-butyl 3-((6-(2-((tert-butyldimethylsilyl)oxy)-2-(2-(4-methoxybenzyl)-2H-tetrazol-5-yl)ethoxy)quinolin-2-yl)amino)azetidine-1-carboxylate. LC/MS: $(M+1)^+=662.6$

Step H: Preparation of Tert-Butyl 3-((6-(2-hydroxy-2-(2-(4-methoxybenzyl)-2H-tetrazol-5-yl)ethoxy)quinolin-2-yl)amino)azetidine-1-carboxylate To a solution of tert-butyl 3-((6-(2-((tert-butyldimethylsilyl)oxy)-2-(2-(4-methoxybenzyl)-2H-tetrazol-5-yl)ethoxy)quinolin-2-yl)amino)azetidine-1-carboxylate (0.53 g, 0.80 mmol) in THF (10 ml) at 0° C. was added TBAF (0.80 ml, 0.80 mmol). The resulting solution was stirred at 0° C. for 1 hour. The solution was concentrated and the residue was purified on silica gel column using MeOH/DCM as eluting solvents to give tert-butyl 3-((6-(2-hydroxy-2-(2-(4-methoxybenzyl)-2H-tetrazol-5-yl)ethoxy)quinolin-2-yl)amino)azetidine-1-carboxylate. LC/MS: $(M+1)^+ = 548.2$

Step I: Preparation of Tert-Butyl 3-((6-(2-((1,3-dioxoisoindolin-2-yl)oxy)-2-(2-(4-methoxybenzyl)-2H-tetrazol-5-yl)ethoxy)quinolin-2-yl)amino)azetidine-1-carboxylate To a solution of triphenylphosphine (0.16 g, 0.59 mmol), tert-butyl 3-((6-(2-hydroxy-2-(2-(4-methoxybenzyl)-2H-tetrazol-5-yl)ethoxy)quinolin-2-yl)amino)azetidine-1-carboxylate (0.25 g, 0.46 mmol), and 2-hydroxyisoindoline-1,3-dione (0.082 g, 0.50 mmol) in THF (20 ml) was added DEAD (0.097 ml, 0.59 mmol). The resulting solution was stirred at room temperature for 3 hours. The solution was then concentrated and the residue was purified on silica gel column using EtOAc/hexane as eluting solvents to give tert-butyl 3-((6-(2-((1,3-dioxoisoindolin-2-yl)oxy)-2-(2-(4-methoxybenzyl)-2H-tetrazol-5-yl)ethoxy)quinolin-2-yl)amino)azetidine-1-carboxylate. LC/MS: $(M+1)^+ = 693.9$

Step J: Preparation of Tert-Butyl 3-((6-(2-(aminooxy)-2-(2-(4-methoxybenzyl)-2H-tetrazol-5-yl)ethoxy)quinolin-2-yl)amino)azetidine-1-carboxylate To a solution of tert-butyl 3-((6-(2-((1,3-dioxoisoindolin-2-yl)oxy)-2-(2-(4-methoxybenzyl)-2H-tetrazol-5-yl)ethoxy)quinolin-2-yl)amino)azetidine-1-carboxylate (0.36 g, 0.52 mmol) in a mixture solvent of ethanol (10 ml) and DCE (20 ml) at 0° C. was added hydrazine (0.018 ml, 0.57 mmol). The resulting solution was stirred at room temperature for 2 hours, the solution was concentrated and the residue was suspended in DCM (10 mL). The resulting mixture was stirred at room temperature for 10 minutes. The precipitate was filtered off, and the filtrate was concentrated to give tert-butyl 3-((6-(2-(aminooxy)-2-(2-(4-methoxybenzyl)-2H-tetrazol-5-yl)ethoxy)quinolin-2-yl)amino)azetidine-1-carboxylate. LC/MS: $(M+1)^+ = 563.4$

Step K: Preparation of (Z)-2-(2-((tert-butoxycarbonyl)amino)thiazol-4-yl)-2-((2-((2-((1-(tert-butoxycarbonyl)azetidin-3-yl)amino)quinolin-6-yl)oxy)-1-(2-(4-methoxybenzyl)-2H-tetrazol-5-yl)ethoxy)imino)acetic Acid To a solution of tert-butyl 3-((6-(2-(aminooxy)-2-(2-(4-methoxybenzyl)-2H-tetrazol-5-yl)ethoxy)quinolin-2-yl)amino)azetidine-1-carboxylate (240 mg, 0.43 mmol) in ethanol (10 ml) and DCE (10 ml) was added 2-(2-((tert-butoxy-carbonyl)amino)thiazol-4-yl)-2-oxoacetic acid (intermediate 3) (139 mg, 0.51 mmol). The resulting solution was stirred at room temperature overnight. The solution was then concentrated to give (Z)-2-(2-((tert-butoxycarbonyl)amino)thiazol-4-yl)-2-((2-((2-((1-(tert-butoxycarbonyl)azetidin-3-yl)amino)quinolin-6-yl)oxy)-1-(2-(4-methoxybenzyl)-2H-tetrazol-5-yl)ethoxy)imino)acetic acid. LC/MS: $(M+1)^+ = 817.4$

Step L: Preparation of (Z)-2-(2-aminothiazol-4-yl)-2-((2-((2-(azetidin-3-ylamino)quinolin-6-yl)oxy)-1-(2H-tetrazol-5-yl)ethoxy)imino)acetic Acid To a flask containing (Z)-2-(2-((tert-butoxycarbonyl)amino)thiazol-4-yl)-2-((2-((2-((1-(tert-butoxycarbonyl)azetidin-3-yl)amino)quinolin-6-yl)oxy)-1-(2-(4-methoxybenzyl)-2H-tetrazol-5-yl)ethoxy)imino)acetic acid (350 mg, 0.43 mmol) was added TFA (4 ml). The resulting solution was stirred at room temperature for 30 minutes, and then concentrated. The residue was re-dissolved in TFA (4 ml), and heated at 70° C. for 1 hour. The solution was concentrated to give (Z)-2-(2-aminothiazol-4-yl)-2-((2-((2-(azetidin-3-ylamino)quinolin-6-yl)oxy)-1-(2H-tetrazol-5-yl)ethoxy)imino)acetic acid. LC/MS: $(M+1)^+ = 497.3$

Step M: Preparation of (Z)-2-(2-aminothiazol-4-yl)-2-((2-((2-((1-(tert-butoxycarbonyl)-azetidin-3-yl)amino)quinolin-6-yl)oxy)-1-(2H-tetrazol-5-yl)ethoxy)imino)acetic Acid To a solution of (Z)-2-(2-aminothiazol-4-yl)-2-((2-((2-(azetidin-3-ylamino)quinolin-6-yl)oxy)-1-(2H-tetrazol-5-yl)ethoxy)imino)acetic acid (210 mg, 0.43 mmol) in DMF (4 ml) at 0° C. was added TEA (0.476 ml, 3.42 mmol) and Boc$_2$O (0.12 ml, 0.51 mmol). The resulting solution was stirred at room temperature for 1 hour. After removing the volatiles, the solution was purified on reverse phase MPLC using acetonitrile (0.05% TFA)/water (0.05% TFA) to give (Z)-2-(2-aminothiazol-4-yl)-2-((2-((2-((2-((1-(tert-butoxycarbonyl)azetidin-3-yl)amino)-quinolin-6-yl)oxy)-1-(2H-tetrazol-5-yl)ethoxy)imino)acetic acid. LC/MS: $(M+1)^+ = 597.4$

Step N: Tert-Butyl 3-((6-(2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)azetidine-1-carboxylate To a solution of (Z)-2-(2-aminothiazol-4-yl)-2-((2-((2-((1-(tert-butoxycarbonyl)azetidin-3-yl)amino)quinolin-6-yl)oxy)-1-(2H-tetrazol-5-yl)ethoxy)imino)acetic acid compound (142 mg, 0.20 mmol) in DMF (6 ml) was added DCC (270 mg, 1.3 mmol) and HOBt (200 mg, 1.3 mmol). The resulting solution was stirred at room temperature for 30 minutes before addition of (S)-3-amino-2,2-dimethyl-4-oxoazetidin-1-yl hydrogen sulfate (168 mg, 0.80 mmol) and sodium bicarbonate (235 mg, 2.8 mmol). The resulting mixture was stirred at room temperature for 4 hours. The solution was filtered and the filtrate was purified on reverse phase HPLC using acetonitrile (0.05% TFA)/water (0.05% TFA) to give tert-butyl 3-((6-(2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)azetidine-1-carboxylate. LC/MS: (M+1)$^+$=789.4

Step O: Preparation of (S)-3-((Z)-2-(2-aminothiazol-4-yl)-2-(((R)-2-((2-(azetidin-3-ylamino)quinolin-6-yl)oxy)-1-(2H-tetrazol-5-yl)ethoxy)imino)acetamido)-2,2-dimethyl-4-oxoazetidin-1-yl hydrogen sulfate and (S)-3-((Z)-2-(2-aminothiazol-4-yl)-2-(((S)-2-((2-(azetidin-3-ylamino)quinolin-6-yl)oxy)-1-(2H-tetrazol-5-yl)ethoxy)imino)acetamido)-2,2-dimethyl-4-oxoazetidin-1-yl Hydrogen Sulfate To a solution of tert-butyl 3-((6-(2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)azetidine-1-carboxylate (135 mg, 0.150 mmol) in CH$_2$Cl$_2$ (5 ml) was added TFA (5 ml, 64.9 mmol), and the resulting solution was stirred at room temperature for 30 minutes. After concentration, the residue was purified on reverse phase HPLC using acetonitrile (0.05% TFA)/water (0.05% TFA) as mobile phase to give (S)-3-((Z)-2-(2-aminothiazol-4-yl)-2-(((R)-2-((2-(azetidin-3-ylamino)quinolin-6-yl)oxy)-1-(2H-tetrazol-5-yl)ethoxy)imino)acetamido)-2,2-dimethyl-4-oxoazetidin-1-yl hydrogen sulfate as a TFA salt (the fast eluant), LC/MS: (M+1)$^+$: 689.2. $^1$HNMR (500 MHz, CD$_3$OD): δ 8.36-8.34 (d, J 9.8 Hz, 1H), 7.83-7.81 (d, J 8.7 Hz, 1H), 7.53-7.48 (m, 2H), 7.12-7.11 (d, J 9.6 Hz, 1H), 7.04 (s, 1H), 6.12-6.10 (m, 1H), 5.18-5.12 (m, 1H), 4.75-4.72 (m, 2H), 4.58-4.55 (m, H), 4.54 (s, 1H), 4.34-4.29 (m, 2H), 1.46 (s, 3H), 1.04 (s, 3H), and (S)-3-((Z)-2-(2-aminothiazol-4-yl)-2-(((S)-2-((2-(azetidin-3-ylamino)quinolin-6-yl)oxy)-1-(2H-tetrazol-5-yl)ethoxy)imino)acetamido)-2,2-dimethyl-4-oxoazetidin-1-yl hydrogen sulfate as a TFA salt (the slow eluant). LC/MS: (M+1)$^+$: 689.2. $^1$HNMR (500 MHz, CD$_3$OD): δ 8.35-8.33 (d, J 10.6 Hz, 1H), 7.81-7.79 (d, J 8.8 Hz, 1H), 7.53-7.51 (m, 1H), 7.49-7.48 (m, 1H), 7.12-7.10 (d, J=9.3 Hz, 1H), 7.02 (s, 1H), 6.08-6.06 (t, J=4.8 Hz, 1H), 5.17-5.11 (m, 1H), 4.83-4.81 (m, 2H), 4.56 (s, 1H), 4.58-4.53 (m, 2H), 4.34-4.30 (m, 2H), 1.5 (s, 3H). 1.28 (s, 3H).

Examples 47 and 48

4-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)piperidin-1-ium 2,2,2-trifluoroacetate (C47) and 4-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxyquinolin-2-yl)amino)piperidin-1-ium 2,2,2-trifluoroacetate (C48)

C47

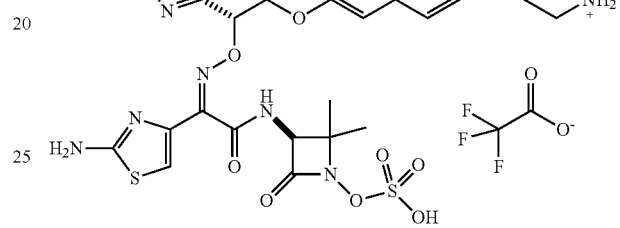

C48

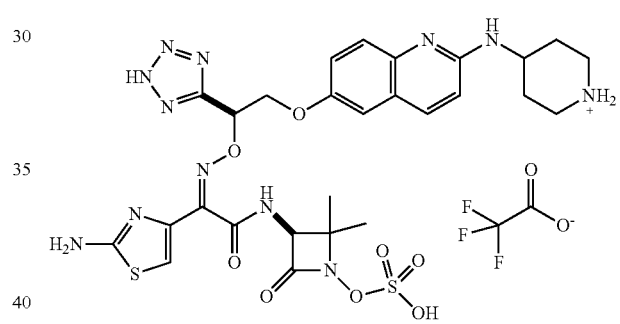

Compounds 47 and 48 were prepared following a similar procedure to that described in Examples 45 and 46.

Compound 47: 4-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)piperidin-1-ium 2,2,2-trifluoroacetate. LC/MS: (M+1)$^+$=717.1, $^1$H-NMR (500 MHz, CD$_3$OD): δ 8.30-8.28 (d, J=10.1 Hz, 1H), 7.86-7.84 (d, J=8.9 Hz, 1H), 7.53-7.51 (m, 1H), 7.47-7.46 (d, J=2.8 Hz, 1H), 7.10-7.08 (m, 1H), 7.04 (s, 1H), 6.12-6.10 (m, 1H), 4.87-4.84 (m, 1H), 4.77-4.73 (m, 1H), 4.55 (s, 1H), 4.25-4.21 (m, 1H), 3.60-3.57 (d, J=13.2 Hz, 2H), 3.25-3.20 (t, J=12.9 Hz, 2H), 2.41-2.38 (d, J=15. Hz, 2H), 1.94-1.88 (m, 2H), 1.47 (s, 3H), 1.09 (s, 3H);

Compound 48: 4-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)quinolin-2-yl)amino)piperidin-1-ium 2,2,2-trifluoroacetate. LC/MS: (M+1)$^+$=717.0, $^1$H-NMR (500 MHz, CD$_3$OD): δ 8.30-8.28 (d, J=9.4 Hz, 1H), 7.85-7.83 (d, J=9.4 Hz, 1H), 7.54-7.51 (m, 1H), 7.48-7.47 (d, J=2.7 Hz, 1H), 7.11-7.08 (m, 1H), 7.03 (s, 1H), 6.08-6.06 (t, J=4.8 Hz, 1H), 4.83-4.82 (d, J=6.8 Hz, 2H), 4.58 (s, 1H), 4.26-4.21 (m, 1H), 3.60-3.57 (d, J 13.2 Hz, 2H), 3.26-3.21 (t, J 13.0 Hz, 2H), 2.40-2.37 (d, J 14.2 Hz, 2H), 1.95-1.87 (m, 2H), 1.50 (s, 3H), 1.30 (s, 3H).

Examples 49 and 50

2-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)isoquinolin-1-yl)amino)ethan-1-aminium 2,2,2-trifluoroacetate (C49) and 2-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)isoquinolin-1-yl)amino)ethan-1-aminium 2,2,2-trifluoroacetate (C50)

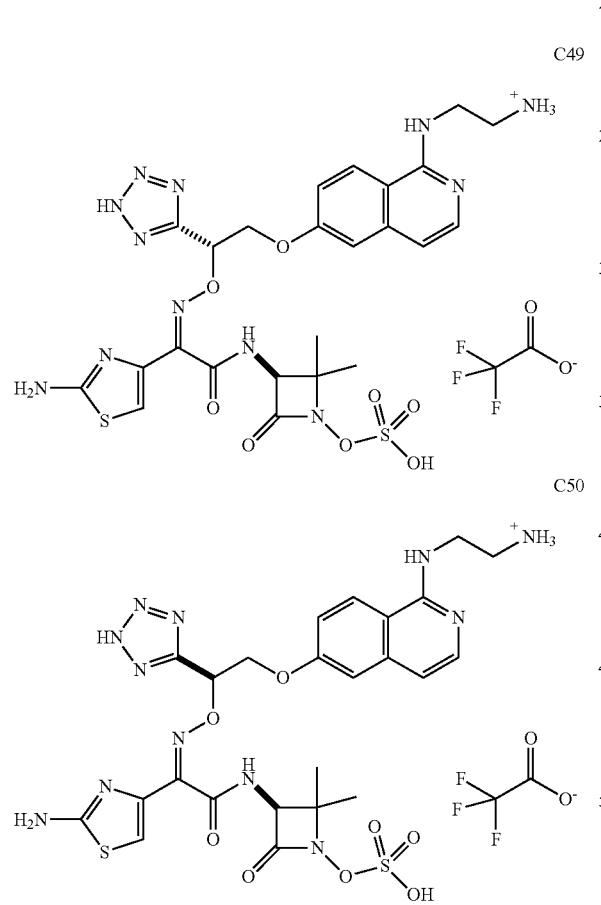

Compounds 49 and 50 were prepared generally following a similar procedure as described in Examples 45 and 46.

Compound 49: 2-((6-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)isoquinolin-1-yl)amino)ethan-1-aminium 2,2,2-trifluoroacetate. LC/MS: (M+1)$^+$=677.1, $^1$H-NMR (500 MHz, CD$_3$OD): δ 8.41-8.40 (d, J 8.9 Hz, 1H), 7.60-7.59 (d, J 6.1 Hz, 1H), 7.49-7.47 (m, 2H), 7.28-7.27 (d, J 7.1 Hz, 1H), 7.04 (s, 1H), 6.17-6.15 (m, 1H), 5.00-4.97 (m, 1H), 4.87-4.82 (m, 2H), 4.53 (s, 1H), 3.99-3.88 (m, 2H), 3.50-3.43 (m, 2H), 1.46 (s, 3H), 1.00 (s, 3H).

Compound 50: 2-((6-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)isoquinolin-1-yl)amino)ethan-1-aminium 2,2,2-trifluoroacetate. LC/MS: (M+1)$^+$=677.3, $^1$H-NMR (500 MHz, CD$_3$OD): δ 4.82-4.80 (d, J 8.5 Hz, 1H), 7.60-7.59 (d, J 6.5 Hz, 1H), 7.51-7.47 (m, 2H), 7.26-7.24 (d, J=6.9 Hz, 1H), 7.01 (s, 1H), 6.13-6.11 (m, 1H), 5.03-4.98 (m, 1H), 4.55 (s, 1H), 3.96-3.92 (m, 2H), 3.47-3.45 (t, J 7.6 Hz, 2H), 1.50 (s, 3H), 1.27 (s, 3H).

Example 51

(S)-3-((Z)-2-(((S)-2-((2-((R)-3-amino-2-hydroxypropyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl Sulfate

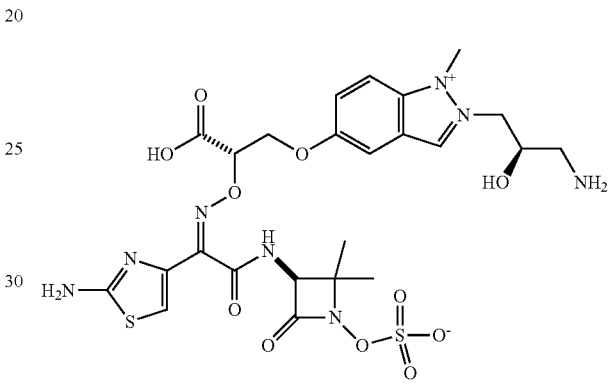

Step A: (R)-tert-butyl 3-((2-((R)-3-((tert-butoxycarbonyl)amino)-2-((tert-butyl-dimethylsilyl)oxy)propyl)-2H-indazol-5-yl)oxy)-2-hydroxypropanoate A solution of (R)-tert-butyl 3-(3-formyl-4-nitrophenoxy)-2-hydroxypropanoate (2.35 g, 7.55 mmol) and (S)-tert-butyl (3-amino-2-((tert-butyldimethylsilyl)-oxy)propyl)carbamate (2.53 g, 8.30 mmol) in 2-propanol (20 ml) was heated at 80° C. for 4 h. Then the solution was cooled to rt, and tri-n-butylphosphine (5.71 ml, 22.6 mmol) was added. The resulting solution was heated at 80° C. for 16 h, and then concentrated. The resulting residue was purified on silica gel column eluting with EtOAc/hexane to give the title compound. LC/MS: [M+1]$^+$=566.5.

Step B: (S)-tert-butyl 3-((2-((R)-3-((tert-butoxycarbonyl)amino)-2-((tert-butyldimethylsilyl)oxy)propyl)-2H-indazol-5-yl)oxy)-2-((1,3-dioxoisoindolin-2-yl)oxy)propanoate To a solution of (R)-tert-butyl 3-((2-((R)-3-((tert-butoxycarbonyl)amino)-2-((tert-butyldimethylsilyl)oxy)propyl)-2H-indazol-5-yl)oxy)-2-hydroxypropanoate (1.31 g, 2.32 mmol) in THF (20 ml) was added 2-hydroxyisoindoline-1,3-dione (0.453 g, 2.78 mmol), triphenylphosphine (0.911 g, 3.47 mmol), and DEAD (0.567 ml, 3.47 mmol). The reaction was stirred at rt for 2 h, and then concentrated. The resulting residue was purified on silica gel column using EtOAc/hexane as eluting solvents to give the title compound. LC/MS: [M+1]$^+$=711.6.

Step C: 5-((S)-3-(tert-butoxy)-2-((1,3-dioxoisoindo-lin-2-yl)oxy)-3-oxopropoxy)-2-((R)-3-((tert-butoxy-carbonyl)amino)-2-((tert-butyldimethylsilyl)oxy) propyl)-1-methyl-2H-indazol-1-ium To a solution of (S)-tert-butyl 3-((2-((R)-3-((tert-butoxy-carbonyl)amino)-2-((tert-butyldimethylsilyl)-oxy)propyl)-2H-indazol-5-yl)oxy)-2-((1,3-dioxoisoindolin-2-yl)oxy) propanoate (2.06 g, 2.32 mmol) in acetonitrile (30 ml) at 0° C. was added methyl trifluoromethanesulfonate (0.306 ml, 2.78 mmol). The resulting solution was stirred at rt for 1.5 h, and then concentrated to give the title compound. LC/MS: [M]+=725.6.

Step D: 5-((S)-2-(aminooxy)-3-(tert-butoxy)-3-oxo-propoxy)-2-((R)-3-((tert-butoxy carbonyl)amino)-2-((tert-butyldimethylsilyl)oxy)propyl)-1-methyl-2H-indazol-1-ium To a solution of 5-((S)-3-(tert-butoxy)-2-((1,3-dioxoisoin-dolin-2-yl)oxy)-3-oxopropoxy)-2-((R)-3-((tert-butoxycar-bonyl)amino)-2-((tert-butyldimethylsilyl)oxy)propyl)-1-methyl-2H-indazol-1-ium (1.68 g, 2.32 mmol) in CH$_2$Cl$_2$ (15 ml) and EtOH (15 ml) at 0° C. was added hydrazine (0.087 ml, 2.78 mmol). The reaction mixture was stirred at rt for 1 h, then concentrated to give the title compound. LC/MS: [M]=595.6.

Step E: 5-((S)-3-(tert-butoxy)-2-(((Z)-((2-((tert-bu-toxycarbonyl)amino)thiazol-4-yl)(carboxy)-methyl-ene)amino)oxy)-3-oxopropoxy)-2-((R)-3-((tert-bu-toxycarbonyl)amino)-2-((tert-butyl-dimethylsilyl) oxy)propyl)-1-methyl-2H-indazol-1-ium To a solution of 5-((S)-2-(aminooxy)-3-(tert-butoxy)-3-oxopropoxy)-2-((R)-3-((tert-butoxycarbonyl)amino)-2-((tert-butyldimethylsilyl)oxy)propyl)-1-methyl-2H-indazol-1-ium (1.25 g, 2.10 mmol) in MeOH (12 mL) and CH$_2$Cl$_2$ (12 mL) was added 2-(2-((tert-butoxycarbonyl)amino)thi-azol-4-yl)-2-oxoacetic acid (0.743 g, 2.73 mmol). The resulting solution was stirred at rt for 2 h, then concentrated to give the title compound. LC-MS: [M]+=849.6.

Step F: 5-((S)-3-(tert-butoxy)-2-(((Z)-((2-((tert-bu-toxycarbonyl)amino)thiazol-4-yl)(carboxy)-methyl-ene)amino)oxy)-3-oxopropoxy)-2-((R)-3-((tert-bu-toxycarbonyl)amino)-2-hydroxypropyl)-1-methyl-2H-indazol-1-ium To a solution of 5-((S)-3-(tert-butoxy)-2-(((Z)-((2-((tert-butoxy-carbonyl)-amino)thiazol-4-yl)(carboxy)methylene) amino)oxy)-3-oxopropoxy)-2-((R)-3-((tert-butoxycarbo-nyl)-amino)-2-((tert-butyldimethylsilyl)oxy)-propyl)-1-methyl-2H-indazol-1-ium (1.78 g, 2.10 mmol) in THF (20 ml) at 0° C. was added TBAF (5.24 ml, 5.24 mmol). The reaction mixture was stirred at rt for 1 h, and then concentrated. The resulting residue was purified on reverse phase MPLC (C18) using acetonitrile (0.05% TFA)/water (0.05% TFA) as eluting solvents to give the title compound. LC/MS: [M]+=735.5.

Step G: 5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((R)-3-((tert-butoxycarbonyl)amino)-2-hydroxypropyl)-1-methyl-2H-indazol-1-ium To a solution of 5-((S)-3-(tert-butoxy)-2-(((Z)-((2-((tert-butoxycarbonyl)-amino)thiazol-4-yl)(carboxy)methylene) amino)oxy)-3-oxopropoxy)-2-((R)-3-((tert-butoxycarbonyl) amino)-2-hydroxypropyl)-1-methyl-2H-indazol-1-ium (1.0 g, 1.36 mmol) in DMF (10 ml) were added DCC (1.68 g, 8.15 mmol) and HOBT (0.832 g, 5.44 mmol). The reaction mixture was stirred at rt for 30 min, then (S)-3-amino-2,2-dimethyl-4-oxoazetidin-1-yl hydrogen sulfate (0.857 g, 4.08 mmol) and sodium bicarbonate (1.14 g, 13.6 mmol) were added. The reaction mixture was stirred at rt overnight. Then the mixture was filtered and the filtrate was purified on reverse phase MPLC (C18) using acetonitrile (0.05% TFA)/water (0.05% TFA) as mobile phase to give the title compound. LC-MS: [M]+=927.8.

Step H: (S)-3-((Z)-2-(((S)-2-((2-((R)-3-amino-2-hydroxypropyl)-1-methyl-2H-indazol-1-ium-5-yl) oxy)-1-carboxyethoxy)imino)-2-(2-aminothiazol-4-yl)acetamido)-2,2-dimethyl-4-oxoazetidin-1-yl Sulfate To a solution of 5-((S)-3-(tert-butoxy)-2-(((Z)-(1-(2-((tert-butoxycarbonyl)amino)thiazol-4-yl)-2-(((S)-2,2-dim-ethyl-4-oxo-1-(sulfooxy)azetidin-3-yl)amino)-2-oxoethyl-idene)amino)oxy)-3-oxopropoxy)-2-((R)-3-((tert-butoxycarbonyl)-amino)-2-hydroxypropyl)-1-methyl-2H-indazol-1-ium (711 mg, 0.766 mmol) in CH$_2$Cl$_2$ (4 ml) was added TFA (8 ml, 104 mmol). The reaction mixture was stirred at rt for 50 min, then concentrated. The resulting residue was precipitated from Et$_2$O. The Et$_2$O phase was transferred to a flask by pipette, and the process was repeated three times. The solid was further dried under vacuum, and then dissolved in DMSO (5.5 mL) and purified on reverse phase HPLC using acetonitrile/water (20 mM NH$_4$OAc) to give the title compound. LCMS: [M+1]+=671.5. $^1$H NMR (500 MHz, D$_2$O): δ 8.74 (s, 1H), 7.64-7.62 (d, J=8.2 Hz, 1H), 7.48-7.46 (d, J=8.2 Hz, 1H), 7.27 (s, 1H), 6.93 (s, 1H), 4.97-4.90 (m, 3H), 4.44-4.35 (m, 3H), 4.20 (s, 3H), 3.38-3.35 (m, 1H), 3.10-3.06 (m, 1H), 1.40 (s, 3H), 1.04 (s, 3H).

Example 52

(S)-3-((Z)-2-(((S)-2-((2-(3-aminopropyl)-1-methyl-2H-indazol-1-ium-5-yl)oxy)-1-carboxyethoxy) imino)-2-(2-aminothiazol-4-yl)acetamido)-2,2-dim-ethyl-4-oxoazetidin-1-yl Sulfate

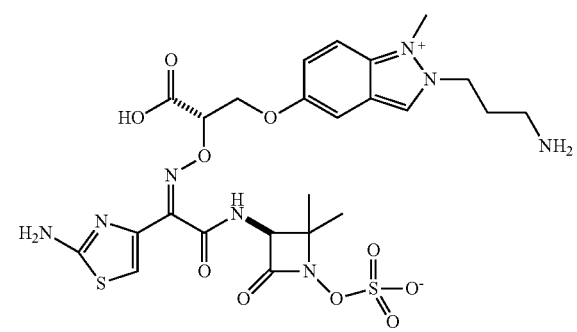

Step A: (R)-tert-butyl 3-((2-(3-((tert-butoxycarbo-nyl)amino)propyl)-2H-indazol-5-yl)oxy)-2-hydroxy-propanoate A solution of (R)-tert-butyl 3-(3-formyl-4-nitrophenoxy)-2-hydroxypropanoate (0.5 g, 1.61 mmol) and tert-butyl (3-aminopropyl)carbamate (0.308 g, 1.77 mmol) in 2-propanol (4 ml) was heated at 80° C. for 4 h. Then the reaction was cooled to rt, and tri-n-butylphosphine (1.22 ml, 4.82 mmol) was added. The reaction mixture was heated at 80° C. for 16 h, then concentrated. The resulting residue was purified on silica gel column using EtOAc/hexane as eluting solvents to give the title compound. LC-MS: [M+1]$^+$: 436.3.

Step B: (S)-Tert-Butyl 3-((2-(3-((tert-butoxycarbonyl)amino)propyl)-2H-indazol-5-yl)oxy)-2-((1,3-dioxoisoindolin-2-yl)oxy)propanoate To a solution of (R)-tert-butyl 3-((2-(3-((tert-butoxycarbonyl)-amino)propyl)-2H-indazol-5-yl)oxy)-2-hydroxypropanoate (0.302 g, 0.693 mmol) in THF (10 ml) was added 2-hydroxy-isoindoline-1,3-dione (0.136 g, 0.832 mmol), triphenylphosphine (0.273 g, 1.04 mmol), and DEAD (0.170 ml, 1.04 mmol). The reaction mixture was stirred at rt for 2 h, and then concentrated. The resulting residue was purified on silica gel column using EtOAc/hexane as eluting solvents to give the title compound. LC/MS: [M+1]$^+$: 581.4.

Step C: (S)-5-(3-(tert-butoxy)-2-((1,3-dioxoisoindolin-2-yl)oxy)-3-oxopropoxy)-2-(3-((tert-butoxycarbonyl)amino)propyl)-1-methyl-2H-indazol-1-ium To a solution of (S)-tert-butyl 3-((2-(3-((tert-butoxycarbonyl)amino)propyl)-2H-indazol-5-yl)oxy)-2-((1,3-dioxoisoindolin-2-yl)oxy)propanoate (379 mg, 0.653 mmol) in acetonitrile (10 ml) at 0° C. was added methyl trifluoromethanesulfonate (0.079 ml, 0.718 mmol). The reaction mixture was stirred at rt for 1 h, then concentrated to give the title compound. LC/MS: M+: 595.4.

Step D: (S)-5-(2-(aminooxy)-3-(tert-butoxy)-3-oxopropoxy)-2-(3-((tert-butoxycarbonyl)amino)propyl)-1-methyl-2H-indazol-1-ium To a solution of (S)-5-(3-(tert-butoxy)-2-((1,3-dioxoisoindolin-2-yl)oxy)-3-oxopropoxy)-2-(3-((tert-butoxycarbonyl)amino)propyl)-1-methyl-2H-indazol-1-ium (389 mg, 0.653 mmol) in ethanol (5 ml) and CH$_2$Cl$_2$ (5 mL) was added hydrazine (0.029 ml, 0.914 mmol). The reaction mixture was stirred at rt for 1 h, and then concentrated to give the title compound. LC/MS: M+: 465.3

Step E: (S)-3-(2-(2-((tert-butoxycarbonyl)amino)thiazol-4-yl)-2-oxoacetamide)-2,2-dimethyl-4-oxoazetidin-1-yl Hydrogen Sulfate To a mixture of 2-(2-((tert-butoxy-carbonyl)amino)thiazol-4-yl)-2-oxoacetic acid hydrochloride (4.02 g, 13.02 mmol) in acetonitrile (60 ml) at 0° C. were added pyridine (3.16 ml, 39.1 mmol), (S)-3-amino-2,2-dimethyl-4-oxoazetidin-1-yl hydrogen sulfate (5.47 g, 26.0 mmol), and EDC (6.24 g, 32.6 mmol). The reaction mixture was stirred at 0° C. for 3 h, then concentrated. The resulting residue was partitioned between 30% IPA/DCM (300 mL) and brine (200 ML). The organic phase was separated, washed with brine, dried over Na$_2$SO$_4$, and concentrated. The resulting residue was purified on reverse phase MPLC using acetonitrile (0.1% formic acid)/water (0.1% formic acid) as eluting solvents to give the title compound. LC/MS: [M+1]$^+$: 465.1.

Step F: 5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-(3-((tert-butoxycarbonyl)amino)propyl)-1-methyl-2H-indazol-1-ium To a solution of (S)-5-(2-(aminooxy)-3-(tert-butoxy)-3-oxopropoxy)-2-(3-((tert-butoxycarbonyl)-amino)propyl)-1-methyl-2H-indazol-1-ium (304 mg, 0.653 mmol) in MeOH (5 ml) and CH$_2$Cl$_2$ (5.00 ml) was added (S)-3-(2-(2-((tert-butoxycarbonyl)amino)thiazol-4-yl)-2-oxoacetamido)-2,2-dimethyl-4-oxoazetidin-1-yl hydrogen sulfate (425 mg, 0.914 mmol). The reaction mixture was stirred at rt overnight, then concentrated. The resulting residue was purified on reverse phase MPLC using acetonitrile (0.1% formic acid)/water (0.1% formic acid) to give the title compound. LC/MS: M+: 911.6.

Step G: (S)-3-((Z)-2-(((S)-2-((2-(3-aminopropyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl Sulfate To a solution of 5-((S)-3-(tert-butoxy)-2-(((Z)-(1-(2-((tert-butoxycarbonyl-)amino)-thiazol-4-yl)-2-(((S)-2,2-dimethyl-4-oxo-1-(sulfooxy)azetidin-3-yl)amino)-2-oxoethylidene)-amino)oxy)-3-oxopropoxy)-2-(3-((tert-butoxycarbonyl)amino)propyl)-1-methyl-2H-indazol-1-ium (306 mg, 0.336 mmol) in CH$_2$Cl$_2$ (2 ml) was added TFA (4 ml, 51.9 mmol). The reaction mixture was stirred at rt for 45 min, and then concentrated. The resulting residue was treated with Et$_2$O three times. The resulting solid was dried under high vacuum, then dissolved in DMSO and purified on reverse phase HPLC using acetonitrile (0.1% formic acid)/water (0.1% formic acid) as eluting solvents to give the title compound. LC/MS: [M+1]$^+$: 655.3. $^1$H NMR (500 MHz, D$_2$O): δ 8.73 (s, 1H), 7.67-7.65 (d, J=9.9 Hz, 1H), 7.49-7.47 (m, 1H), 7.29 (s, 1H), 7.07 (s, 1H), 5.10 (s, 1H), 4.79-4.75 (d, J=8.8 Hz, 2H), 4.53-4.44 (m, 3H), 4.19 (s, 3H), 3.13-3.10 (t, J=7.8 Hz, 2H), 2.40-2.35 (m, 2H), 1.37 (s, 3H), 0.94 (s, 1H).

Example 53

(S)-3-((Z)-2-(2-aminothiazol-4-yl)-2-(((S)-1-carboxy-2-((2-((3-hydroxyazetidin-3-yl)methyl)-1-methyl-2H-indazol-1-ium-5-yl)oxy)ethoxy)imino)acetamido)-2,2-dimethyl-4-oxoazetidin-1-yl Sulfate

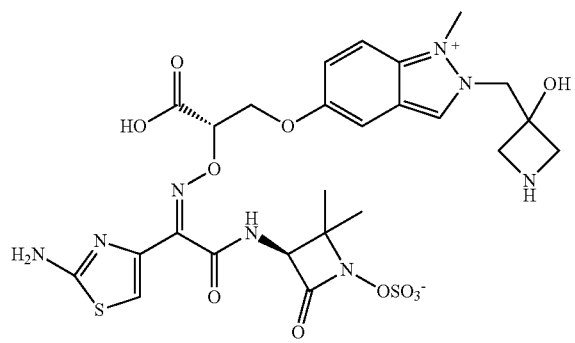

Step A: (R)-Tert-Butyl 3-((5-(3-(tert-butoxy)-2-hydroxy-3-oxopropoxy)-2H-indazol-2-yl)methyl)-3-hydroxyazetidine-1-carboxylate A solution of (R)-tert-butyl 3-(3-formyl-4-nitrophenoxy)-2-hydroxy-propanoate (1.4 g, 4.50 mmol) and tert-butyl 3-(aminomethyl)-3-hydroxyazetidine-1-carboxylate (1.00 g, 4.95 mmol) in 2-propanol (7 ml) was heated at 80° C. for 4 h. Then the solution was cooled to rt, and tri-n-butylphosphine (3.40 ml, 13.49 mmol) was added. The reaction mixture was heated at 80° C. for 16 h, and then concentrated. The resulting residue was purified on silica gel column using EtOAc/hexane as eluting solvents to give the title compound. LC/MS: $[M+1]^+=464.3$.

Step B: (S)-Tert-Butyl 3-((5-(3-(tert-butoxy)-2-((1,3-dioxoisoindolin-2-yl)oxy)-3-oxo-propoxy)-2H-indazol-2-yl)methyl)-3-hydroxyazetidine-1-carboxylate To a solution of (R)-tert-butyl 3-((5-(3-(tert-butoxy)-2-hydroxy-3-oxopropoxy)-2H-indazol-2-yl)methyl)-3-hydroxyazetidine-1-carboxylate (1.17 g, 2.52 mmol) in THF (20 ml) were added dropwise 2-hydroxyisoindoline-1,3-dione (0.453 g, 2.78 mmol), triphenylphosphine (0.993 g, 3.79 mmol), and DEAD (0.599 ml, 3.79 mmol). The reaction mixture was stirred at rt for 2 h, and then concentrated. The resulting residue was purified on silica gel column using EtOAc/hexane as eluting solvents to give the title compound. LC/MS: $[M+1]^+=609.4$.

Step C: (S)-5-(3-(tert-butoxy)-2-((1,3-dioxoisoindolin-2-yl)oxy)-3-oxopropoxy)-2-((1-(tert-butoxy-carbonyl)-3-hydroxyazetidin-3-yl)methyl)-1-methyl-2H-indazol-1-ium To a solution of (S)-tert-butyl 3-((5-(3-(tert-butoxy)-2-((1,3-dioxoisoindolin-2-yl)oxy)-3-oxopropoxy)-2H-indazol-2-yl)methyl)-3-hydroxyazetidine-1-carboxylate (500 mg, 0.822 mmol) in acetonitrile (4 ml) at 0° C. was added methyl trifluoromethanesulfonate (0.109 ml, 0.986 mmol). The resulting solution was stirred at 0° C. and then stirred at rt for 1 hr. Then the reaction mixture was concentrated to give the title compound. LC/MS: $[M]^+=623.4$.

Step D: (S)-5-(2-(aminooxy)-3-(tert-butoxy)-3-oxopropoxy)-2-((1-(tert-butoxycarbonyl)-3-hydroxyazetidin-3-yl)methyl)-1-methyl-2H-indazol-1-ium To a solution of (S)-5-(3-(tert-butoxy)-2-((1,3-dioxoisoindolin-2-yl)oxy)-3-oxopropoxy)-2-((1-(tert-butoxycarbonyl)-3-hydroxyazetidin-3-yl)methyl)-1-methyl-2H-indazol-1-ium (512 mg, 0.821 mmol) in ethanol (5 ml) and $CH_2Cl_2$ (5 mL) was added hydrazine (0.028 ml, 0.903 mmol) at ° C. The reaction mixture was stirred at rt for 1 h, and then concentrated. The resulting residue was treated with DCM (5 mL) and the mixture was stirred at rt for 15 min, and then filtered. The filtrate was concentrated to give the title compound. LC/MS: $[M]^+=493.3$.

Step E: (S,Z)-5-(3-(tert-butoxy)-2-((((2-((tert-butoxycarbonyl)amino)thiazol-4-yl)(carboxy)-methylene)amino)oxy)-3-oxopropoxy)-2-((1-(tert-butoxycarbonyl)-3-hydroxyazetidin-3-yl)methyl)-1-methyl-2H-indazol-1-ium To a solution of (S)-5-(2-(aminooxy)-3-(tert-butoxy)-3-oxopropoxy)-2-((1-(tert-butoxy-carbonyl)-3-hydroxyazetidin-3-yl)methyl)-1-methyl-2H-indazol-1-ium (405 mg, 0.821 mmol) in MeOH (2 mL) and $CH_2Cl_2$ (2 mL) was added 2-(2-((tert-butoxycarbonyl)-amino)thiazol-4-yl)-2-oxoacetic acid (268 mg, 0.985 mmol). The reaction mixture was stirred at rt for 2 h, then concentrated to give the title compound. LC/MS: $[M]^+=747.4$.

Step F: 5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-3-hydroxyazetidin-3-yl)methyl)-1-methyl-2H-indazol-1-ium To a solution of (S,Z)-5-(3-(tert-butoxy)-2-((((2-((tert-butoxycarbonyl)-amino)thiazol-4-yl)(carboxy)methylene)amino)-oxy)-3-oxopropoxy)-2-((1-(tert-butoxy-carbonyl)-3-hydroxy-azetidin-3-yl)methyl)-1-methyl-2H-indazol-1-ium (614 mg, 0.821 mmol) in DMF (8 ml) was added DCC (678 mg, 3.28 mmol) and HOBT (377 mg, 2.463 mmol). The resulting mixture was stirred at rt for 0.5 h, then (S)-3-amino-2,2-dimethyl-4-oxoazetidin-1-yl hydrogen sulfate (518 mg, 2.46 mmol) and sodium bicarbonate (690 mg, 8.21 mmol) were added. The reaction mixture was stirred at rt overnight. Then the mixture was filtered and the filtrate was purified on reverse phase MPLC using acetonitrile (0.05% TFA)/water (0.05% TFA) as eluting solvents to give the title compound. LC/MS: $[M]^+=939.5$.

Step G: (S)-3-(((Z)-2-(2-aminothiazol-4-yl)-2-(((S)-1-carboxy-2-((2-(((3-hydroxyazetidin-3-yl)methyl)-1-methyl-2H-indazol-1-ium-5-yl)oxy)ethoxy)imino)acetamido)-2,2-dimethyl-4-oxoazetidin-1-yl Sulfate To a solution of 5-((S)-3-(tert-butoxy)-2-(((Z)-(1-(2-((tert-butoxy-carbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-3-hydroxyazetidin-3-yl)methyl)-1-methyl-2H-indazol-1-ium (287 mg, 0.305 mmol) in $CH_2Cl_2$ (2 ml) was added TFA (4 ml, 51.9 mmol). The reaction mixture was stirred at rt for 45 min, and then concentrated. The resulting residue was treated with $Et_2O$. The resulting solid was dried under high vacuum, dissolved in DMSO (3 mL) and purified on reverse phase HPLC using acetonitrile (0.1% formic acid)/water (0.1% formic acid). The resulting product was re-purified on reverse phase HPLC using acetonitrile/ammonium acetate (20 mM) buffer to give the title compound. LC/MS: $[M+1]^+=683.4$. $^1H$ NMR (500 MHz, $D_2O$): δ 8.79 (s, 1H), 7.62-7.60 (d, J=9 Hz, 1H), 7.47-7.45 (dd, J=2.3 Hz and 9.0 Hz, 1H), 7.24 (d, J=2.3 Hz, 1H), 6.90 (s, 1H), 5.08 (s, 2H), 4.96-4.94 (m, 1H), 4.41-4.36 (m, 4H), 4.17 (s, 3H), 4.11-4.06 (t, J=8.8 Hz, 2H), 1.35 (s, 3H), 0.98 (s, 3H).

Example 54

(S)-3-((Z)-2-(2-aminothiazol-4-yl)-2-(((S)-2-((2-((3-carbamoylazetidin-3-yl)methyl)-1-methyl-2H-indazol-1-ium-5-yl)oxy)-1-carboxyethoxy)imino)acetamido)-2,2-dimethyl-4-oxoazetidin-1-yl Sulfate

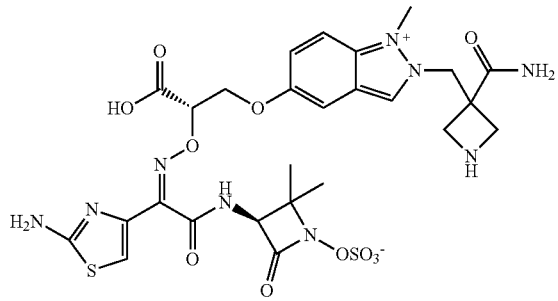

Step A: (R)-tert-butyl 3-((5-(3-(tert-butoxy)-2-hydroxy-3-oxopropoxy)-2H-indazol-2-yl)methyl)-3-carbamoylazetidine-1-carboxylate A solution of tert-butyl 3-(aminomethyl)-3-carbamoylazetidine-1-carboxylate (1 g, 4.36 mmol) and (R)-tert-butyl 3-(3-formyl-4-nitrophenoxy)-2-hydroxypropanoate (1.36 g, 4.36 mmol) in 2-propanol (8 ml) was heated at 80° C. for 4 h. After cooling to rt, tributylphosphine (3.30 ml, 13.1 mmol) was added, and the reaction was heated at 80° C. for 16 h. Then the reaction mixture was concentrated, and the resulting residue was purified on silica gel column using EtOAc/hexane as eluting solvents to give the title compound. LC/MS: [M+1]$^+$=491.4.

Step B: (S)-Tert-Butyl 3-((5-(3-(tert-butoxy)-2-((1,3-dioxoisoindolin-2-yl)oxy)-3-oxo-propoxy)-2H-indazol-2-yl)methyl)-3-carbamoylazetidine-1-carboxylate To a solution of (R)-tert-butyl 3-((5-(3-(tert-butoxy)-2-hydroxy-3-oxopropoxy)-2H-indazol-2-yl)methyl)-3-carbamoylazetidine-1-carboxylate (325 mg, 0.663 mmol) in THF (5 ml) were added 2-hydroxyisoindoline-1,3-dione (130 mg, 0.795 mmol), triphenylphosphine (261 mg, 0.994 mmol), and DEAD (0.157 ml, 0.994 mmol). The reaction mixture was stirred at rt for 3 h, then concentrated. The resulting residue was purified on silica gel column using EtOAc/hexane as eluting solvents to give the title compound. LC/MS: [M+1]$^+$=636.5.

Step C: (S)-Tert-Butyl 3-((5-(2-(aminooxy)-3-(tert-butoxy)-3-oxopropoxy)-2H-indazol-2-yl)methyl)-3-carbamoylazetidine-1-carboxylate To a solution of (S)-tert-butyl 3-((5-(3-(tert-butoxy)-2-((1,3-dioxoisoindolin-2-yl)oxy)-3-oxopropoxy)-2H-indazol-2-yl)methyl)-3-carbamoylazetidine-1-carboxylate (421 mg, 0.662 mmol) in CH$_2$Cl$_2$ (8 ml) and EtOH (8 ml) was added hydrazine (0.025 ml, 0.795 mmol) at 0° C. The reaction mixture was stirred at rt for 1 h, then concentrated. The resulting residue was stirred in DCM (20 mL) for 10 min. The resulting precipitate was filtered off and the filtrate was concentrated to give the title compound. LC/MS: [M+1]$^+$=506.5.

Step D: (S,Z)-2-(((1-(tert-butoxy)-3-((2-((1-(tert-butoxycarbonyl)-3-carbamoylazetidin-3-yl)methyl)-2H-indazol-5-yl)oxy)-1-oxopropan-2-yl)oxy)imino)-2-(2-((tert-butoxycarbonyl)-amino)thiazol-4-yl) acetic Acid To a solution of (S)-tert-butyl 3-((5-(2-(aminooxy)-3-(tert-butoxy)-3-oxopropoxy)-2H-indazol-2-yl)methyl)-3-carbamoylazetidine-1-carboxylate (335 mg, 0.663 mmol) in CH$_2$Cl$_2$ (10 ml) and MeOH (10 ml) was added 2-(2-((tert-butoxy-carbonyl)amino)thiazol-4-yl)-2-oxoacetic acid (180 mg, 0.663 mmol). The reaction mixture was stirred at rt for 2 h, then concentrated. The resulting residue was purified on reverse phase MPLC (C18) using acetonitrile (0.05% TFA)/water (0.05% TFA) as mobile phase to give the title compound. LC/MS: [M+1]$^+$=760.5.

Step E: tert-butyl 3-((5-((S)-3-(tert-butoxy)-2-(((Z)-(1-(2-((tert-butoxycarbonyl)amino)-thiazol-4-yl)-2-(((S)-2,2-dimethyl-4-oxo-1-(sulfooxy)azetidin-3-yl)amino)-2-oxo-ethylidene)amino)oxy)-3-oxopropoxy)-2H-indazol-2-yl)methyl)-3-carbamoylazetidine-1-carboxylate To a solution of (S,Z)-2-(((1-(tert-butoxy)-3-((2-((1-(tert-butoxycarbonyl)-3-carbamoylazetidin-3-yl)methyl)-2H-indazol-5-yl)oxy)-1-oxopropan-2-yl)oxy)imino)-2-(2-((tert-butoxycarbonyl)amino)thiazol-4-yl)acetic acid (313 mg, 0.412 mmol) in acetonitrile (10 ml) at 0° C. were added EDC (237 mg, 1.24 mmol), (S)-3-amino-2,2-dimethyl-4-oxoazetidin-1-yl hydrogen sulfate (260 mg, 1.24 mmol), and pyridine (0.133 ml, 1.65 mmol). The reaction mixture was stirred at 0° C. for 2 h, then concentrated. The resulting residue was purified on reverse phase MPLC (C18) using acetonitrile (0.05% TFA)/water (0.05% TFA) to give the title compound. LC/MS: [M+1]$^+$=952.6.

Step F: 5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-3-carbamoylazetidin-3-yl)methyl)-1-methyl-2H-indazol-1-ium To a solution of tert-butyl 3-((5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2H-indazol-2-yl)methyl)-3-carbamoylazetidine-1-carboxylate (203 mg, 0.213 mmol) in acetonitrile (5 ml) at 0° C. were added sodium bicarbonate (35.8 mg, 0.426 mmol) and methyl trifluoromethanesulfonate (0.028 ml, 0.256 mmol). The reaction mixture was stirred at rt overnight, and filtered. The filtrate was concentrated, and the resulting residue was purified on reverse phase MPLC (C18) using acetonitrile (0.05% TFA)/water (0.05% TFA) as mobile phase to give the title compound. LC/MS: M$^+$=966.6.

Step G: (S)-3-((Z)-2-(2-aminothiazol-4-yl)-2-(((S)-2-((2-((3-carbamoylazetidin-3-yl)-methyl)-1-methyl-2H-indazol-1-ium-5-yl)oxy)-1-carboxyethoxy)imino)acetamido)-2,2-dimethyl-4-oxoazetidin-1-yl Sulfate To a solution of 5-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)-3-carbamoylazetidin-3-yl)methyl)-1-methyl-2H-indazol-1-ium (80 mg, 0.083 mmol) in CH$_2$Cl$_2$ (2 ml) was added TFA (4 mL, 51.9 mmol). The reaction mixture was stirred at rt for 45 min, and then concentrated under vacuum. The resulting residue was treated with Et$_2$O, and the resulting solid was dried under vacuum, then purified on reverse phase HPLC (C18) using acetonitrile (0.05% TFA)/water (0.05% TFA) as mobile phase to give the title compound. LC/MS: [M+1]$^+$=710.5. $^1$H NMR (500 MHz, D$_2$O): δ 8.77 (s, 1H), 7.65-7.65 (d, J=10.7 Hz, 1), 7.51-7.49 (d, J=10.7 Hz, 1H), 7.26 (s, 1H), 7.04 (s, 1H), 5.32 (s, 1H), 5.08-5.06 (m, 1H), 4.50-4.45 (m, 4H), 4.40-4.36 (m, 2H), 4.13 (s, 3H), 1.35 (s, 3H), 0.95 (s, 3H).

Example 55

(S)-3-((Z)-2-(((S)-2-((2-(3-amino-2-(aminomethyl)propyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl Sulfate

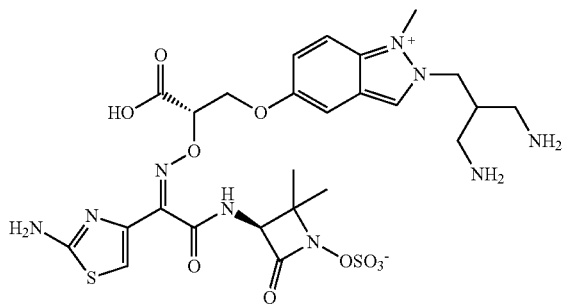

Step A: (R)-Tert-Butyl 3-((2-(3-((tert-butoxycarbonyl)amino)-2-(((tert-butoxycarbonyl)-amino)methyl)-propyl)-2H-indazol-5-yl)oxy)-2-hydroxypropanoate A solution of (R)-tert-butyl 3-(3-formyl-4-nitrophenoxy)-2-hydroxypropanoate (1.32 g, 4.25 mmol) and di-tert-butyl (2-(aminomethyl)propane-1,3-diyl)dicarbamate (1.29 g, 4.25 mmol) in 2-propanol (10 ml) was heated at 80° C. for 4 h. Then the reaction was cooled to rt, and tri-n-butylphosphine (3.22 ml, 12.8 mmol) was added. The reaction mixture was heated at 80° C. for 16 h, then concentrated. The resulting residue was purified on silica gel column using EtOAc/hexane as eluting solvents to give the title compound. LC/MS: [M+1]$^+$: 565.5.

Step B: (S)-Tert-Butyl 3-((2-(3-((tert-butoxycarbonyl)amino)-2-(((tert-butoxycarbonyl)-amino)-methyl)propyl)-2H-indazol-5-yl)oxy)-2-((1,3-dioxoisoindolin-2-yl)oxy)propanoate To a solution of (R)-tert-butyl 3-((2-(3-((tert-butoxycarbonyl)amino)-2-(((tert-butoxy-carbonyl)amino)methyl)propyl)-2H-indazol-5-yl)oxy)-2-hydroxypropanoate (1.1 g, 1.95 mmol) in THF (20 ml) were added 2-hydroxy-isoindoline-1,3-dione (0.381 g, 2.34 mmol), triphenylphosphine (60.8 g, 2.92 mmol), and DEAD (0.463 ml, 2.92 mmol). The reaction mixture was stirred at rt for 2 h, then concentrated. The resulting residue was purified on silica gel column using EtOAc/hexane as eluting solvents to give the title compound. LC/MS: [M+1]$^+$: 710.6

Step C: (S)-5-(3-(tert-butoxy)-2-((1,3-dioxoisoindolin-2-yl)oxy)-3-oxopropoxy)-2-(3-((tert-butoxy-carbonyl)amino)-2-(((tert-butoxycarbonyl)amino)methyl)propyl)-1-methyl-2H-indazol-1-ium To a solution of (S)-tert-butyl 3-((2-(3-((tert-butoxycarbonyl)amino)-2-(((tert-butoxycarbonyl)amino)-methyl)propyl)-2H-indazol-5-yl)oxy)-2-((1,3-dioxoisoindolin-2-yl)oxy)propanoate (1.29 g, 1.82 mmol) in acetonitrile (20 ml) at 0° C. was added methyl trifluoromethanesulfonate (0.240 ml, 2.18 mmol). The reaction mixture was stirred at rt for 1 h, then concentrated to give the title compound. LC/MS: M+: 724.6.

Step D: (S)-5-(2-(aminooxy)-3-(tert-butoxy)-3-oxopropoxy)-2-(3-((tert-butoxycarbonyl)-amino)-2-(((tert-butoxycarbonyl)amino)methyl)propyl)-1-methyl-2H-indazol-1-ium To a solution of (S)-5-(3-(tert-butoxy)-2-((1,3-dioxoisoindolin-2-yl)oxy)-3-oxopropoxy)-2-(3-((tert-butoxycarbonyl)amino)-2-(((tert-butoxycarbonyl)amino)methyl)propyl)-1-methyl-2H-indazol-1-ium (1.32 g, 1.82 mmol) in CH$_2$Cl$_2$ (10 ml) and EtOH (10.00 ml) at 0° C. was added hydrazine (0.068 ml, 2.180 mmol). The reaction mixture was stirred at rt for 1 h, then concentrated to give the title compound. LC/MS: M+: 594.6.

Step E: (S,Z)-5-(3-(tert-butoxy)-2-((((2-((tert-butoxycarbonyl)amino)thiazol-4-yl)(carboxy)-methylene)amino)oxy)-3-oxopropoxy)-2-(3-((tert-butoxycarbonyl)-amino)-2-(((tert-butoxy-carbonyl)-amino)methyl)propyl)-1-methyl-2H-indazol-1-ium To a solution of (S)-5-(2-(aminooxy)-3-(tert-butoxy)-3-oxopropoxy)-2-(3-((tert-butoxycarbonyl)amino)-2-(((tert-butoxycarbonyl)amino)methyl)propyl)-1-methyl-2H-indazol-1-ium (1.08 g, 1.82 mmol) in CH$_2$Cl$_2$ (10 ml) and MeOH (10 ml) was added 2-(2-((tert-butoxycarbonyl)amino)thiazol-4-yl)-2-oxoacetic acid (0.643 g, 2.36 mmol). The reaction mixture was stirred at rt for 2 h, then concentrated to give the title compound. LC/MS: M+: 848.7.

Step F: 5-(((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-(3-((tert-butoxycarbonyl)amino)-2-(((tert-butoxycarbonyl)amino)methyl)-propyl)-1-methyl-2H-indazol-1-ium To a solution of (S,Z)-5-(3-(tert-butoxy)-2-((((2-((tert-butoxycarbonyl)amino)thiazol-4-yl) (carboxy)methylene)amino)oxy)-3-oxopropoxy)-2-(3-((tert-butoxycarbonyl)amino)-2-(((tert-butoxy-carbonyl)amino)methyl)propyl)-1-methyl-2H-indazol-1-ium (1.52 g, 1.79 mmol) in DMF (10 ml) were added DCC (1.48 g, 7.16 mmol) and HOBT (0.823 g, 5.37 mmol). The reaction mixture was stirred at rt for 30 min, then (S)-3-amino-2,2-dimethyl-4-oxoazetidin-1-yl hydrogen sulfate (1.13 g, 5.37 mmol) and sodium bicarbonate (1.50 g, 17.9 mmol) were added. The reaction mixture was stirred at rt overnight, then filtered. The filtrate was purified on reverse phase MPLC (C18 column) using acetonitrile (0.05% TFA)/water (0.05% TFA) as mobile phase to give the title compound. LC/MS: M+: 1041.4.

Step G: (S)-3-((Z)-2-(((S)-2-((2-(3-amino-2-(aminomethyl)propyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl Sulfate To a solution of 5-((S)-3-(tert-butoxy)-2-(((Z)-(1-(2-((tert-butoxy-carbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-(3-((tert-butoxycarbonyl)amino)-2-(((tert-butoxycarbonyl)amino)methyl)propyl)-1-methyl-2H-indazol-1-ium (780 mg, 0.749 mmol) in $CH_2Cl_2$ (4 ml) was added TFA (8 mL, 104 mmol). The reaction mixture was stirred at rt for 70 min, and then concentrated at rt. The resulting residue was treated with $Et_2O$ (10 mL). The resulting solid was collected, and $Et_2O$ solution was concentrated and combined with the solid. The solid was dissolved in DMSO (6.5 mL) and purified on reverse phase HPLC (C18 column) using acetonitrile (0.1% formic acid)/water (0.1% formic acid) to give the title compound. LC/MS: [M+1]$^+$: 684.5. $^1$H NMR (500 MHz, $D_2O$): δ 8.80 (s, 1H), 7.64-7.62 (d, J=10.1 Hz, 1H), 7.49-7.47 (d, J=10.1 Hz, 1H), 7.25 (s, 1H), 6.94 (s, 1H), 4.98 (s, 1H), 4.88-4.87 (d, J=7.2 Hz, 2H), 4.46-4.43 (m, 2H), 4.21 (s, 3H), 3.53-3.48 (m, 1H), 3.27-3.22 (m, 2H), 3.10-3.06 (m, 2H), 2.86-2.80 (m, 1H), 1.40 (s, 3H), 1.00 (s, 3H).

Example 56

(S)-3-((Z)-2-(2-Aminothiazol-4-yl)-2-(((S)-1-carboxy-2-((1-methyl-2-((R)-pyrrolidin-3-yl)-2H-indazol-1-ium-5-yl)oxy)ethoxy)imino)acetamido)-2,2-dimethyl-4-oxoazetidin-1-yl Sulfate

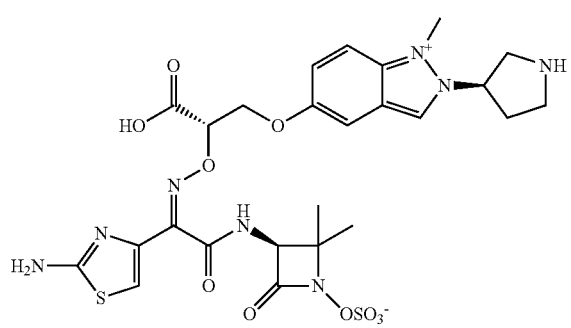

Step A: Tert-Butyl (R)-3-(5-((R)-3-(tert-butoxy)-2-hydroxy-3-oxopropoxy)-2H-indazol-2-yl)pyrrolidine-1-carboxylate A solution of (R)-tert-butyl 3-(3-formyl-4-nitrophenoxy)-2-hydroxypropanoate (300 mg, 0.964 mmol) and (R)-(+)-1-Boc-3-aminopyrrolidine in 2-propanol (2 ml) was heated at 80° C. for 4 h. Then the reaction was cooled to rt, and tri-n-butylphosphine (0.729 ml, 2.89 mmol) was added. The reaction mixture was heated at 80° C. for 16 h, then concentrated. The resulting residue was purified on silica gel column (40 g) using 0-60% EtOAc/hexane to give the title compound. LC/MS: m/e 448.21 (M+H)$^+$.

Step B: Tert-Butyl (R)-3-(5-((S)-3-(tert-butoxy)-2-((1,3-dioxoisoindolin-2-yl)oxy)-3-oxo-propoxy)-2H-indazol-2-yl)pyrrolidine-1-carboxylate To a solution of (R)-tert-butyl 3-(5-((R)-3-(tert-butoxy)-2-hydroxy-3-oxopropoxy)-2H-indazol-2-yl)pyrrolidine-1-carboxylate (288 mg, 0.644 mmol) in THF (4.29 ml) at rt were added dropwise 2-hydroxyisoindoline-1,3-dione (126 mg, 0.772 mmol), triphenylphosphine (253 mg, 0.965 mmol), and diisopropyl azodicarboxylate (190 µl, 0.965 mmol). The reaction mixture was stirred at rt overnight, then concentrated. The resulting residue was purified on silica gel column (40 g) using 0-70% EtOAc/hexane to give the title compound. LC/MS: m/e 593.17 (M+H)$^+$.

Step C: 5-((S)-3-(tert-Butoxy)-2-((1, 3-dioxoisoindolin-2-yl)oxy)-3-oxopropoxy)-2-((R)-1-(tert-butoxycarbonyl)pyrrolidin-3-yl)-1-methyl-2H-indazol-1-ium To a solution of (R)-tert-butyl 3-(5-((S)-3-(tert-butoxy)-2-((1,3-dioxoisoindolin-2-yl)oxy)-3-oxopropoxy)-2H-indazol-2-yl)pyrrolidine-1-carboxylate (360 mg, 0.607 mmol) in acetonitrile (6 ml) at 0° C. was added methyl trifluoromethane-sulfonate (73.6 µl, 0.668 mmol). The reaction mixture was stirred at rt for 1 h, then concentrated to give the title compound, which was used in the next step without further purification. LC/MS: m/e 607.23 (M)$^+$.

Step D: 5-((S)-2-(Aminooxy)-3-(tert-butoxy)-3-oxopropoxy)-2-((R)-1-(tert-butoxy carbonyl)pyrrolidin-3-yl)-1-methyl-2H-indazol-1-ium To a solution of 5-((S)-3-(tert-butoxy)-2-((1,3-dioxoisoindolin-2-yl)oxy)-3-oxopropoxy)-2-((R)-1-(tert-butoxycarbonyl)-pyrrolidin-3-yl)-1-methyl-2H-indazol-1-ium (0.369 g, 0.607 mmol) in ethanol (4.1 ml) and $CH_2Cl_2$ (4.1 ml) was added hydrazine (0.023 ml, 0.728 mmol). The reaction mixture was stirred at rt for 1 h, then concentrated. The resulting residue was treated with $CH_2Cl_2$ (10 mL), and the mixture was stirred at rt for 30 min. The mixture was filtered, and the filtrate was concentrated to give title compound. LC/MS: m/e 477.21 (M)$^+$.

Step E: 5-((S)-3-(tert-Butoxy)-2-((((Z)-(2-((tert-Butoxycarbonyl)amino)thiazol-4-yl)-(carboxy)-methylene)amino)oxy)-3-oxopropoxy)-2-((R)-1-(tert-butoxycarbonyl)pyrrolidin-3-yl)-1-methyl-2H-indazol-1-ium To a solution of 5-((S)-2-(aminooxy)-3-(tert-butoxy)-3-oxopropoxy)-2-((R)-1-(tert-butoxycarbonyl) pyrrolidin-3-yl)-1-methyl-2H-indazol-1-ium (0.290 g, 0.607 mmol) in MeOH (3.04 ml) and $CH_2Cl_2$ (3.04 ml) was added 2-(2-((tert-butoxycarbonyl)amino)thiazol-4-yl)-2-oxoacetic acid (0.198 g, 0.728 mmol). The reaction was stirred at rt for 2 h, then concentrated to give the title compound. LC/MS: m/e 731.24 (M)$^+$.

Step F: 5-((S)-3-(tert-Butoxy)-2-((((Z)-1-(2-((tert-Butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((R)-1-(tert-butoxycarbonyl)pyrrolidin-3-yl)-1-methyl-2H-indazol-1-ium To a solution of 5-((S)-3-(tert-butoxy)-2-(((Z)-((2-((tert-butoxy-carbonyl)amino)-thiazol-4-yl)(carboxy)methylene)

amino)oxy)-3-oxopropoxy)-2-((R)-1-(tert-butoxycarbonyl)-pyrrolidin-3-yl)-1-methyl-2H-indazol-1-ium (444 mg, 0.607 mmol) in DMF (4047 µl) at rt were added DCC (376 mg, 1.82 mmol) and HOBT (279 mg, 1.82 mmol). The reaction mixture was stirred at rt for 0.5 hr, then (S)-3-amino-2,2-dimethyl-4-oxoazetidin-1-yl hydrogen sulfate (383 mg, 1.82 mmol) and NaHCO$_3$ (510 mg, 6.07 mmol) were added. The resulting mixture was stirred at rt overnight. Then the mixture was filtered and the filtrate was purified on reverse phase MPLC (C18, 100 g column) using 10-100% acetonitrile (0.05% TFA)/water (0.05% TFA) to give the title compound. LC/MS: m/e 923.22 (M+H)$^+$.

Step G: (S)-3-((Z)-2-(2-Aminothiazol-4-yl)-2-(((S)-1-carboxy-2-((1-methyl-2-((R)-pyrrolidin-3-yl)-2H-indazol-1-ium-5-yl)oxy)ethoxy)imino)acetamido)-2,2-dimethyl-4-oxoazetidin-1-yl Sulfate To a solution of 5-((S)-3-(tert-butoxy)-2-(((Z)-(1-(2-((tert-butoxy-carbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((R)-1-(tert-butoxycarbonyl)-pyrrolidin-3-yl)-1-methyl-2H-indazol-1-ium (70 mg, 0.076 mmol) in CH$_2$Cl$_2$ (2 ml) was added TFA (4 ml, 51.9 mmol). The reaction mixture was stirred at rt for 40 min, then concentrated. washed with Et$_2$O twice, and dried under vacuum. The resulting crude product was purified on RP-HPLC (Gilson) (Sunfire, prep C$_{18}$, OBD, 10 um, 30×150 mm, 5-25% MeCN/H$_2$O with 0.05% TFA, 12 min) to give the title compound. LC/MS: m/e 667.06 (M+H)$^+$. $^1$H NMR (500 MHz, D$_2$O): δ (ppm) 0.86 (s, 3H); 1.30 (s, 3H); 2.67-2.59 (m, 1H); 2.83 (dt, J=14.7, 7.4 Hz, 1H); 3.68-3.54 (m, 2H); 3.79 (dd, J=13.7, 4.9 Hz, 1H); 4.07 (dd, J=13.7, 7.9 Hz, 1H); 4.17 (s, 3H); 4.40 (dd, J=11.2, 5.8 Hz, 1H); 4.48-4.46 (m, 1H); 4.64 (s, 1H); 5.07 (dd, J=5.6, 2.1 Hz, 1H); 5.76 (t, J=6.7 Hz, 1H); 7.02 (s, 1H); 7.24 (d, J=2.3 Hz, 1H); 7.44 (dd, J=9.5, 2.3 Hz, 1H); 7.61 (d, J=9.5 Hz, 1H); 8.88 (s, 1H).

TABLE 6

The compounds in Examples 57 to 63 were prepared according to the procedure of Example 56 using the appropriate starting materials and reagents.

| Example | Name | Structure | LC/MS(M) |
|---|---|---|---|
| 57 | (S)-3-((Z)-2-(2-aminothiazol-4-yl)-2-(((S)-1-carboxy-2-((1-methyl-2-(((R)-pyrrolidin-3-yl)methyl)-2H-indazol-1-ium-5-yl)oxy)ethoxy)imino)acetamido)-2,2-dimethyl-4-oxoazetidin-1-yl sulfate | 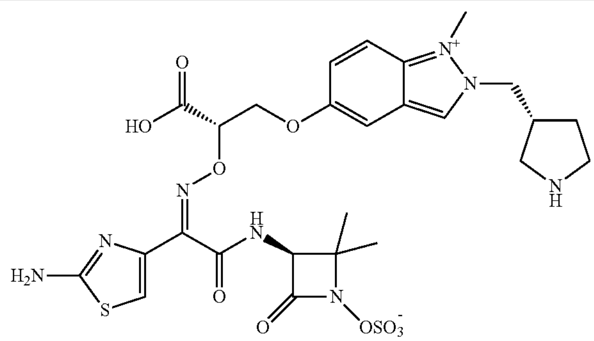 | 680.1 |
| 58 | (S)-3-((Z)-2-(2-aminothiazol-4-yl)-2-(((S)-1-carboxy-2-((1-methyl-2-(piperidin-4-ylmethyl)-2H-indazol-1-ium-5-yl)oxy)ethoxy)imino)acetamido)-2,2-dimethyl-4-oxoazetidin-1-yl sulfate | 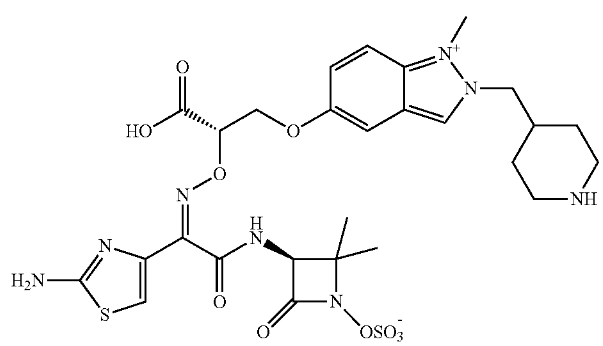 | 694.1 |
| 59 | (S)-3-((Z)-2-(2-aminothiazol-4-yl)-2-(((S)-1-carboxy-2-((1-methyl-2-(piperidin-4-yl)-2H-indazol-1-ium-5-yl)oxy)ethoxy)imino)acetamido)-2,2-dimethyl-4-oxoazetidin-1-yl sulfate | 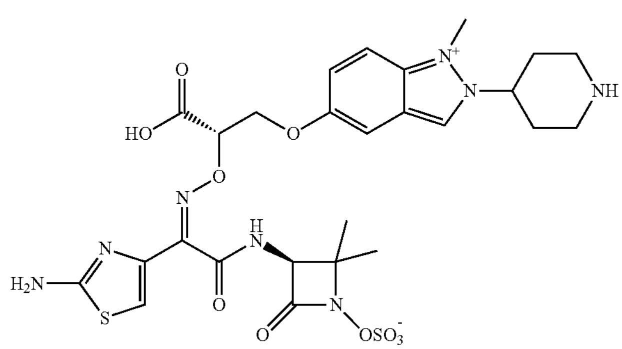 | 679.9 |

TABLE 6-continued

The compounds in Examples 57 to 63 were prepared according to the procedure of Example 56 using the appropriate starting materials and reagents.

| Example | Name | Structure | LC/MS(M) |
|---|---|---|---|
| 60 | (S)-3-((Z)-2-(((S)-2-((2-((R)-2-aminopropyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl sulfate | 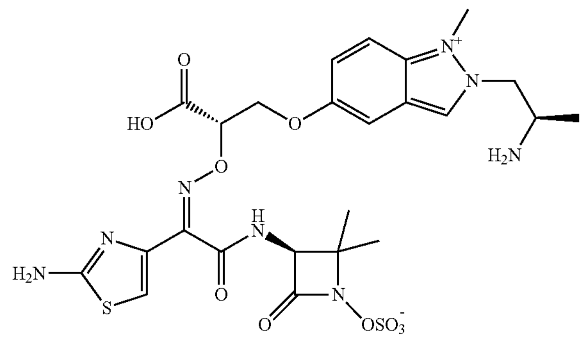 | 654.2 |
| 61 | (S)-3-((Z)-2-(((S)-2-((2-((1r,4S)-4-aminocyclohexyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl sulfate | 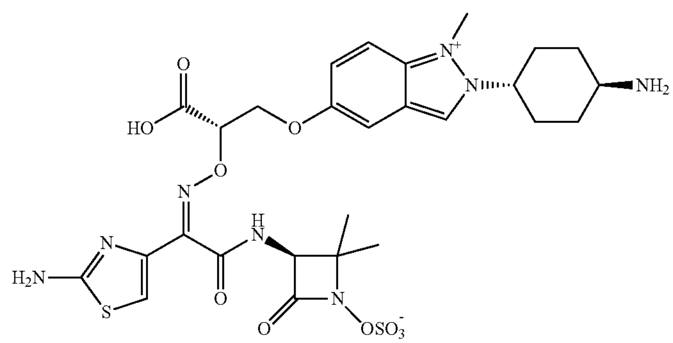 | 694.3 |
| 62 | (S)-3-((Z)-2-(((S)-2-((2-(3-amino-2,2-difluoropropyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl sulfate | 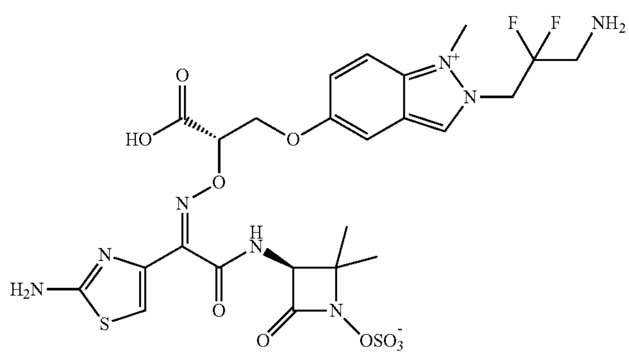 | 690.0 |
| 63 | (S)-3-((Z)-2-(((S)-2-((2-((1s,4R)-4-aminocyclohexyl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl sulfate | 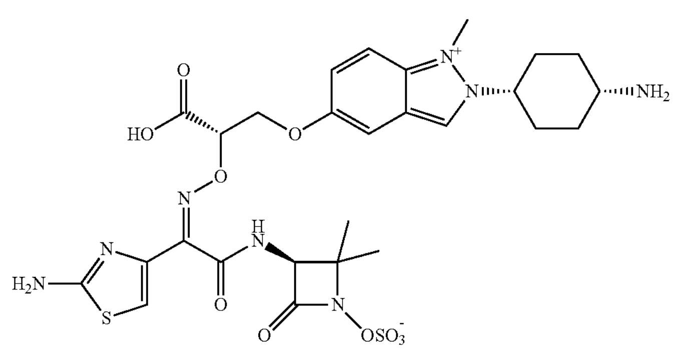 | 694.1 |

Example 64

(S)-3-((Z)-2-(2-Aminothiazol-4-yl)-2-(((S)-1-carboxy-2-((2-((3R,4S)-4-hydroxypyrrolidin-3-yl)-1-methyl-2H-indazol-1-ium-5-yl)oxy)ethoxy)imino)acetamido)-2,2-dimethyl-4-oxoazetidin-1-yl Sulfate

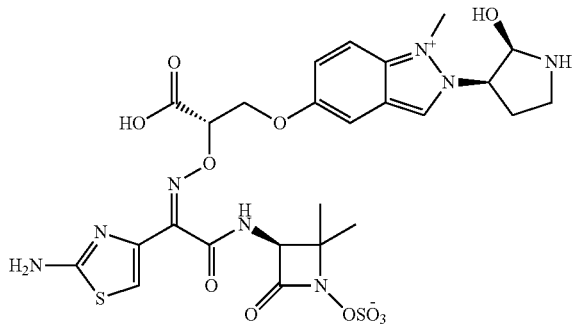

Step A: tert-Butyl (3R,4S)-3-amino-4-((tert-butyldimethylsilyl)oxy)pyrrolidine-1-carboxylate To a solution of (3R,4S)-tert-butyl 3-amino-4-hydroxypyrrolidine-1-carboxylate (250 mg, 1.24 mmol) and imidazole (210 mg, 3.09 mmol) in DCM (12 ml) was added TBDMS-Cl (224 mg, 1.48 mmol) at rt. The reaction was stirred at rt overnight, then partitioned between EtOAc and water. The organic layer was washed with brine, dried over MgSO$_4$, filtered, concentrated and purified on silica gel column (40 g) using 10-10% MeOH/DCM to give the title compound.

Step B: tert-Butyl (3R,4S)-3-(5-((R)-3-(tert-butoxy)-2-hydroxy-3-oxopropoxy)-2H-indazol-2-yl)-4-((tert-butyldimethylsilyl)oxy)pyrrolidine-1-carboxylate The title compound was prepared according to the procedure described for Example 56 using tert-Butyl (3R,4S)-3-amino-4-((tert-butyldimethylsilyl)oxy) pyrrolidine-1-carboxylate. LC/MS: m/e 578.23 (M+H)$^+$.

Step C: Tert-Butyl (3R, 4S)-3-(5-((S)-3-(tert-butoxy)-2-((1, 3-dioxoisoindolin-2-yl)oxy)-3-oxopropoxy)-2H-indazol-2-yl)-4-((tert-butyldimethylsilyl)oxy)pyrrolidine-1-carboxylate The title compound was prepared according to the procedure described for Example 56 using tert-Butyl (3R, 4S)-3-(5-((R)-3-(tert-butoxy)-2-hydroxy-3-oxopropoxy)-2H-indazol-2-yl)-4-((tert-butyldimethylsilyl)oxy)pyrrolidine-1-carboxylate. LC/MS: m/e 723.24 (M+H)$^+$.

Step D: 5-((S)-3-(tert-Butoxy)-2-((1,3-dioxoisoindolin-2-yl)oxy)-3-oxopropoxy)-2-((3R,4S)-1-(tert-butoxycarbonyl)-4-((tert-butyldimethylsilyl)oxy)pyrrolidin-3-yl)-1-methyl-2H-indazol-1-ium The title compound was prepared according to the procedure described for Example 56 using tert-Butyl (3R,4S)-3-(5-((S)-3-(tert-butoxy)-2-((1,3-dioxoisoindolin-2-yl)oxy)-3-oxopropoxy)-2H-indazol-2-yl)-4-((tert-butyldimethylsilyl)oxy)pyrrolidine-1-carboxylate. LC/MS: m/e 737.22 (M)$^+$.

Step E: 5-((S)-2-(Aminooxy)-3-(tert-butoxy)-3-oxopropoxy)-2-((3R, 4S)-1-(tert-butoxycarbonyl)-4-((tert-butyldimethylsilyl)oxy)pyrrolidin-3-yl)-1-methyl-2H-indazol-1-ium The title compound was prepared according to the procedure described for Example 56 using 5-((S)-3-(tert-Butoxy)-2-((1,3-dioxoisoindolin-2-yl)oxy)-3-oxopropoxy)-2-((3R,4S)-1-(tert-butoxycarbonyl)-4-((tert-butyldimethylsilyl)oxy)pyrrolidin-3-yl)-1-methyl-2H-indazol-1-ium. LC/MS: m/e 607.28 (M)$^+$.

Step F: 5-((S)-3-(tert-butoxy)-2-(((Z)-(2-((tert-butoxycarbonyl)amino)thiazol-4-yl)(carboxy)methylene)amino)oxy)-3-oxopropoxy)-2-((3R,4S)-1-(tert-butoxycarbonyl)-4-((tert-butyldimethylsilyl)oxy)pyrrolidin-3-yl)-1-methyl-2H-indazol-1-ium The title compound was prepared according to the procedure described for Example 56 using 5-((S)-2-(Aminooxy)-3-(tert-butoxy)-3-oxopropoxy)-2-((3R,4S)-1-(tert-butoxycarbonyl)-4-((tert-butyldimethylsilyl)oxy)pyrrolidin-3-yl)-1-methyl-2H-indazol-1-ium. LC/MS: m/e 861.47 (M)$^+$.

Step G: 5-((S)-3-(tert-Butoxy)-2-(((Z)-(2-((tert-butoxycarbonyl)amino)thiazol-4-yl)(carboxy)methylene)amino)oxy)-3-oxopropoxy)-2-((3R,4S)-1-(tert-butoxycarbonyl)-4-hydroxypyrrolidin-3-yl)-1-methyl-2H-indazol-1-ium To a solution of 5-((S)-3-(tert-butoxy)-2-(((Z)-((2-((tert-butoxycarbonyl)amino)thiazol-4-yl)(carboxy)methylene)amino)oxy)-3-oxopropoxy)-2-((3R,4S)-1-(tert-butoxycarbonyl)-4-((tert-butyldimethylsilyl)oxy) pyrrolidin-3-yl)-1-methyl-2H-indazol-1-ium (274 mg, 0.318 mmol) in THF (3 ml) at rt was added TBAF (382 µl, 0.382 mmol). The reaction mixture was stirred at rt for 2 h, then concentrated to dryness, and purified by C18 column (150 g, 10-100% MeCN (0.05% TFA)/H$_2$O (0.05% TFA)) to give the title compound. LC/MS: m/e 747.22 (M)$^+$.

Step H: 5-((S)-3-(tert-Butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((3R, 4S)-1-(tert-butoxycarbonyl)-4-hydroxypyrrolidin-3-yl)-1-methyl-2H-indazol-1-ium The title compound was prepared according to the procedure described for Example 56 using 5-((S)-3-(tert-Butoxy)-2-((((Z)-(2-((tert-butoxycarbonyl)amino) thiazol-4-yl)(carboxy)methylene)amino)oxy)-3-oxopropoxy)-2-((3R, 4S)-1-(tert-butoxycarbonyl)-4-hydroxypyrrolidin-3-yl)-1-methyl-2H-indazol-1-ium. LC/MS: m/e 939.31 (M+H)$^+$.

Step I: (S)-3-((Z)-2-(2-Aminothiazol-4-yl)-2-(((S)-1-carboxy-2-((2-((3R,4S)-4-hydroxypyrrolidin-3-yl)-1-methyl-2H-indazol-1-ium-5-yl)oxy)ethoxy)imino)acetamido)-2,2-dimethyl-4-oxoazetidin-1-yl Sulfate The title compound was prepared according to the procedure described for Example 56 using 5-((S)-3-(tert-butoxy)-2-(((((Z)-1-(2-((tert-butoxycarbonyl)amino) thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((3R,4S)-1-(tert-butoxycarbonyl)-4-hydroxypyrrolidin-3-yl)-1-methyl-2H-indazol-1-ium. ¹H NMR (500 MHz, D₂O): δ (ppm) 0.92 (s, 3H); 1.37 (s, 3H); 3.68 (m, 2H); 4.06 (d, J=10.8 Hz, 1H); 4.15 (d, J=10.4 Hz, 1H); 4.26 (s, 3H); 4.50 (m, 1H); 4.55 (m, 1H); 4.82 (s, 1H); 5.15 (s, 1H); 5.80 (m, 1H); 7.10 (s, 1H); 7.33 (s, 1H); 7.53 (d, J=9.4 Hz, 1H); 7.70 (d, J=9.5 Hz, 1H); 9.02 (s, 1H). LC/MS: m/e 683.67 (M+H)⁺.

TABLE 7

The compounds in Examples 65 and 66 were prepared according to the procedure of Example 64 using the appropriate starting materials and reagents.

| Example | Name | Structure | LC/MS (M)⁺ |
|---|---|---|---|
| 65 | (S)-3-((Z)-2-(((S)-2-((2-((S)-1-amino-3-hydroxypropan-2-yl)-1-methyl-2H-indazol-1-ium-5-yl)oxy)-1-carboxyethoxy)imino)-2-(2-aminothiazol-4-yl)acetamido)-2,2-dimethyl-4-oxoazetidin-1-yl sulfate | 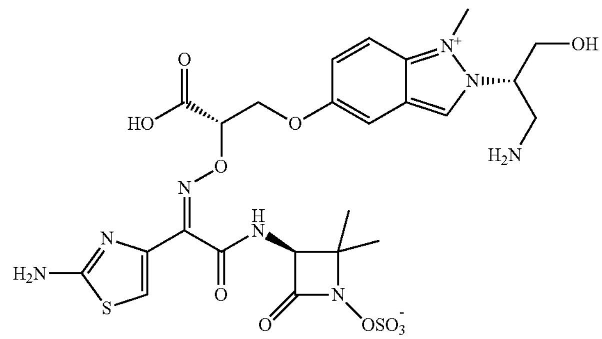 | 670.2 |
| 66 | (S)-3-((Z)-2-(2-aminothiazol-4-yl)-2-(((S)-1-carboxy-2-((2-(((3R,4S)-4-hydroxypyrrolidin-3-yl)methyl)-1-methyl-2H-indazol-1-ium-5-yl)oxy)ethoxy)imino)acetamido)-2,2-dimethyl-4-oxoazetidin-1-yl sulfate | 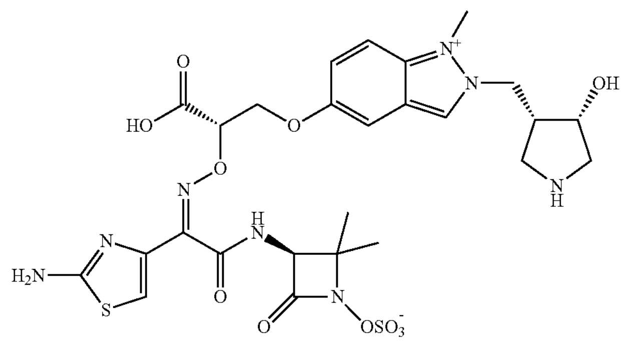 | 696.7 |

Example 67

(3S)-3-((Z)-2-(2-aminothiazol-4-yl)-2-(((1S)-2-((2-(azetidin-3-ylmethyl)-1-(2,3-dihydroxypropyl)-2H-indazol-1-ium-5-yl)oxy)-1-carboxyethoxy)imino)acetamido)-2,2-dimethyl-4-oxoazetidin-1-yl Sulfate

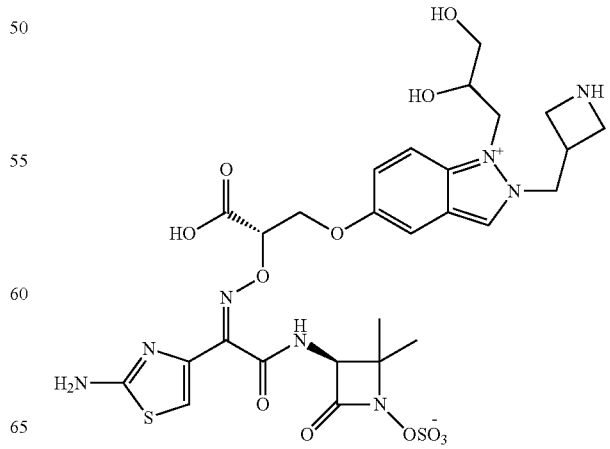

Step A: (S)-1-allyl-5-(3-(tert-butoxy)-2-((1,3-dioxoisoindolin-2-yl)oxy)-3-oxopropoxy)-2-((1-(tert-butoxycarbonyl)azetidin-3-yl)methyl)-2H-indazol-1-ium 3-iodoprop-1-ene (569 µl, 6.22 mmol) was added to a solution of (S)-tert-butyl 3-((5-(3-(tert-butoxy)-2-((1,3-dioxoisoindolin-2-yl)oxy)-3-oxopropoxy)-2H-indazol-2-yl)methyl) azetidine-1-carboxylate (737 mg, 1.244 mmol) in CH$_3$CN at rt. The reaction mixture was stirred at 60° C. for 72 h, then cooled to rt and concentrated. The resulting residue was purified by column chromatography on silica gel (80 g), eluting with MeOH/DCM (0-15%), re-purified by C18 column (150 g, 0-100% MeCN/H$_2$O (0.05% TFA) to give the title compound.
LC/MS: m/e 633.45 (M)$^+$.

Step B: 5-((S)-3-(tert-Butoxy)-2-((1,3-dioxoisoindolin-2-yl)oxy)-3-oxopropoxy)-2-((1-(tert-butoxycarbonyl)azetidin-3-yl)methyl)-1-(2, 3-dihydroxypropyl)-2H-indazol-1-ium To a solution of(S)-1-allyl-5-(3-(tert-butoxy)-2-((1,3-dioxoisoindolin-2-yl)oxy)-3-oxopropoxy)-2-((1-(tert-butoxycarbonyl)-azetidin-3-yl)methyl)-2H-indazol-1-ium (294 mg, 0.464 mmol) in CH$_2$Cl$_2$ (9 ml) at rt were added 4-methylmorpholine N-oxide (163 mg, 1.392 mmol) and osmium tetroxide (2.36 mg, 9.28 µmol). The reaction mixture was stirred at rt overnight, then quenched with saturated Na$_2$S$_2$O$_3$, extracted with IPA/CHCl$_3$ (1:3) (3×), dried over MgSO$_4$, filtered, and concentrated. The resulting residue was purified by C-18 column (150 g, 0-100% MeCN/H$_2$O w/0.05% TFA) to give the title compound.

Step C: 5-((S)-2-(Aminooxy)-3-(tert-butoxy)-3-oxopropoxy)-2-((1-(tert-butoxycarbonyl)-azetidin-3-yl)methyl)-1-(2,3-dihydroxypropyl)-2H-indazol-1-ium The title compound was prepared according to the procedure described for Example 56 using 5-((S)-3-(tert-Butoxy)-2-((1,3-dioxoisoindolin-2-yl)oxy)-3-oxopropoxy)-2-((1-(tert-butoxycarbonyl)azetidin-3-yl)methyl)-1-(2,3-dihydroxypropyl)-2H-indazol-1-ium. LC/MS: m/e 537.67 (M)$^+$.

Step D: 5-((S)-3-(tert-Butoxy)-2-((((Z)-(2-((tert-butoxycarbonyl)amino)thiazol-4-yl)-(carboxy)methylene)-amino)oxy)-3-oxopropoxy)-2-((1-(tert-butoxycarbonyl)azetidin-3-yl)methyl)-1-(2,3-dihydroxypropyl)-2H-indazol-1-ium The title compound was prepared according to the procedure described for Example 56 using 5-((S)-2-(aminooxy)-3-(tert-butoxy)-3-oxopropoxy)-2-((1-(tert-butoxycarbonyl)azetidin-3-yl)methyl)-1-(2, 3-dihydroxypropyl)-2H-indazol-1-ium. LC/MS: m/e 791.00 (M)$^+$.

Step E: 5-((S)-3-(tert-Butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-((1-(tert-butoxycarbonyl)azetidin-3-yl)methyl)-1-(2,3-dihydroxypropyl)-2H-indazol-1-ium The title compound was prepared according to the procedure described for Example 56 using 5-((S)-3-(tert-Butoxy)-2-((((Z)-2-((tert-butoxycarbonyl)amino)thiazol-4-yl) (carboxy)methylene)amino)oxy)-3-oxopropoxy)-2-((1-(tert-butoxycarbonyl)azetidin-3-yl)methyl)-1-(2,3-dihydroxypropyl)-2H-indazol-1-ium. LC/MS: m/e 983.92 (M+H)$^+$.

Step F: (3S)-3-((Z)-2-(2-aminothiazol-4-yl)-2-(((1S)-2-((2-(azetidin-3-ylmethyl)-1-(2,3-dihydroxypropyl)-2H-indazol-1-ium-5-yl)oxy)-1-carboxyethoxy)imino)acetamido)-2,2-dimethyl-4-oxoazetidin-1-yl Sulfate The above compound was prepared according to the procedure described for Example 56 using 5-((S)-3-(tert-Butoxy)-2-((((Z)-1-(2-((tert-butoxycarbonyl)amino)thiazol-4-yl)-2-(((S)-2,2-dimethyl-4-oxo-1-(sulfooxy)azetidin-3-yl) amino)-2-oxoethylidene)amino)oxy)-3-oxopropoxy)-2-((1-(tert-butoxycarbonyl)azetidin-3-yl)methyl)-1-(2,3-dihydroxypropyl)-2H-indazol-1-ium. $^1$H NMR (500 MHz, D$_2$O): δ (ppm) 0.89 (d, J=7.3 Hz, 3H); 1.30 (s, 3H); 3.58-3.55 (m, 3H); 4.03 (m, 3H); 4.18 (m, 2H); 4.45-4.40 (m, 2H); 4.64-4.67 (m, 2H): 4.75-4.79 (m, 1H); 5.04-5.00 (m, 3H); 7.01 (s, 1H); 7.24 (s, 1H); 7.44 (d, J=9.6 Hz, 1H); 7.64 (d, J=9.5 Hz, 1H); 8.72 (s, 1H). LC/MS: m/e 727.22 (M+H)$^+$.

Example 68

(S)-3-((Z)-2-(2-Aminothiazol-4-yl)-2-(((S)-2-((3-((azetidin-3-ylmethyl)amino)-2-methylisoquinolin-2-ium-7-yl)oxy)-1-carboxyethoxy)imino)acetamido)-2,2-dimethyl-4-oxoazetidin-1-yl Sulfate

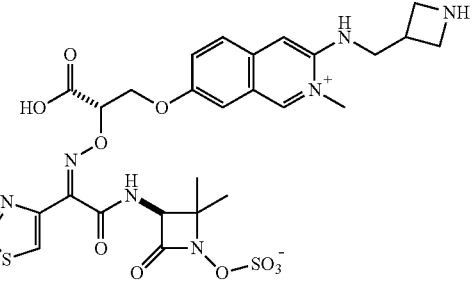

Step A. Preparation of Tert-Butyl (R)-3-(((7-(3-(tert-butoxy)-2-((tert-butyldimethylsilyl)oxy)-3-oxopropoxy)isoquinolin-3-yl)amino)methyl)azetidine-1-carboxylate To a solution of (R)-tert-butyl 2-((tert-butyldimethylsilyl)oxy)-3-((3-chloroisoquinolin-7-yl)oxy)propanoate (1-4, 300 mg, 0.685 mmol) in dioxane (5 ml) were added tert-butyl 3-(aminomethyl)azetidine-1-carboxylate (191 mg, 1.03 mmol), 2nd generation Ruphos precatalyst (106 mg, 0.137 mmol) and Cs$_2$CO$_3$ (558 mg, 1.71 mmol). After degassing and refilling with N$_2$, the reaction was heated at 70° C. overnight. Then the reaction mixture was diluted with EtOAc, washed with NH$_4$Cl, water, and brine. The solvent was removed, and the resulting residue was purified by column chromatography on silica gel (40 g), eluting with EtOAc/hexane (40%) to give the title compound. LC-MS [M+H]$^+$: m/z 589.52.

Step B. Preparation of Tert-Butyl (R)-3-(((7-(3-(tert-butoxy)-2-hydroxy-3-oxopropoxy) isoquinolin-3-yl)amino)methyl)azetidine-1-carboxylate To a solution of (R)-tert-butyl 3-(((7-(3-(tert-butoxy)-2-((tert-butyldimethylsilyl)oxy)-3-oxopropoxy)isoquinolin-3-yl)amino)methyl)azetidine-1-carboxylate (0.13 g, 0.221 mmol) in THF (3 ml) was added TBAF in THF (0.221 ml, 0.221 mmol). The reaction was stirred at rt for 1 h, then the solvent was removed. The resulting residue was purified by column chromatography on silica gel (12 g), eluting with EtOAc/hexane (30%, 15 cv) to give the title compound. LC-MS [M+H]: m/z 474.42.

Step C. Preparation of Tert-Butyl (S)-3-(((7-(3-(tert-butoxy)-2-((1,3-dioxoisoindolin-2-yl)oxy)-3-oxopropoxy)isoquinolin-3-yl)amino)methyl)azetidine-1-carboxylate A solution of (R)-tert-butyl 3-(((7-(3-(tert-butoxy)-2-hydroxy-3-oxopropoxy)isoquinolin-3-yl)amino)methyl)azetidine-1-carboxylate (0.12 g, 0.253 mmol) in THF (1 ml) were added 2-hydroxyisoindoline-1,3-dione (0.050 g, 0.304 mmol), and triphenylphosphine (0.080 g, 0.304 mmol), followed by DIAD (0.059 ml, 0.304 mmol) at rt. The reaction mixture was stirred overnight, then the solvent was removed. The resulting residue was purified by column chromatography on silica gel (24 g), eluting with EtOAc/Hexane (70% 15 cv) to give the title compound. LC-MS [M+H]: m/z 619.36

Step D. Preparation of (S)-7-(3-(tert-butoxy)-2-((1,3-dioxoisoindolin-2-yl)oxy)-3-oxopropoxy)-3-(((1-(tert-butoxycarbonyl)azetidin-3-yl)methyl)amino)-2-methylisoquinolin-2-ium Iodide To a solution of (S)-tert-butyl 3-(((7-(3-(tert-butoxy)-2-((1,3-dioxoisoindolin-2-yl)oxy)-3-oxopropoxy)isoquinolin-3-yl)amino)methyl)azetidine-1-carboxylate (80 mg, 0.129 mmol) in ACN (0.5 ml) was added MeI (0.081 ml, 1.29 mmol). The reaction mixture was heated at 75° C. overnight, then the solvent was removed to give the title compound. LC-MS [M+H]: m/z 633.44

Step E. Preparation of (S)-7-(2-(aminooxy)-3-(tert-butoxy)-3-oxopropoxy)-3-(((1-(tert-butoxycarbonyl)azetidin-3-yl)methyl)amino)-2-methylisoquinolin-2-ium Iodide To a solution of (S)-7-(3-(tert-butoxy)-2-((1,3-dioxoisoindolin-2-yl)oxy)-3-oxopropoxy)-3-(((1-(tert-butoxycarbonyl)azetidin-3-yl)methyl)amino)-2-methylisoquinolin-2-ium iodide in ACN (1 ml) was added hydrazine (3.96 μl, 0.126 mmol). The reaction was stirred at rt for 1 h and then concentrated. To the resulting residue was added DCM (3 ml), and the mixture was stirred at rt for 1 h. Then the solid was filtered off, and the solvent was removed to give the title compound. LC-MS [M+H]: m/z 503.28

Step F. Preparation of (S,Z)-7-(3-(tert-butoxy)-2-(((((2-((tert-butoxycarbonyl)amino)thiazol-4-yl)(carboxy)methylene)amino)oxy)-3-oxopropoxy)-3-(((1-(tert-butoxycarbonyl)azetidin-3-yl)methyl)amino)-2-methylisoquinolin-2-ium,iodide A solution of (S)-7-(2-(aminooxy)-3-(tert-butoxy)-3-oxopropoxy)-3-(((1-(tert-butoxycarbonyl)azetidin-3-yl)methyl)amino)-2-methylisoquinolin-2-ium, Iodide (60 mg, 0.095 mmol) and 2-(2-((tert-butoxycarbonyl)-amino)thiazol-4-yl)-2-oxoacetic acid (33 mg, 0.12 mmol) in EtOH (1.5 ml) and $CH_2C_1CH_2C_1$ (0.5 ml) was stirred at rt overnight. Then the reaction mixture was concentrated to give the title compound. LC-MS [M+H]: m/z 757.49

Step G. Preparation of (S)-3-((Z)-2-(((((S)-1-(tert-butoxy)-3-((3-(((1-(tert-butoxycarbonyl)azetidin-3-yl)methyl)amino)-2-methylisoquinolin-2-ium-7-yl)oxy)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate To a solution of (S,Z)-7-(3-(tert-butoxy)-2-(((((2-((tert-butoxycarbonyl)amino)thiazol-4-yl)(carboxy)methylene)-amino)oxy)-3-oxopropoxy)-3-(((1-(tert-butoxycarbonyl)azetidin-3-yl)methyl)amino)-2-methyl-isoquinolin-2-ium (84 mg, 0.095 mmol) in DMF (2 ml) were added DCC (58.8 mg, 0.285 mmol), and HOBt (43.6 mg, 0.285 mmol). The reaction mixture was stirred at rt for 30 min, then (S)-3-amino-2,2-dimethyl-4-oxoazetidin-1-yl hydrogen sulfate (49.9 mg, 0.238 mmol) and sodium bicarbonate (39.9 mg, 0.475 mmol) were added. The reaction mixture was stirred at rt overnight, then the solid was filtered off. The filtrate was purified on RP (C-18 column) (130 g), eluting with 20-100% ACN/Water containing 0.05% TFA (10 CV) to give the title compound. LC-MS [M+H]: m/z 949.83

Step H: Preparation of (S)-3-((Z)-2-(2-aminothiazol-4-yl)-2-(((S)-2-((3-((azetidin-3-ylmethyl)amino)-2-methylisoquinolin-2-ium-7-yl)oxy)-1-carboxyethoxy)imino)acetamido)-2,2-dimethyl-4-oxoazetidin-1-yl Sulfate To a solution of (S)-3-((Z)-2-(((((S)-1-(tert-butoxy)-3-((3-(((1-(tert-butoxycarbonyl)azetidin-3-yl)methyl)amino)-2-methylisoquinolin-2-ium-7-yl)oxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (30 mg, 0.032 mmol) in $CH_2Cl_2$ (1 ml) was added TFA (2 ml, 51.9 mmol). The reaction mixture was stirred at rt for 40 min, then the solvent was removed under vacuum. The resulting residue was washed with $Et_2O$ twice, then dissolved in DMSO (0.5 mL), and purified on RP-HPLC (Gilson) (C-18 column) eluting with 2-40% ACN/Water containing 0.05% TFA (12 min) to give the title compound as the TFA salt. LC-MS [M+H]: m/z 692.23. $^1$HNMR (500 MHz, $CDCl_3$) δ 8.84 (1H, s), 7.73 (1H, d), 7.45 (1H, d), 7.35 (1H, s), 7.26 (1H, s), 7.09 (1H, s), 5.18 (1H, s), 4.62-4.54 (4H, m), 4.21 (2H, t), 4.05 (3H, s), 3.98 (2H, t), 3.71 (2H, d), 3.39 (1H, m), 3.15 (1H, m), 1.37 (3H, s), 0.94 (3H, s).

Example 69

(S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-((1-(azetidin-3-ylmethyl)piperidin-4-yl)amino)quinolin-6-yl)oxy) propanoic Acid

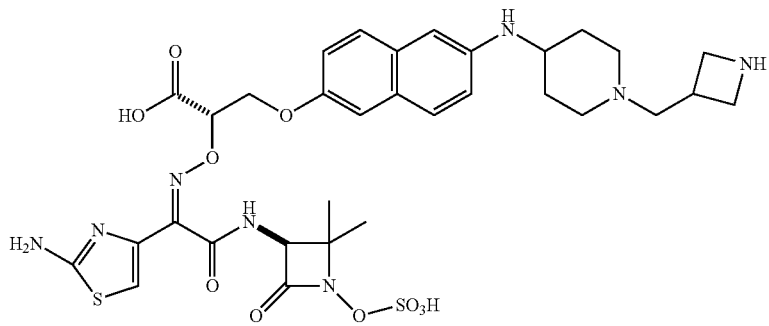

Step A: (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-3-((2-((1-((1-(tert-butoxycarbonyl)-azetidin-3-yl)methyl)piperidin-4-yl)amino)quinolin-6-yl)oxy)propanoic Acid To a solution of (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-(piperidin-4-ylamino)quinolin-6-yl)oxy)-propanoic acid (Example 3, 15 mg, 0.019 mmol) in DMSO (0.5 ml) was added tert-butyl 3-formylazetidine-1-carboxylate (6.89 mg, 0.037 mmol). The reaction was stirred at rt for 1 h. Then sodium triacetoxyborohydride (7.88 mg, 0.037 mmol) was added and the reaction was stirred at rt overnight. Then the reaction mixture was directly loaded onto a RP-HPLC (Gilson C-18 column (eluting with 20-100% ACN/water containing 0.05% TFA (12 min)) to give the title compound. LC-MS [M+H]: m/z 862.79.

Step B: (S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-3-((2-((1-(azetidin-3-ylmethyl)piperidin-4-yl)amino)quinolin-6-yl)oxy)propanoic Acid To a solution of (S)-2-((((Z)-1-(2-aminothiazol-4-yl)-2-(((S)-2,2-dimethyl-4-oxo-1-(sulfooxy)azetidin-3-yl)amino)-2-oxoethylidene)-amino)oxy)-3-((2-((1-((1-(tert-butoxycarbonyl)-azetidin-3-yl)methyl)-piperidin-4-yl)amino)-quinolin-6-yl)oxy)propanoic acid (5 mg, 5.12 µmol) in $CH_2Cl_2$ (0.25 ml) was added TFA (0.5 ml, 6.49 mmol). The reaction was stirred at rt for 0.5 h, then the solvent was removed. The resulting residue was washed with $Et_2O$ twice and dried under vacuum, and then purified on RP-HPLC (Gilson) (C-18 column), eluting with 0-40% ACN/Water containing 0.05% TFA (12 min) to give the title compound as the TFA salt. LC-MS [M+H]: m/z 760.57. $^1$HNMR (500 MHz, $CDCl_3$) δ 8.08 (1H, s), 7.68 (1H, d), 7.32 (1H, d), 7.25 (1H, s), 6.99 (1H, s), 6.94 (1H, s), 5.04 (1H, d), 4.64-4.42 (4H, m), 4.21 (2H, t), 4.12 (1H, m), 4.02 (2H, t), 3.58 (2H, d), 3.49 (3H, m), 3.16 (2H, m), 2.33 (2H, m), 1.85 (2H, m), 1.31 (3H, s), 0.91 (3H, s).

TABLE 8

The compounds in Examples 70 and 71 were prepared according to the procedure of Example 69 starting with the Example 9 and using the appropriate reagents

| Example | Name | Structure | LCMS |
|---|---|---|---|
| 70 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-((3-((azetidin-3-ylmethyl)amino)propyl)amino)quinolin-6-yl)oxy)propanoic acid | 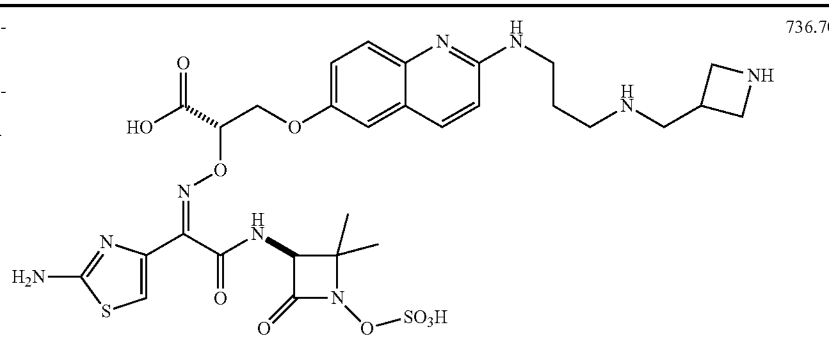 | 736.70 |

TABLE 8-continued

The compounds in Examples 70 and 71 were prepared according to the procedure of Example 69 starting with the Example 9 and using the appropriate reagents

| Example | Name | Structure | LCMS |
|---|---|---|---|
| 71 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-((2-((3-(bis(azetidin-3-yl-methyl)amino)propyl)amino)quinolin-6-yl)oxy)propanoic acid | 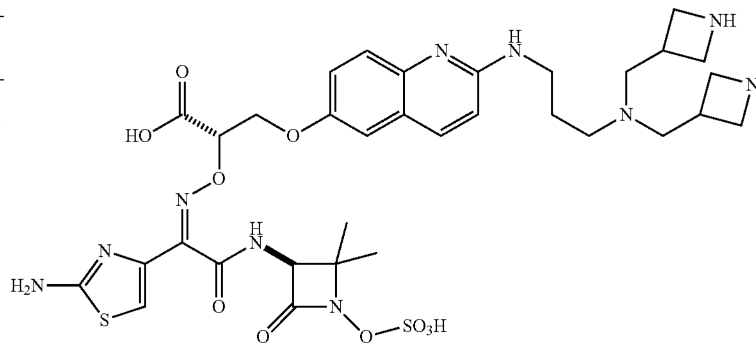 | 805.33 |

Example 72

(S)-3-((2-((3-aminopropyl)(azetidin-3-ylmethyl)amino)quinolin-6-yl)oxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic Acid

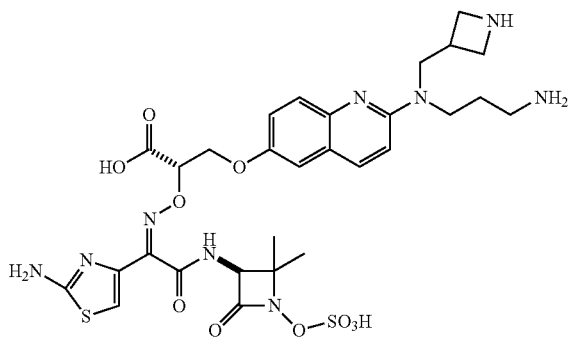

Step A. Preparation of Tert-Butyl (R)-3-(((6-(3-(tert-butoxy)-2-((tert-butyldimethylsilyl)oxy)-3-oxopropoxy)quinolin-2-yl)(3-((tert-butoxycarbonyl)amino)propyl)amino)methyl)-azetidine-1-carboxylate To a solution of (R)-tert-butyl 2-((tert-butyldimethylsilyl)oxy)-3-((2-chloroquinolin-6-yl)oxy)propanoate (1-4, 1 g, 2.28 mmol) in dioxane (18 ml) was added tert-butyl 3-(((3-((tert-butoxycarbonyl)amino)propyl)-amino)methyl)azetidine-1-carboxylate (1.18 g, 3.42 mmol), 2nd generation Ruphos precatalyst (0.266 g, 0.342 mmol) and Cs$_2$CO$_3$ (1.49 g, 4.57 mmol). The reaction vial was degassed and refilled with N$_2$. The reaction was heated at 75° C. overnight, then the solid was filtered off and solvent was removed. The resulting residue was purified by column chromatography on silica gel Redi 40 g gold, eluting with EtOAc/Hexane 30% to give the title compound. LC-MS [M+H]: m/z 745.87.

Step B. Preparation of Tert-Butyl (S)-3-(((6-(3-(tert-butoxy)-2-hydroxy-3-oxopropoxy)-quinolin-2-yl)(3-((tert-butoxycarbonyl)amino)propyl)amino)methyl)azetidine-1-carboxylate To a solution of (R)-tert-butyl 3-(((6-(3-(tert-butoxy)-2-((tert-butyldimethylsilyl)oxy)-3-oxopropoxy)quinolin-2-yl)(3-((tert-butoxycarbonyl)amino)propyl)amino)methyl)azetidine-1-carboxylate (0.3 g, 0.403 mmol) in THF (5 ml) was added TBAF in THF (0.403 ml, 0.403 mmol, 1M). The solution was stirred at rt for 2 h, then the solvent was removed. The resulting residue was purified by column chromatography on silica gel (Redi 12 g gold), eluting with EtOAc/hexane (0-70%, 6 cv; 70%, 10 cv) to give the title compound. LC-MS [M+H]: m/z 631.59.

Step C. Preparation of Tert-Butyl (S)-3-(((6-(3-(tert-butoxy)-2-((1,3-dioxoisoindolin-2-yl)oxy)-3-oxopropoxy)quinolin-2-yl)(3-((tert-butoxycarbonyl)amino)propyl)amino)-methyl)azetidine-1-carboxylate To a solution of (R)-tert-butyl 3-(((6-(3-(tert-butoxy)-2-hydroxy-3-oxopropoxy)quinolin-2-yl)(3-((tert-butoxycarbonyl)amino)-propyl)amino)-methyl)azetidine-1-carboxylate (0.22 g, 0.349 mmol) in THF (2 ml) were added 2-hydroxyisoindoline-1,3-dione (0.068 g, 0.419 mmol) and triphenylphosphine (0.110 g, 0.419 mmol), followed by DIAD (0.081 ml, 0.419 mmol) at rt. The reaction was stirred overnight and then concentrated. The resulting residue was purified by silica gel column chromatography (Redi 24 g gold), eluting with EtOAc/Hexane (70%, 15 cv) to give the title compound. LC-MS [M+H]: m/z 776.82.

Steps D-G followed the same procedure as Steps E-H of Example 1 to give the title compound. LC-MS [M+H]$^+$: m/z 736.89. $^1$HNMR (500 MHz, CDCl$_3$) δ 8.22 (1H, d), 7.78 (1H, d), 7.46 (1H, d), 7.38 (1H, s), 7.31 (1H, d), 7.09 (1H, s), 5.17 (1H, d), 4.58-4.50 (2H, m), 4.19 (1H, m), 3.89-3.80 (2H, m), 3.59 (1H, m), 3.25 (2H, d), 3.10 (2H, m), 2.82 (1H, m), 2.11 (2H, m), 1.35 (3H, s), 0.86 (3H, s).

Example 73

(S)-3-((4-amino-2-((azetidin-3-ylmethyl)amino)quinolin-6-yl)oxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic Acid

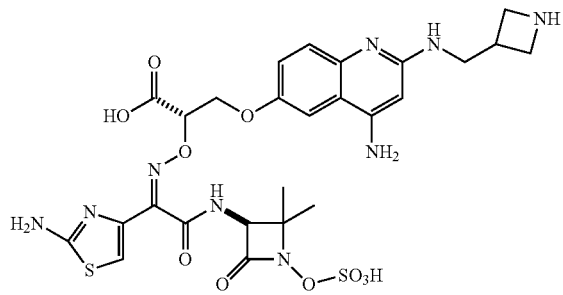

The compound of Example 73 was synthesized according to the procedure of Example 72 using intermediate 12 and tert-butyl 3-(aminomethyl)azetidine-1-carboxylate as starting materials. LC-MS [M+H]$^+$: m/z 692.5. $^1$HNMR (500 MHz, CDCl$_3$) δ 8.18 (1H, s), 7.53 (1H, s), 7.15 (1H, s), 6.85 (1H, s), 6.55 (1H, s), 5.82 (1H, s), 4.77 (1H, d), 4.73 (1H, d), 4.51-4.41 (2H, m), 4.02 (2H, m), 3.82 (2H, m), 3.50 (1H, m), 3.06 (2H, m), 1.47 (3H, s), 1.30 (3H, s)

BIOLOGICAL ASSAY

Antibiotic Activity: Determination of Growth Inhibitory Concentration

The concentrations of compounds required to inhibit the growth of various strains of bacteria were determined in an assay that assessed bacterial growth by measuring optical density at 600 nm (OD600). The bacterial strains tested included the clinical strains *Escherichia coli* expressing NDM-1 (CLB30016), *Klebsiella pneumoniae* expressing KPC-1 (CL6569), *Acinetobacter baumannii* expressing TEM-1, AmpC, and Oxa-24/40 (CL6188) and *Pseudomonas aeruginosa* expressing AmpC (CL5701). All compounds were tested in the presence of a β lactamase inhibitor (BLi, Relebactam) in 384-well microplates. The clinical strains were stored as frozen single use stocks, thawed and diluted into 1.1× cation-adjusted Mueller-Hinton II broth to achieve approximately 2×10$^5$ CFU/mL. Test compounds were dissolved in DMSO and diluted 1:50 in the assay, resulting in a final concentration range of 100 μM to 0.098 μM. On the day of the assay, 1 μL of test compound was added to the plate followed by 4 μL of 50 μg/mL BLi in MOPS buffer and 45 L of diluted bacteria. Plates were centrifuged at 1000 rpm for 30 seconds, shaken at approximately 800 rpm for 1 minute, and incubated at 35±2° C. for 22 hours. The concentration of BLi used in the assay was 4 μg/mL. At the end of the incubation, absorbance at 600 nm was determined using a spectrophotometer. Inhibition was quantitated by identifying the lowest concentration of test compound that was required to inhibit 95% of the growth of the bacteria. The results for Examples 1-73 are reported in Table I, expressed as the concentration of compound that inhibited 95% of bacterial growth (Minimum Inhibitory Threshold Concentration; MITC95).

Representative compounds of the present invention display a growth inhibitory effect. For example, representative compounds of Examples 1-73 were determined to inhibit growth at concentrations of 100 μM or less.

TABLE I

Antibacterial activity of Compounds 1-73

| EXAMPLE # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 1 | 6.2 | 3.1 | 0.39 | 3.1 |
| 2 | 3.1 | 3.1 | 0.20 | 3.1 |
| 3 | 6.2 | 6.2 | 0.39 | 6.2 |
| 4 | 25 | 6.2 | 0.39 | 6.2 |
| 5 | 12.5 | 3.1 | 0.39 | 3.1 |
| 6 | 50 | 12.5 | 0.78 | 12.5 |
| 7 | 25 | 6.2 | 0.39 | 6.2 |
| 8 | 12.5 | 6.2 | 0.39 | 3.1 |
| 9 | 12.5 | 6.2 | 0.39 | 6.2 |
| 10 | 50 | 6.2 | 0.78 | 6.2 |
| 11 | 6.2 | 6.2 | 0.39 | 6.2 |
| 12 | 50 | 12.5 | 0.78 | 12.5 |
| 13 | 3.1 | 6.2 | 0.39 | 3.1 |
| 14 | 25 | 9.4 | 0.78 | 9.4 |
| 15 | 4.7 | 6.2 | 0.39 | 6.2 |
| 16 | 3.1 | 12.5 | 0.39 | 6.2 |
| 17 | 25 | 12.5 | 0.78 | 12.5 |
| 18 | 12.5 | 6.2 | 1.2 | 12.5 |
| 19 | 3.1 | 12.5 | 1.6 | 6.2 |
| 20 | 12.5 | 12.5 | 0.78 | 6.2 |
| 21 | 12.5 | 100 | 0.39 | 3.1 |
| 22 | 75 | 100 | 12.5 | 100 |
| 23 | 9.4 | 12.5 | 1.5 | 12.5 |
| 24 | 12.5 | 12.5 | 1.8 | 12.5 |
| 25 | 10.4 | 50 | 1.3 | 38 |
| 26 | 50 | 12.5 | 0.78 | 12.5 |
| 27 | 100 | 100 | 6.2 | 50 |
| 28 | 11 | 38 | 3.4 | 22 |
| 29 | 6.2 | 25 | 1.3 | 19 |
| 30 | 1.6 | 6.2 | 0.39 | 3.1 |
| 31 | 12.5 | 100 | 6.2 | 12.5 |
| 32 | 6.2 | 25 | 0.78 | 6.2 |

TABLE I-continued

Antibacterial activity of Compounds 1-73

| EXAMPLE # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 33 | 25 | 100 | 25 | 25 |
| 34 | 3.1 | 25 | 0.78 | 6.2 |
| 35 | 25 | 100 | 12.5 | 25 |
| 36 | 25 | 50 | 1.6 | 3.1 |
| 37 | 25 | 12.5 | 0.78 | 6.25 |
| 38 | 50 | 100 | 6.2 | 50 |
| 39 | 6.2 | 12.5 | 0.78 | 6.2 |
| 40 | 25 | 100 | 12.5 | 100 |
| 41 | 25 | 12.5 | 0.78 | 6.2 |
| 42 | 100 | 100 | 12.5 | 25 |
| 43 | 12.5 | 6.2 | 0.39 | 6.2 |
| 44 | 25 | 12.5 | 0.78 | 6.2 |
| 45 | 3.9 | 4.3 | 0.53 | 2.1 |
| 46 | 19 | 62 | 3.1 | 14 |
| 47 | 19 | 6.2 | 0.78 | 3.1 |
| 48 | 50 | 100 | 3.1 | 12.5 |
| 49 | 12.5 | 12.5 | 0.78 | 6.2 |
| 50 | 50 | 200 | 6.2 | 25 |
| 51 | 6.25 | 25 | 0.78 | 12.5 |
| 52 | 3.13 | 6.25 | 0.39 | 3.13 |
| 53 | 1.56 | 6.25 | 0.39 | 3.13 |
| 54 | 6.25 | 12.5 | 0.78 | 6.25 |
| 55 | 6.25 | 6.25 | 0.78 | 6.25 |
| 56 | 6.25 | 6.25 | 0.78 | 6.25 |
| 57 | 3.13 | 12.5 | 0.39 | 6.25 |
| 58 | 1.56 | 6.25 | 0.39 | 6.25 |
| 59 | 3.13 | 6.25 | 0.39 | 6.25 |
| 60 | 12.5 | 12.5 | 1.56 | 12.5 |
| 61 | 25 | 25 | 3.13 | 25 |
| 62 | 25 | 12.5 | 0.78 | 12.5 |
| 63 | 1.56 | 3.13 | 0.39 | 3.13 |
| 64 | 6.25 | 12.5 | 0.78 | 12.5 |
| 65 | 25 | 25 | 1.56 | 12.5 |
| 66 | 6.25 | 12.5 | 0.78 | 6.25 |
| 67 | 3.13 | 12.5 | 0.78 | 3.13 |
| 68 | 3.13 | 6.25 | 0.39 | 6.25 |
| 69 | 3.13 | 1.56 | 0.39 | 3.13 |
| 70 | 3.13 | 3.13 | 0.39 | 3.13 |
| 71 | 6.25 | 3.13 | 0.39 | 6.25 |
| 72 | 1.56 | 1.56 | 0.098 | 1.56 |
| 73 | 3.13 | 3.13 | 0.39 | 3.13 |

What is claimed is:

1. A compound of Formula I

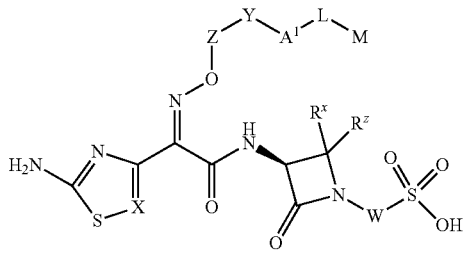

(I)

or a pharmaceutically acceptable salt thereof, wherein:

W is a bond or O;

$R^x$ and $R^z$ are independently hydrogen, —$SC_1$-$C_3$alkyl, $C_1$-$C_3$ alkyl, —($C_1$-$C_3$alkylene)$_n$$OC_1$-$C_3$alkyl, or —($C_1$-$C_3$alkylene)$_n$$NC_1$-$C_3$alkyl, wherein said —$SC_1$-$C_3$alkyl, $C_1$-$C_3$ alkyl, —($C_1$-$C_3$alkylene)$_n$$OC_1$-$C_3$alkyl and —($C_1$-$C_3$alkylene)$_n$$NC_1$-$C_3$alkyl are optionally substituted with one to seven fluorines;

or, alternatively, $R^x$ and $R^z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and $C_4$-$C_7$ heterocycloalkyl are optionally substituted with one to three substituents independently selected from —F, —OH and —$OC_1$-$C_3$alkyl;

X is N or $CR^1$;

$R^1$ is hydrogen, $C_1$-$C_3$ alkyl, or halogen; wherein said $C_1$-$C_3$ alkyl is optionally substituted with one to three $R^a$;

each occurrence of $R^a$ is independently hydrogen, halogen, $C_1$-$C_3$alkyl, —$NR^cR^d$, —$OR^e$, or —$C(O)NR^cR^d$;

Z is $C_1$-$C_3$ alkylene, optionally substituted with one to three $R^b$;

each occurrence of $R^b$ is independently —$C_1$-$C_6$ alkyl, —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or $P(O)(R^e)_p$ wherein said —$C_1$-$C_6$ alkyl and —$C_3$-$C_7$ cycloalkyl are optionally substituted with one to three $R^a$ and wherein said AryA and HetA are optionally substituted with one to four $R^4$;

AryA is a 5- or 6-membered monocyclic aromatic ring with 0, 1, 2, or 3 heteroatom ring atoms independently selected from N, N as a quaternary salt, O and S;

HetA is a 4- to 6-membered saturated or monounsaturated monocyclic ring with 1, 2, or 3 heteroatom ring atoms independently selected from N, NH, N as a quaternary salt, O and S;

Y is a bond, O, $NR^2$, S, or $CH_2$;

$R^2$ is hydrogen, —$C_1$-$C_3$ alkyl, —$C(O)R^e$, —$C(O)NR^cR^d$, —$S(O)_mR^e$, or —$S(O)_mNR^cR^d$, wherein said —$C_1$-$C_3$ alkyl is optionally substituted with one to three $R^a$;

$A^1$ is a 9- to 11-membered bicyclic aromatic ring with 0, 1, 2, 3, or 4 heteroatom ring atoms independently selected from N, NH, N as a quaternary salt, O and S, optionally substituted with one to four $R^4$;

each occurrence of $R^4$ is independently:
(a) —$C_1$-$C_6$ alkyl,
(b) —$C_2$-$C_6$ alkenyl,
(c) —$C_2$-$C_6$ alkynyl,
(d) halogen,
(e) —$OR^e$,
(f) —$S(O)_mR^e$,
(g) —$S(O)_mNR^cR^d$,
(h) —$C(O)R^e$,
(i) —$OC(O)R^e$,
(j) —$C(O)OR^e$,
(k) —CN,
(l) —$C(O)NR^cR^d$,
(m) —$NR^cR^d$,
(n) —$NR^cC(O)R^e$,
(o) —$NR^cC(O)OR^e$,
(p) —$NR^cC(O)NR^cR^d$,
(q) —$NR^cS(O)_mR^e$,
(r) =NH,
(s) —$CF_3$,
(t) —$OCF_3$,
(u) —$OCHF_2$,
(v) —$C_3$-$C_6$ cycloalkyl,
(w) —O—$C_3$-$C_6$cycloalkyl,
(x) —$C_1$-$C_3$alkylene-$C_3$-$C_6$cycloalkyl,
(y) —O—$C_1$-$C_3$ alkylene-$C_3$-$C_6$cycloalkyl,
(z) HetA,
(aa) —O-HetA,
(bb) —$C_1$-$C_3$alkylene-HetA,
(cc) —O— $C_1$-$C_3$alkylene-HetA,
(dd) AryA,
(ee) —O-AryA,
(ff) —$C_1$-$C_3$ alkylene-AryA, or
(gg) —O—$C_1$-$C_3$alkylene-AryA, wherein said $C_1$-$C_6$ alkyl, —$C_2$-$C_6$ alkenyl, —$C_2$-$C_6$ alkynyl, —$C_3$-$C_6$cycloalkyl, —O—$C_3$-$C_6$cycloalkyl, —$C_1$-$C_3$alkylene-$C_3$-$C_6$cycloalkyl, —O—$C_1$-$C_3$alkylene-$C_3$-$C_6$cycloalkyl, HetA, O-HetA, —$C_1$-$C_3$alkylene-HetA, —O— $C_1$-$C_3$ alkylene-HetA, AryA, —O-AryA, —$C_1$-$C_3$ alkylene-AryA, and —O—$C_1$-$C_3$alkylene-AryA are optionally substituted with one to three $R^a$;

L is a bond, —O—, —$C_1$-$C_6$alkylene-, —NHC(O)—, —C(O)—, —C(=NH)—, —$S(O)_m$—, —$SC_1$-$C_6$alkylene-, —$NR^3(CH_2)_n$—, —NHC(=NH)—, or —$NHS(O)_m$—, wherein —$C_1$-$C_6$alkylene-, —NHC(O)—, —C(=NH)—, —$SC_1$-$C_6$alkylene-, —$NR^3(CH_2)_n$—, —NHC(=NH)—, and —$NHS(O)_m$— are optionally substituted with one to four $R^7$;

$R^3$ is hydrogen or —$C_1$-$C_3$ alkyl;

M is —$CH_2OH$, $N(R^3)_2$, $N^+(C_1$-$C_3$alkyl$)_3$, $C_2$-$C_6$alkyl, $C_3$-$C_7$ cycloalkyl, HetA, or AryA, wherein —$CH_2OH$, $N(R^3)_2$, $N^+(C_1$-$C_3$alkyl$)_3$, $C_2$-$C_6$alkyl, $C_3$-$C_7$ cycloalkyl, HetA, and AryA are optionally substituted with one to four $R^6$;

each occurrence of $R^6$ is independently selected from the group consisting of: halogen, —$C_1$-$C_6$alkyl, —$(CH_2)_nNR^cR^d$, —$(CH_2)_qOR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$C(NH)NR^cR^d$, —$NR^cR^d$, —$N(R^c)(C(O)R^e)$, —$N(R^c)(C(O)OR^e)$, —$N(R^c)(C(O)NR^cR^d)$, —$N(R^c)(S(O)_mR^e)$, HetA, and —$C_1$-$C_3$alkylene-HetA;

each occurrence of $R^7$ is independently selected from the group consisting of: halogen, —$C_1$-$C_6$alkyl, —$(CH_2)_nNR^cR^d$, —$(CH_2)_qOR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$C(NH)NR^cR^d$, —$NR^cR^d$, —$N(R^c)(C(O)R^e)$, —$N(R^c)(C(O)OR^e)$, —$N(R^c)(C(O)NR^cR^d)$, —$N(R^c)(S(O)_mR^e)$, HetA, and —$C_1$-$C_3$alkylene-HetA;

each occurrence of $R^c$ and $R^d$ is independently: hydrogen, —$C_1$-$C_6$ alkyl, —$C_2$-$C_6$ alkenyl, —$C_3$-$C_6$ cycloalkyl, —$C_1$-$C_3$ alkylene-$C_3$-$C_6$ cycloalkyl, HetA, —$C_1$-$C_3$alkylene-HetA, AryA, —$C_1$-$C_3$ alkylene-AryA, or —$C_1$-$C_3$alkylene-HetA, wherein each $R^c$ and $R^d$ is optionally substituted with one to three $R^f$;

or, alternatively, $R^c$ and $R^d$ together with the nitrogen atom to which they are attached, come together to form a 4- to 7-membered cycloheteroalkyl optionally containing one or two additional heteroatoms independently selected from O, S and —$NR^g$;

each occurrence of $R^e$ is independently: hydrogen, —$C_1$-$C_6$alkyl, —$C_2$-$C_6$ alkenyl, —OH, —$OC_1$-$C_6$ alkyl, —$C_3$-$C_6$ cycloalkyl, —$C_1$-$C_3$ alkylene-$C_3$-$C_6$ cycloalkyl, HetA, AryA, —$C_1$-$C_3$ alkylene-AryA, or —$C_1$-$C_3$ alkylene-HetA; wherein each $R^e$ is optionally substituted with one to three $R^h$;

each occurrence of $R^f$ is independently: halogen, —$C_1$-$C_6$alkyl, —OH, —$OC_1$-$C_4$ alkyl, —$S(O)_mC_1$-$C_4$ alkyl, —CN, —$CF_3$, —$OCHF_2$, or —$OCF_3$; wherein said —$C_1$-$C_6$ alkyl, —$OC_1$-$C_4$ alkyl and —$S(O)_mC_1$-$C_4$ alkyl are optionally substituted with one to three substituents independently selected from: —OH, halogen, cyano, and —$S(O)_2CH_3$;

each occurrence of $R^g$ is independently: hydrogen, —$C(O)R^e$, or —$C_1$-$C_6$ alkyl, wherein said —$C_1$-$C_6$alkyl is optionally substituted with one to five fluorines;

each occurrence of $R^h$ is independently: halogen, —$C_1$-$C_6$alkyl, —OH, —$OC_1$-$C_4$ alkyl, —$S(O)_mC_1$-$C_4$ alkyl, —CN, —$CF_3$, —$OCHF_2$, or —$OCF_3$; wherein said —$C_1$-$C_6$ alkyl, —$OC_1$-$C_4$ alkyl, and —$S(O)_mC_1$-$C_4$ alkyl are optionally substituted with one to three substituents independently selected from: —OH, halogen, cyano, and —$S(O)_2CH_3$;

each n is independently 0, 1, 2, 3 or 4;

each m is independently 0, 1 or 2;

each p is 1 or 2; and each q is 0, 1, 2 or 3.

2. A compound of Formula I

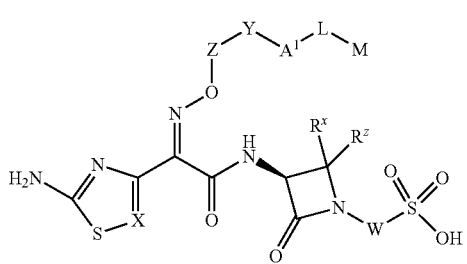

or a pharmaceutically acceptable salt thereof, wherein:
W is a bond or O;
$R^X$ and $R^Z$ are independently hydrogen, —$SC_1$-$C_3$alkyl, $C_1$-$C_3$ alkyl, —$(C_1$-$C_3$alkylene$)_n$O$C_1$-$C_3$alkyl, or —$(C_1$-$C_3$alkylene$)_n$N$C_1$-$C_3$alkyl, wherein said —$SC_1$-$C_3$alkyl, $C_1$-$C_3$ alkyl, —$(C_1$-$C_3$alkylene$)_n$O$C_1$-$C_3$alkyl and —$(C_1$-$C_3$alkylene$)_n$N$C_1$-$C_3$alkyl are optionally substituted with one to seven fluorines;
or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and $C_4$-$C_7$ heterocycloalkyl are optionally substituted with one to three substituents independently selected from —F, —OH and —O$C_1$-$C_3$alkyl;
X is N or $CR^1$;
$R^1$ is hydrogen, $C_1$-$C_3$ alkyl, or halogen; wherein said $C_1$-$C_3$ alkyl is optionally substituted with one to three $R^a$;
each occurrence of $R^a$ is independently hydrogen, halogen, $C_1$-$C_3$alkyl, —$NR^cR^d$ or —$OR^e$;
Z is $C_1$-$C_3$ alkylene, optionally substituted with one to three $R^b$;
each occurrence of $R^b$ is independently —$C_1$-$C_6$ alkyl, —$C_3$-$C_7$ cycloalkyl, —C(O)O$R^e$, —C(O)$NR^cR^d$, tetrazolyl, oxadiazolonyl, HetA, AryA, —S(O)$_m R^e$, —S(O)$_m NR^cR^d$, or P(O)($R^e$)$_p$ wherein said —$C_1$-$C_6$ alkyl and —$C_3$-$C_7$ cycloalkyl are optionally substituted with one to three $R^a$ and wherein said AryA and HetA are optionally substituted with one to four $R^4$;
AryA is a 5- or 6-membered monocyclic aromatic ring with 0, 1, 2, or 3 heteroatom ring atoms independently selected from N, N as a quaternary salt, O and S;
HetA is a 4- to 6-membered saturated or monounsaturated monocyclic ring with 1, 2, or 3 heteroatom ring atoms independently selected from N, N as a quaternary salt, O and S;
Y is a bond, O, $NR^2$, S, or $CH_2$;
$R^2$ is hydrogen, —$C_1$-$C_3$ alkyl, —C(O)$R^e$, —C(O)$NR^cR^d$, —S(O)$_m R^e$, or —S(O)$_m NR^cR^d$, wherein said —$C_1$-$C_3$ alkyl is optionally substituted with one to three $R^a$;
$A^1$ is a 9- to 11-membered bicyclic aromatic ring with 0, 1, 2, 3, or 4 heteroatom ring atoms independently selected from N, N as a quaternary salt, O and S, optionally substituted with one to four $R^4$;
each occurrence of $R^4$ is independently:
(a) —$C_1$-$C_6$ alkyl,
(b) —$C_2$-$C_6$ alkenyl,
(c) —$C_2$-$C_6$ alkynyl,
(d) halogen,
(e) —$OR^e$,
(f) —S(O)$_m R^e$,
(g) —S(O)$_m NR^cR^d$,
(h) —C(O)$R^e$,
(i) —OC(O)$R^e$,
(j) —C(O)O$R^e$,
(k) —CN,
(l) —C(O)$NR^cR^d$,
(m) —$NR^cR^d$,
(n) —$NR^c$C(O)$R^e$,
(o) —$NR^c$C(O)O$R^e$,
(p) —$NR^c$C(O)$NR^cR^d$,
(q) —$NR^c$S(O)$_m R^e$,
(r) =NH,
(s) —$CF_3$,
(t) —$OCF_3$,
(u) —$OCHF_2$,
(v) —$C_3$-$C_6$ cycloalkyl,
(w) —O—$C_3$-$C_6$cycloalkyl,
(x) —$C_1$-$C_3$alkylene-$C_3$-$C_6$cycloalkyl,
(y) —O—$C_1$-$C_3$ alkylene-$C_3$-$C_6$cycloalkyl,
(z) HetA,
(aa) —O-HetA,
(bb) —$C_1$-$C_3$alkylene-HetA,
(cc) —O—$C_1$-$C_3$alkylene-HetA,
(dd) AryA,
(ee) —O-AryA,
(ff) —$C_1$-$C_3$ alkylene-AryA, or
(gg) —O—$C_1$-$C_3$alkylene-AryA,
wherein said $C_1$-$C_6$ alkyl, —$C_2$-$C_6$ alkenyl, —$C_2$-$C_6$ alkynyl, —$C_3$-$C_6$ cycloalkyl, —O—$C_3$-$C_6$cycloalkyl, —$C_1$-$C_3$alkylene-$C_3$-$C_6$cycloalkyl, —O—$C_1$-$C_3$ alkylene-$C_3$-$C_6$cycloalkyl, HetA, O-HetA, —$C_1$-$C_3$alkylene-HetA, —O—$C_1$-$C_3$ alkylene-HetA, AryA, —O-AryA, —$C_1$-$C_3$ alkylene-AryA, and –O—$C_1$-$C_3$alkylene-AryA are optionally substituted with one to three $R^a$;
L is a bond, —O—, —$C_1$-$C_6$alkylene-, —NHC(O)—, —C(O)—, —C(=NH)—, —S(O)$_m$—, —S$C_1$-$C_6$alkylene-, —$NR^3$($CH_2$)$_n$—, —NHC(=NH)—, or —NHS(O)$_m$—;
$R^3$ is hydrogen or —$C_1$-$C_3$ alkyl;
M is N($R^3$)$_2$, $N^+$($C_1$-$C_3$alkyl)$_3$, $C_2$-$C_6$alkyl, $C_3$-$C_7$ cycloalkyl, HetA, or AryA, wherein said $C_2$-$C_6$alkyl, $C_3$-$C_7$ cycloalkyl, HetA, and AryA are optionally substituted with one to three $R^6$;
each occurrence of $R^6$ is independently selected from the group consisting of: halogen, —$C_1$-$C_6$alkyl, —($CH_2$)$_n NR^cR^d$, —$OR^e$, —S(O)$_m R^e$, —S(O)$_m NR^cR^d$, —C(O)$R^e$, —OC(O)$R^e$, —C(O)O$R^e$, —CN, —C(O)$NR^cR^d$, —C(NH)$NR^cR^d$, —$NR^cR^d$, —N($R^c$)(C(O)$R^e$), —N($R^c$)(C(O)O$R^e$), —N($R^c$)(C(O)$NR^cR^d$), and —N($R^c$)(S(O)$_m R^e$);
each occurrence of $R^c$ and $R^d$ is independently: hydrogen, —$C_1$-$C_6$ alkyl, —$C_2$-$C_6$ alkenyl, —$C_3$-$C_6$ cycloalkyl, —$C_1$-$C_3$ alkylene-$C_3$-$C_6$ cycloalkyl, HetA, —$C_1$-$C_3$alkylene-HetA, AryA, —$C_1$-$C_3$ alkylene-AryA, or —$C_1$-$C_3$alkylene-HetA, wherein each $R^c$ and $R^d$ is optionally substituted with one to three $R^f$;
or, alternatively, $R^c$ and $R^d$ together with the nitrogen atom to which they are attached, come together to form a 4- to 7-membered cycloheteroalkyl optionally containing one or two additional heteroatoms independently selected from O, S and —$NR^g$;
each occurrence of $R^e$ is independently: hydrogen, —$C_1$-$C_6$alkyl, —$C_2$-$C_6$ alkenyl, —OH, —O$C_1$-$C_6$ alkyl, —$C_3$-$C_6$ cycloalkyl, —$C_1$-$C_3$ alkylene-$C_3$-$C_6$ cycloalkyl, HetA, AryA, —$C_1$-$C_3$ alkylene-AryA, or —C$_1$-C$_3$ alkylene-HetA; wherein each R$^e$ is optionally substituted with one to three R$^h$;

each occurrence of R$^f$ is independently: halogen, —C$_1$-C$_6$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_6$ alkyl, —OC$_1$-C$_4$ alkyl and —S(O)$_m$C$_1$-C$_4$ alkyl are optionally substituted with one to three substituents independently selected from: —OH, halogen, cyano, and —S(O)$_2$CH$_3$;

each occurrence of R$^g$ is independently: hydrogen, —C(O)R$^e$, or —C$_1$-C$_6$ alkyl, wherein said —C$_1$-C$_6$alkyl is optionally substituted with one to five fluorines;

each occurrence of R$^h$ is independently: halogen, —C$_1$-C$_6$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_6$ alkyl, —OC$_1$-C$_4$ alkyl, and —S(O)$_m$C$_1$-C$_4$ alkyl are optionally substituted with one to three substituents independently selected from: —OH, halogen, cyano, and —S(O)$_2$CH$_3$;

each n is independently 0, 1, 2, 3 or 4;
each m is independently 0, 1 or 2; and
each p is 1 or 2.

3. The compound of claim 1, or a pharmaceutically acceptable salt thereof, wherein X is CR$^1$.

4. The compound of claim 1, or a pharmaceutically acceptable salt thereof, wherein X is N.

5. The compound of claim 1, or a pharmaceutically acceptable salt thereof, wherein W is O.

6. The compound of claim 2, or a pharmaceutically acceptable salt thereof, having the Formula (IA) or (IB):

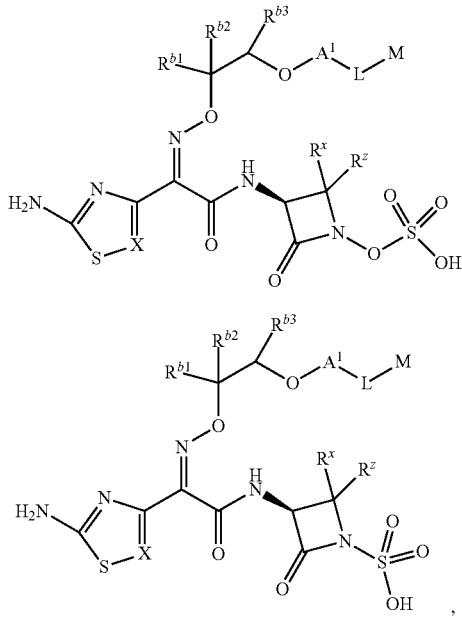

wherein:
R$^x$ and R$^z$ are independently hydrogen, —SC$_1$-C$_3$alkyl, C$_1$-C$_3$ alkyl, —(C$_1$-C$_3$alkylene)$_n$OC$_1$-C$_3$alkyl, or —(C$_1$-C$_3$alkylene)$_n$NC$_1$-C$_3$alkyl, wherein said —SC$_1$-C$_3$alkyl, C$_1$-C$_3$ alkyl, —(C$_1$-C$_3$alkylene)$_n$OC$_1$-C$_3$alkyl and —(C$_1$-C$_3$alkylene)$_n$NC$_1$-C$_3$alkyl are optionally substituted with one to seven fluorines;

R$^{b1}$, R$^{b2}$, and R$^{b3}$ are independently hydrogen, C$_1$-C$_6$ alkyl, C$_3$-C$_7$ cycloalkyl, —C(O)OR$^e$, —C(O)NR$^c$R$^d$, tetrazolyl, oxadiazolonyl, HetA, AryA, —S(O)$_m$R$^e$, —S(O)$_m$NR$^c$R$^d$, or —P(O)(R$^e$)$_p$, wherein said C$_1$-C$_6$ alkyl and C$_3$-C$_7$ cycloalkyl are optionally substituted with one to three R$^a$ and wherein said AryA and HetA are optionally substituted with one to four R$^4$;

A$^1$ is a 9- to 11-membered bicyclic aromatic ring containing one heteroatom ring atom selected from N and N as a quaternary salt, and containing 0, 1, 2, or 3, additional heteroatoms independently selected from N, O and S, optionally substituted with one to four R$^4$, M is selected from the group consisting of:
(a) N(R$^3$)$_2$,
(b) N$^+$(C$_1$-C$_3$alkyl)$_3$,
(c) C$_3$-C$_7$ cycloalkyl, substituted with N(R$^3$)$_2$, and optionally substituted with one to three additional substituents, independently selected from halogen, C$_1$-C$_3$alkyl, —NR$^c$R$^d$ and —OR$^e$,
(d) a 5- or 6-membered monocyclic aromatic ring containing one heteroatom ring atom selected from N and N as a quaternary salt, and containing 0, 1, or 2 additional heteroatom ring atoms independently selected from N, O and S, optionally substituted with one to four R$^6$; and
(e) a 4- to 6-membered saturated or monounsaturated monocyclic ring containing one heteroatom ring atom selected from N and N as a quaternary salt, and containing 0, 1, or 2, additional heteroatom ring atoms independently selected from N, O and S, optionally substituted with one to four R$^6$;

and all other variables are as defined in claim 1.

7. The compound of claim 6, or a pharmaceutically acceptable salt thereof, wherein R$^{b1}$ and R$^{b2}$ are independently hydrogen, C$_1$-C$_3$ alkyl, tetrazolyl, oxadiazolonyl or —C(O)OR$^e$; and R$^{b3}$ is hydrogen.

8. The compound of claim 1, wherein A$^1$ is a 9- or 10-membered bicyclic aromatic ring containing one ring atom selected from N and N as a quaternary salt, and optionally containing an additional ring atom selected from N, O and S, optionally substituted with one or two C$_1$-C$_6$ alkyl or halogen.

9. The compound of claim 1, or a pharmaceutically acceptable salt thereof, wherein A$^1$ is quinoline, isoquinoline, imidazo[1,2-a]pyridine, indazole, benzo[d]imidazole, benzo[d]thiazole, or naphthalene, wherein A$^1$ is optionally substituted with one to four R$^4$.

10. The compound of claim 1, or a pharmaceutically acceptable salt thereof, wherein A$^1$ is:

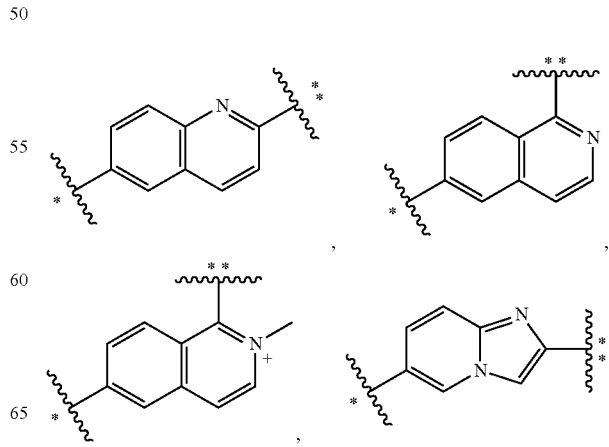

-continued

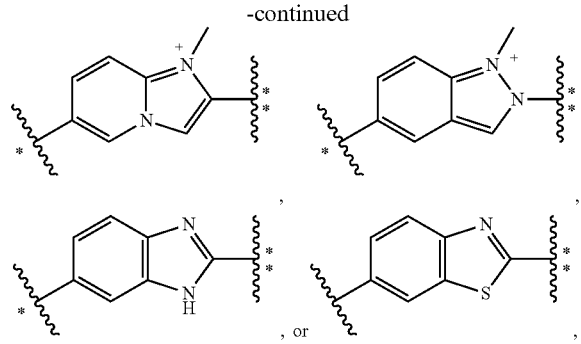

wherein ** indicates the point of attachment to L and * indicates the point of attachment to the rest of the compound.

11. The compound of any of claim 1, or a pharmaceutically acceptable salt thereof, wherein M is: —CH$_2$OH, —NH$_2$, —NHCH$_3$, or —N$^+$(CH$_3$)$_3$, wherein M is optionally substituted with one or two R$^6$.

12. The compound of any of claim 1, or a pharmaceutically acceptable salt thereof, wherein M is: —NH$_2$, —NHCH$_3$, or —N$^+$(CH$_3$)$_3$.

13. The compound of any of claim 1, or a pharmaceutically acceptable salt thereof, wherein M is: C$_3$-C$_7$ cycloalkyl, substituted with N(R$^3$)$_2$,
 a 5- or 6-membered monocyclic aromatic ring containing one heteroatom ring atom selected from N and N as a quaternary salt, and containing 0, 1, or 2 additional heteroatom ring atoms independently selected from N, O and S, optionally substituted with one or two C$_1$-C$_6$alkyl; or
 a 4- to 6-membered saturated or monounsaturated monocyclic ring containing one heteroatom ring atom selected from N and N as a quaternary salt, and containing 0, 1, or 2, additional heteroatom ring atoms independently selected from N, O and S, optionally substituted with one or two C$_1$-C$_6$alkyl.

14. The compound of claim 1, or a pharmaceutically acceptable salt thereof, wherein M is:

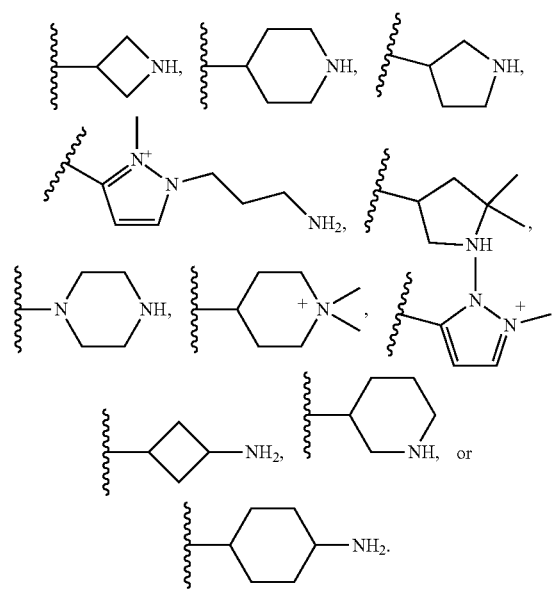

15. The compound of claim 1, or a pharmaceutically acceptable salt thereof, wherein M is:

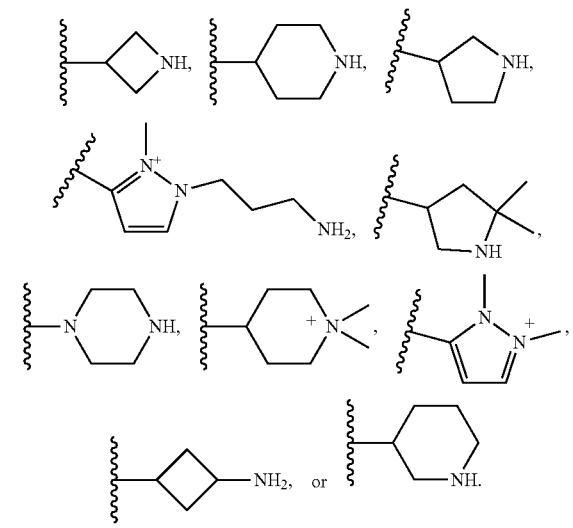

16. The compound of claim 1, or a pharmaceutically acceptable salt thereof, wherein R$^x$ and R$^z$ are methyl, or R$^x$ is methyl and R$^z$ is hydrogen.

17. A compound of claim 2, having the structure:

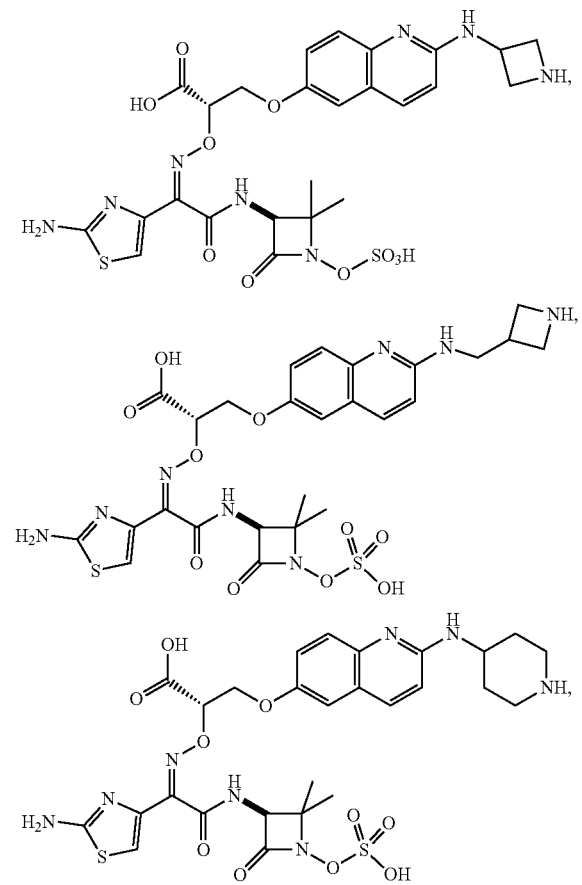

213
-continued
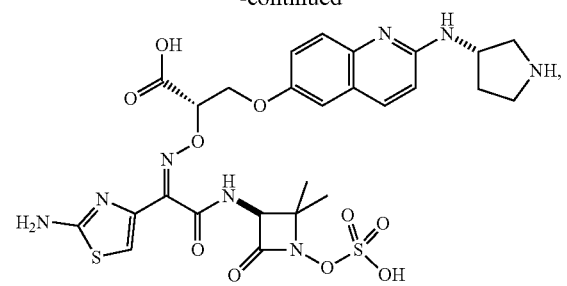
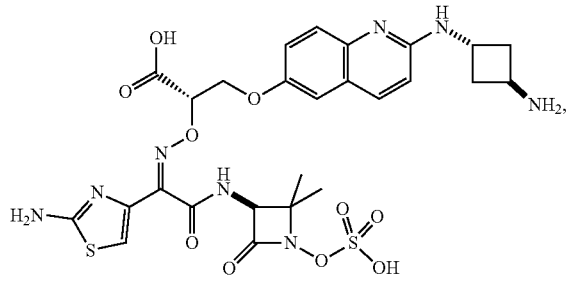
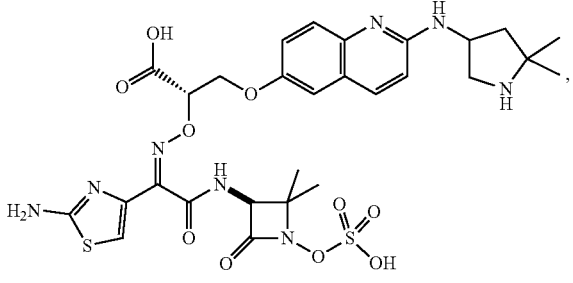
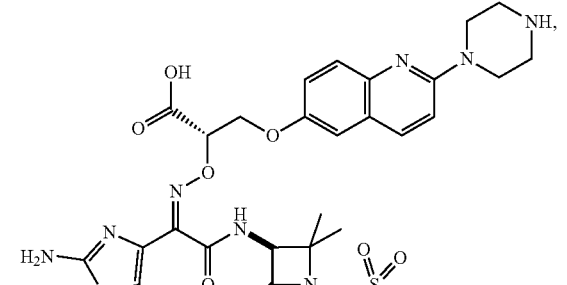
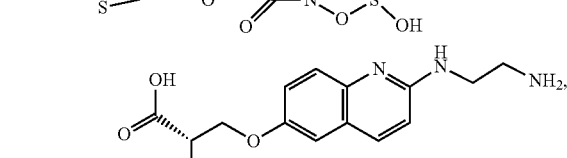
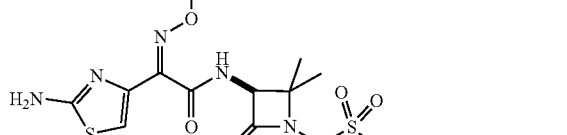
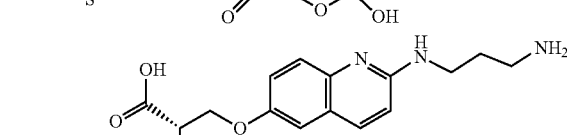
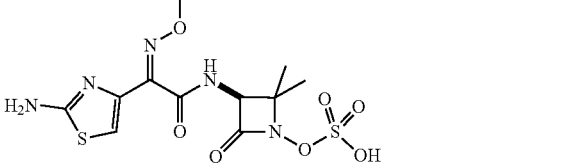
214
-continued
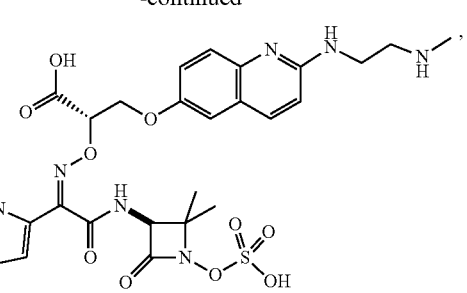
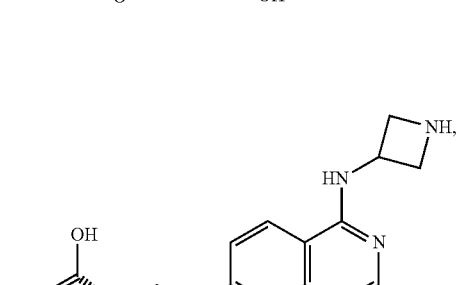
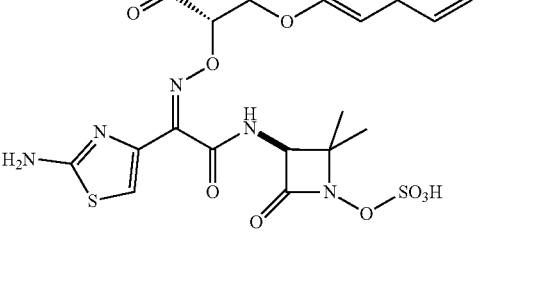
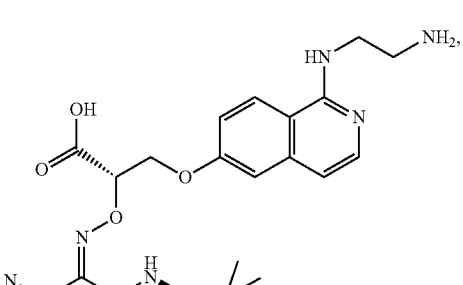
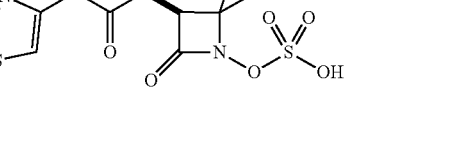
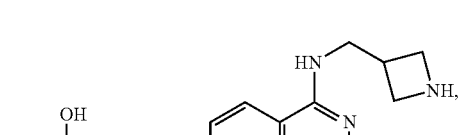
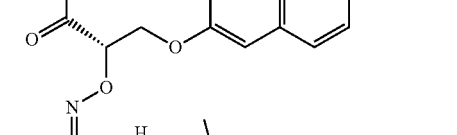
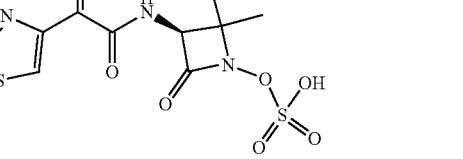

215
-continued
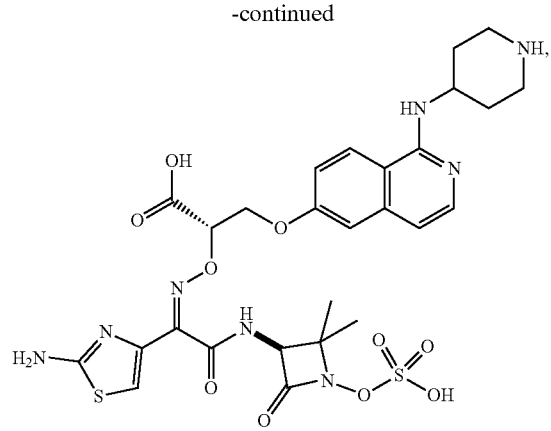
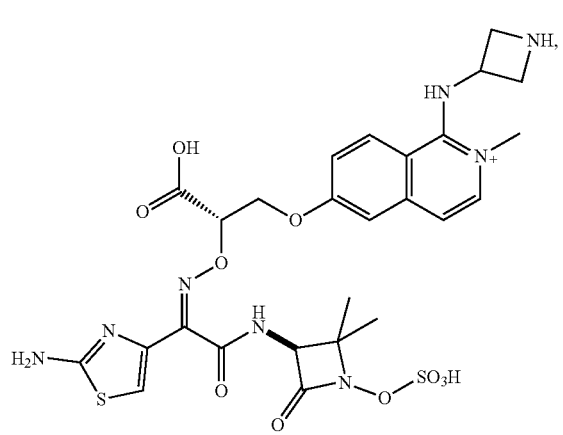
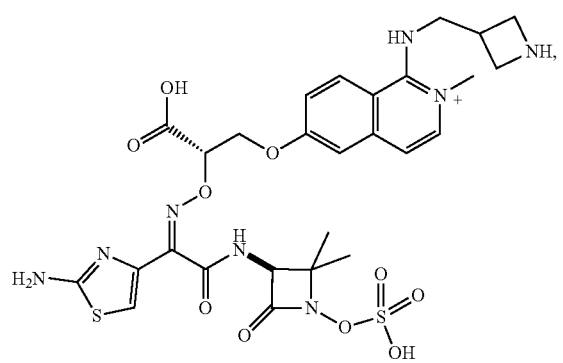
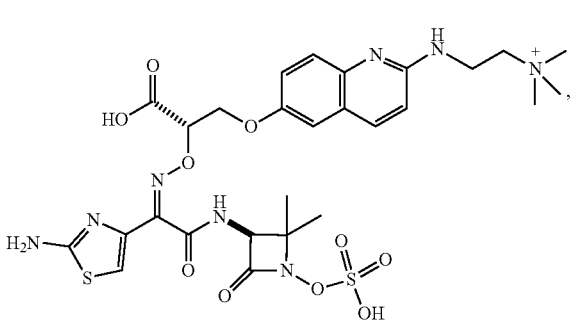
216
-continued
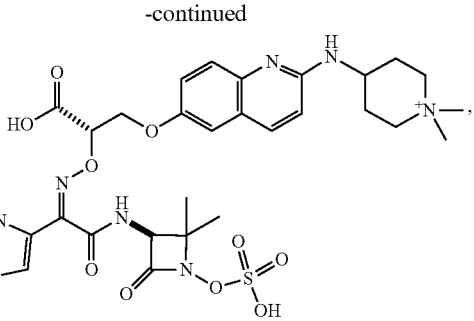
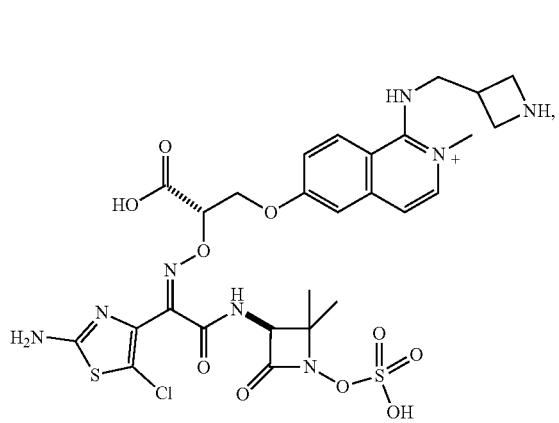
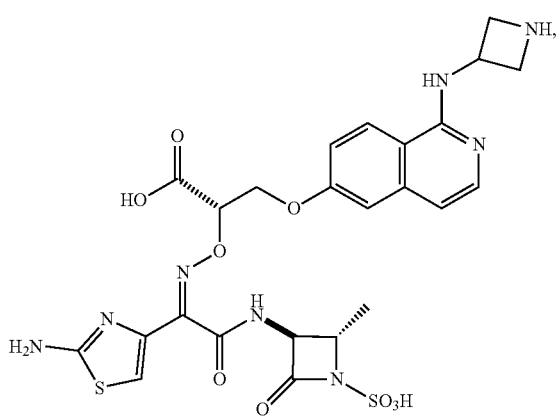
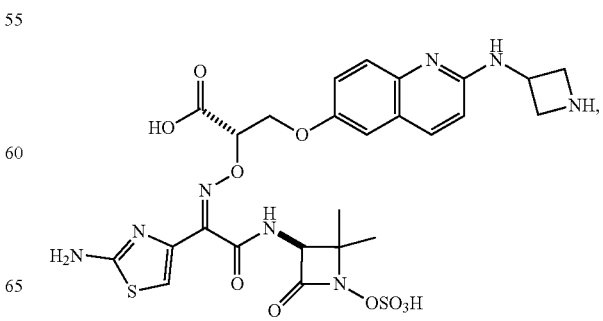

217
-continued
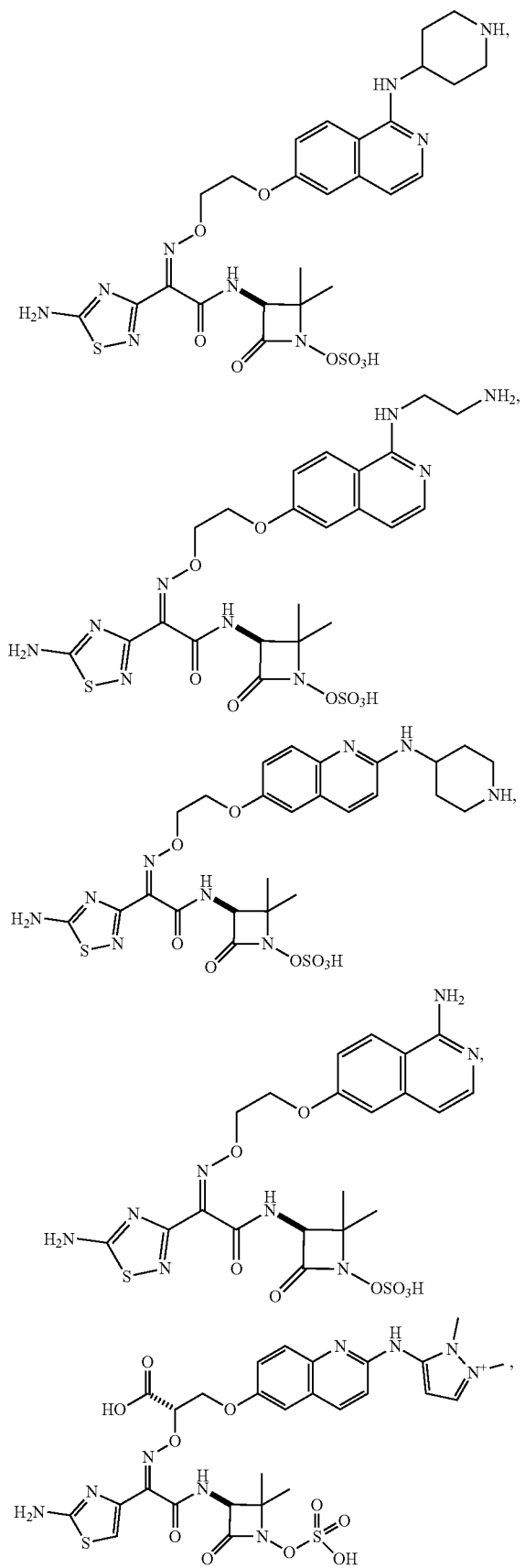
218
-continued
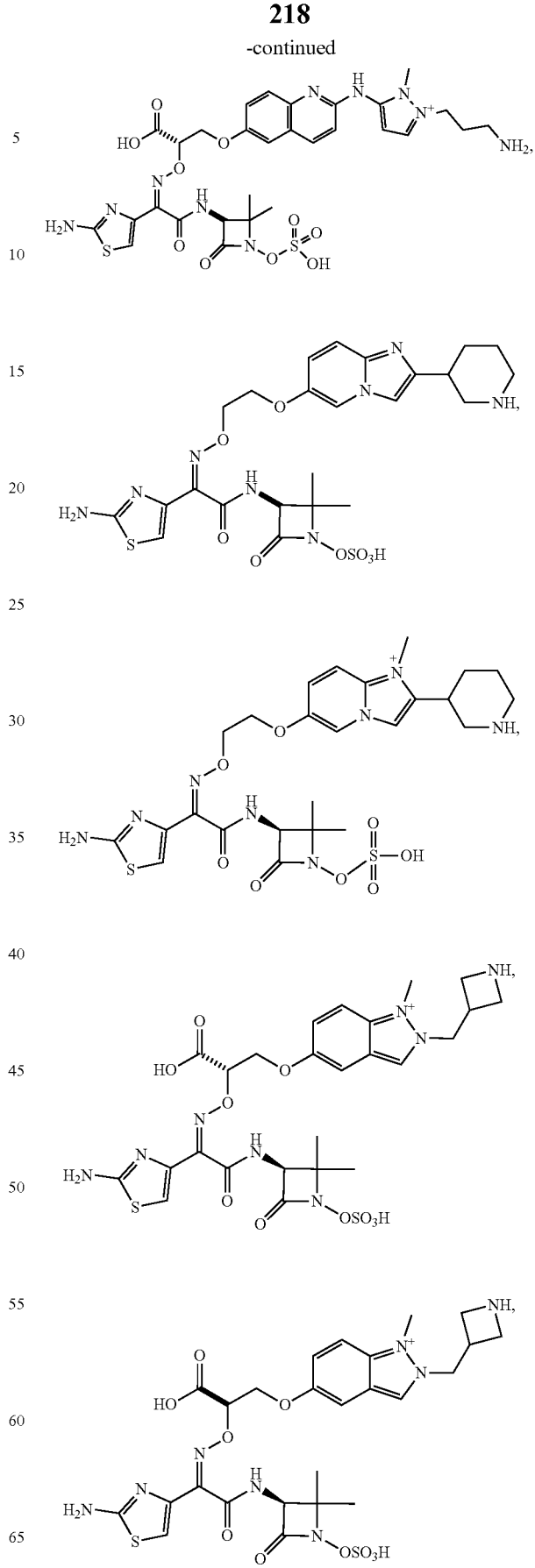

219
-continued
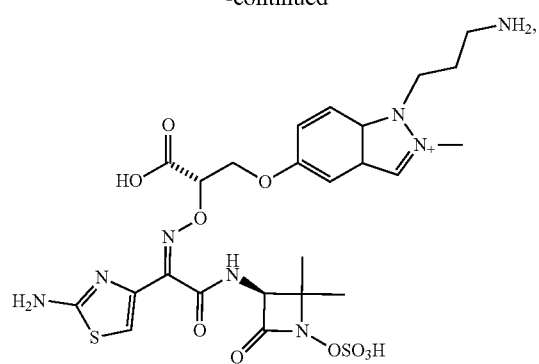
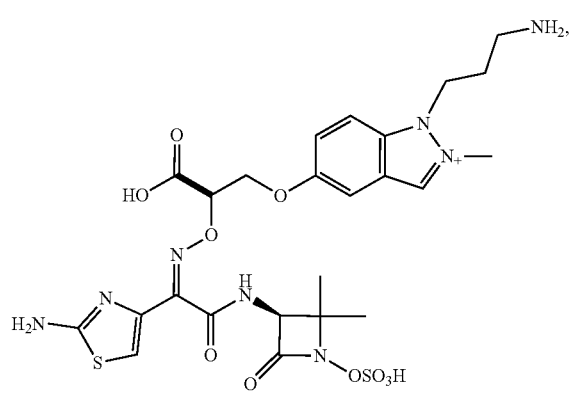
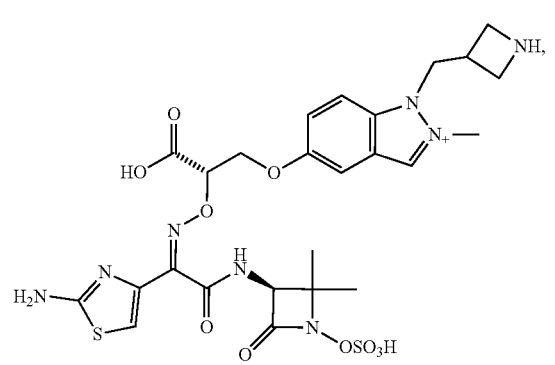
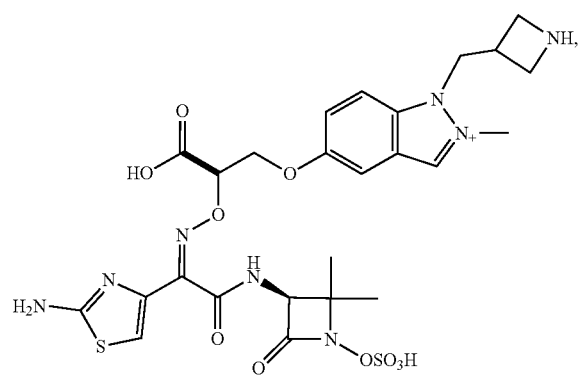
220
-continued
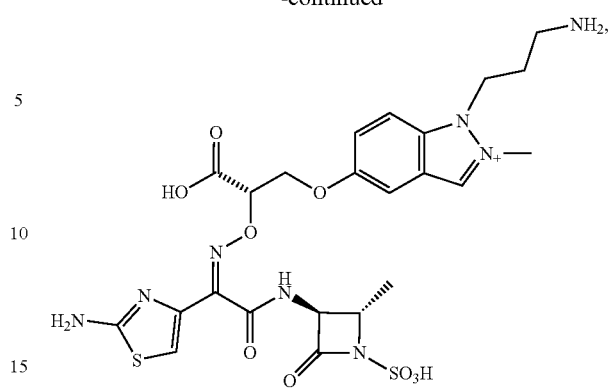
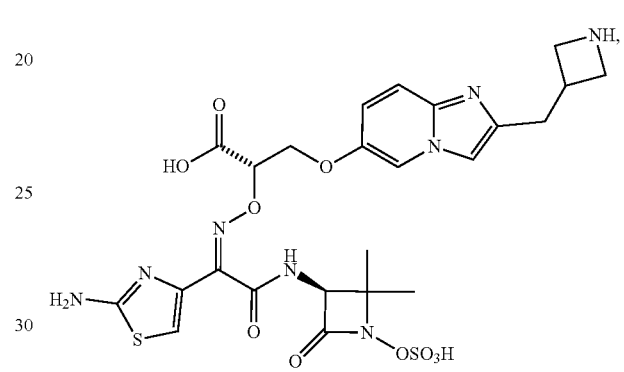
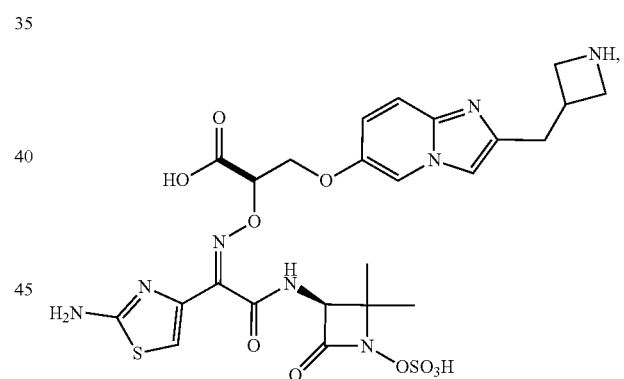
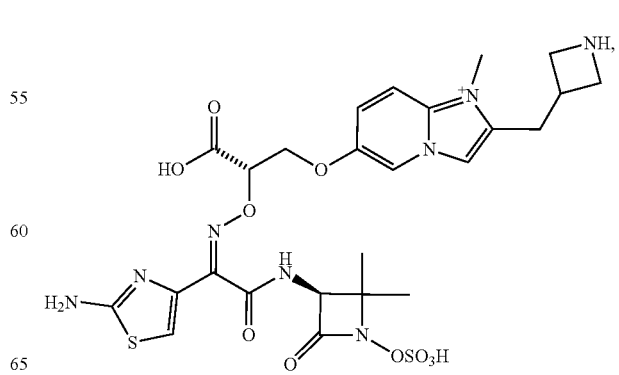

221
-continued
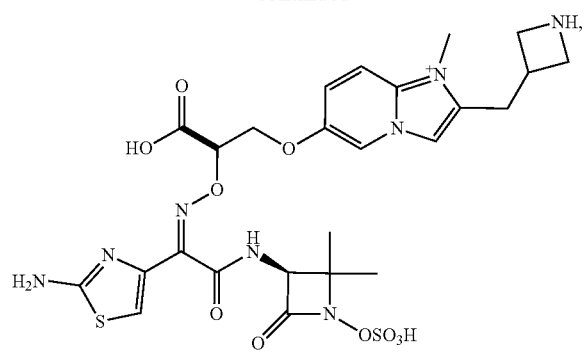
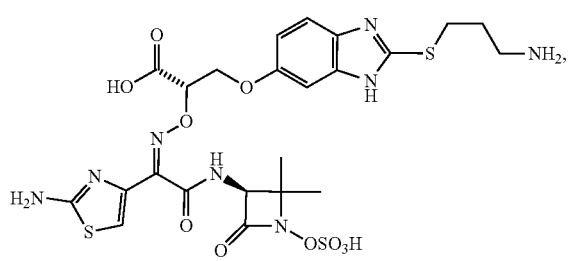
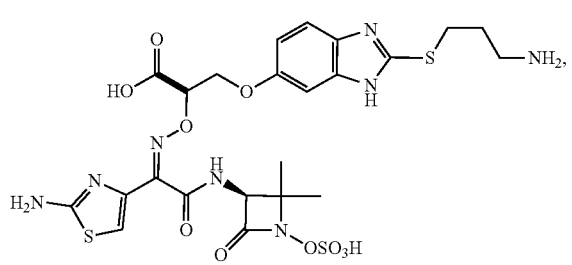
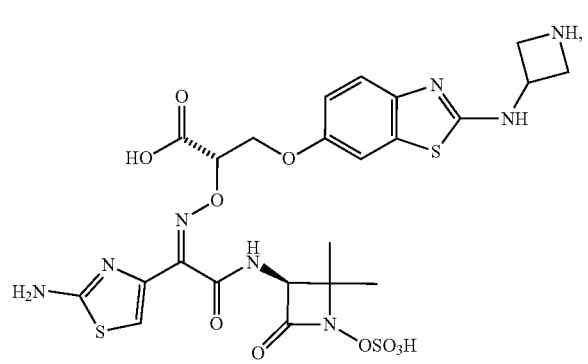
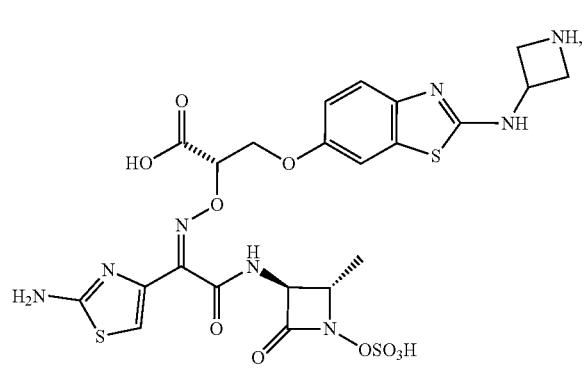
222
-continued
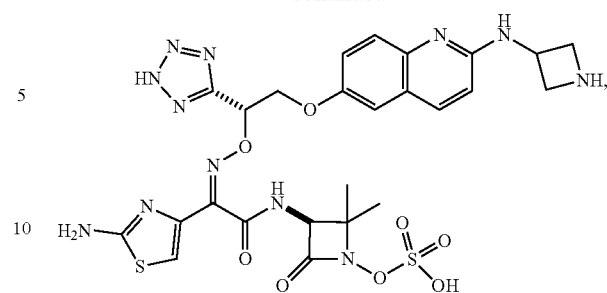
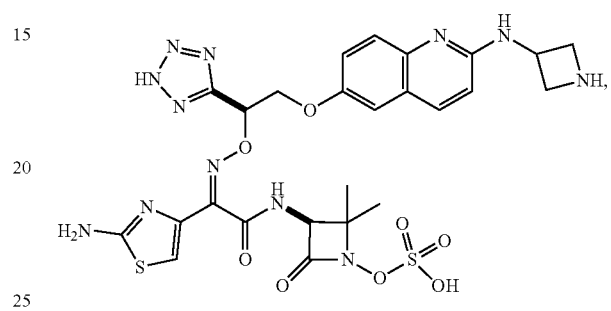
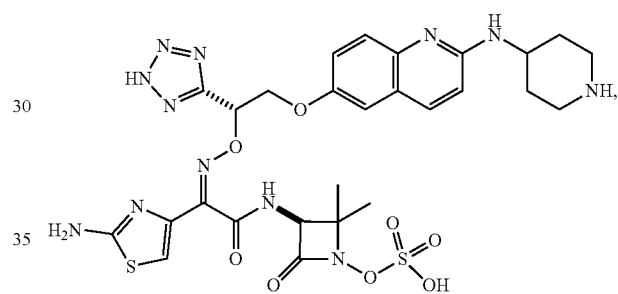
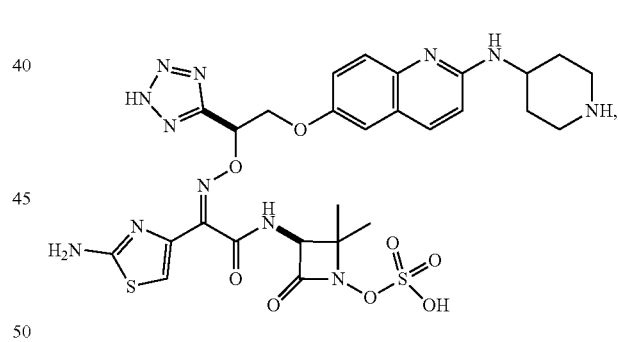
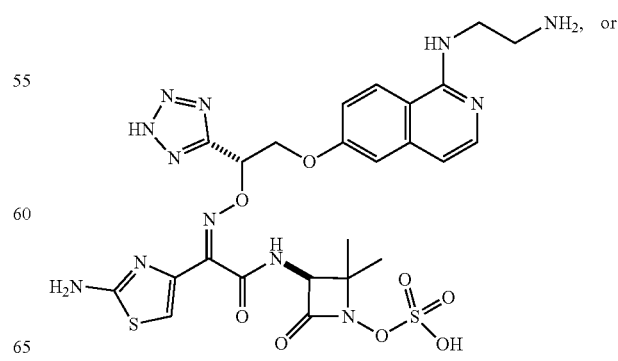

or a pharmaceutically acceptable salt thereof.
18. The compound of claim 1 selected from:
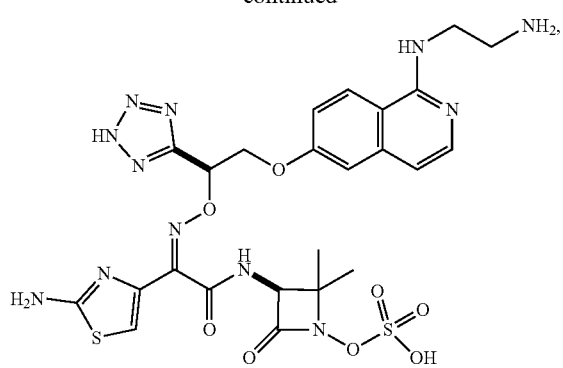
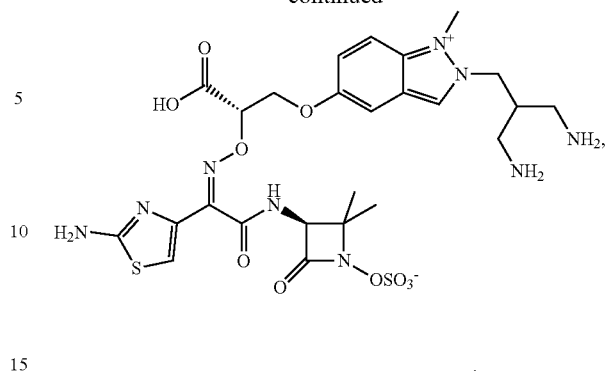

225
-continued
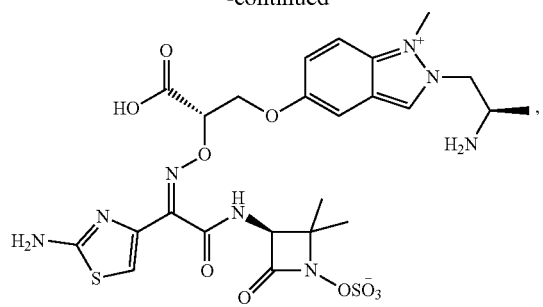
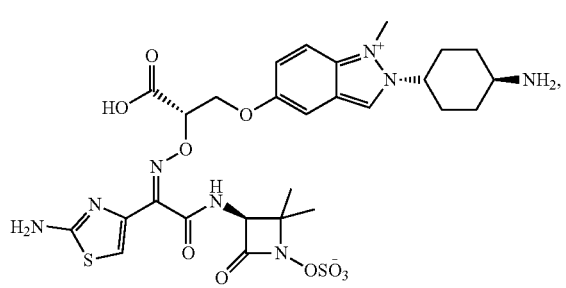
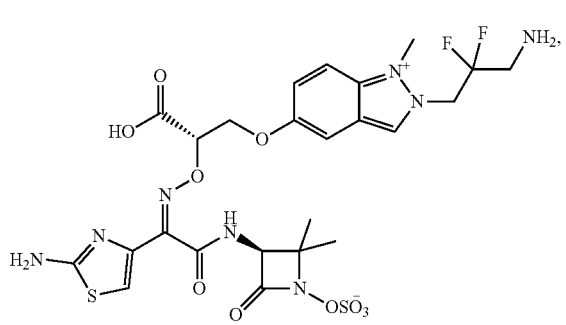
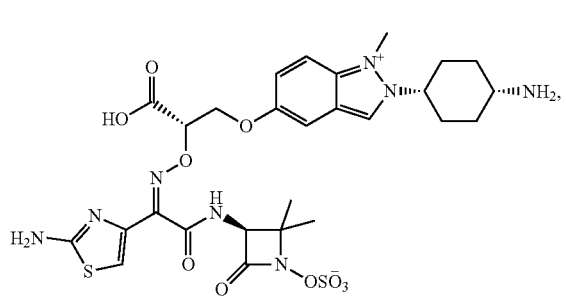
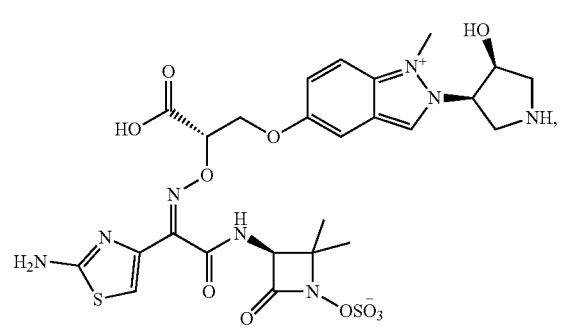
226
-continued
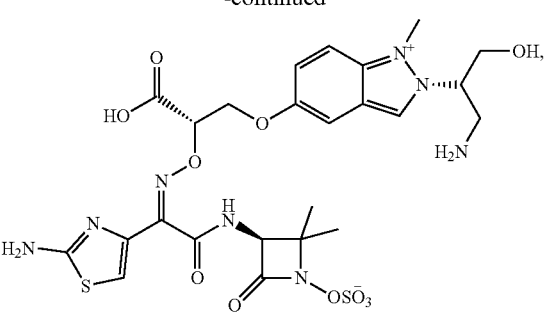
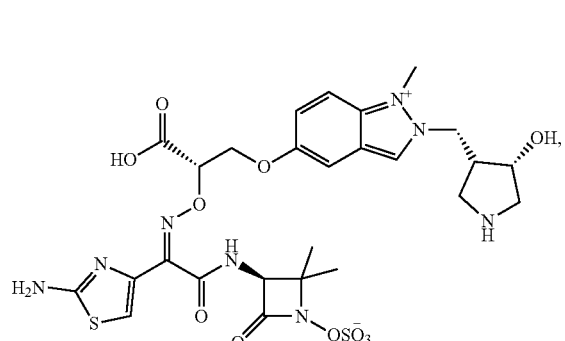
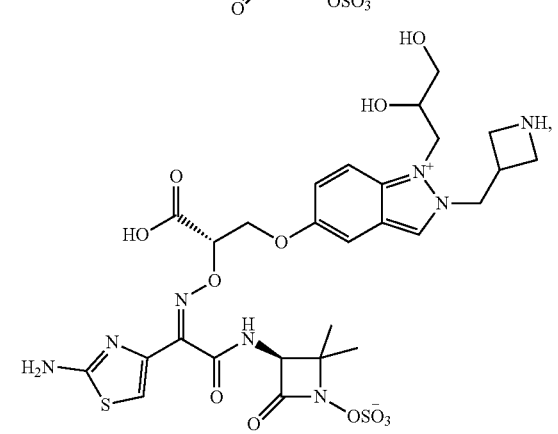
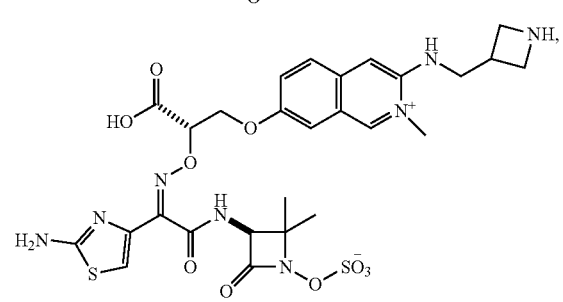
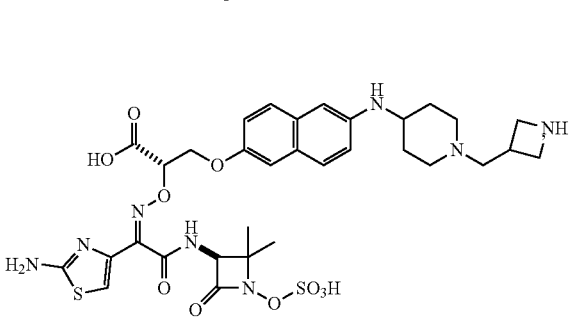

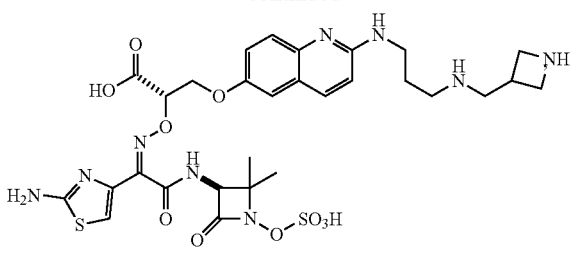
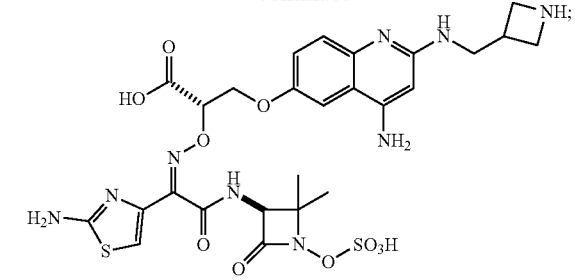
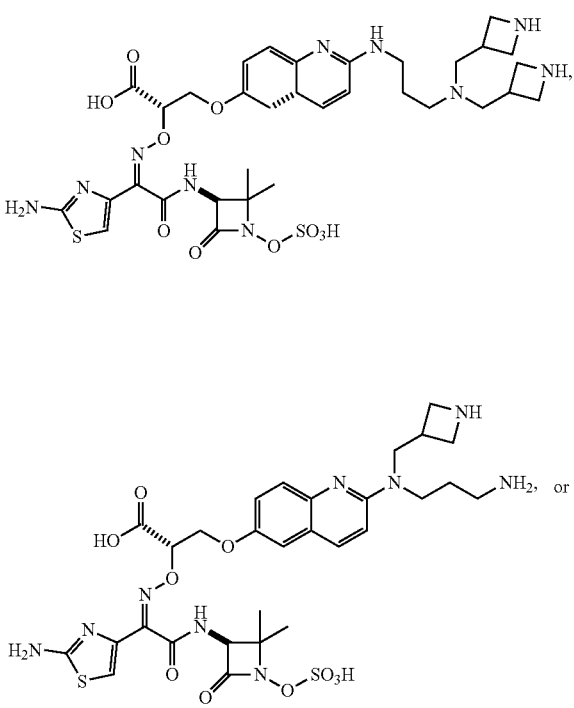

or a pharmaceutically acceptable salt thereof.

19. A trifluoroacetic acid salt of the compound of claim 1.

20. A trifluoroacetic acid salt of the compounds of claim 2.

21. A pharmaceutical composition comprising a therapeutically effective amount of a compound according to claim 1, or a pharmaceutically acceptable salt thereof, and a pharmaceutically acceptable carrier.

22. A pharmaceutical composition according to claim 21, which further comprises a therapeutically effective amount of one or more beta-lactamase inhibitor compounds.

23. A pharmaceutical composition according to claim 22, wherein at least one of the one or more beta-lactamase inhibitor compounds is selected from the group consisting of relebactam, tazobactam, clavulanic acid, sulbactam, and avibactam.

24. A method for treating a bacterial infection which comprises administering to a subject in need of such treatment (i) a therapeutically effective amount of a compound according to claim 1, or a pharmaceutically acceptable salt thereof, optionally in combination with one or more beta-lactamase inhibitor compounds.

25. The method of claim 24, wherein at least one of the one or more beta-lactamase inhibitor compounds is selected from the group consisting of relebactam, tazobactam, clavulanic acid, sulbactam, and avibactam.

26. The method of claim 24, wherein the bacterial infection is due to *Pseudomonas* spp., *Klebsiella* spp., *Enterobacter* spp., *Escherichia* spp., *Morganella* spp., *Citrobacter* spp., *Serratia* spp. or *Acintetobacter* spp.

* * * * *